United States Patent [19]

Marinier et al.

[11] Patent Number: 5,747,463
[45] Date of Patent: May 5, 1998

[54] MALONATE DERIVATIVES OF GLYCOLIPIDS AS CELL ADHESION INHIBITORS

[75] Inventors: Anne Marinier, Kirkland; Alain Martel, Delson, both of Canada

[73] Assignee: Bristol-Myers Squibb Company, Princeton, N.J.

[21] Appl. No.: 725,147

[22] Filed: Oct. 2, 1996

Related U.S. Application Data

[60] Provisional application No. 60/006,468 Nov. 13, 1995.

[51] Int. Cl.$^6$ .......................... A61K 31/70; C07H 15/00
[52] U.S. Cl. ............................................. 514/25; 536/17.9
[58] Field of Search ............................... 536/17.9; 514/25

[56] References Cited

FOREIGN PATENT DOCUMENTS

| | | |
|---|---|---|
| WO 92/01718 | 2/1992 | WIPO. |
| WO 93/05803 | 4/1993 | WIPO. |
| WO 93/10796 | 6/1993 | WIPO. |

OTHER PUBLICATIONS

Hsu-Lin, S., et al., "A Platelet Membrane Protein Expressed during Platelet Activation and Secretion" *J. Biol. Chem.*, 259/14, 9121-9126 (Jul. 1984).

Stenberg, P.E., et al., "A Platelet Alpha-Granule Membrane Protein (GMP-140) Is Expressed on the Plasma Membrane after Activation," *J. Cell Biol.*, 101, 880-886 (Sep. 1985).

McEver, R.P., et al., "GMP-140, a Platelet Alpha-Granule Membrane Protein, Is Also Synthesized by Vascular Endothelial Cells and Is Localized in Weibel-Palade Bodies" *J. Clin. Invest.*, 84, 92-99 (Jul. 1989).

Bonfanti, R., et al., "PADGEM (GMP 140) Is a component of Weibel-Palade Bodies of Human Endothelial Cells." *Blood*, 73, 1109-1112 (Apr. 1989).

Hattori, R., et al., "Complement Proteins C5b-9 Induces Secretion of High Molecular Weight Multimers of Endothelial von Willebrand Factor and Translocation of Granule Membrane Protein GMP-140 to the Cell Surface," *J. Biol. Chem.*, 264, 9053-9060 (May 1989).

Patel, K.D., et al., "Oxygen Radicals Induce Human Endothelial Cells to Express GMP-140 and Bind Neutrophils," *J. Cell Biol.*, 112, 749-759 (Feb. 1991).

Larsen, et al., "PADGEM-Dependent Adhesion of Platelets to Monocytes and Neutrophils is Mediated by a Lineage-Specific Carbohydrate, LNF III (CD15)," *Cell*, 63, 467-474 (Nov. 1990).

Erbe, et al., "Identification of an E-selectin Region Critical for Carbohydrate Recognition and Cell Adhesion," *J. Cell Biol.*, 112, 749-759 (Oct. 1991).

Skinner, et al., "Characterization of Human Platelet GMP-140 as a Heparin-Binding Protein," *Biochem. Biophys. Res. Commun.*, 164, 1373-1379 (Nov. 1989).

Skinner, et al., "GMP-140 Binding to Neutrophils is Inhibited by Sulfated Glycans," *J. Biol. Chem.*, 266, 5371-5374 (Mar. 1991).

Aruffo, et al., "CD62/P-Selectin Recognition of Myeloid and Tumor Cell Sulfatides," *Cell*, 67, 35-44 (Oct. 1991).

Suzuki, et al., "Sulfated Glycolipids are Ligands for a Lymphocyte Homing Receptor, L-Selectin (LECAM-1), Binding Epitope in Sulfated Sugar Chain," *Biochem. Biophys. Res. Commun.*, 190, 426-434 (Jan. 1993).

M.S. Mulligan, et al., "Protective Effects of Oligosaccharides in P-selectin-dependent Lung Inury," *Nature*, 364, 149-151 (Jul. 1993).

*Primary Examiner*—Kathleen K. Fonda
*Attorney, Agent, or Firm*—Aldo A. Algieri

[57] ABSTRACT

There is provided a novel series of malonate derivatives of glycolipid compounds of the formula

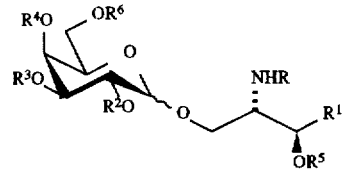

wherein R is an acyl residue of a fatty acid;
$R^1$ is $-(CH=CH)_m-(CH_2)_n-CH_3$;
$R^2$, $R^3$, $R^4$, $R^5$ and $R^6$ each are independently hydrogen, unsubstituted or substituted (lower)alkanoyl, arylalkyl or arylcarbonyl wherein said substituent is selected from the group consisting of halogen, $C_{1-4}$ alkyl, trifluoromethyl, hydroxy and $C_{1-4}$ alkoxy provided that one of $R^2$, $R^3$, $R^4$ and $R^6$ substituents is $-(CH_2)_p-CH(CO_2R^7)_2$;
m is an integer of 0 or 1;
n is an integer of from 5 to 14 inclusive;
p is an integer of from 2 to 6 inclusive; and
$R^7$ is hydrogen, a hydrolyzable ester group or a cation to form a non-toxic pharmaceutically acceptable salt;
or a solvate or hydrate thereof which are inhibitors of selectin-mediated cellular adhesion and are useful in the treatment or prevention of inflammatory diseases and other pathological conditions in mammals.

20 Claims, No Drawings

MALONATE DERIVATIVES OF GLYCOLIPIDS AS CELL ADHESION INHIBITORS

CROSS-REFERENCE TO RELATED APPLICATION

This nonprovisional application claims the benefit of copending provisional application, U.S. Ser. No. 60/006, 468, filed Nov. 13, 1995.

FIELD OF THE INVENTION

The present invention provides a novel series of malonate derivatives of glycolipid compounds, pharmaceutically acceptable salts and pharmaceutical compositions thereof as inhibitors of selectin-mediated cellular adhesion which are useful in the treatment or prevention of inflammatory disease processes and other pathological conditions mediated by the binding of selectins involved in intercellular adhesion.

BACKGROUND OF THE INVENTION

P-selectin (CD62, GMP140, PADGEM) is a membrane glycoprotein of ~140 kDa expressed by activated platelets and vascular endothelial cells. In resting platelets and vascular endothelial cells P-selectin is sequestered in α granules [Hsu-Lin, S., et al., *J. Biol. Chem.*, 259, 9121–9126 (1984); and Stenberg, P. E., *J. Cell Biol.*, 101,880–886 (1985)] and Weibel-Palade bodies [McEver, R. P. et al., *J. Clin. Invest.*, 84, 92–99 (1989); and Bonfanti, R., et al., *Blood*, 73, 1109–1112 (1989)], respectively. In response to inflammatory mediators such as thrombin [Hsu-Lin, S., et al., *J. Biol. Chem.*, 29121–9126 (1984); and Stenberg, P. E., *J. Cell Biol.*, 101, 880–886 (1985)], histamine [Hattori, R., et al., *J. Biol. Chem.*, 264, 9053–9060 (1989)], or peroxides [Patel, K. D., et al., *J. Cell Biol.*, 112, 749–759 (1991)] and cytokines such as interleukin-1 and tumor necrosis factor, P-selectin is rapidly mobilized from these intracellular stores to the cell surface where it mediates the initial binding interactions of activated platelets with leukocytes and the vascular wall, and of leukocytes with activated vascular endothelial cells. P-selectin is a member of a family of adhesion molecules which includes E-selectin (ELAM-1), which is expressed by activated vascular endothelial cells, and L-selectin (Leu 8, LAM-1, LECAM), which is expressed by leukocytes. These proteins are type 1 membrane proteins and are composed of an amino terminal lectin domain followed by an epidermal growth factor (EGF) like domain, a variable number of complement receptor related repeats (CR), a hydrophobic membrane spanning region and a cytoplasmic domain. As indicated by high sequence homology, these proteins are not only structurally but also functionally related, modulating the trafficking of peripheral blood leukocyte by permitting adhesive interactions between leukocytes and endothelial cells. These binding interactions are predominately mediated by contact between the lectin domain of the selectin and various carbohydrate ligands.

Although it is now widely accepted that a lectin domain/carbohydrate interaction is primarily reponsible for mediating P-selectin/myeloid cell binding, the exact molecular nature of the P-selectin ligand is not known. Binding of P-selectin to myeloid cells is $Ca^{2+}$ dependent as well as neuraminidase and protease sensitive. The binding of P-selectin to myeloid cell lines can be inhibited by growing the cells in the presence of sodium selenate and inhibitor of sulfation. P-selectin has been shown to bind to the carbohydrate $Le^x$ (CD15) [Larsen, et al., *Cell*, 63, 467–474 (1990)] and its sialylated form, sialyl-Lewis$^x$ (sLe$^x$) [Erbe, et al., *J. Cell Biol.*, 119, 215–217 (1992)], and there is evidence that these carbohydrates and/or others like them are presented to P-selectin by a discrete number of cell surface proteins including L-selectin. Various anionic polymers, including heparin, fucoidan, and dextran sulfate have also been shown to inhibit P-selectin mediated adhesion [Skinner, et al., *Biochem. Biophys. Res. Commun.*, 164, 1373–1379 (1989); and *J. Biol. Chem.*, 266, 5371–5374 (1991)]. In addition, P-selectin has been shown to bind 3-sulfated galactosyl ceramides (sulfatides) [Aruffo, et al., *Cell*, 67, 35–44 (1991)]. Although the physiological relevance of this interaction remains to be elucidated, it is known that myeloid cells can excrete large quantities of sulfatides on activation. This suggests that sulfatides might participate in leukocyte extravasation at sites of inflammation by displacing the adhesion-mediating leukocyte surface ligand(s), thereby permitting the efficient exit of leukocytes from the blood stream at sites of inflammation.

A number of publications have appeared which describe new agents as inhibitors of cellular adhesion. Some of these publications, but not limited to, include the use of peptides and carbohydrate sutructures in International patent application WO 92/01718 published Feb. 6, 1992; the use of substituted lactose and lactosamine derivatives in International patent application WO 93/10796 published Jun. 10, 1993; the use of glycoconjugates in International patent application WO 93/05803 published Apr. 1, 1993; the use of sulfated glycolipid derivatives by Suzuki, et al., *Biochem. Biophys. Res. Commun.*, 190, 426–434 (1993) and the use of oligosaccharides by M. S. Mulligan, et al., *Nature*, 364, 149–151 (1993).

However, there are many situations in which the recruitment of leukocytes by adhesion to the endothelial cells is abnormal or in excess, and the end result is tissue damage instead of repair. Thus, there is a need to develop specific and potent compounds which can inhibit the initial cellular adhesion process. It is the object of the present invention to provide new malonate derivatives of glycolipids which are inhibitors of cell adhesion and, therefore, useful in man for the treatment and/or prevention of acute or chronic inflammatory diseases such as rheumatoid arthritis, asthma, allergy conditions, psoriasis, septic shock and other indications such as reperfusion injury, adult respiratory distress syndrom, ischemia, ulcerative colitis, vasculitides, atherosclerosis and inflammatory bowel disease, chemical and thermal burn injuries, multiple sclerosis and tumor metastases.

SUMMARY OF THE INVENTION

The present invention provides novel O-dicarboxyalkylated glycolipids having the formula

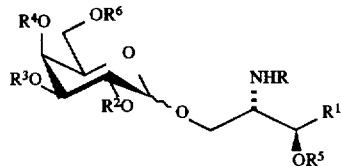

wherein R, $R^1$, $R^2$, $R^3$, $R^4$, $R^5$ and $R^6$ are as defined below, or a solvate or hydrate thereof which are inhibitors of selectin-mediated cellular adhesion. The present invention also provides pharmaceutical compositions comprising said dicarboxyalkylated glycolipids and to the method of treatment or prevention of conditions characterized by selectin-mediated cellular adhesion such as inflammatory diseases and other pathological conditions in mammals.

DESCRIPTION OF THE INVENTION

The present invention provides novel O-dicarboxyalkylated α- and β-glycolipid compounds which are inhibitors of selectin-mediated cellular adhesion and which have the formula

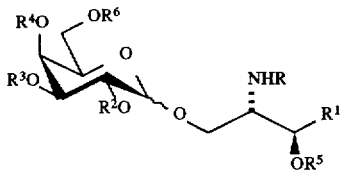

wherein

R is an acyl residue of a fatty acid:

$R^1$ is —$(CH=CH)_m$—$(CH_2)_n$—$CH_3$;

$R^2$, $R^3$, $R^4$, $R^5$ and $R^6$ each are independently hydrogen, unsubstituted or substituted (lower)alkanoyl, arylalkyl or arylcarbonyl wherein said substituent is selected from the group consisting of halogen, $C_{1-4}$ alkyl, trifluoromethyl, hydroxy and $C_{1-4}$ alkoxy provided that one of $R^2$, $R^3$, $R^4$ and $R^6$ substituents is —$(CH_2)_p$—$CH(CO_2R^7)_2$;

m is an integer of 0 or 1;

n is an integer of from 5 to 14 inclusive;

p is an integer of from 2 to 6 inclusive; and $R^7$ is hydrogen, a hydrolyzable ester group or a cation to form a non-toxic pharmaceutically acceptable salt;

or a solvate or hydrate thereof.

The present invention also provides a method for the treatment or prevention of inflammatory diseases and other pathological conditions characterized by selectin-mediated cellular adhesion, which comprises administering a therapeutically effective amount of a compound of Formula I or in combination with a pharmaceutical carrier or diluent.

The terms "$C_{1-4}$ alkyl", $C_{1-4}$ alkoxy", "(lower) alkyl" and "(lower) alkoxy" as used herein and in the claims (unless the context indicates otherwise) mean straight or branched chain alkyl or alkoxy groups such as methyl, ethyl, propyl, isopropyl, butyl, isobutyl, t-butyl. Preferably, these groups contain from 1 to 2 carbon atoms. The term "arylalkyl" as used herein and in the claims means a phenyl group attached via an alkyl moiety containing from 1 to 4 carbon atoms such as methyl, ethyl, propyl, butyl and the like, and most preferably means benzyl or phenylethyl. Unless otherwise specified, the term "halogen" as used herein and in the claims is intended to include bromine, chlorine, iodine and fluorine while the term "halide" is intended to include bromide, chloride and iodide anion. Preferably, halogen is chlorine or fluorine. The term "(lower) alkanoyl" as used herein and in the claims means an alkanoyl containing from 2 to 6 carbon atoms such as acetyl, propionyl and the like.

The term "provided that one of the $R^2$, $R^3$, $R^4$ and $R^6$ substituents is —$(CH_2)_p$—$CH(CO_2R^7)_2$," as used herein and in the claims means that one substituent selected from $R^2$, $R^3$, $R^4$ and $R^6$ must be —$(CH_2)_p$—$CH(CO_2R^7)_2$ to provide a O-dicarboxyalkylated glycolipid. The wavy bond "~" in the structural formula to which the bond to the anomeric carbon is attached as used herein and in the claims means that the bond may be either in the axial or equatorial configuration as occurs in the monosaccharide galactose.

The term "a cation to form a non-toxic pharmaceutically acceptable salt" as used herein and in the claims is intended to include non-toxic base addition salts with inorganic and organic bases. Suitable inorganic bases such as alkali and alkaline earth metal bases include metallic cations such as sodium, potassium, magnesium, calcium and the like. Suitable organic bases include amines such as ammonium, trialkylamines, pyridine, dibenzylamine, ethanolamine, N-methylglucamine, N-methylpiperidine, N-methylmorpholine, lysine, arginine and other amines which have been used to form salts of carboxylic acids. Unless otherwise specified, the term "a hydrolyzable ester group" as used herein and in the claims is intended to include an ester group which is physiologically acceptable and hydrolyzable such as $C_{1-6}$ alkyl, benzyl, 4-methoxybenzyl, (lower)-alkanoyloxy(lower)alkyl, e.g. acetoxymethyl, propionyloxymethyl or pivaloyloxymethyl, (lower)alkoxycarbonyloxy(lower)alkyl, e.g., methoxycarbonyloxymethyl or ethoxycarbonyloxymethyl, (lower)-alkoxycarbonyl(lower)alkyl, e.g., methoxycarbonylmethyl, or t-butoxycarbonylmethyl, 2-methoxycarbonyloxyethyl, (5-methyl-2-oxo-1,3-dioxol-4-yl)methyl, dihydroxypropyl and the like.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

The compounds of the present invention contain a monosaccharide selected from galactose. The natural occurring sulfatides from brain tissue are part of a class of compounds known as sulfated cerebrosides [Radin *Handbook of Neurochemistry*, Vol. 3 415–424 (1969)]. The commercially available sulfatides are a mixture of compounds in which the hexose moiety is mainly galactose and the configuration of the hexose in the natural sulfatides is in the β-anomeric form. [Sweeley, *Pure and Appl. Chem.*, 61(7) 1307–1312 (1989)].

In the method of the present invention, the term "therapeutically effective amount" means the total amount of each active component of the method that is sufficient to show a meaningful patient benefit, i.e. healing of chronic conditions characterized by selectin-mediated cellular adhesion or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with selectin-mediated cellular adhesion.

The term "acyl residue of a fatty acid" as used herein and in the claims means the acyl residue of a naturally occuring saturated or unsaturated fatty acid or a fatty acid derived therefrom such as 9-methoxycarbonyl nonanoic acid. Suitable saturated fatty acids are those described herein and other known fatty acids such as butyric, isovaleric, caproic, caprylic, capric, lauric, myristic, palmitic, stearic, arachidic, behenic, lignoceric, cerotic and the like. Suitable unsaturated fatty acids include the cis and trans isomers of fatty acids such as $\Delta^9$-decylenic, stillingic, $\Delta^9$-dodecylenic, palmitoleic, oleic, ricinoleic, petroselinic, vaccenic, linoleic, linolenic, eleostearic, punicic, licanic, parinaric, gadoleic, arachidonic, 5-eicosenic, 5-docosenic, cetoleic, erucic, 5,13-docosadienic, nervonic and the like.

Hydroxy-protecting groups which can be employed in the present invention to block or protect the hydroxyl group are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Hydroxy-protecting (blocking) groups which are advantageously used are those which are common in carbohydrate chemistry especially for primary alcohols, secondary alcohols and vicinal cis and trans diols.

Suitable hydroxy-protecting groups may be, for example, acyl groups such as acetyl, trichloroacetyl, phenoxycarbonyl, benzyloxycarbonyl, benzhydryloxycarbonyl, trityloxycarbonyl and 2,2,2-trichloroethoxycarbonyl, ether groups such as methoxymethyl, benzyloxymethyl, allyl, benzyl, p-methoxybenzyl, p-nitrobenzyl, benzhydryl, trityl or triorganosilyl groups such as tri($C_1$–$C_6$)alkylsilyl (e.g., trimethylsilyl, triethylsilyl, triisopropylsilyl, isopropyidimethylsilyl, t-butyldimethylsilyl, methyldiisopropylsilyl or methyldi-t-butylsilyl), t-butyldiphenylsilyl, triarylsilyl (e.g. triphenylsilyl, tri-p-xylylsilyl) or triaralkylsilyl (e.g. tribenzylsilyl). Examples of these and other suitable hydroxy-protecting groups and methods for their formation and removal are known in the art, e.g., see *Protective Groups in Organic Synthesis*, second ed., Greene et al., John Wiley & Sons, New York, 1991, Chapter 2 and references therein.

The compounds of Formula I may be prepared by various procedures such as those illustrated herein in the examples, in the Reaction Schemes 6, 7, 8 and 9 and variations thereof which would be evident to those skilled in the art. The various O-carboxyalkyl substituted glycolipids of Formula I wherein the carbohydrate moiety is galactose are advantageously prepared from the intermediates of Formula Va, Vb, Vc, Vd and Ve which are prepared by various procedures such as those illustrated in Reaction Schemes 2, 3, 4 and 5 and the azido alcohol of Formula III illustrated in Reaction Scheme 1.

The preparation of a generic azido diol lipid of Formula II (occasionally referred to as azidosphingosine) wherein $R^1$ is as previously defined is illustrated in the process shown in Reaction Scheme 1. Thus, 2,4-O-benzylidene-D-threose is advantageously reacted with the desired phosphonium salt in a Wittig reaction by the general procedures described by P. Zimmerman, et al., *Liebigs Ann. Chem.*, 663–667 (1988) to produce the desired trans olefin wherein n=5–14. The olefin moiety may be retained in the process to provide compounds of Formula I wherein m=1 in the definition of $R^1$ or, if desired, the olefin may be reduced by conventional hydrogenation procedures to eventually provide compounds of Formula I wherein m=0 in the definition of $R^1$. The hydroxy function of the intermediate is treated with triflic anhydride and sodium azide to produce the cyclic azido intermediate with inversion of configuration followed by acid treatment to remove the benzylidene blocking group to produce the desired azido diol intermediate of Formula II wherein $R^1$ is —(CH=CH)$_m$—(CH$_2$)$_n$—CH$_3$. It is advantageous in the present process to block (protect) the secondary alcohol or allylic alcohol as the case may be in the compound of Formula II by first readily blocking the primary alcohol by conventional blocking (protecting) groups with an organosilyl group such as t-butyldimethylsilyl followed by the reaction with the desired $R^5$ substituent, as previously defined and wherein X is a conventional leaving group well-known in the art such as chloro, bromo, iodo, fluorosulfonyl and the like. After the displacement is completed, the silyl blocking group may readily be removed with, for example, tetrabutylammonium fluoride to give the desired compound of Formula III which is now suitable for use in the coupling reaction with a carbohydrate moiety, as illustrated in Reaction Schemes 6, 7, 8 and 9.

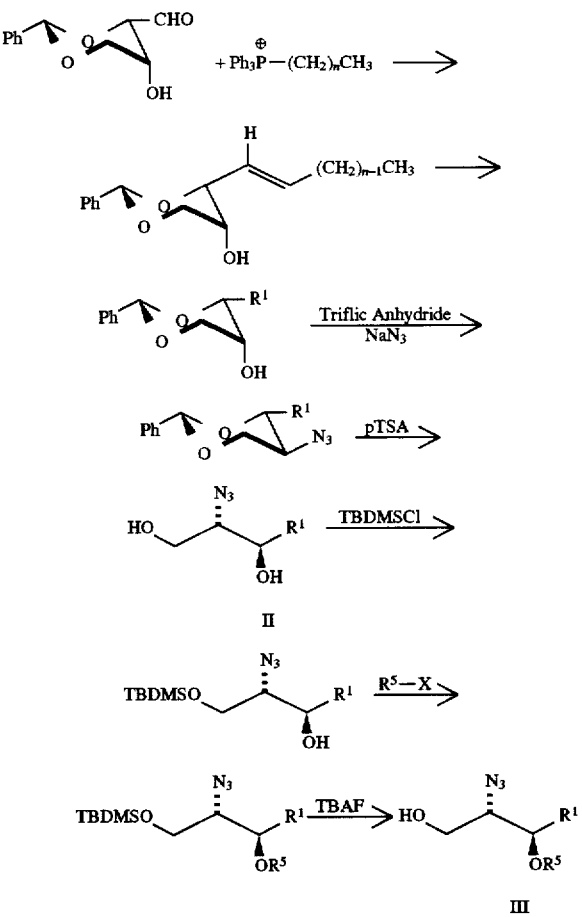

There are various processes which are useful for the preparation of the pyranoside compounds of Formula Va, Vb, Vc, Vd and Ve. It should be appreciated by those skilled in the art that selective blocking and deblocking of carbohydrates which are used to prepare the various positional dicarboxyalkylated isomers are well-known in the art such as those illustrated herein and in *Protective Groups in Organic Synthesis*, second ed., T. W. Greene and P. G. M. Wuts, John Wiley & Sons, New York, 1991, Chapter 2 and references therein. It should further be appreciated by those skilled in the art that the specific blocking group to be used will vary with the axial or equatorial position of the hydroxyl groups in the preferred carbohydrate moiety of the instant invention. Thus, Reaction Schemes 2, 3, 4 and 5 exemplify the preparation of the 2-dicarboxyalkylated galactopyranosides of Formula Va and Vb, the 6-dicarboxyalkylated galactopyranosides of Formula Vc, the 3-dicarboxyalkylated galactopyranosides of Formula Vd and the 4-dicarboxyalkylated galactopyranosides of Formula Ve. Some of the processes for the preparation of compounds of Formula Va to Ve are exemplified in the examples described herein, some are illustrated in Reaction Schemes and other processes will be evident to those skilled in the art.

The process for the preparation of O-dicarboxyalkylated α- and β-glycolipids of Formula I are conveniently illustrated and summarized in Reaction Schemes 6, 7, 8 and 9. When it is desired to prepare a dicarboxyalkylated glycolipid of Formula 1, the possible combinations of the instant invention are set forth in Reaction Schemes 6, 7, 8 and 9. The sequence in Reaction Scheme 6 exemplifies the preparation of both the α-anomer of Formula Ia and the β-anomer of Formula Ib of 2-dicarboxyalkylated glycolipids of galactopyranosides of Formula 1, from the corresponding pyranoside intermediate of Formula Va or Vb. The reaction sequence in Reaction Scheme 7 exemplifies the preparation of both the α-anomer of Formula Ic and the β-anomer of Formula Id of 6-dicarboxyalkylated glycolipids of galactopyranosides of Formula I, from the corresponding pyranoside intermediate of Formula Vc. The process in Reaction Scheme 8 exemplifies the preparation of both the α-anomer of Formula Ie and the β-anomer of Formula If of 3-dicarboxyalkylated glycolipids of galactopyranosides of Formula I, from the corresponding pyranoside intermediate of Formula Vd. The sequence in Reaction Scheme 9 exemplifies the preparation of both the α-anomer of Formula Ig and the β-anomer of Formula Ih of 4-dicarboxyalkylated glycolipids of galactopyranosides of Formula I, from the corresponding pyranoside intermediate of Formula Ve.

In the process for the preparation of dicarboxyalkylated α- and β-glycolipids of Formula I several known procedures are contemplated which generally follow the sequence of reaction steps as illustrated in Reaction Schemes 2 to 9. Each reaction step is generally well-known to those skilled in the art and, advantageously, the appropriate use of protecting (blocking) groups are used when necessary to effect the desired results. In the compounds of Formula I, the $R^2$, $R^3$, $R^4$, $R^5$ and $R^6$ substituents may also be changed by standard well-known procedures to achieve a different but desirable modification of the compounds of Formula I. This is conveniently illustrated in the reaction scheme by the double arrows indicating that the chemical structures may be interchanged by well-known hydrolysis and esterification or etherification procedures. It should be understood by those skilled in the art that the selection and therefore the result will depend on the nature, number and position of the substituents. It should also be understood that the illustration in the schemes is not intended to be limiting since slight modifications are often deemed desirable or necessary to achieve a particular result.

As used herein and in the reaction schemes the term "reduction" is intended to include well-known reduction procedures for the azido group such as reducing metals, i.e., activated zinc; hydrogenolysis with hydrogen and palladium; hydrogen transfer reactions with cyclohexane/formic acid/palladium; and preferably with hydrogen sulfide in aqueous pyridine. The term "reduction" is also intended to include well-known reduction procedures for the ester group such as aluminum or boron hydrides.

As used herein and in the reaction schemes the term "acylation" is intended to include conventional and well-known acylation procedures for the preparation of amides such as the use of leaving groups and activating groups on the acyl portion of the fatty acid. For example, the use of acid chlorides and carbodiimide as activating groups in organic solvent such as tetrahydrofuran, dichloromethane or mixture of aqueous-organic solvents in the presence of a base such as triethylamine, pyridine, dimethylaminopyridine and 50% sodium acetate.

As used herein and in the reaction schemes the term "alkylation" is intended to include conventional and well-known alkylation procedures. Thus, in one method, the desired hydroxy groups which are to be alkylated are treated in the presence of an organic or inorganic base such as sodium hydride, potassium hydride, lithium diisopropylamine or lithium bis(trimethylsilyl)amide in an inert organic solvent such as tetrahydrofuran, dimethylformamide, hexamethylphosphoramide, dimethylsulfoxide, N-methylpyrolidinone and the like with an alkylating agent such as an ester of bromoacetate [Westerduin, et al., *Carbohydrate Research*, 234, 131–140 (1992)], i.e. t-butyl ester or any other suitable carboxy-protecting group, or an alkyl halide, an alkyl mesylate or tosylate. In a second method, the alkylation may be carried out under phase transfer catalysis conditions [Keller. et al., *Helvetica Chim. Acta*, 76, 884 (1993)]. This method is well-known to those skilled in the art and the alkylation reaction proceeds at the interface of the aqueous solution and the immisible solvent such as methylene chloride, diethyl ether, diisopropyl ether, and other similar water-immisible solvents. The alkylation reaction proceeds with the addition of a phase-transfer catalyst which are well-known and are readily available from commercial sources such as tetraorganoammonium salts, i.e. tetrabutylammonium chloride, tetrabutylammonium bromide, and tributylbenzylammonium chloride. Advantageously an excess of alkylating agent is utilized in the two methods described above to alkylate the desired hydroxy groups while the hydroxy groups to be retained are blocked (protected). The term "alkylation" is also intended to include conventional and well-known procedures involving the displacement of a leaving group such as halide, mesylate or tosylate by the carbon anion of a malonate ester, i.e., methyl, ethyl, t-butyl ester or any other suitable carboxy-protecting group produced by an organic or inorganic base such as sodium hydride, potassium hydride, lithium diisopropylamine, lithium bis(trimethylsilyl)amide, potassium tert-butoxide or sodium ethoxide in an inert organic solvent such as tetrahydrofuran, dimethylformamide, hexamethylphosphoramide, dimethylsulfoxide, N-methylpyrolidinone and the like.

As used herein and in the reaction schemes the term "substitution" is intended to include well-known transformation procedures of a hydroxy group to an alkylsulfonate or substituted alkylsulfonate or arylsulfonate group such as methanesulfonate (mesylate), trifluoromethanesulfonate (triflate) and p-toluenesulfonate (tosylate). These well-known procedures involve for example the use of alkylsulfonyl or arylsulfonyl chlorides in an organic solvent such as dichloromethane or tetrahydrofuran in the presence of a base such as triethylamine, pyridine and dimethylaminopyridine. The term "substitution" is also intended to include well-known conversion procedures of an hydroxy group to a halide group such as chloride, bromide or iodide, by the use of carbon tetrachloride or carbon tetrabromide in the presence of triphenylphosphine, or sodium iodide in an organic solvent such as acetone, dimethylformamide and the like.

As used herein and in the reaction schemes the terms "blocking" and "protecting" are intended to include conventional and well-known protecting groups in the art such as those illustrated herein and in *Protective Groups In Organic Synthesis*, second ed., Green et al., John Wiley and Sons, New York, 1991, Chapter 2 and references therein. For example, the formation of acetals and ketals with an acid catalyst; the use of trisubstituted organosilyl reagents such as tert-butyldimethylsilyl chloride and triethylsilyl chloride;

methoxymethyl bromide; benzyl bromide; benzoyl chloride and the like. The reaction may be carried out in tetrahydrofuran, dichloromethane, dimethylformamide and the like in the presence of a base such as triethylamine, dimethylaminopyridine, pyridine, sodium hydride and the like, and optionally with imidazole or 4-dimethylaminopyridine as a catalyst.

As used herein and in the reaction schemes, the term "hydrolysis" is intended to include conventional hydrolysis procedures well-known to those skilled in the art. For example, the hydrolysis of benzylidene, isopropylidene, p-methoxybenzyl (PMB), methoxymethyl (MOM) and the like may be carried out under acidic conditions such as 90% trifluoroacetic acid, 3N hydrochloric acid, p-toluenesulfonic acid and the like in solvents such as dichloromethane and tetrahydrofuran. Also, p-methoxybenzyl may be removed with the use of dichlorodicyanobenzoquinone. Furthermore, organosilyl blocking groups such as tert-butyldimethylsilyl and triethylsilyl may advantageously be removed by the use of tetrabutylammonium fluoride (TBAF) in tetrahydrofuran and acetic acid. Still further, benzoate and acetate blocking groups may also be removed by the use of sodium or potassium alkoxides.

The preparation of the 2-dicarboxyalkylated galactopyranosides of Formula Va and Vb is advantageously carried out from the corresponding ethyl 1-thio-β-galactopyranoside of Formula IV as shown in Reaction Scheme 2A. The galactopyranoside of Formula IV is selectively treated with two different blocking groups. It is advantageous to first block the 3- and 4-hydroxy groups with 2,2-dimethoxypropane and the partially blocked intermediate is then selectively blocked at position 6 with a different protecting group such as tert-butyldimethylsilyl. The resulting unblocked 2-hydroxy group in the intermediate of Formula VI is then alkylated preferably with t-butyl ester of bromoacetate when it is desired to prepare the pyranoside intermediate of Formula Va' or Vb' wherein p=2 as shown in Reaction Scheme 2B or with a dihalogenated alkane when it is desired to prepare the pyranoside intermediate of Formula Va or Vb wherein p>2, under conditions described herein and as illustrated in Reaction Scheme 2A. The halogenated galactopyranoside resulting from the alkylation with a dihalogenated alkane is then submitted to a malonate condensation to produce the 2-dicarboxyalkylated galactopyranoside of Formula Va. If desired, further modification of protecting groups can be performed by hydrolysis of the isopropylidene and tert-butyldimethylsilyl groups and subsequent selective blocking with benzaldehyde acetal and benzoyl chloride, producing the 2-dicarboxyalkylated galactopyranoside of Formula Vb. When it is desired to prepare an intermediate of Formula Va' or Vb' wherein p=2, the monocarboxymethylated galactopyranoside resulting from the alkylation of the galactopyranoside of Formula VI with the t-butyl ester of bromoacetate is reduced under conditions described herein and as illustrated in Reaction Scheme 2B. The free hydroxy group produced is then converted to a leaving group such as halide, tosylate or preferably mesylate which is submitted to a malonate condensation to produce the 2-dicarboxypropylated intermediate of Formula Va'. It should be appreciated by those skilled in the art that the 2-dicarboxypropylated intermediate of Formula Vb' can be produced, if desired, by following the general synthetic steps outlined for the pyranoside intermediate of Formula Vb wherein p>2.

Reaction Scheme 2A

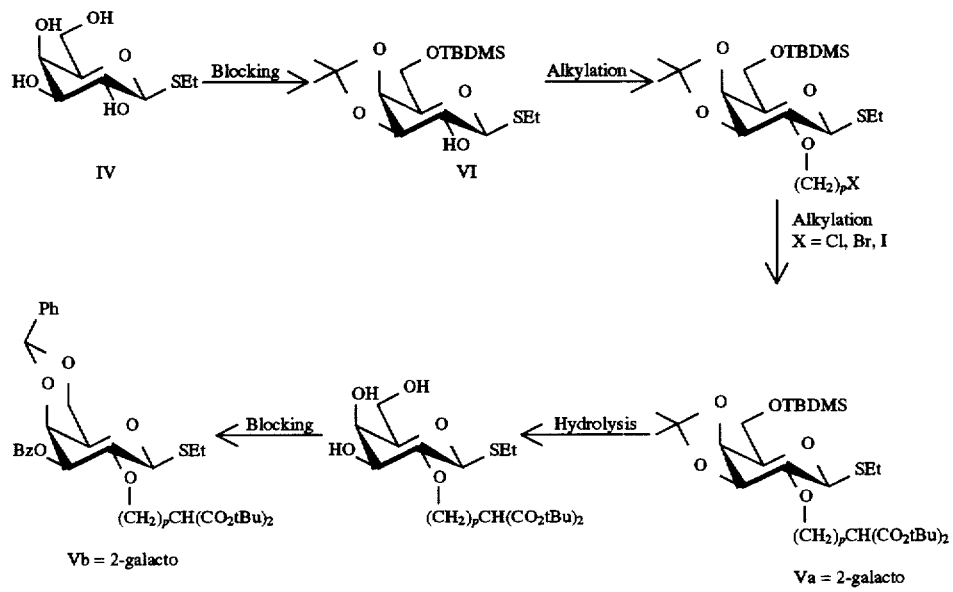

Reaction Scheme 2B

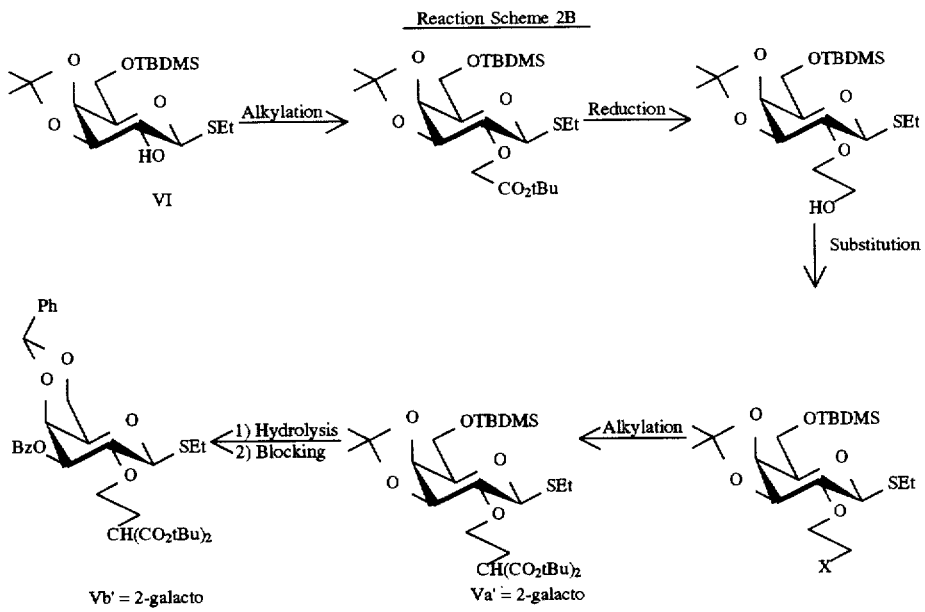

When it is desired to prepare the 6-dicarboxyalkylated galactopyranosides of Formula Vc, the intermediate of Formula IV is treated with 2,2-dimethoxypropane in the presence of an acid catalyst and the resulting unblocked 2-hydroxy group is protected preferably with p-methoxybenzyl chloride as outlined in Reaction Scheme 3A. After selective hydrolysis, the unblocked 6-hydroxy group in the intermediate of Formula VII is alkylated preferably with a dihalogenated alkane when it is desired to prepare 6-carboxylalkylated galactopyranosides of Formula Vc wherein p>2. The halogenated galactopyranoside resulting from the alkylation with a dihalogenated alkane is then submitted to a malonate condensation under well-known conditions to produce the 6-dicarboxyalkylated galactopyranoside of Formula Vc wherein p>2. When it is desired to prepare an intermediate of Formula Vc' wherein p=2, the monocarboxymethylated galactopyranoside resulting from the alkylation of the intermediate of Formula VII with the t-butyl ester of bromoacetate is reduced under conditions described herein and illustrated in Reaction Scheme 3B. The free hydroxy group is then converted to a leaving group such as halide or preferably mesylate which is then submitted to a malonate condensation to produce the 6-dicarboxypropylated pyranoside intermediate of Formula Vc'.

Reaction Scheme 3A

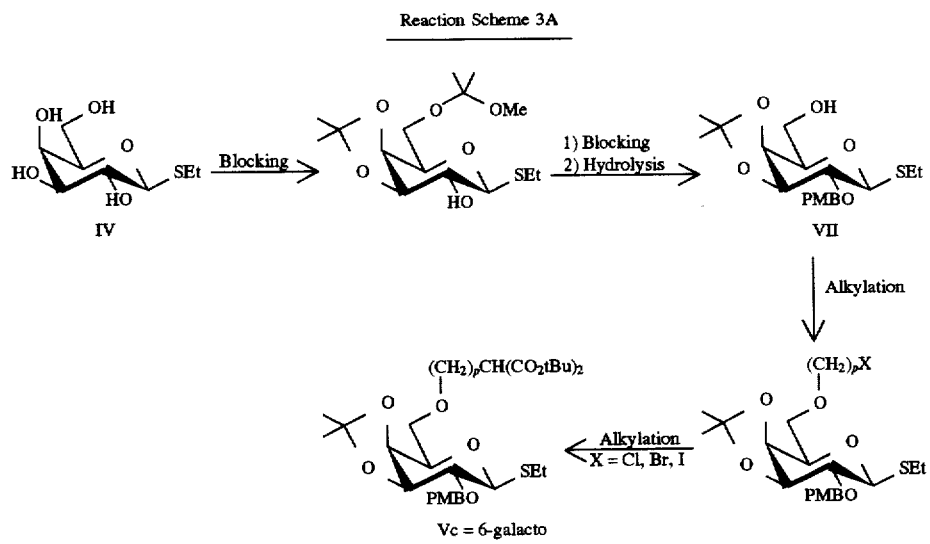

Reaction Scheme 3B

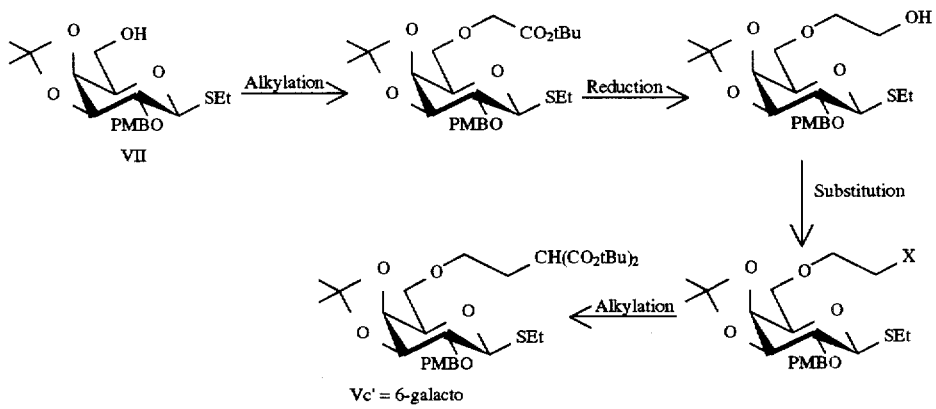

Vc' = 6-galacto

The reaction sequence advantageously used to prepare the 3-dicarboxyalkylated galactopyranosides of Formula Vd is illustrated in Reaction Scheme 4A. The intermediate of Formula VII which is prepared from ethyl 1-thio-β-galactopyranoside of Formula IV as outlined in Reaction Scheme 3A, is selectively hydrolyzed and then treated with a blocking group, preferably with benzaldehyde dimethylacetal to block the 4- and 6-hydroxy groups. The unblocked 3-hydroxy group in the intermediate of Formula VIII is alkylated with a dihalogenated alkane when it is desired to prepare 3-carboxylalkylated galactopyranosides of Formula Vd wherein p>2, under conditions described herein. The halogenated galactopyranoside resulting from the alkylation with a dihalogenated alkane is then submitted to a malonate condensation to produce the 3-dicarboxyalkylated galactopyranoside of Formula Vd wherein p>2. When it is desired to prepare an intermediate of Formula Vd' wherein p=2, the monocarboxymethylated galactopyranoside resulting from the alkylation of the intermediate of Formula VIII with the t-butyl ester of bromoacetate is reduced under conditions described herein and illustrated in Reaction Scheme 4B. As described above, the free hydroxy group produced is then converted to a leaving group such as halide or preferably mesylate which is submitted to a malonate condensation to produce the 3-dicarboxypropylated pyranoside intermediate of Formula Vd'.

Reaction Scheme 4A

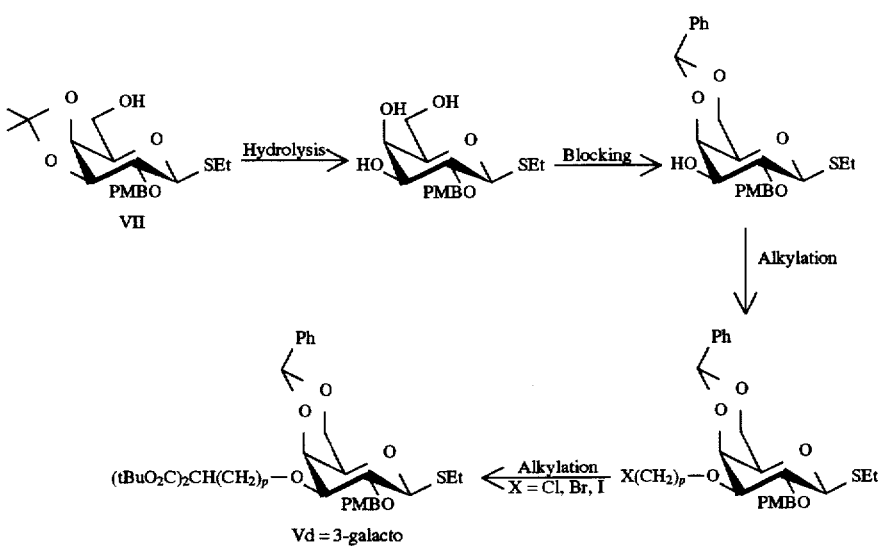

Vd = 3-galacto

Reaction Scheme 4B

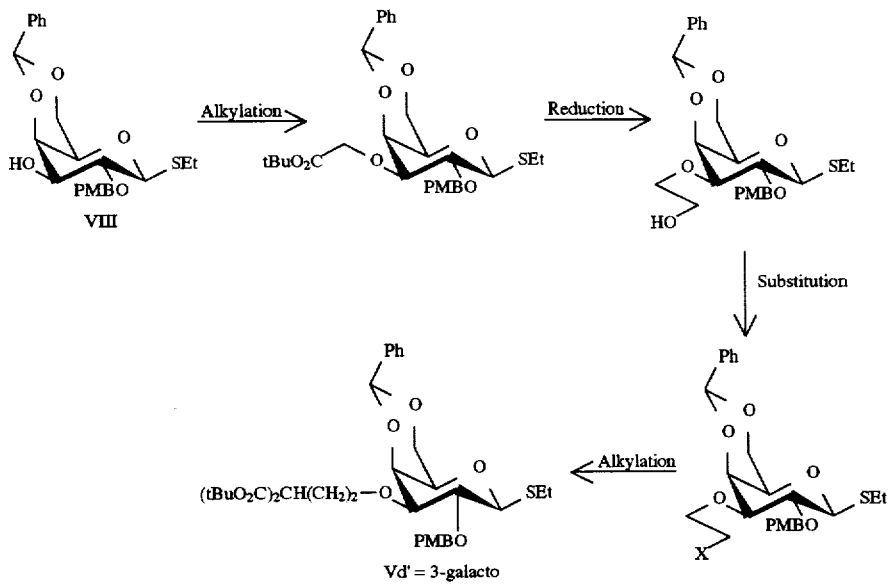

The preparation of the 4-dicarboxyalkylated galactopyranosides of Formula Ve may be carried out from the compound of Formula IV, following the reaction sequences outlined in Reaction Scheme 5A. Ethyl 1-thio-β-galactopyranoside of Formula IV is selectively treated with two different blocking groups. It is advantageous to first block the 4- and 6-hydroxy groups with benzaldehyde dimethylacetal and the 2- and 3-hydroxy groups are then selectively blocked with a different blocking group such as p-methoxybenzyl. The fully protected pyranoside compound is subjected to conventional hydrolysis to remove the benzylidene acetal blocking group. The primary 6-hydroxy group of the resulting 4,6-diol is then selectively blocked, preferably with p-methoxybenzyl chloride to produce the intermediate of Formula IX and the remaining unblocked 4-hydroxy group is then alkylated under conditions described herein. When it is desired to prepare the intermediate of Formula Ve wherein p>2, it is advantageous to use a dihalogenated alkane as an alkylating agent. The halogenated galactopyranoside resulting from the alkylation with a dihalogenated alkane is then submitted to a malonate condensation to produce the 4-dicarboxyalkylated galactopyranoside of Formula Ve wherein p>2. When it is desired to prepare an intermediate of Formula Ve' wherein p=2, the monocarboxymethylated galactopyranoside resulting from the alkylation of the intermediate of Formula IX with the t-butyl ester of bromoacetate is reduced under conditions described herein and illustrated in Reaction Scheme 5B. As described previously, the resulting free hydroxy group is then converted to a leaving group such as halide or preferably mesylate which is submitted to a malonate condensation to produce the 4-dicarboxypropylated pyranoside intermediate of Formula Ve'.

Reaction Scheme 5A

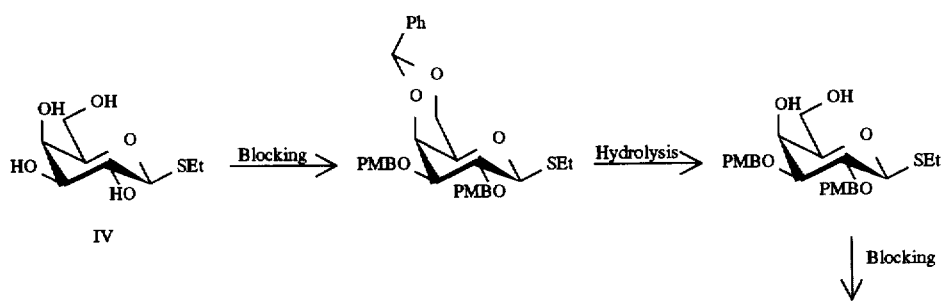

-continued
Reaction Scheme 5A

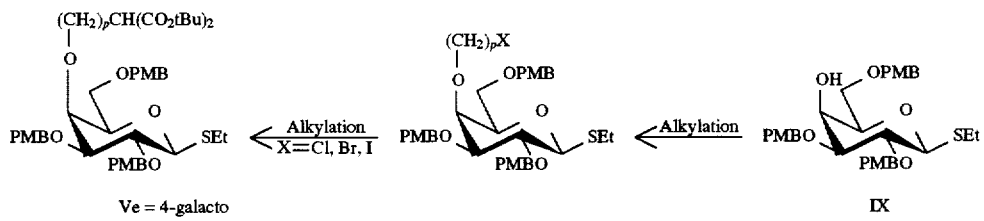

Ve = 4-galacto

Reaction Scheme 5B

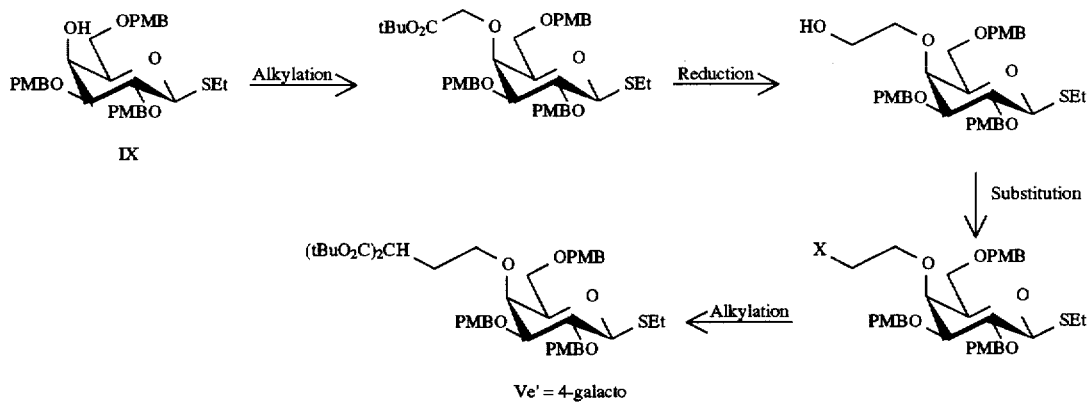

Ve' = 4-galacto

In the process for the preparation of O-dicarboxyalkylated α- and β-glycolipids of Formula I several known procedures are contemplated which generally follow the sequence of reaction steps as illustrated in Reaction Schemes 6, 7, 8 and 9. Each reaction step is generally well-known to those skilled in the art and, advantageously, the appropriate use of protecting (blocking) groups are used when necessary to effect the desired results. In the compounds of Formula I, the $R^2$, $R^3$, $R^4$, $R^5$ and $R^6$ substituents may also be changed by standard well-known procedures to achieve a different but desirable modification of the compounds of Formula I. This is conveniently illustrated in the reaction schemes by the double arrows indicating that the chemical structures may be interchanged by well-known hydrolysis and esterification or etherification procedures. It should be understood by those skilled in the art that the selection and therefore the result will depend on the nature, number and position of the substituents. It should also be understood that the illustration in the schemes is not intended to be limiting since slight modifications are often deemed desirable or necessary to achieve a particular result.

When it is desired to prepare the 2-dicarboxyalkylated α- and β-anomer compounds of Formula Ia and Ib, respectively, the fully protected galactopyranoside of Formula Va or Vb is reacted with the azido alcohol of Formula III under well-known coupling procedures as shown in Reaction Scheme 6. Procedures which may be used are described by H. Paulsen, Angew. Chem. Int. Ed. Engil., 21, 155–173 (1982) and K. Toshima et al, Chem. Rev., 93, 1503–1531 (1993). Preferably, dimethyl(methylthio) sulfonium triflate is used in the coupling procedure in an inert organic solvent in the presence of an organic base. Inert organic solvents, such as dioxane, dimethylformamide, methylene chloride, benzene, or mixtures thereof may be used in the coupling reaction and the selection of solvent will depend on the desired ratio of anomeric products to be produced. It should be understood that the selection of solvents for the reaction will influence the ratio of anomeric products obtained as described in the above references and illustrated in the examples herein. In a preferred embodiment, the azido alcohol of Formula IIIa wherein $R^5$ is benzoyl is illustrated in Reaction Scheme 6 and in subsequent Reaction Schemes 7 to 9. The use of $R^5$ being benzoyl is for illustration purposes only and is not intended to be limiting. The resulting azido glycolipid from the reaction of the pyranoside of Formula Va or Vb and the alcohol of Formula IIIa is a mixture of α- and β-anomers of the desired azido glycolipid compound. It should be appreciated by those skilled in the art that the mixture of anomers produced in the coupling reaction can be readily separated by methods such as fractional crystallization and preferably, chromatography as described herein. It should further be appreciated by those skilled in the art that the separation may be carried out at this step while the glycolipid compound is fully protected (blocked) or, if desired, after the blocking groups on the 3-, 4- and/or 6- hydroxy groups have been removed. It should be understood by those skilled in the art that if the separation is not complete at this step, then the separation can be completed in the next step. The choice of when the separation of anomers is carried out is dependent on the nature of the substituents, the ratio of anomers and the ease of separation based on the relative differences between the anomers and the desired anomer.

Reaction Scheme 6

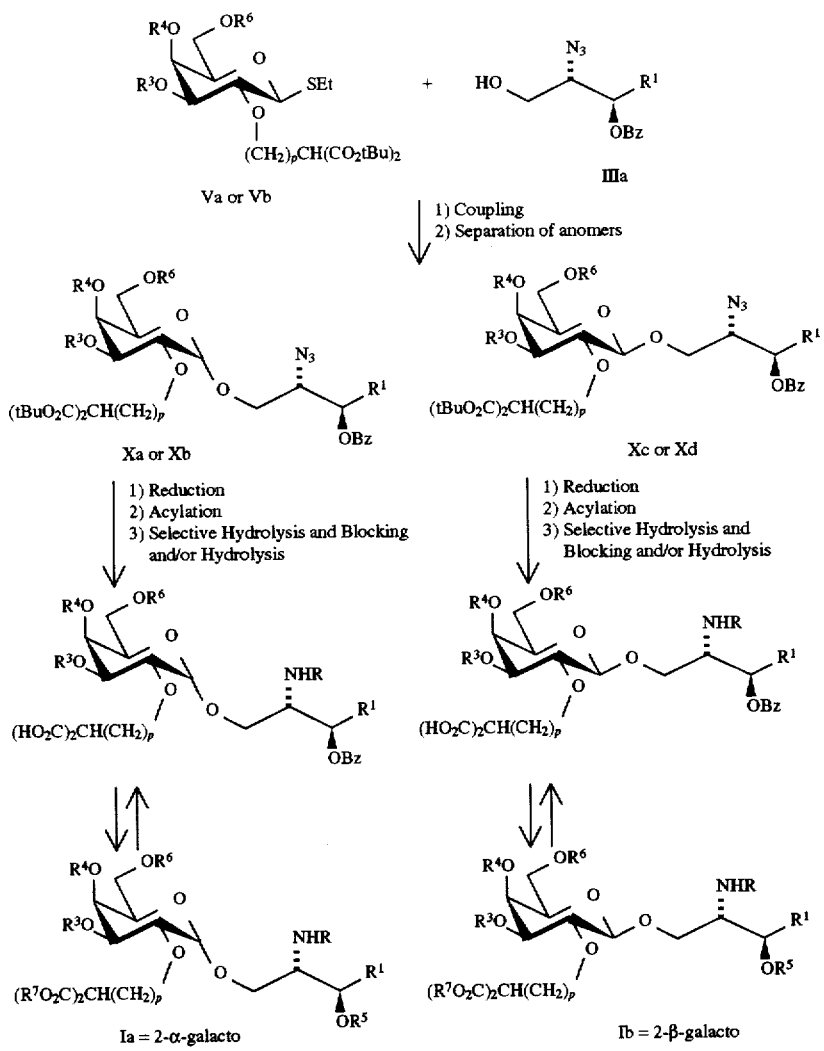

To prepare the 2-dicarboxyalkylated α-galacto type glycolipids of Formula Ia, the corresponding separated α-anomer of the azido glycolipid of Formula Xa or Xb is subjected to reduction of the azido group followed by acylation of the resulting amino group with the desired activated acyl residue of a fatty acid having the definitions of R as defined herein. The resulting glycolipid is subjected, if desired, to conventional hydrolysis of the blocking groups and of the carboxylic acid esters to produce the dicarboxylic acid of the compound of Formula Ia or a non-toxic pharmaceutically acceptable salt thereof. If desired, the glycolipid protecting groups may also be selectively hydrolyzed and the resulting hydroxy groups are subsequently blocked to interchange $R^3$, $R^4$ and $R^6$ substituents prior to the hydrolysis of the blocking groups of the carboxylic acids. It should be appreciated by those skilled in the art that the removal and insertion of the desired $R^3$, $R^4$, $R^5$, $R^6$ and $R^7$ moieties in the compound of Formula Ia can be interchanged, or left untouched depending on the particular substituent which is desired in the preparation of compounds having the dicarboxyalkylated moiety in the 2-position of the α-galacto type glycolipids of Formula Ia.

Similarly, to prepare the 2-dicarboxyalkylated β-galacto type glycolipids of Formula Ib, the corresponding separated β-anomer of the azido glycolipid of Formula Xc or Xd is subjected to reduction and acylation of the resulting amino group and, if desired, complete or partial hydrolysis. The substituents may then be interchanged or converted to the desired compound of Formula Ib having the dicarboxyalkylated moiety in the 2-position of the β-galacto type glycolipids.

When it is desired to prepare the 6-dicarboxyalkylated α- and β-anomer compounds of Formula Ic and Id respectively, the fully protected galactopyranoside of Formula Vc is reacted with the azido alcohol of Formula IIIa under well-known coupling procedures as shown in Reaction Scheme 7 and as previously described. The resulting azido glycolipid from the reaction of the pyranoside of Formula Vc and the alcohol of Formula IIIa is a mixture of α- and β-anomers of the desired azido glycolipid compound. It should be appreciated by those skilled in the art that the mixture of anomers produced in the coupling reaction can be readily separated by methods such as fractional crystallization and preferably, chromatography as described herein. It should further be appreciated by those skilled in the art that the separation may be carried out at this step while the glycolipid compound is fully protected (blocked) or, if desired, after the blocking groups on the 2-, 3- and/or 4-hydroxy groups have been removed. It should be understood by those skilled in the art that if the separation is not complete at this step, then the separation can be completed in the next step. The choice of when the separation of anomers is carried out is dependent on the nature of the substituents, the ratio of anomers and the ease of separation based on the relative differences between the anomers and the desired anomer.

To prepare the 6-dicarboxyalkylated α-galacto type glycolipids of Formula Ic, the corresponding separated a-anomer of the azido glycolipid of Formula Xe is subjected to reduction of the azido group followed by acylation of the resulting amino group with the desired activated acyl residue of a fatty acid having the definitions of R as defined herein. The resulting glycolipid is subjected, if desired, to conventional hydrolysis of the blocking groups and of the carboxylic acid esters to produce the dicarboxylic acid of the desired $R^2$, $R^3$, $R^4$, $R^5$ or $R^7$ moieties in the compound of Formula Ic can be interchanged, or left untouched depending on the particular substituent which is desired in the preparation of compounds having the dicarboxyalkylated moiety in the 6-position of the α-galacto type glycolipids of Formula Ic.

Similarly, to prepare the 6-dicarboxyalkylated β-galacto type glycolipids of Formula Id, the corresponding separated β-anomer of the azido glycolipid of Formula Xf is subjected to reduction and acylation of the resulting amino group and, if desired, complete or partial hydrolysis. The substituents may then be interchanged or converted to the desired compound of Formula Id having the dicarboxyalkylated moiety in the 6-position of the β-galacto type glycolipids.

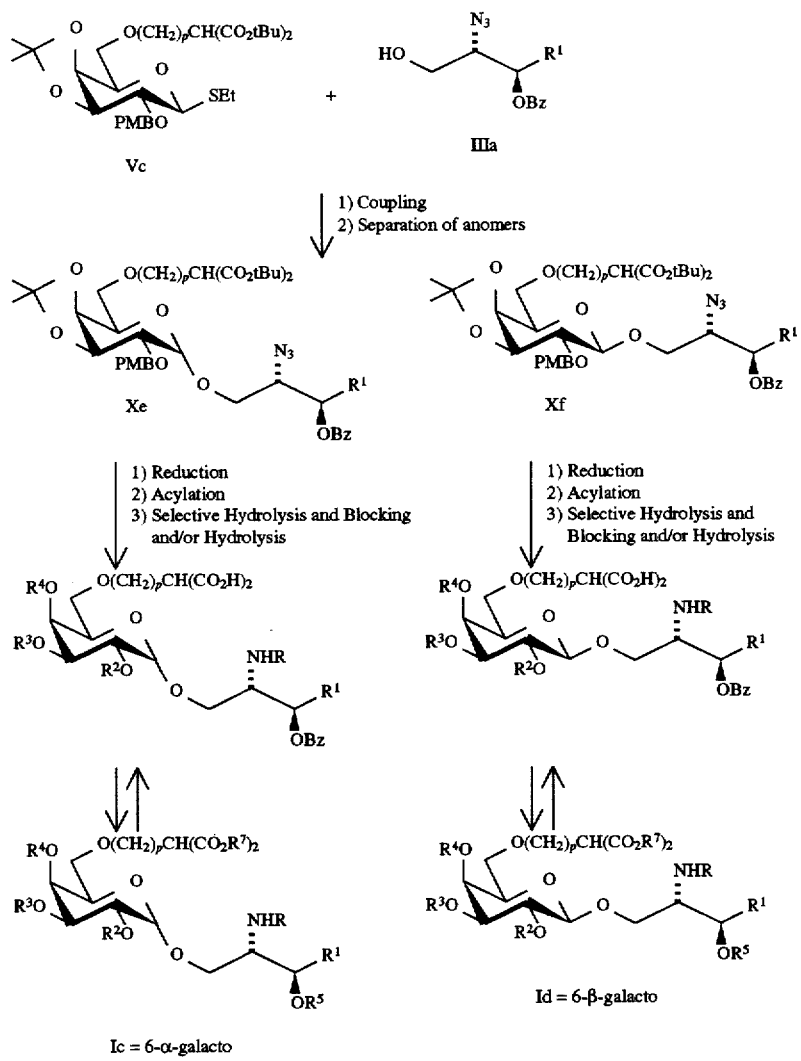

compound of Formula Ic or a non-toxic pharmaceutically acceptable salt thereof. If desired, the glycolipid protecting groups may also be selectively hydrolyzed and the resulting hydroxy groups are subsequently blocked to interchange $R^2$, $R^3$ and $R^4$ substituents prior to the hydrolysis of the blocking groups of the carboxylic acids. It should be appreciated by those skilled in the art that the removal and insertion of the When it is desired to prepare the 3-dicarboxyalkylated α- and β-anomer compounds of Formula Ie and If, respectively, the fully protected galactopyranoside of Formula Vd is reacted with the azido alcohol of Formula IIIa under well-known coupling procedures as shown in Reaction Scheme 8 and as previously described. The resulting azido glycolipid from the reaction of the pyranoside of Formula Vd and the alcohol of Formula IIIa is a mixture of α- and β-anomers of the desired azido glycolipid compound. It should be appreciated by those skilled in the art that the mixture of anomers produced in the coupling reaction can be readily separated by methods such as fractional crystallization and preferably, chromatography as described herein. It should further be appreciated by those skilled in the art that the separation may be carried out at this step while the glycolipid compound is fully protected (blocked) or, if desired, after the blocking groups on the 2-, 4- and/or 6-hydroxy groups have been removed. It should be understood by those skilled in the art that if the separation is not complete at this step, then the separation can be completed in the next step. The choice of when the separation of anomers is carried out is dependent on the nature of the substituents, the ratio of anomers and the ease of separation based on the relative differences between the anomers and the desired anomer.

To prepare the 3-dicarboxyalkylated α-galacto type glycolipids of Formula Ie, the corresponding separated α-anomer of the azido glycolipid of Formula Xg is subjected to reduction of the azido group followed by acylation of the resulting amino group with the desired activated acyl residue of a fatty acid having the definitions of R as defined herein. The resulting glycolipid is subjected, if desired, to conventional hydrolysis of the blocking groups and of the carboxylic acid esters to produce the dicarboxylic acid of the compound of Formula Ie or a non-toxic pharmaceutically acceptable salt thereof. If desired, the resulting glycolipid protecting groups may also be selectively hydrolyzed and the resulting hydroxy groups are subsequently blocked to interchange $R^2$, $R^4$ and $R^6$ substituents prior to the hydrolysis of the blocking groups of the carboxylic acids. It should be appreciated by those skilled in the art that the removal and insertion of the desired $R^2$, $R^4$, $R^5$, $R^6$ or $R^7$ moieties in the compound of Formula Ie can be interchanged, or left untouched depending on the particular substituent which is desired in the preparation of compounds having the dicarboxyalkylated moiety in the 3-position of the α-galacto type glycolipids of Formula Ie.

Similarly, to prepare the 3-dicarboxyalkylated β-galacto type glycolipids of Formula If, the corresponding separated β-anomer of the azido glycolipid of Formula Xh is subjected to reduction and acylation of the resulting amino group and, if desired, complete or partial hydrolysis. The substituents may then be interchanged or converted to the desired compound of Formula If having the dicarboxyalkylated moiety in the 3-position of the β-galacto type glycolipids.

Reaction Scheme 8

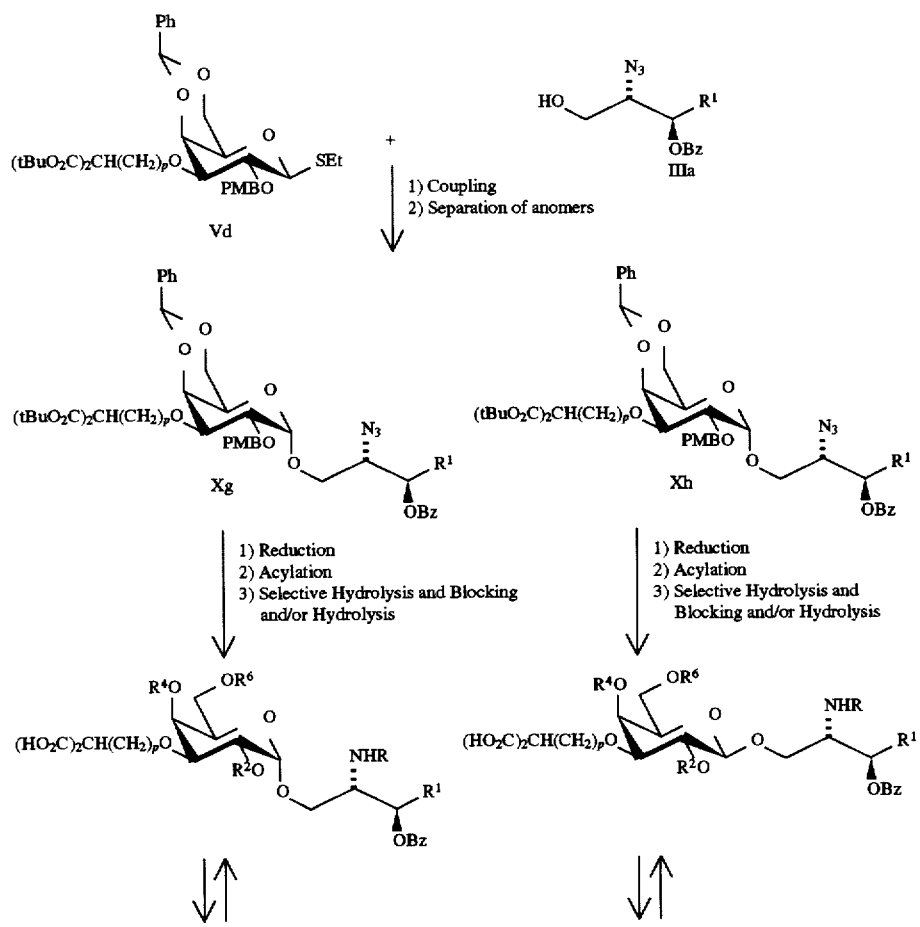

-continued
Reaction Scheme 8

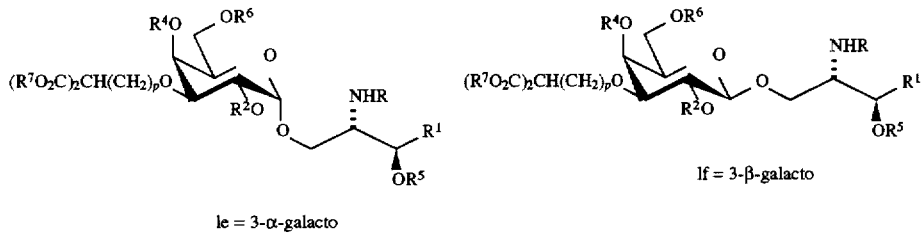

Ie = 3-α-galacto

If = 3-β-galacto

When it is desired to prepare the 4-dicarboxyalkylated α- and β-anomer compounds of Formula Ig and Ih respectively, the fully protected galactopyranoside of Formula Ve is reacted with the azido alcohol of Formula IIIa under well-known coupling procedures as shown in Reaction Scheme 9 and as previously described. The resulting azido glycolipid from the reaction of the pyranoside of Formula Ve and the alcohol of Formula IIIa is a mixture of α- and β-anomers of the desired azido glycolipid compound. It should be appreciated by those skilled in the art that the mixture of anomers produced in the coupling reaction can be readily separated by methods such as fractional crystallization and preferably, chromatography as described herein. It should further be appreciated by those skilled in the art that the separation may be carried out at this step while the glycolipid compound is fully protected (blocked) or, if desired, after the blocking groups on the 2-, 3- and/or 6-hydroxy groups have been removed. It should be understood by those skilled in the art that if the separation is not complete at this step, then the separation can be completed in the next step. The choice of when the separation of anomers is carried out is dependent on the nature of the substituents, the ratio of anomers and the ease of separation based on the relative differences between the anomers and the desired anomer.

To prepare the 4-dicarboxyalkylated α-galacto type glycolipids of Formula Ig, the corresponding separated α-anomer of the azido glycolipid of Formula Xi is subjected to reduction of the azido group followed by acylation of the resulting amino group with the desired activated acyl residue of a fatty acid having the definitions of R as defined herein. The resulting glycolipid is subjected, if desired, to conventional hydrolysis of the blocking groups and of the carboxylic acid esters to produce the dicarboxylic acid of the compound of Formula Ig or a non-toxic pharmaceutically acceptable salt thereof. If desired, the glycolipid protecting groups may also be selectively hydrolyzed and the resulting hydroxy groups are subsequently blocked to interchange $R^2$, $R^3$ and $R^6$ substituents prior to the hydrolysis of the blocking groups of the carboxylic acids. It should be appreciated by those skilled in the art that the removal and insertion of the desired $R^2$, $R^3$, $R^5$, $R^6$ or $R^7$ moieties in the compound of Formula Ig can be interchanged, or left untouched depending on the particular substituent which is desired in the preparation of compounds having the dicarboxyalkylated moiety in the 4-position of the α-galacto type glycolipids of Formula Ig.

Similarly, to prepare the 4-dicarboxyalkylated β-galacto type glycolipids of Formula Ih, the corresponding separated β-anomer of the azido glycolipid of Formula Xj is subjected to reduction and acylation of the resulting amino group and, if desired, complete or partial hydrolysis. The substituents may then be interchanged or converted to the desired compound of Formula Ih having the dicarboxyalkylated moiety in the 4-position of the β-galacto type glycolipids.

Reaction Scheme 9

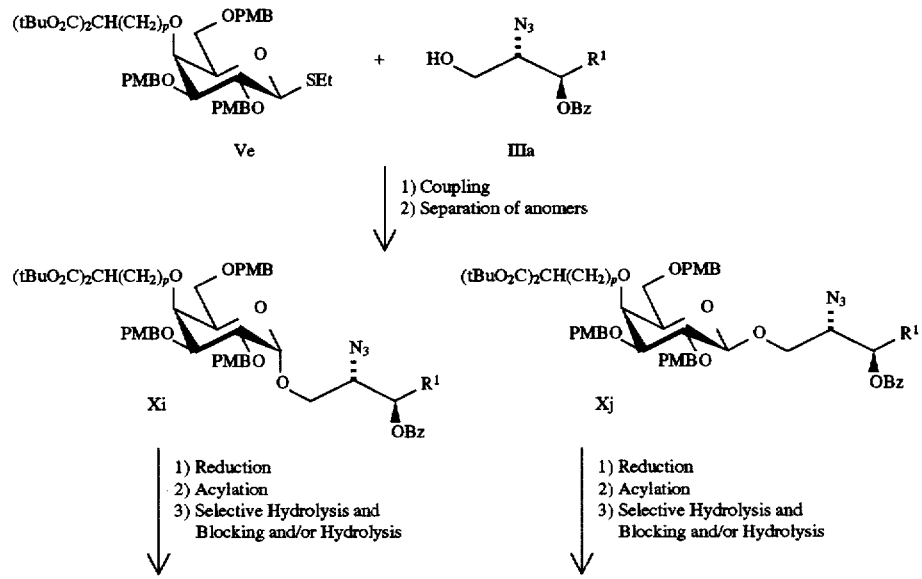

-continued
Reaction Scheme 9

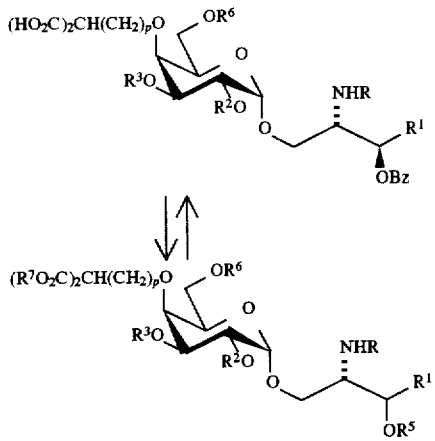

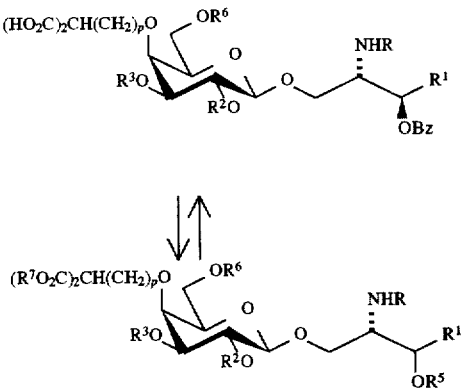

Ig = 4-α-galacto

Ih = 4-β-galacto

In a preferred embodiment of the invention, the compounds of Formula I have the formula

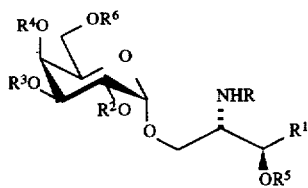

wherein R is an acyl residue of a fatty acid; $R^1$ is $-(CH=CH)_m-(CH_2)_n-CH_3$; $R^2$, $R^3$, $R^4$, $R^5$ and $R^6$ each are independently hydrogen, unsubstituted or substituted (lower) alkanoyl, arylalkyl or arylcarbonyl wherein said substituent is selected from the group consisting of halogen, $C_{1-4}$ alkyl, trifluoromethyl, hydroxy and $C_{1-4}$ alkoxy, provided that one of the $R^2$, $R^3$, $R^4$ and $R^6$ substituents is $-(CH_2)_p-CH(CO_2R_7)_2$; m is an integer of 0 or 1; n is an integer of from 5 to 14 inclusive; p is an integer of from 2 to 6 inclusive; $R^7$ is hydrogen, a hydrolyzable ester group or a cation to form a non-toxic pharmaceutically acceptable salt; or a solvate or hydrate thereof. In a particularly preferred embodiment, $R^2$ is $-(CH_2)_p-CH(CO_2R^7)_2$ and $R^3$, $R^4$, $R^5$ and $R^6$ each are independently hydrogen or benzoyl. In another particularly preferred embodiment $R^3$ is $-(CH_2)_p-CH(CO_2R^7)_2$ and $R^2$, $R^4$, $R^5$ and $R^6$ each are independently hydrogen or benzoyl. In still another particularly preferred embodiment $R^4$ is $-(CH_2)_p-CH(CO_2R^7)_2$ and $R^2$, $R^3$, $R^5$ and $R^6$ each are independently hydrogen or benzoyl. In still another particularly preferred embodiment $R^6$ is $-(CH_2)_p-CH(CO_2R^7)_2$ and $R^2$, $R^3$, $R^4$ and $R^5$ each are independently hydrogen or benzoyl.

In another preferred embodiment of the invention, the compounds of Formula I have the formula

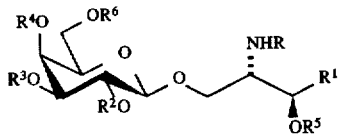

wherein R is an acyl residue of a fatty acid; $R^1$ is $-(CH=CH)_m-(CH_2)_n-CH_3$; $R^2$, $R^3$, $R^4$, $R^5$ and $R^6$ each are independently hydrogen, unsubstituted or substituted (lower) alkanoyl, arylakyl or arylcarbonyl wherein said substituent is selected from the group consisting of halogen, $C_{1-4}$ alkyl, trifluoromethyl, hydroxy and $C_{1-4}$ alkoxy, provided that one of the $R^2$, $R^3$, $R^4$, and $R^6$ substituents is $-(CH_2)_p-CH(CO_2R^7)_2$; m is an integer of 0 or 1; n is an integer of from 5 to 14 inclusive; p is an integer of from 2 to 6 inclusive; $R^7$ is hydrogen, a hydrolyzable ester group or a cation to form a non-toxic pharmaceutically acceptable salt; or a solvate or hydrate thereof. In a particularly preferred embodiement, $R^2$ is $-(CH_2)_p-CH(CO_2R^7)_2$ and $R^3$, $R^4$, $R^5$ and $R^6$ each are independently hydrogen or benzoyl. In another particularly preferred embodiment $R^3$ is $-(CH_2)_p-CH(CO_2R^7)_2$ and $R^2$, $R^4$, $R^5$ and $R^6$ each are independently hydrogen or benzoyl. In still another particularly preferred embodiment $R^4$ is $-(CH_2)_p-CH(CO_2R^7)_2$ and $R^2$, $R^3$, $R^5$ and $R^6$ each are independently hydrogen or benzoyl. In still another particularly preferred embodiment $R^6$ is $-(CH_2)_p-CH(CO_2R^7)_2$ and $R^2$, $R^3$, $R^4$ and $R^5$ each are independently hydrogen or benzoyl.

In another aspect, this invention provides novel intermediates of the Formula XI

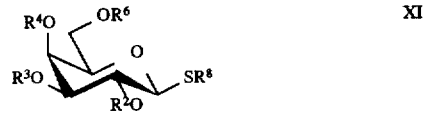

wherein
$R^2$, $R^3$, $R^4$ and $R^6$ each are independently hydrogen, unsubstituted or substituted (lower) alkanoyl, arylalkyl or arylcarbonyl wherein said substituent is selected from the group consisting of halogen, $C_{1-4}$ alkyl, trifluoromethyl, hydroxy and $C_{1-4}$ alkoxy, provided at least one of the $R^2$, $R^3$, $R^4$ and $R^6$ substituents is $-(CH_2)_p-CH(CO_2R^{7a})_2$;

p is an integer of from 2 to 6 inclusive;
$R^{7a}$ is a hydrolyzable ester group; and
$R^8$ is (lower)alkyl, unsubstituted or substituted aryl, or aryl(lower)alkyl wherein said substituent is selected from the group consisting of halogen, $C_{1-4}$ alkyl, trifluoromethyl and $C_{1-4}$ alkoxy.

In yet another aspect, this invention provides a method for the treatment or prevention of diseases mediated by the inhibition of selectin-mediated cellular adhesion in a mammal in need thereof, which comprises administering to said mammal a therapeutically effective amount of a compound of Formula I or a non-toxic pharmaceutically acceptable salt, solvate or hydrate thereof. In a particularly preferred embodiment, this invention provides a method for the treatment of inflammatory related diseases or other pathological conditions in a mammal in need thereof, which comprises administering to said mammal a therapeutically effective amount of a compound of Formula I or a non-toxic pharmaceutically acceptable salt or a solvate or hydrate thereof.

In still yet another aspect, this invention provides pharmaceutical compositions comprising at least one compound of Formula I in combination with a pharmaceutical carrier or diluent.

CELL ADHESION ACTIVITY

1. P-Selectin Adhesion Receptor Binding

P-selectin (GMP140, granule membrane protein-140, PADGEM, or CD62) is a calcium-dependent transmembrane protein found in alpha granules of endothelial cells and platelets. It is an inducible selectin produced on activated endothelium and platelets which recognize alpha(2-3)sialylated and alpha(1-3)fucosylated lactosaminoglycans which include the sequence, Lewis x (Zhou et al., *J. Cell. Biol.*, (1991) 115 (2): 557–564) and sulfatides (3-sulfated galactosyl ceramides, Aruffo et al., *Cell* (1991) 67: 35–44). P-selectin may be responsible for the initial adhesion events between endothelium and neutrophils as evidenced by leukocyte rolling induced by P-selectin in flow cells (Lawrence et al., *Cell* (1991) 65: 859–873).

Based on the availability of soluble forms of P-selectin prepared as described by Aruffo, A. et al., *Cell*, 67, 35–44 (1991), a binding ELISA based assay modified from Foxall, et al., *J. Cell Biol.*, 117, 1895–902 (1992) was developed to measure inhibitors of P-selectin binding to immobilized sulfatides. Such inhibitors were tested in the assay described below.

0.1 ml of sulfatide (SIGMA) at 1 µg/ml in MeOH was added to 48 wells of a 96-well ELISA plate (ProBind, Falcon) and allowed to dry overnight at room temperature. Another set of 48 wells were incubated with the solvent (methanol, Fisher Scientific). The next day the antigen/ solvent coated plates were blocked for 1.5 hours at room temperature with 5% BSA (ICN) in buffer containing 20 mM Hepes, 1 mM $CaCl_2$ and 0.15M NaCl, pH 8.0. Wild type P-selectin was first mixed with HRP-conjugated goat anti-human IgG (1:5000 dilution, Fisher Scientific), and incubated for 30 minutes at 37° C. in buffer containing 20 mM Hepes, 0.15M NaCl, 1% BSA and 1 mM $CaCl_2$, pH 8.0 prior to addition to the BSA blocked plates. Following the 30 minute preincubation, the fusion protein-HRP conjugate immunocomplexes were incubated on the blocked antigen coated plates for 45 minutes at 37° C. in the presence or absence of the test compounds and then washed to remove any unbound proteins. Bound complexes were detected by addition of substrate buffer (95 mM $NaOAc.3H_2O$, 5 mM citric acid monohydrate, 1.4 mM urea/$H_2O_2$) containing 3,3',5,5'-tetramethylbenzidine (SIGMA). Reactions were stopped by the addition of 3N sulfuric acid and the absorbance read on an ELISA reader at dual wavelengths 450 and 630 nm. The efficacy of these compounds was compared to that of sulfatide (positive control) or to MeOH (negative control). The data is obtained as percent inhibition of specific binding $$\% \text{ inhibition} = \left[ 1 - \left( \frac{\text{Specific binding:Test Compound}}{\text{Specific binding:Vehicle}} \right) \right] \times 100$$

and a plot of dose vs. percent inhibition of Rg binding is generated in which $IC_{50}$ (µM) is calculated and reported as cell free data in Table 1.

2. HL-60 Platelet Cell Adhesion Assay

HL-60 cells, obtained from American Type Culture Collection, were cultured in RPMI 1640 medium (GIBCO) supplemented with 20% fetal calf serum (Sigma) and 50 µg/ml gentamicin (GIBCO). Cells in log phase growth were harvested, washed and resuspended in Tyrodes buffer containing 5 mM HEPES and 0.2% bovine serum albumin and were fixed with 1% buffered formalin.

Blood from normal human donors was anticoagulated with citrate, layered over 1-Step Platelets (Accurate Chemical Co.) and centrifuged at 350 g for 20 minutes at room temperature. The platelet band was collected, diluted in 2 volumes of Tyrode's Buffer with 5 mM HEPES, 10 mM EDTA, and 0.2% BSA (pH 7.4) (THEB) and centrifuged at 600 g for 10 minutes. The platelet pellet was resuspended in THEB and incubated at room temperature for 1 hour. Calcein-acetoxy methylester (Calcein-Am, Molecular Probes) was added to the platelets at a final concentration of 10 µM and incubated for 10 minutes at 37° C. to label the platelets. Without washing, the platelets were counted on a Coulter counter model ZM, and the concentration was adjusted to $1 \times 10^7$/ml. The platelets were activated with 2 U/ml of human thrombin for 10 minutes in Tyrode's containing 2 mM $CaCl_2$, 5 mM HEPES, and 0.2% BSA (pH 7.4) (THB) at 37° C. and immediately fixed with 1% buffered formalin for 1 to 2 hours at room temperature. A small aliquot of labeled platelets was removed before activation and designated as non-activated.

Both platelets and HL-60 were washed in a $\geq 25$ fold excess volume of Hanks Balanced Salt Solution (HBSS), resuspended in THB and counted. Cell concentrations were adjusted to $2 \times 10^7$/ml for platelets and $4 \times 10^6$/ml for HL-60, this ratio determined to be optimum for platelet: HL-60 cell adhesion. Compounds were incubated with 50 µl of platelets for 30 minutes at room temperature before addition of 50 µl of HL-60. This ratio of 5:1 platelets to HL-60 was incubated for 30 minutes at room temperature before addition of 0.2 ml of THB to increase the volume so the samples could be analyzed on a FACScan cytometer (Becton Dickinson). Non-activated platelets, and activated platelets with 10 mM EDTA were included as controls. Data were collected within a region set for the forward scatter channel corresponding to HL-60 size events.

The HL-60 cells were present in two populations: one was non-fluorescent and did not contain platelets; the other was fluorescent due to bound platelets. The percent HL-60 cells which contained bound platelets was determined for each test condition. The inhibition of binding was determined by comparison to standards which were treated with vehicle alone (representing 0% inhibition) and standards whose specific binding had been blocked by the use of EDTA (representing 100% inhibition), by the following formula:

$$\left\{ 1 - \frac{x-b}{a-b} \right\} \times 100 = z$$

where
x=HL-60 cells containing bound platelets in the presence of the compound;
b=HL-60 cells containing bound platelets in the presence of EDTA;

a=HL-60 cells containing bound platelets in the presence of compound vehicle;

z=% inhibition of platelet: HL-60 cell adhesion

3. Reverse Passive Arthus Reaction in Rats

The reverse passive Arthus reaction in rats is a modification of the method by Mulligan et al., as described in *J. Clin. Invest.* (1991) 88: 1396–1406. This is an experimental model in which the interaction of antigen-antibody complexes and complement leads to a severe vasculitis that is associated with edema, induration, erythema and hemorrhage. The interaction between the antigen-antibody complexes and complement leads to a localized influx of neutrophils. These neutrophils release a variety of mediators that are associated with tissue damage and vascular permeability. The localized inflammatory reaction is measured using different techniques i.e., vascular permeability and neutrophil influx which is evaluated both biochemically and microscopically.

Male Sprague Dawley specific pathogen-free rats with jugular vein cannulae (280–320 g, Hill Top Labs, Pennsylvania) are used in these studies. Animals are acclimated for at least 1 day and individually housed in stainless steel cages. The dorsal region of the rats is closely clipped 2 days prior to the experiments and divided into 4 sites on each side of the midline. Prior to all injections the rats are sedated with 0.4 ml per 300 gm rat of ketamine/rompun [1000 mg (10 ml) of ketamine HCl is mixed with 40 mg (2.0 ml) Rompun] administered IP and or inhalation anesthesia with metafane (methoxyflurane).

Bovin Serum Albumin (BSA) and rabbit polyclonal IgG rich in anti-BSA are purchased from Sigma Chemical Co. (St. Louis, Mo.). Radiolabelled $^{125}$I-BSA (spAct 1–5 μCi/μg) is purchased from Dupont NEN (Boston, Mass.).

Each rat is administered intradermal (ID) injection of (0.4 mg, 0.6 mg and 0.8 mg) anti-BSA in a volume of 100 μl per injection in normal saline. The ID injections are randomized near the mid dorsal region on both sides of the back bone. Immediately after the ID injections of the anti-BSA, the rats are administered intravenous (IV) injections of BSA (10 mg in 1.0 ml) in normal saline containing $^{125}$I labeled BSA (1 μCi/ml BSA or 5.0 μCi/kg body/wt) for quantification of dermal valscular injury. Anti-inflammatory agents such as inhibitors of adhesion molecules of the present invention are administered IV at a single dose of 3 mg immediately after BSA. Four (4) hours after the IV injection of BSA, the rats are anesthetized with metafane and 2 to 3 ml of blood is withdrawn via the cannula into an anticoagulant containing (EDTA or Heparin) tube and plasma separated and saved for neutrophil and albumin quantitation. The rats are killed and the skin surrounding the injection site (15 mm diameter) is punched out and weighed. The skin sample and a fixed volume of plasma (0.1 to 1.0 ml) is analyzed in a gamma-counter for $^{125}$I content. Skin samples from the contralateral side are processed and analyzed for myeloperoxidase activity (MPO) as a measure of neutrophil accumulation. As needed, samples are also processed for histological evaluation of the reacted sites.

Vascular Permeability (VP)

The calculation of the plasma protein exudation into skin is made by determining the radioactivity in the tissue and relating this to the level of radioactive albumin in the blood at the time of sacrifice. The equation below shows the calculation for microliter plasma extravasated (Issekutz and Issekutz, Pharmacological methods in the control of inflammation, (1989) 129–150).

$$\mu l \text{ plasma extravasated} = \frac{CPM \text{ in tissue}}{CPM/\mu l \text{ plasma}}$$

Percent inhibition of the test compound at 3 mg was determined as follows:

% inhibition =

$$\left[ 1 - \left( \frac{\mu l \text{ plasma extravasated with test compound}}{\mu l \text{ plasma extravasated with vehicle}} \right) \right] \times 100$$

Myeloperoxidase (MPO)

MPO is located in the azurophil granules of polymorphonuclear leukocytes (PMN). Because of its abundance in these cells (5% dry weight), this enzyme is used as a marker for tissue neutrophil content. For tissue MPO content, the method of Bradley, et al., was used as described in *J. Invest. Dermatol.* (1982) 78: 206–209. Biopsies from each treatment group were placed in plastic tubes (15×100 mm) containing 10 ml of 0.5% hexadecyltrimethylammonium bromide (HTAB) in 0.05M potassium phosphate buffer pH 6.0. The tissue was then homogenized with a Brinkmann Polytron homogenizer (10s). The supernatant (0.05 ml) was assayed by mixing with 0.150 ml o-dianisidine (0.334 mg/ml) and 0.0005% hydrogen peroxide in 0.05M potassium phosphate buffer pH 6.0 in a 96-well microtiter plate. Change in absorbance at 450 nm was measured at room temperature using a $V_{max}$ kinetic plate reader (Molecular Devices, Palo Alto, Calif., U.S.A.). Percent inhibition of the test compound at 3 mg dose was determined as follows:

% inhibition =

$$\left[ 1 - \left( \frac{\text{Absorbance of test compound treated Biopsies}}{\text{Absorbance of vehicle treated Biopsies}} \right) \right] \times 100$$

The in vivo experimental results as measured by vascular permeability (VP) and myeloperoxidase (MPO) at a single dose of the test compound are shown in Table 1.

TABLE 1

| | P-selectin | | RPA | |
|---|---|---|---|---|
| Example No. | Cell Free IC$_{50}$ (μM) | HL-60 Platelets | VP % Inhib.* | MPO % Inhib.* |
| 2 | 8.2 | 12 | 41 | 96 |
| 4 | 7 | 19 | 60 | 84 |
| 6 | NA** | 13 | NS*** | 25 |
| 12 | NA** | 22.9 | 33 | 82 |
| 14 | NA** | 45 | 15.5 | 30.9 |
| 18 | NA** | 8.8 | 4.3 | 61.6 |
| 24 | NA** | 51 | 33.5 | 35 |

*% Inhibition at 3 mg
**not available
***no significant inhibition at 3 mg

The biological results of representative compounds according to this invention are shown in Table 1. Both the cell and cell-free in vitro assays and the in vivo tests carried out in the RPA rat model show that the compounds of Formula I are inhibitors of P-selectin mediated binding and, more importantly, confirm that the compounds of the instant invention are selectin inhibitors useful to treat inflammatory conditions in a mammal.

Therefore, the compound of Formula I or pharmaceutical compositions thereof are useful in the treatment and/or prevention of diseases or other pathological conditions which are mediated by the binding of selectins in cellular adhesion. Such diseases and conditions include acute or chronic inflammatory diseases such as rheumatoid arthritis, asthma, allergy conditions, psoriasis, septic shock, adult respiratory distress syndrome, inflammatory bowel disease and ophtalmic inflammatory diseases; autoimmune diseases; thrombosis or inappropriate platelet aggregation conditions, and cardiovascular disease; reperfusion injury; multiple sclerosis; chemical and thermal burn injuries and neoplastic disease including metastasis conditions.

In another embodiment, this invention includes pharmaceutical compositions comprising at least one compound of Formula I in combination with a pharmaceutical carrier or diluent.

In still another embodiment, this invention relates to a method of treatment or prevention of diseases or other pathological conditions characterized by selectin-mediated cellular adhesion in a mammal in need thereof, which comprises administering to said mammal a therapeutically effective amount of a compound of Formula I or a non-toxic pharmaceutically acceptable salt, solvate or hydrate thereof.

In yet another embodiment, this invention relates to a method for inhibiting or reducing inflammatory disease processes in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), transdermal, bronchial, rectal, topical, ophthalmic, intraarticular or nasal administation. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in transdermal formulations with permeation enhancers such as DMSO and iontophoresis. Other topical compositions well-known in the art can be administered to treat dermal inflammation. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of cell adhesion inhibition desired and the potency of the particular compound being utilized for the particular disorder of disease concerned. It is also contemplated that the treatment and dosage of the particular compound may be similar to the treatment and dosage used with dexamethasone phosphate and that the dosage would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention for the satisfactory inhibition of reduction of selectin-mediated cell adhesion.

A suitable dose of a compound of Formula I or pharmaceutical composition thereof for a mammal suffering from, or likely to suffer from any condition as described herein is an amount of active ingredient form 0.1 µg/kg to 100 mg/kg body weight. For systemic administration, the dose may be in the range of 0.1 to 100 mg/kg body weight to the active ingredient, and preferably, in the range of 0.1 to 50 mg/kg body weight. For topical administration, for example to the skin or eye, a suitable dose of active ingredient may be in the range of 0.1 µg to about 100 mg/ml of liquid carrier or excipient, and preferably, about 0.1 mg to 10 mg/ml. For oral dosing including the treatment of prophylaxis of inflammatory diseases or conditions, a suitable dose may be in the range of about 1 mg to 100 mg/kg of mammal body weight, and preferably, from about 1 mg to about 50 mg/kg body weight. The active ingredient will preferably be administered in equal doses from one to four times a day. However, usually a small dosage is administered, and the dosage is gradually increased until the optimal dosage for the host under treatment is determined.

The following examples are given by way of illustration and are not to be construed as limiting the invention in any way inasmuch as many variations of the invention are possible within the spirit of the invention.

DESCRIPTION OF SPECIFIC EMBODIMENTS

EXAMPLE 1

(2S,3R,4E)-3-Benzoyloxy-2-hexadecanoylamino-1-[2-O-(3,3-di-tert-butyloxycarbonylprop-1-yl)-3- O-benzoyl-α-D-galactopyranosyloxyl-4-octadecene A. Ethyl 3,4-O-isopropylidene-1-thio-β-D-galactopyranoside

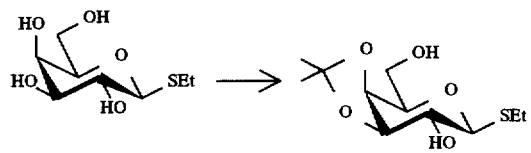

A mixture of ethyl 1-thio-β-D-galactopyranoside [Lemieux, *Can. J. Chem.*, 29, 1079 (1951)] (24.86 g, 0.111 mol) and 2,2-dimethoxypropane (500 mL) was treated with p-toluenesulfonic acid (0.625 g) and stirred at 22° C. for 24 hours. Water (80 mL) was added and after 15 minutes the reaction mixture was cooled in an ice water bath and stirred for another 30 minutes. Then triethylamine (5 mL) was added and the mixture was stirred for 20 minutes. The solvent was evaporated under vacuum and the residue was purified by silica gel chromatography (9×12 cm, 50% to 70% ethyl acetate/toluene) to give the title material (25.50 g, 87%) as a white solid. Recrystallization from ethyl acetate and hexane gave white prisms.

$[\alpha]_D^{22}$: +20.8° (c=2.8, CHCl$_3$).

IR (KBr) $v_{max}$ (cm$^{-1}$): 3200 (broad, OH).

$^1$H NMR 400 MHz (CDCl$_3$) δ (ppm): 1.33 (3H, t, J=7.3 Hz, —SCH$_2$CH$_3$), 1.36 and 1.52 (2×3H, 2s, —CH$_3$ of isopropylidene), 2.2 and 2.5 (broad, OH), 2.75 (2H, m, —SCH$_2$CH$_3$), 3.57 (1H, dd, J=10.2 and 7.0 Hz, H-2), 3.81 (1H, dd, J=11.5 and 4.0 Hz, H-6), 3.89 (1H, m, H-5), 3.98 (1H, dd, J=11.5 and 7.2 Hz, H-6), 4.09 (1H, dd, J=7.0 and 5.6 Hz, H-3), 4.21 (1H, dd, J=5.6 and 2.2 Hz, H-4), 4.27 (1H, d, J=10.2 Hz, H-1).

Anal. Calcd. for C$_{11}$H$_{20}$O$_5$S: C, 49.98; H, 7.63; S, 12.13. Found: C, 49.89; H, 7.49; S, 12.33.

B. Ethyl 6-O-t-butyldimethylsilyl-3,4-O-isopropylidene-1-thio-β-D-galactopyranoside

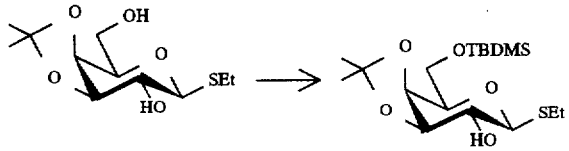

A solution of ethyl 3,4-O-isopropylidene-1-thio-β-D-galactopyranoside (8.65 g, 32.7 mmol) in dry pyridine (125 mL) was treated at 0°–5° C. with tert-butyldimethylsilyl chloride (5.92 g, 39.2 mmol) and the resulting mixture was stirred for 5 hours. Methanol (15 mL) was then added and the solution was stirred for another 15 min. The solvent was then evaporated under vacuum and the residue was diluted with ethyl acetate (500 mL) washed with cold 2N hydrochloric acid, saturated sodium bicarbonate, brine and dried over anhydrous magnesium sulfate. Evaporation of the solvent under vacuum gave an oil which was purified by chromatography on silica gel (9×11 cm, 10% to 20% ethyl acetate/toluene) and afforded the title compound (12.4 g, 100%) as an oil.

$[\alpha]_D^{22}$: +2.8° (c=1.0, CHCl$_3$).

$^1$H NMR 400 MHz (CDCl$_3$) δ ppm: 0.08 (6H, s, SiCH$_3$), 0.9 (9H, s,Si-t-Bu), 1.32 (3H, t, J=7.5 Hz, —SCH$_2$CH$_3$) 1.35 and 1.53 (2×3H, 2s, —CH$_3$ of isopropylidene), 2.7 (2H, m, —SCH$_2$CH$_3$), 3.56 (1H, dd, J=10.2 and 7.0 Hz, H-2), 3.8–3.9 (3H, m, H-5 and H-6), 4.05 (1H, dd, J=7.0 and J=5.5 Hz, H-3), 4.24 (1H, d, J=10.2 Hz, H-1) 4.26 (1H, dd, J=5.5 and 2.0 Hz, H-4).

C. Ethyl 6-O-t-butyldimethylsilyl-3,4-O-isopropylidene-2-O-tert-butyloxycarbonylmethyl-1-thio-β-D-galactopyranoside

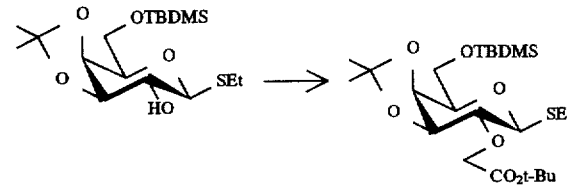

A solution of ethyl 6-O-t-butyldimethylsilyl-3,4-O-isopropylidene-1-thio-β-D-galactopyranoside (6.7 g, 17.7 mmol) in dimethylformamide (120 mL) was added to sodium hydride (4.25 g, 50% suspension in oil, previously washed with hexane, 88 mmol) under argon. The resulting suspension was stirred at 22° C. for 0.75 hour. Tert-butyl bromoacetate (16.5 mL, 102 mmol) was added dropwise to this mixture which was stirred for an additional hour. The mixture was then diluted with cold 1M aqueous sodium bicarbonate (150 mL) and ethyl acetate (250 mL). The organic phase was washed with water (4×150 mL), 1M aqueous sodium bicarbonate (150 mL) and brine (150 mL), dried over anhydrous magnesium sulfate, filtered and concentrated. The residue was purified by silica gel column chromatography (300 g, 2 to 10% ethyl acetate/hexane) to give the title compound (8.03 g, 92%) as a yellow oil.

IR (CH$_2$Cl$_2$) $v_{max}$ (cm$^{-1}$): 3055, 2990, 2835 (C—H), 1745 (C=O).

$^1$H NMR 400 MHz (CDCl$_3$) δ (ppm): 0.07 (6H, s, —Si(CH$_3$)$_2$), 0.90 (9H, s, —SiC(CH$_3$)$_3$), 1.30 (3H, t, J=7.4 Hz, —CH$_3$), 1.33 and 1.50 (6H, 2s, —C(CH$_3$)$_2$), 1.48 (9H, s, tert-butyl), 2.67–2.82 (2H, m, —SCH$_2$—), 3.48 (1H, dd, J=9.7 and 6.0 Hz, H-2), 3.75 (1H, td, J=6.6 and 1.3 Hz, H-5), 3.82–3.89 (2H, m, H-6), 4.21 (1H, d, J=16.2, —OCH$_2$CO—), 4.19–4.25 (2H, m, H-3 and H-4), 4.33 (1H, d, J=16.2, —OCH$_2$CO—), 4.42 (1H, d, J=9.7 Hz, H-1).

Anal. Calcd. for C$_{23}$H$_{44}$O$_7$SSi: C, 56.06; H, 9.00; S, 6.51. Found: C, 56.20; H, 8.79; S, 6.67.

D. Ethyl 6-O-t-butyldimethylsilyl-3,4-O-isopropylidene-2-O-(2-hydroxyeth-1-yl)-1-thio-β-D-galactopyranoside

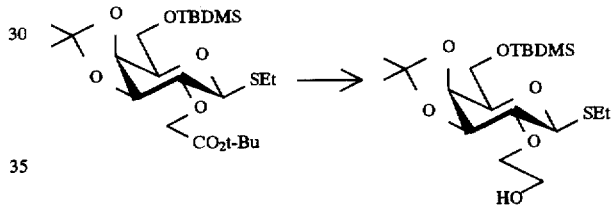

A solution of ethyl 6-O-t-butyldimethylsilyl-3,4-O-isopropylidene-2-O-tert-butyloxycarbonylmethyl-1-thio-β-D-galactopyranoside (4.0 g, 8.1 mmol) in tetrahydrofuran (40 mL) was treated with lithium aluminium hydride (0.31 g, 8.1 mmol) which was added by portions at 5° C. The reaction mixture was stirred for 1 hour. The same quantity of lithium aluminium hydride is added again and the mixture was stirred for another hour. The mixture was then diluted with ethyl ether, cooled down to −15° C. and treated with a 3N aqueous solution of sodium hydroxide. This was stirred for 0.75 hour, then the organic layer was separated and the residual gum was washed with ethyl ether (3×100 mL). The combined organic layers were then dried over anhydrous magnesium sulfate, filtered and concentrated. The residue (2.73 g, 80%) without any purification was used for the next reaction.

IR (CH$_2$Cl$_2$) $v_{max}$ (cm$^{-1}$): 3490 (OH), 3050, 2990, 2935, 2860 (C—H).

$^1$H NMR 400 MHz (CDCl$_3$) δ (ppm): 0.08 (6H, s, —Si(CH$_3$)$_2$), 0.90 (9H, s, —SiC(CH$_3$)$_3$), 1.31 (3H, t, J=7.4 Hz, —CH$_3$), 1.35 and 1.54 (6H, 2s, —C(CH$_3$)$_2$), 2.66–2.82 (2H, m, —SCH$_2$—), 2.92 (1H, t, J=6.5 Hz, —OH), 3.55 (1H, dd, J=10.0 and 7.0 Hz, H-2), 3.63–3.74 (2H, m, —CH$_2$OH), 3.77 (1H, br td, H-5), 3.82–3.90 (4H, m, —OCH$_2$— and H-6), 4.12 (1H, dd, J=6.8 and 5.5 Hz, H-3), 4.26 (1H, dd, J=5.5 and 2.1 Hz, H-4), 4.33 (1H, d, J=10.0 Hz, H-1).

Anal. Calcd. for C$_{19}$H$_{38}$O$_6$SSi: C, 53.99; H, 9.06; S, 7.59. Found: C, 53.82; H, 8.91; S, 7.65.

E. Ethyl 3,4-O-isopropylidene-6-O-tert-butyldimethylsilyl-2-O-(2-methanesulfonyloxyeth-1-yl)-1-thio-β-D-galactopyranoside

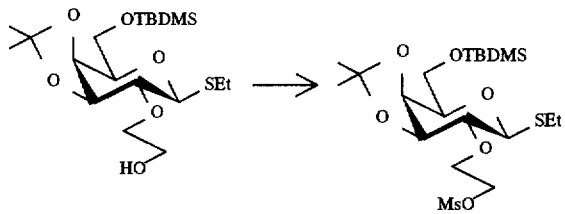

Triethylamine (99 μL, 0.711 mmol) followed by methanesulfonyl chloride (44 μL, 0.569 mmol) were added to a stirred solution of ethyl 3,4-O-isopropylidene-6-O-tert-butyldimethylsilyl-2-O-(2-hydroxyeth-1-yl)-1-thio-β-D-galactopyranoside (0.200 g, 0.474 mmol) in methylene chloride (2 mL) at 0° C. The mixture was stirred for 30 minutes then water (~2 mL) was added. The aqueous layer was extracted with methylene chloride (3×3 mL). The combined organic layers were dried over anhydrous magnesium sulfate, filtered and concentrated. The residue was purified by silica gel column chromatography (30% ethyl acetate/hexane) and afforded the title compound (0.229 g, 97%) as an oil.

$^1$H NMR 200 MHz (CDCl$_3$) δ (ppm): 0.07 (6H, s, —Si(CH$_3$)$_2$—), 0.89 (9H, s, tert-butyl), 1.28 (3H, t, J=5.2 Hz, —CH$_3$), 1.33 and 1.52 (6H, 2s, —C(CH$_3$)$_2$), 2.72 (2H, m, —SCH$_2$—), 3.09 (3H, s, —SO$_2$CH$_3$), 3.31 (1H, dd, J=9.9 and 6.6 Hz, H-2), 3.74–4.17 (7H, m, H-6, H-5, —OCH$_2$— and —CH$_2$OMs), 4.24 (1H, dd, J=5.4 and 1.8 Hz, H-4), 4.35–4.41 (2H, m, H-1 and H-3).

F. Ethyl 3,4-O-isopropylidene-6-O-tert-butyldimethylsilyl-2-O-(3,3-di-tert-butyloxycarbonylprop-1-yl)-1-thio-β-D-galactopyranoside

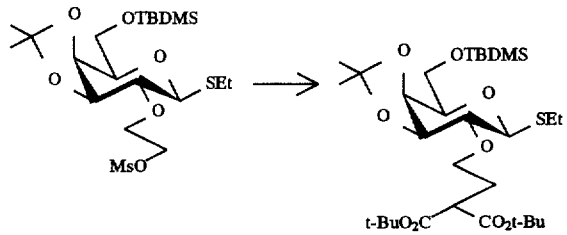

Tert-butyl malonate (225 μL, 1.00 mmol) was added to a suspension of sodium hydride (36 mg, 80% suspension in oil, 1.20 mmol) in dimethylformamide (2 mL) at 0° C. This mixture was stirred at 22° C. for 0.75 hour, then a solution of ethyl 3,4-O-isopropylidene-6-O-tert-butyldimethylsilyl-2-O-(2-methanesulfonyloxyeth-1-yl)-1-thio-β-D-galactopyranoside (0.102 g, 0.204 mmol) in tetrahydrofuran (4 mL) was added in dropwise, followed by solid potassium iodide (~7 mg, 0.04 mmol). The resulting mixture was stirred at 65° C. for 12 hours, then diluted with ethyl acetate (~10 mL) and quenched with saturated ammonium chloride. The organic layers were washed with water (10 mL), dried over anhydrous magnesium sulfate, filtered and concentrated. The residue was purified by silica gel column chromatography (5 to 10% ethyl acetate/hexane) and afforded the title material (0.330 g, contaminated with tert-butyl malonate). An aliquot of pure material was purified.

$^1$H NMR 200 MHz (CDCl$_3$) δ (ppm): 0.06 (6H, s, —Si(CH$_3$)$_2$), 0.88 (9H, s, —SiC(CH$_3$)$_3$), 1.28 (3H, t, J=3.2 Hz, —CH$_3$), 1.31 and 1.49 (6H, 2s, —C(CH$_3$)$_2$), 1.45 (18H, br s, 2×tert-butyl), 2.08 (2H, m, —CH$_2$—CH(CO$_2$tBu)$_2$), 2.70 (2H, m, —SCH$_2$—), 3.24 (1H, dd, J=9.8 and 6.6 Hz, H-2), 3.46 (1H, t, J=7.4 Hz, —CH(CO$_2$tBu)$_2$), 3.63–3.85 (5H, m, H-5, H-6, —OCH$_2$—), 4.08 (1H, br t, H-3), 4.21 (1H, dd, J=5.5 and 1.8 Hz, H-4), 4.30 (1H, d, J=9.8 Hz, H-1).

G. Ethyl 3,4-O-isopropylidene-2-O-(3,3-di-tert-butyloxycarbonylprop-1-yl)-1-thio-β-D-galactopyranoside

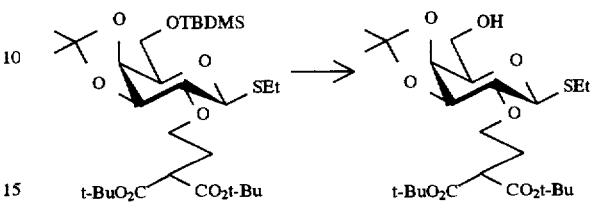

A solution of ethyl 3,4-O-isopropylidene-6-O-tert-butyldimethylsilyl-2-O-(3,3-di-tert-butyloxycarbonylprop-1-yl)-1-thio-β-D-galactopyranoside (0.330 g, contaminated with tert-butyl malonate) in tetrahydrofuran (2 mL) was treated with tetra-butylammonium fluoride (204 μL, 1M solution in tetrahydrofuran, 0.204 mmol) at 0° C. The mixture was stirred at 22° C. for ~2 hours, then diluted with ethyl acetate (~5 mL) and washed with water (~5 mL). The organic layer was dried over anhydrous magnesium sulfate, filtered and concentrated. The residue was purified by silica gel column chromatography and gave the title compound (0.069 g, 67% for 2 steps) as an oil.

$[\alpha]_D^{22}$: -1.2° (c=1.2, CHCl$_3$).

IR (film) $v_{max}$ (cm$^{-1}$): 3700–3020 (OH), 2970, 2920 (C—H), 1720 (C=O).

$^1$H NMR 400 MHz (CDCl$_3$) δ (ppm): 1.31 (3H, t, J=7.7 Hz, —CH$_3$), 1.34 and 1.51 (6H, 2s, —C(CH$_3$)$_2$), 1.47 (18H, s, 2×tert-butyl), 2.05–2.12 (3H, m, —CH$_2$CH(CO$_2$tBu)$_2$ and —OH), 2.74 (2H, m, —SCH$_2$—), 3.28 (1H, dd, J=9.5 and 6.2 Hz, H-2), 3.47 (1H, t, J=7.4 Hz, —CH(CO$_2$tBu)$_2$), 3.68 (1H, dt, J=9.6 and 6.3 Hz, —OCH$_2$—), 3.76–3.84 and 3.92–3.99 (4H, 2 sets of m, —OCH$_2$—, H-6 and H-5), 4.14 (1H, br t, H-3), 4.18 (1H, dd, J=5.8 and 1.7 Hz, H-4), 4.35 (1H, d, J=9.5 Hz, H-1).

Anal. Calcd. for C$_{24}$H$_{42}$O$_9$S: C, 56.90; H, 8.36; S, 6.33. Found: C, 56.83; H, 8.14; S, 6.59.

H. Ethyl 2-O-(3,3-di-tert-butyloxycarbonylprop-1-yl)-1-thio-β-D-galactopyranoside

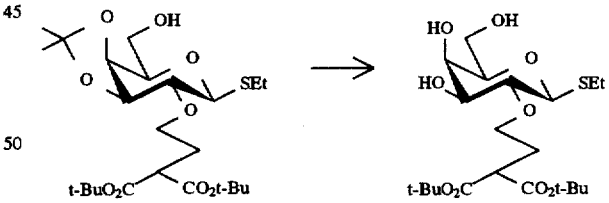

A solution of ethyl 3,4-O-isopropylidene-2-O-(3,3-di-tert-butyloxycarbonylprop-1-yl)-1-thio-β-D-galactopyranoside (0.885 g, 1.75 mmol) in tetrahydrofuran (20 mL) was treated with aqueous hydrochloric acid (2N, 5 mL). The mixture was stirred at 220° C. for 12 hours and then diluted with ethyl acetate (25 mL). Solid sodium bicarbonate was added at 0° C., followed by anhydrous magnesium sulfate. The mixture was filtered and the solvents were evaporated. The residue was purified by silica gel column chromatography (30% ethyl acetate/hexane to pure ethyl acetate) to give the title compound (0.758 g, 93%) as an oil.

$[\alpha]_D^{22}$: -25.9° (c=1.1, CHCl$_3$).

IR (film) $v_{max}$ (cm$^{-1}$): 3700–3020 (OH), 2970, 2920 (C—H), 1720 (C=O).

¹H NMR 400 MHz (CDCl₃) δ (ppm): 1.32 (3H, t, J=7.5 Hz, —CH₃), 1.47 and 1.48 (18H, 2s, 2×tert-butyl), 1.98–2.06 (1H, m, —OH), 2.15–2.28 (2H, m, —CH₂CH(CO₂tBu)₂), 2.76 (2H, m, —SCH₂—), 2.80 (1H, br s, —OH), 3.34 (1H, br t, H-2), 3.45–3.54 (3H, m, H-5, —CH(CO₂tBu)₂ and —OCH₂—), 3.59 (1H, td, J=8.8 and 3.3 Hz, —OCH₂—), 3.82 (1H, ddd, J=11.8, 8.4 and 4.3 Hz, H-6), 3.97 (1H, ddd, J=11.8, 6.6 and 4.4 Hz, H-6), 4.04 (1H, d, J=1.2 Hz, —OH-4), 4.17 (1H, dt, J=8.9 and 4.4 Hz, H-3), 4.31 (1H, d, J=9.7 Hz, H-1), 4.38 (1H, br d, J=3.2 Hz, H-4).

Anal. Calcd. for C₂₁H₃₈O₉S·0.3H₂O: C, 53.44; H, 8.24; S, 6.79. Found: C, 53.39; H, 7.95; S, 6.76.

I. Ethyl 2-O-(3,3-di-tert-butyloxycarbonylprop-1-yl)-4,6-O-benzylidene-1-thio-β-D-galactopyranoside

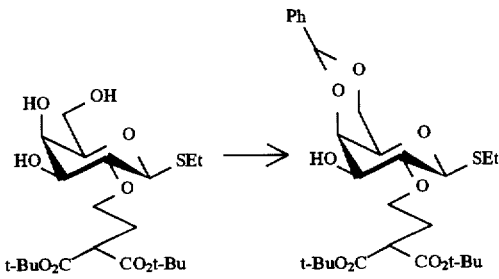

A solution of ethyl 2-O-(3,3-di-tert-butyloxycarbonylprop-1-yl)-1-thio-β-D-galactopyranoside (0.724 g, 1.55 mmol) in acetonitrile (20 mL) was treated with benzaldehyde dimethylacetal (1.16 mL, 7.76 mmol) and p-toluenesulfonic acid (40 mg). The mixture was stirred at 22° C. for 1 hour, then was diluted with ethyl acetate (20 mL) and washed with aqueous 1M sodium bicarbonate (~10 mL) and brine (~10 mL). The organic layer was dried over anhydrous magnesium sulfate, filtered and concentrated. The residue was purified by silica gel column chromatography (30 to 50% ethyl acetate/hexane) and afforded the title material (0.77 g, 89%) as an oil.

[α]_D²²: –32.8° (c=1.2, CHCl₃).

IR (film) ν_max (cm⁻¹): 3600–3200 (OH), 2970, 2920, 2880 (C—H), 1735, 1720 (C=O).

¹H NMR 400 MHz (CDCl₃) δ (ppm): 1.34 (3H, t, J=7.5 Hz, —CH₃), 1.45 and 1.46 (18H, 2s, 2×tert-butyl), 2.02–2.21 (2H, m, —CH₂—CH(CO₂tBu)₂), 2.79 (2H, m, —SCH₂—), 3.44 (1H, br s, H-5), 3.46–3.51 (2H, m, —CH(CO₂Bu)₂ and H-2), 3.55 (1H, J=6.4 Hz, —OH), 3.64–3.69 and 4.05–4.08 (3H, 2 sets of m, H-3 and —OCH₂—), 4.03 (1H, dd, J=12.7 and 1.7 Hz, H-6), 4.26 (1H, d, J=3.5 Hz, H-4), 4.32 (1H, d, J=9.5 Hz, H-1), 4.32 (1H, d, J=12.7 Hz, H-6), 5.55 (1H, s, —OCHO—), 7.35–7.39 and 7.50–7.53 (5H, 2 sets of m, —C₆H₅).

Anal. Calcd. for C₂₈H₄₂O₉S: C, 60.63; H, 7.63; S, 5.78. Found: C, 60.74; H, 7.46; S, 6.23.

J. Ethyl 2-O-(3,3-di-tert-butyloxycarbonylprop-1-yl)-3-O-benzoyl-4,6-O-benzylidene-1-thio-β-D-galactopyranoside

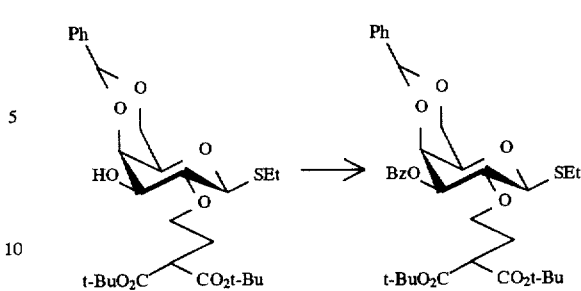

A stirred solution of ethyl 2-O-(3,3-di-tert-butyloxycarbonylprop-1-yl)-4,6-O-benzylidene-1-thio-β-D-galactopyranoside (0.751 g, 1.35 mmol) in methylene chloride (8 mL) and pyridine (7 mL) was treated with benzoyl chloride (204 μL, 1.76 mmol) and 4-dimethylaminopyridine (~10 mg) at 22° C. The mixture was stirred for 4 hours then diluted with methylene chloride (15 mL) and washed with aqueous 1M sodium bicarbonate (~15 mL) and brine (~15 mL). The organic layer was dried over anhydrous magnesium sulfate, filtered and concentrated. The residue was purified by silica gel column chromatography (10 to 30% ethyl acetate/hexane) and gave the title material (0.888 g, 99%) as an oil.

[α]_D²²: +51° (c=1.1, CHCl₃).

IR (film) ν_max (cm⁻¹): 3035, 3010, 2970, 2920, 2860 (C—H), 1720 (C=O).

¹H NMR 400 MHz (CDCl₃) δ (ppm): 1.36 (3H, t, J=7.6 Hz, —CH₃), 1.37 and 1.42 (18H, 2s, 2×tert-butyl), 2.00 (2H, m, —CH₂—CH(CO₂tBu)₂), 2.82 (2H, m, —SCH₂—), 3.37 (1H, dd, J=7.9 and 6.6 Hz, —CH(CO₂tBu)₂), 3.58 (1H, br s, H-5), 3.75 (1H, dt, J=9.2 and 5.9 Hz, —OCH₂—), 3.81–3.87 (1H, m, —OCH₂—), 3.87 (1H, t, J=9.6 Hz, H-2), 4.03 (1H, dd, J=12.4 and 1.6 Hz, H-6), 4.36 (1H, dd, J=12.4 and 1.3 Hz, H-6), 4.50 (1H, d, J=9.6 Hz, H-1), 4.53 (1H, d, J=3.5 Hz, H-4), 5.12 (1H, dd, J=9.6 and 3.5 Hz, H-3), 5.49 (1H, s, —OCHO—), 7.34–7.38, 7.43–7.48, 7.56–7.60 and 8.08–8.10 (10H, 4 sets of m, 2×—C₆H₅).

Anal. Calcd. for C₃₅H₄₆O₁₀S: C, 63.81; H, 7.04; S, 4.87. Found: C, 63.94; H, 6.89; S, 5.41.

K. (2S,3R,4E)-3-Benzoyloxy-2-azido-1-[2-O-(3,3-di-tert-butyloxycarbonylprop-1-yl)-3-O-benzoyl-4,6-O-benzylidene-α-D-galactopyranosyloxy]-4-octadecene and (2S 3R,4E)-3-benzoyloxy-2-azido-1-[2-O-(3,3-di-tert-butyloxycarbonylprop-1-yl)-3-O-benzoyl-4,6-O-benzylidene-β-D-galactopyranosyloxy]-4-octadecene

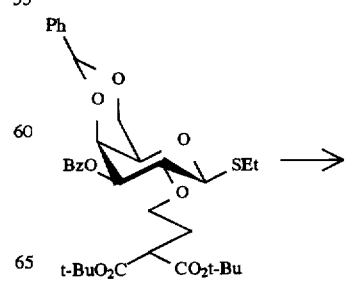

-continued

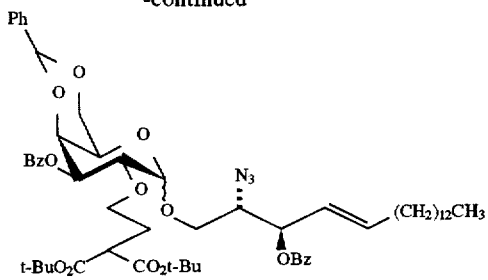

A solution of ethyl 2-O-(3,3-di-tert-butyloxycarbonylprop-1-yl)-3-O-benzoyl-4,6-O-benzylidene-1-thio-β-D-galactopyranoside (1.97 g, 3.00 mmol), 2,6-di-tert-butyl-4-methylpyridine (1.23 g, 6.0 mmol) and (2S,3R,4E)-2-azido-3-benzoyloxy-4-octadecen-1-ol [P. Zimmermann and R. R. Schmidt, Liebigs Ann. Chem. 1988, 663–6671](1.1 g, 2.5 mmol) in dioxane (25 mL) was stirred with molecular sieves (4 Å, previously heated with a Bunsen flame) for 1 hour at 22° C. Then dimethyl(methylthio)sulfonium triflate (1.5 g, 6.0 mmol) was added in and stirring was continued for 1 hour. The mixture was diluted with ethyl acetate (25 mL) and filtered through celite. The filtrate was washed with 1M aqueous sodium bicarbonate (25 mL) and brine (25 mL), dried over anhydrous magnesium sulfate, filtered and concentrated. The residue was purified by silica gel column chromatography (5 to 30% ethyl acetate/hexane) and gave the α-anomer (1.64 g, 64%) and the β-anomer (0.51 g, 20%) of the title compound as oils.

α-anomer $[\alpha]_D^{22}$: +71.8° (c=1.2, CHCl$_3$).

IR (film) $v_{max}$ (cm$^{-1}$): 3035, 3010, 2970, 2925, 2855 (C—H), 2100 (N$_3$), 1722 (C=O).

$^1$H NMR 400 MHz (CDCl$_3$) δ (ppm): 0.89 (3H, t, J=6.8 Hz, —CH$_3$), 1.26 (20H, br s, —(CH$_2$)$_{10}$—), 1.39–1.42 (20H, m, 2×tert-butyl and —CH$_2$—), 2.01–2.12 (4H, m, =CH—CH$_2$— and —CH$_2$—CH(CO$_2$tBu)$_2$), 3.41 (1H, t, J=7.4 Hz, —CH(CO$_2$tBu)$_2$), 3.64–3.72 (3H, m, H-2, H-2' and —OCH$_2$—), 3.89 (1H, dd, J=10.7 and 4.2 Hz, H-1), 3.90 (1H, br s, H-5'), 4.04 (1H, dt, J=7.8 and 4.0 Hz, —OCH$_2$—), 4.10 (1H, br d, J=12.5 Hz, H-6'), 4.14 (1H, dd overlapped by H-6', H-1), 4.30 (1H, br d, J=12.5 Hz, H-6'), 4.64 (1H, d, J=3.4 Hz, H-4'), 5.19 (1H, d, J=3.4 Hz, H-1'), 5.45 (1H, dd, J=10.5 and 3.4 Hz, H-3'), 5.52 (1H, s, —OCHO—), 5.62 (1H, dd, J=14.3 and 8.0 Hz, H-4), 5.66 (1H, dd, J=8.0 and 4.1Hz, H-3), 5.98 (1H, dt, J=14.3 and 6.8 Hz, H-5), 7.33–7.34, 7.43–7.49, 7.56–7.60 and 8.07–8.13 (15H, 4 sets of m, 3×—C$_6$H$_5$).

Anal. Calcd. for C$_{58}$H$_{79}$N$_3$O$_{13}$: C, 67.88; H, 7.76; N, 4.09. Found: C, 67.83; H, 7.64; N, 4.20.

β-anomer $[\alpha]_D^{22}$: +28° (c=0.97, CHCl$_3$).

IR (film) $v_{max}$ (cm$^{-1}$): 2930, 2850 (C—H), 2100 (—N$_3$), 1725 (C=O).

$^1$H NMR 400 MHz (CDCl$_3$) δ (ppm): 0.89 (3H, t, J=6.8 Hz, —CH$_3$), 1.20–1.50 (22H, m, —(CH$_2$)$_{11}$—), 1.35 and 1.36 (18H, 2 s, 2×—OtBu), 1.96–2.11 (4H, m, =CH—CH$_2$— and —CH$_2$—CH(CO$_2$tBu)$_2$), 3.28 (1H, t, J=7.3 Hz, —CH(CO$_2$tBu)$_2$), 3.54 (1H, br s, H-5'), 3.69 (1H, dt, J=9.9 and 6.6 Hz, —OCH$_2$—), 3.72 (1H, dd, J=10.2 and 4.6 Hz, H-1), 3.86 (1H, dd, J=10.1 and 7.7 Hz, H-2'), 3.94 (1H, dt, J=9.9 and 6.0 Hz, —OCH$_2$—), 4.02 (1H, dd, J=10.2 and 7.9 Hz, H-1), 4.07 (1H, d, J=12.2 Hz, H-6'), 4.10–4.13 (1H, m, H-2), 4.34 (1H, d, J=12.2 Hz H-6'), 4.47–4.50 (2H, m, H-1' and H-4'), 5.07 (1H, dd, J=10.1 and 3.6 Hz, H-3'), 5.50 (1H, s, —OCHO—), 5.60 (1H, dd, J=14.4 and 8.0 Hz, H-4), 5.64 (1H, dd, J=8.0 and 4.0 Hz, H-3), 5.95 (1H, dt, J=14.4 and 6.7 Hz, H-5), 7.33–7.37, 7.43–7.49, 7.53–7.59 and 8.07–8.13 (15H, 4 sets of m, aromatic H).

Anal. Calcd. for C$_{58}$H$_{79}$N$_3$O$_{13}$.CH$_2$Cl$_2$: C, 63.77; H, 7.35; N, 3.78. Found: C, 64.00; H, 7.35; N, 3.89.

L. (2S,3R,4E)-3-Benzoyloxy-2-hexadecanoylamino-1-[2-O-(3,3-di-tert-butyloxycarbonylprop-1-yl)-3-O-benzoyl-4,6-O-benzylidene-α-D-galactopyranosyloxy]-4-octadecene

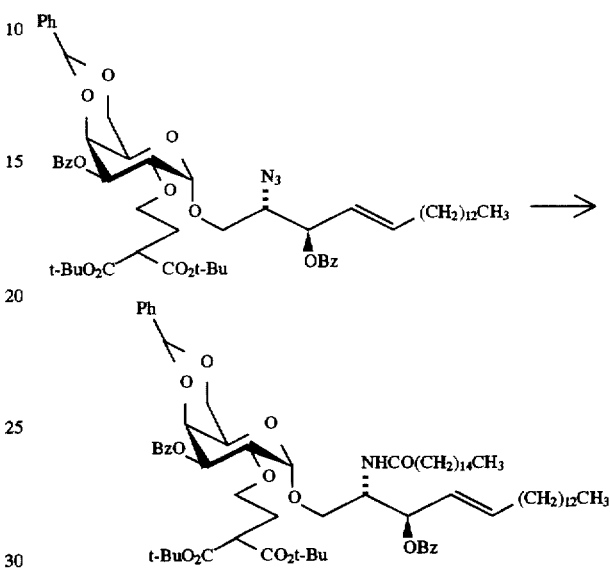

A solution of (2S,3R,4E)-3-benzoyloxy-2-azido-1-[2-O-(3,3-di-tert-butyloxycarbonylprop-1-yl)-3-O-benzoyl-4,6-O-benzylidene-α-D-galactopyranosyloxy]-4-octadecene (0.477 g, 0.464 mmol) in pyridine (15 mL) and water (3 mL) was treated with a stream of hydrogen sulfide for ~10 minutes. The solution was stirred for 12 hours, then hydrogen sulfide was bubbled again for ~10 minutes. The reaction mixture was stirred for another 12 hours. The solvents were evaporated under vacuum and the residue was co-evaporated with toluene (2×). The residue was then dissolved in tetrahydrofuran (15 mL) and an aqueous solution of sodium acetate (50%, 3 mL) was added followed by palmitoyl chloride (184 μL, 0.603 mmol) at 0° C. The mixture was stirred for 30 minutes at 22° C. and then diluted with ethyl acetate (~15 mL). The organic layer was separated, washed with 1M aqueous sodium bicarbonate (~15 mL) and brine (~15 mL), dried over anhydrous magnesium sulfate, filtered and concentrated. The residue was purified by silica gel column chromatography (20 to 50% ethyl acetate/hexane) to afford the title compound (0.527 g, 92%) as an oil.

$[\alpha]_D^{22}$: +61.5° (c=1.1, CHCl$_3$).

IR (film) $v_{max}$ (cm$^{-1}$): 3500–3240 (NH), 2925, 2855 (C—H), 1722, 1650 (C=O).

$^1$H NMR 400 MHz (CDCl$_3$) δ (ppm): 0.87–0.91 (6H, m, 2×—CH$_3$), 1.24–1.44 (44H, m, —(CH$_2$)$_{10}$— and —(CH$_2$)$_{12}$—), 1.37 and 1.39 (18H, 2s, 2×tert-butyl), 1.53–1.65 (4H, m, 2×—CH$_2$—), 2.00–2.09 and 2.19–2.40 (6H, 2 sets of m, —NHCOCH$_2$—, =CH—CH$_2$— and —CH$_2$—CH(CO$_2$tBu)$_2$), 3.39 (1H, t, J=7.3 Hz, —CH(CO$_2$tBu)$_2$), 3.62 (1H, dt, J=9.5 and 5.8 Hz, —OCH$_2$—), 3.72–3.82 (2H, m, —OCH$_2$— and H-1), 3.80 (1H, br s, H-5'), 3.91 (1H, dd, J=10.9 and 3.4 Hz, H-1), 4.05 (1H, dd, J=12.4 and 1.3 Hz, H-6'), 4.08 (1H, dd, J=10.6 and 3.4 Hz, H-2'), 4.25 (1H, d, J=12.4 Hz, H-6'), 4.52 (1H, m, H-2), 4.59 (1H, d, J=3.4 Hz, H-4'), 5.08 (1H, d, J=3.4 Hz, H-1'), 5.39 (1H, dd, J=10.6 and 3.4 Hz, H-3'), 5.50 (1H, s, —OCHO—), 5.55 (1H, dd, J=15.3 and 7.5 Hz, H-4), 5.67 (1H, t, J=7.3 Hz, H-3), 5.92 (1H, dt, J=15.3 and 6.8 Hz, H-5), 6.44 (1H, d, J=9.0 Hz, —NH—), 7.31–7.33, 7.42–7.48, 7.54–7.60, 8.04–8.12 (15H, 4 sets of m, 3×—C$_6$H$_5$).

Anal. Calcd. for C$_{74}$H$_{111}$NO$_{14}$: C, 71.75; H, 9.03;N,1.13. Found: C, 72.02; H, 9.12; N, 1.33.

M. (2S,3R,4E)-3-Benzoyloxy-2-hexadecanoylamino-1-[2-O-(3,3-di-tert-butyloxycarbonylprop-1-yl)-3-O-benzoyl-α-D-galactopyranosyloxy]-4-octadecene

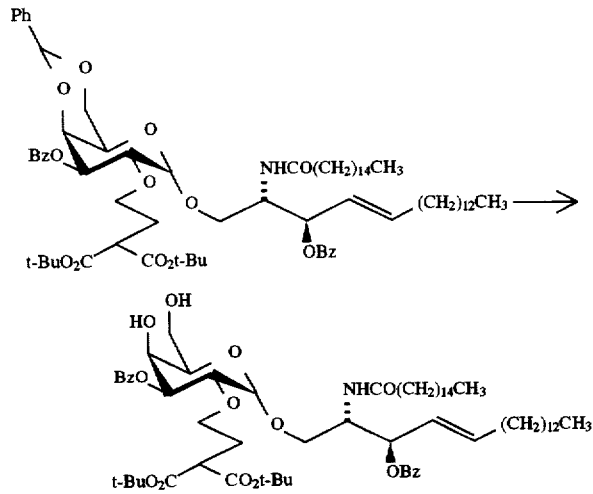

A stirred solution of (2S,3R,4E)-3-benzoyloxy-2-hexadecanoylamino-1-[2-O-(3,3-di-tert-butyloxycarbonylprop-1-yl)-3-O-benzoyl-4,6-O-benzylidene-α-D-galactopyranosyloxy]-4-octadecene (0.242 g, 0.195 mmol) in methylene chloride (10 mL) was treated at 0° C. with aqueous trifluoroacetic acid (90%, 1 mL). The solution was stirred at 0° C. for 3 hours, then solid sodium bicarbonate followed by anhydrous magnesium sulfate were added. The mixture was filtered and evaporated. The residue was purified by silica gel column chromatography (20 to 50% ethyl acetate/hexane) and afforded the title material (0.187 g, 83%) as an oil.

[α]$_D^{22}$: +60.1° (c=1.0, CHCl$_3$).

IR (film) ν$_{max}$ (cm$^{-1}$): 3600–3100 (OH and NH), 2920, 2850 (C—H), 1720, 1650 (C=O).

$^1$H NMR 400 MHz (CDCl$_3$) δ (ppm): 0.89 (6H, t, J=6.7 Hz, 2×—CH$_3$), 1.24–1.47 (62H, m, —(CH$_2$)$_{10}$—, —(CH$_2$)$_{12}$— and 2×tert-butyl), 1.63 (5H, m, 2×—CH$_2$— and —OH), 2.00–2.08 (4H, m, =CH—CH$_2$— and —CH$_2$—CH(CO$_2$tBu)$_2$), 2.22 (2H, m, —NHCOCH$_2$—), 2.65 (1H, br s, —OH), 3.35 (1H, t, J=7.4 Hz, —CH(CO$_2$tBu)$_2$), 3.61 (1H, dt, J=9.5 and 6.0 Hz, —OCH$_2$—), 3.73 (1H, dt, J=9.5 and 6.2 Hz, —OCH$_2$—), 3.82–3.94 (4H, m, H-1 and H-6'), 3.92 (1H, br s, H-5'), 4.00 (1H, dd, J=10.5 and 3.6 Hz, H-2'), 4.37 (1H, d, J=2.9 Hz, H-4'), 4.56 (1H, m, H-2), 5.07 (1H, d, J=3.6 Hz, H-1'), 5.32 (1H, dd, J=10.5 and 3.0 Hz, H-3'), 5.54 (1H, dd, J=15.3 and 7.4 Hz, H-4), 5.64 (1H, t, J=7.2 Hz, H-3), 5.91 (1H, dt, J=15.3 and 6.8 Hz, H-5), 6.38 (1H, d, J=9.1 Hz, —NH—), 7.43–7.49, 7.55–7.61 and 8.04–8.11 (10H, 3 sets of m, 3×—C$_6$H$_5$).

EXAMPLE 2

(2S,3R,4E)-3-Benzoyloxy-2-hexadecanoylamino-1-[2-O-(3,3-di-carboxyprop-1-yl)-3-O-benzoyl-α-D-galactopyranosyloxy]-4-octadecene Procedure No. 1:

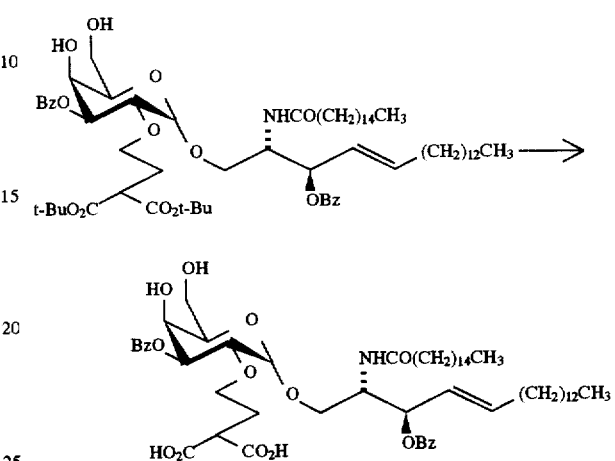

Aqueous trifluoroacetic acid (90%, 1 mL) was added to (2S,3R,4E)-3-benzoyloxy-2-hexadecanoylamino-1-[2-O-(3,3-di-tert-butyloxycarbonylprop-1-yl)-3-O-benzoyl-α-D-galactopyranosyloxy]-4-octadecene (0.083 g, 0.072 mmol) at 22° C. The resulting solution was stirred for 5 minutes then toluene (1 mL) was added and the solvents were evaporated under vacuum. This procedure was repeated until there was no starting material left. The residue was purified by silica gel column chromatography (1 to 20% methanol/methylene chloride) and, after evaporation of the solvents, was redissolved in methylene chloride/methanol (1:1) and treated with Amberlite H$^+$ resin for 0.5 hour at 0° C. The solution was evaporated and the residue was lyophilized in dioxane to afford the title compound (0.074 g, 98%) as a white fluffy solid.

Procedure No. 2:

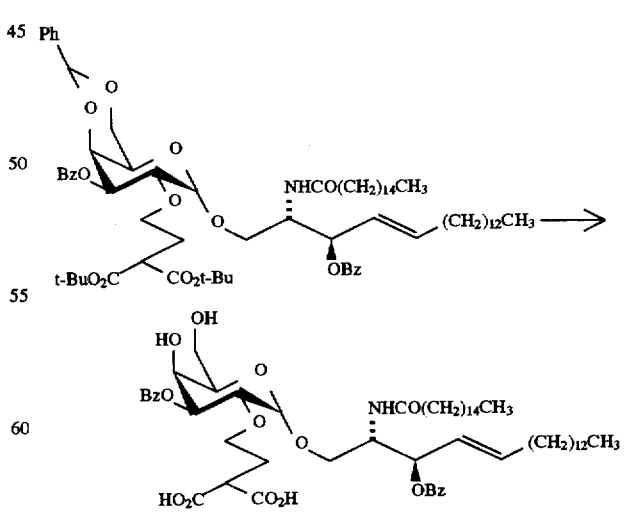

Aqueous trifluoroacetic acid (90%, 1 mL) was added to (2S,3R,4E)-3-benzoyloxy-2-hexadecanoylamino-1-[2-O-(3,3-di-tert-butyloxycarbonylprop-1-yl)-3-O-benzoyl-4,6-O- benzylidene-(α-D-galactopyranosyloxy]-4-octadecene (0.193 g, 0.156 mmol) at 22° C. The resulting solution was stirred for 5 minutes then toluene (1 mL) was added and the solvents were evaporated under vacuum. This procedure was repeated until there was no starting material left. The residue was purified by silica gel column chromatography (1 to 20% methanol/methylene chloride) and, after evaporation of the solvents, was redissolved in methylene chloride/methanol (1:1) and treated with Amberlite H+ resin for 0.5 hour at 0° C. The solution was evaporated and the residue was lyophilized in dioxane to afford the title compound (0.103 g, 64%) as a white fluffy solid.

$[\alpha]_D^{22}$: +66° (c=0.5, CHCl$_3$).

IR (film) $v_{max}$ (cm$^{-1}$): 3700–3000 (OH and NH), 2920, 2850 (C—H), 1720, 1650 (C=O).

$^1$H NMR 400 MHz (DMSO-d$_6$) δ (ppm): 0.85 (6H, t, J=6.8 Hz, 2×—CH$_3$), 1.19–1.35 (46H, m, —(CH$_2$)$_{11}$— and —(CH$_2$)$_{12}$—), 1.47, 1.85, 2.00 and 2.09 (8H, 4 sets of m, —CH$_2$—, —NHCOCH$_2$—, =CH—CH$_2$— and —CH$_2$CH(CO$_2$H)$_2$), 3.42 (1H, dd, J=10.9 and 6.5 Hz, H-1), 3.47–3.49, 3.51–3.58 and 3.73–3.76 (7H, 3 sets of m, H-5', H-6', H-1, —OCH$_2$— and —CH(CO$_2$H)$_2$), 3.85 (1H, dd, J=10.5 and 3.4 Hz, H-2'), 4.10 (1H, br s, H-4'), 4.37 (1H, m, H-2), 4.6 (1H, br s, —OH-6'), 4.97 (1H, d, J=3.4 Hz, H-1'), 5.06 (1H, dd, J=10.5 and 3.0 Hz, H-3'), 5.09 (1H, s, —OH-4'), 5.48 (1H, br t, H-3), 5.55 (1H, dd, J=15.1 and 7.5 Hz, H-4), 5.7 (1H, dt, J=15.1 and 6.8 Hz, H-5), 7.47–7.52, 7.61–7.67 and 7.94–8.01 (11H, 3 sets of m, 2×—C$_6$H$_5$ and —NH—), 12.63 (1H, br s, —COOH).

Preparation of the sodium salt of the title compound

The diacid from the above procedure (0.350 g, 0.337 mmol) was dissolved in dioxane and water. This solution was cooled down to −10° C. and treated with sodium bicarbonate (57 mg, 0.674 mmol). The resulting solution was filtered on glass paper and on Millex LCR 0.5 μm, then lyophilized to give the sodium salt of the title compound (0.348 g, 100%) as a white fluffy solid.

IR (neat) $v_{max}$ (cm$^{-1}$): 3700–3100 (NH and OH), 2920, 2850 (C—H), 1720, 1645, 1600 (C=O).

$^1$H NMR 400 MHz (CD$_3$OD) δ (ppm): 0.83 (6H, t, J=6.8 Hz, 2×—CH$_3$), 1.17–1.34 (46H, m, —(CH$_2$)$_{11}$— and —(CH$_2$)$_{12}$—), 1.52–1.56 (2H, m, —CH$_2$—), 1.99–2.04 (4H, m, =CH—CH$_2$— and —CH$_2$—CH(CO$_2$Na)$_2$), 2.21 (2H, t, J=7.3 Hz, —NHCOCH$_2$—), 3.08 (1H, t, J=7.3 Hz, —CH(CO$_2$Na)$_2$), 3.58–3.71 (5H, m, H-1, H-6' and —OCH$_2$—), 3.86 (1H, t, J=6.4 Hz, H-5'), 3.90 (1H, dd, J=10.5 and 3.7 Hz, H-1), 3.98 (1H, dd, J=10.6 and 3.5 Hz, H-2'), 4.13 (1H, d, J=2.6 Hz, H-4'), 4.41 (1H, m, H-2), 5.03 (1H, d, J=3.5 Hz, H-1'), 5.17 (1H, dd, J=10.6 and 3.1 Hz, H-3'), 5.51 (1H, dd, J=14.6 and 7.6 Hz, H-4), 5.56 (1H, br t, H-3), 5.85 (1H, dt, J=14.6 and 6.8 Hz, H-5), 7.39–7.44, 7.51–7.55 and 7.98–8.03 (10H, 3 sets of m, aromatic H).

EXAMPLE 3

(2S,3R,4E)-3-Benzoyloxy-2-hexadecanoylamino-1-[2-O-(5,5-di-tert-butyloxycarbonylpentyl)-3-O-benzoyl-α-D-galactopyranosyloxy]-4-octadecene A. Ethyl 3,4-O-isopropylidene-6-O-tert-butyldimethylsilyl-2-O-(4-bromobut-1-yl)-1-thio-β-D-galactopyranoside

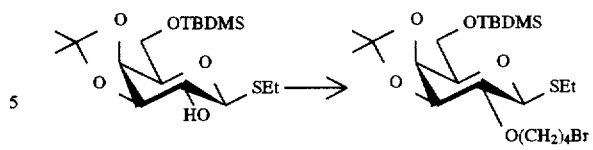

A stirred solution of ethyl 6-O-t-butyldimethylsilyl-3,4-O-isopropylidene-1-thio-β-D-galactopyranoside described in Example 1-B (0.89 g, 2.35 mmol) in N,N-dimethylformamide (20 mL) was treated with sodium hydride (60% in mineral oil, 0.90 g, 22.5 mmol) at 0C. The mixture was stirred at room temperature for 10 minutes, then 1,4-dibromobutane (6 mL, 50.2 mmol) was added. The mixture was stirred for ~30 minutes at 22° C., then diluted with ethyl ether and washed with saturated ammonium chloride, water and brine. The residue was purified by silica gel chromatography (5 to 8% ethyl acetate/hexane) to give the title compound (0.950 g, 79%).

IR (CH$_2$Cl$_2$) $v_{max}$ (cm$^{-1}$): 2940, 2920, 2840 (C—H).

$^1$H NMR 200 MHz (CDCl$_3$) δ (ppm): 0.07 (6H, s, —Si(CH$_3$)$_2$), 0.89 (9H, s, —SitBu), 1.29 (3H, t, J=7.5 Hz, —CH$_2$—CH$_3$), 1.34 and 1.52 (6H, 2s, —(CH$_3$)$_2$C—), 1.67–1.80 and 1.92–2.06 (4H, 2m, —(CH$_2$)$_2$—), 2.62–2.82 (2H, m, —SCH$_2$—), 3.26 (1H, dd, J=9.9 and 6.7 Hz, H-2), 3.47 (2H, t, J=6.7 Hz, —CH$_2$Br), 3.62–3.83 (4H, m, H-6 and —OCH$_2$—), 3.86 (1H, d, J=1.9 Hz, H-5'), 4.07 (1H, dd, J=5.5 and 6.7 Hz, H-3), 4.22 (1H, dd, J=5.5 and 1.9 Hz, H-4), 4.32 (1H, d, J=9.9 Hz, H-1).

B. Ethyl 3,4-O-isopropylidene-6-O-tert-butyldimethylsilyl-2-O-(5,5-di-tert-butyloxycarbonylpent-1-yl)-1-thio-β-D-galactopyranoside

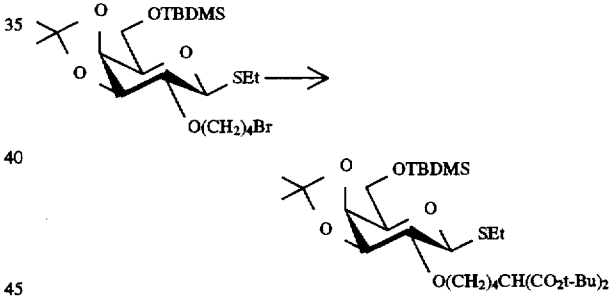

A stirred solution of di-tert-butylmalonate (3.0 mL, 13.4 mmol) in tetrahydrofuran (20 mL) was treated with a solution of potassium tert-butoxide in tert-butanol (1.0M, 15.0 mL, 15 mmol) at 0° C. The mixture was stirred for ~30 minutes. A solution of ethyl 3,4-O-isopropylidene-6-O-tert-butyldimethylsilyl-2-O-(4-bromobut-1-yl)-1-thio-β-D-galactopyranoside (4.00 g, 7.79 mmol) in N,N-dimethylformamide (20 mL) was then added to this mixture and the ice-cooled bath was removed. The mixture was heated to ~50°–60° C. for ~2 hours, then diluted with ethyl acetate. A saturated solution of ammonium chloride was added and the two phases were separated. The organic layer was then washed with water and brine, dried over anhydrous magnesium sulfate, filtered and concentrated. The residue was purified by silica gel chromatography (5 to 10% ethyl acetate/hexane) and afforded the title compound (5.2 g, 100%).

IR (CH$_2$Cl$_2$) $v_{max}$ (cm$^{-1}$): 2930, 2850 (C—H), 1740,1725 (C=O).

$^1$H NMR 400 MHz (CDCl$_3$) δ (ppm): 0.08 (6H, s, -Si(CH$_3$)$_2$), 0.90 (9H, s, —SitBu), 1.29 (3H, t, J=7.4 Hz, —CH$_2$—CH$_3$), 1.34 (3H, s, —C(CH$_3$)$_2$—), 1.36-1.43 (2H, m, —CH$_2$—), 1.47 (18H, s, 2×—OtBu), 1.52 (3H, s, —C(CH$_3$)$_2$—), 1.60-1.67 and 1.83 (4H, 2m, —(CH$_2$)$_2$—), 2.64-2.80 (2H, m, —SCH$_2$—), 3.13 (1H, t, —CH(CO$_2$tBu)$_2$), 3.28 (1H, dd, J=9.8 and 6.7 Hz, H-2), 3.65 (1H, dt, J=9.3 and 6.8 Hz, —OCH$_2$—), 3.72-3.79 and 3.82-3.89 (4H, 2m, —OCH$_2$—, H-5 and H-6), 4.09 (1H, br t, H-3), 4.22 (1H, dd, J=5.5 and 2.0 Hz, H-4), 4.33 (1H, d, J=9.8 Hz, H-1).

C. Ethyl 3,4-O-isopropylidene-2-O-(5,5-di-tert-butyloxycarbonylpent-1-yl)-1-thio-β-D-galactopyranoside

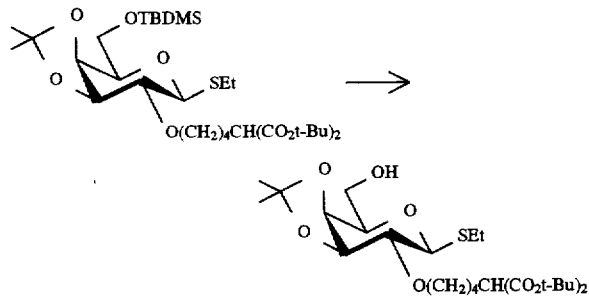

Ethyl 3,4-O-isopropylidene-6-O-tert-butyldimethylsilyl-2-O-(5,5-di-tert-butyloxycarbonylpent-1-yl)-1-thio-β-D-galactopyranoside (5.0 g, 7.7 mmol) was reacted as described in Example 1-G and afforded the title compound (3.8 g, 86%).

IR (CH$_2$Cl$_2$) ν$_{max}$ (cm$^{-1}$): 3700-3100 (OH), 2980, 2930, 2860 (C—H), 1745, 1725 (C=O).

$^1$H NMR 400 MHz (DMSO-d$_6$) δ (ppm): 1.19 (3H, t, J=7.4 Hz, —CH$_2$—CH$_3$), 1.24-1.42 (23H, m, 2×—OtBu, —CH$_2$—, —C(CH$_3$)$_2$—), 1.26 (3H, s, —C(CH$_3$)$_2$—), 1.47 (2H, br qa, —CH$_2$—), 1.67 (2H, br qa, —CH$_2$—), 2.63 (2H, m, —SCH$_2$—), 3.09 (1H, dd, J=9.8 and 6.8 Hz, H-2), 3.14 (1H, t, J=7.5 Hz, —CH(CO$_2$tBu)$_2$), 3.50-3.55 (3H, m, H-6 and —OCH$_2$—), 3.62 (1H, dt, J=9.5 and 6.2 Hz, —OCH$_2$—), 3.74 (1H, td, J=6.3 and 1.8 Hz, H-5), 4.05 (1H, br t, H-3), 4.15 (1H, dd, J=5.5 and 1.9 Hz, H-4), 4.38 (1H, d, J=9.8 Hz, H-1), 4.78 (1H, t, J=5.6 Hz, —OH).

D. Ethyl 2-O-(5,5-di-tert-butyloxycarbonylpent-1-yl)-1-thio-β-D-galactopyranoside

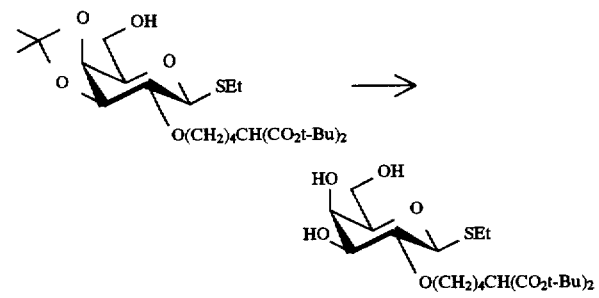

A solution of ethyl 3,4-O-isopropylidene-2-O-(5,5-di-tert-butyloxycarbonylpent-1-yl)-1-thio-β-D-galactopyranoside (3.5 g, 6.1 mmol) in 80% acetic acid (20 mL) was stirred for ~72 hours at 22° C. The solvents were evaporated and the residue was purified by silica gel chromatography (0 to 5% methanol/ethyl acetate) to give the title compound (3.0 g, 99%).

IR (nujol) ν$_{max}$ (cm$^{-1}$): 3700-3000 (br, OH), 2910 (br, C—H), 1740, 1710 (C=O).

$^1$H NMR 400 MHz (DMSO-d$_6$) δ (ppm): 4.78 (1H, d, J=6.6 Hz, —OH), 4.54 (1H, t, J=5.6 Hz, —OH-6), 4.48 (1H, d, J=4.6 Hz, —OH), 4.24 (1H, d, J=9.6 Hz, H-1), 3.67-3.62, 3.57-3.52, 3.50-3.42, 3.40-3.29 and 3.15-3.11 (9H, 5 sets of m, H-2, H-3, H-4, H-5, H-6, —OCH$_2$— and —CH (CO$_2$tBu)$_2$), 2.62 (2H, m, —SCH$_2$—), 1.67 (2H, qa, J=7.7 Hz, —CH$_2$—), 1.56-1.45 (2H, m, —CH$_2$—), 1.40 (18H, s, 2×—OtBu), 1.36-1.24 (2H, m, —CH$_2$—), 1.19 (3H, t, J=7.4 Hz, —CH$_3$).

E. Ethyl 4,6-O-benzylidene-2-O-(5,5-di-tert-butyloxycarbonylpent-1-yl)-1-thio-β-D-galactopyranoside

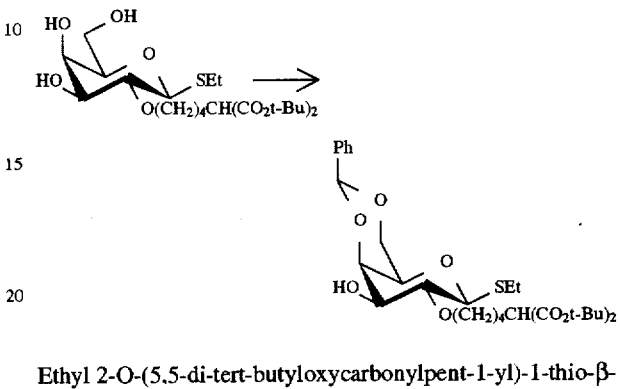

Ethyl 2-O-(5,5-di-tert-butyloxycarbonylpent-1-yl)-1-thio-β-D-galactopyranoside (3.0 g, 6.05 mmol) was reacted as described in Example 1-I and afforded the title compound (2.1 g, 59%).

1H NMR 400 MHz (CDCl$_3$) δ (ppm): 1.34 (3H, t, J=7.5 Hz, —CH$_2$—CH$_3$), 1.37-1.49 (2H, m, —CH$_2$—), 1.46 (18H, 2s, 2×—OtBu), 1.62-1.68 and 1.78-1.87 (4H, 2m, —(CH$_2$)$_2$—), 2.71-2.86 (3H, m, —SCH$_2$— and —OH), 3.13 (1H, t, J=7.5 Hz, —CH(CO$_2$tBu)$_2$), 3.43-3.48 (2H, m, H-2 and H-5), 3.68 (1H, dd, J=8.4 and 3.6 Hz, H-3), 3.70-3.77 (1H, m, —OCH$_2$—), 3.84 (1H, dt, J=8.8 and 6.4 Hz, —OCH$_2$—), 4.03 (1H, dd, J=12.4 and 1.7 Hz, H-6), 4.26 (1H, d, J=3.5 Hz, H-4), 4.34 (1H, dd, J=12.4 and 1.3 Hz, H-6), 4.36 (1H, d, J=9.5 Hz, H-1), 5.55 (1H, s, —OCHO—), 7.37-7.41 and 7.51-7.53 (5H, 2 sets of m, aromatic H).

F. Ethyl 3-O-benzoyl-4,6-O-benzylidene-2-O-(5,5-di-tert-butyloxycarbonylpent-1-yl)-1-thio-β-D-galactopyranoside

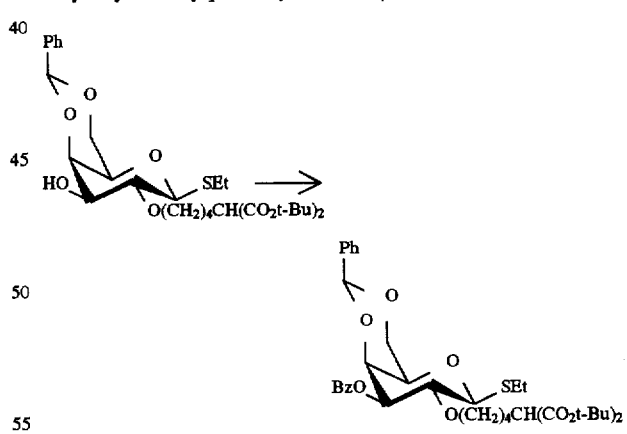

Ethyl 4,6-O-benzylidene-2-O-(5,5-di-tert-butyloxycarbonylpent-1-yl)-1-thio-β-D-galactopyranoside (2.1 g, 3.56 mmol) was reacted as described in Example 1-J and afforded the title compound (2.1 g, 85%).

IR (CH$_2$Cl$_2$) ν$_{max}$ (cm$^{-1}$): 2970, 2920, 2860 (C—H), 1740,1720 (C=O).

$^1$H NMR 400 MHz (CDCl$_3$) δ (ppm): 1.18-1.30 (2H, m, —CH$_2$—),1.34 (3H, t, J=7.5 Hz, —CH$_2$—CH$_3$), 1.42 and 1.43 (18H, 2s, 2×—OtBu), 1.48-1.54 (2H, m, —CH$_2$—), 1.60-1.73 (2H, m, —CH$_2$—), 2.73-2.90 (2H, m, —SCH$_2$—), 2.95 (1H, t, J=7.6 Hz, —CH(CO$_2$Bu)$_2$), 5.58

(1H, br s, H-5), 3.64 (1H, dt, J=8.9 and 6.6 Hz, —OCH₂—), 3.81 (1H, dt, J=8.9 and 6.7 Hz, —OCH₂—), 3.85 (1H, t, J=9.6 Hz, H-2), 4.03 (1H, dd, J=12.4 and 1.6 Hz, H-6), 4.36 (1H, dd, J=12.4 and 1.3 Hz, H-6), 4.50 (1H, d, J=3.5 Hz, H-4), 4.51 (1H, d, J=9.5 Hz, H-1), 5.14 (1H, dd, J=9.6 and 3.5 Hz, H-3), 5.50 (1H, s, —OCHO—), 7.35–7.39, 7.44–7.50, 7.55–7.60 and 8.07–8.09 (10H, 4 sets of m, aromatic H).

G. (2S,3R,4E)-3-Benzoyloxy-2-azido-1-[2-O-(5,5-di-tert-butyloxycarbonylpent-1-yl)-3-O-benzoyl-4,6-O-benzylidene-α-D-galactopyranosyloxy]-4-octadecene and (2S,3R,4E)-3-benzoyloxy-2-azido-1-[2-O-(5,5-di-tert-butyloxycarbonylpent-1-yl)-3-O-benzoyl-4,6-O-benzylidene-β-D-galactopyranosyloxy]-4-octadecene

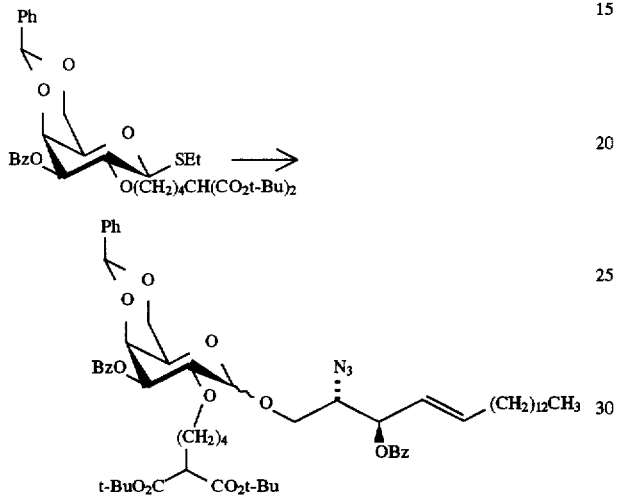

Ethyl 3-O-benzoyl-4,6-O-benzylidene-2-O-(5,5-di-tert-butyloxycarbonylpent-1-yl)-1-thio-β-D-galactopyranoside (0.780 g, 1.12 mmol) and (2S,3R,4E)-2-azido-3-benzoyloxy-4-octadecen-1-ol (0.423 g, 0.99 mmol) were reacted as described in Example 1-K and afforded the α-anomer to the title compound (0.630 g, 60%) and the β-anomer of the title compound (~300 mg, ~29%).

α-anomer

IR (CH₂Cl₂) ν$_{max}$ (cm⁻¹): 2920, 2850 (C—H), 1720 (C=O).

¹H NMR 400 MHz (CDCl₃) δ (ppm): 0.88 (3H, t, J=6.8 Hz, —CH₃), 1.25–1.38 (22H, m, —(CH₂)₁₁—), 1.42 (18H, s, 2×—OtBu), 1.42–1.44, 1.51–1.57 and 1.68–1.74 (3×2H, 3m, —(CH₂)₃—), 2.09 (2H, qa, J=6.8 Hz, =CH—CH₂—), 2.96 (1H, t, J=7.5 Hz, —CH(CO₂tBu)₂), 3.55–3.48 (3H, m, H-1 and —OCH₂—), 3.87 (1H, dd, J=10.8 and 4.2 Hz, H-1), 3.88 (1H, br s, H-5'), 4.03 (1H, m, H-2), 4.09 (1H, dd, J=12.5 and 1.2 Hz, H-6'), 4.12 (1H, dd, J=10.5 and 3.4 Hz, H-2'), 4.29 (1H, dd, J=12.5 and 0.7 Hz, H-6'), 4.61 (1H, d, J=3.5 Hz, H-4'), 5.18 (1H, d, J=3.4 Hz, H-1'), 5.45 (1H, dd, J=10.5 and 3.5 Hz, H-3'), 5.52 (1H, s, —OCHO—), 5.57–5.66 (2H, m, H-3 and H-4), 5.97 (1H, dt, J=14.4 and 6.8 Hz, H-5), 7.34–7.36, 7.44–7.49, 7.55–7.60 and 8.06–8.08 (15H, 4 sets of m, aromatic H).

Anal. Calcd. for C₆₀H₈₃N₃O₁₃: C, 68.35; H, 7.93; N, 3.99. Found: C, 68.19; H, 7.79; N, 4.03.

β-anomer

IR (CH₂Cl₂) ν$_{max}$ (cm⁻¹): 3025, 2980, 2930, 2850 (C—H), 2100 (—N₃), 1720 (C=O).

¹H NMR 400 MHz (CDCl₃) δ (ppm): 0.89 (3H, t, J=6.8 Hz, —CH₃), 1.12–1.33 (22H, m, —(CH₂)₁₁—), 1.38–1.46 (2H, m, —CH₂—), 1.41 and 1.42 (18H, 2s, 2×—OtBu), 1.47–1.60 (2H, m, —CH₂—), 1.62–1.70 (2H, m, —CH₂—), 2.09 (2H, qa, J=6.9 Hz, =CH—CH₂—), 2.90 (1H, t, J=7.5 Hz, —CH(CO₂tBu)₂), 3.54 (1H, s, H-5'), 3.60–3.69 (2H, m, —OCH₂— and H-1), 3.84 (1H, dd, J=10.1 and 7.6 Hz, H-2'), 3.82–3.91 (1H, m, —OCH₂—), 4.02–4.09 (3H, m, H-6', H-1 and H-2), 4.34 (1H, dd, J=0.7 and 11.9 Hz, H-6'), 4.46–4.48 (2H, m, H-1' and H-4'), 5.10 (1H, dd, J=10.1 and 3.6 Hz, H-3'), 5.51 (1H, s, —OCHO—), 5.60 (1H, dd, J=15.0 and 8.0 Hz, H-4), 5.67 (1H, dd, J=8.0 and 3.4 Hz, H-3), 5.96 (1H, dt, J=15.0 and 6.9 Hz, H-5), 7.32–7.39, 7.41–7.53, 7.56–7.60 and 8.05–8.13 (15H, 4 sets of m, aromatic H).

Anal. Calcd. for C₆₀H₈₃N₃O₁₃: C, 68.35; H, 7.93; N, 3.99. Found: C, 68.14; H, 7.92; N, 3.83.

H. (2S,3R,4E)-3-Benzoyloxy-2-hexadecanoylamino-1-[2-O-(5,5-di-tert-butyloxycarbonylpent-1-yl)-3-O-benzoyl-4,6-O-benzylidene-α-D-galactopyranosyloxy]-4-octadecene

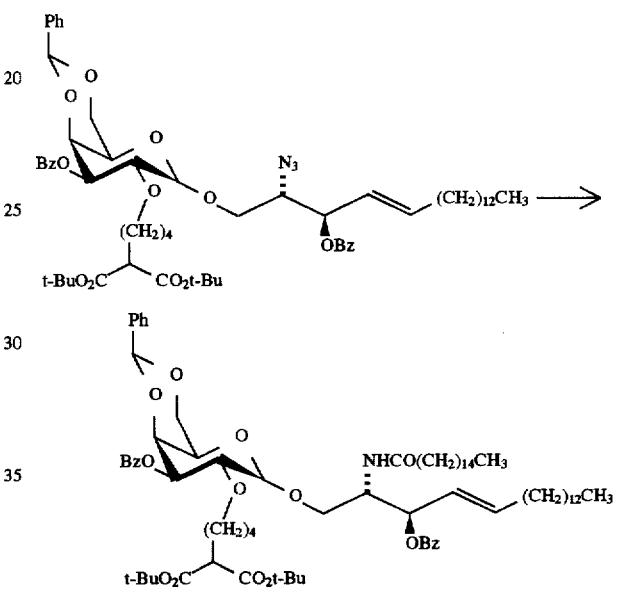

(2S,3R,4E)-3-Benzoyloxy-2-azido-1-[2-O-(5,5-di-tert-butyloxycarbonylpent-1-yl)-3-O-benzoyl-4,6-O-benzylidene-α-D-galactopyranosyloxy]-4-octadecene (0.620 g, 0.588 mmol) was reacted as described in Example 1-L to give the title compound (0.600 g, 81%).

IR (CH₂Cl₂) ν$_{max}$ (cm⁻¹): 3300 (NH), 2920, 2850 (C—H), 1720,1675(C=O).

¹H NMR 400 MHz (CDCl₃) δ (ppm): 0.89 (6H, t, J=6.6 Hz, 2×—CH₃), 1.23–1.30 (48H, br s, —(CH₂)₁₁— and —(CH₂)₁₃—), 1.42 (18H, s, 2×—OtBu), 1.52–1.74 (6H, m, —(CH₂)₃—), 2.03 (2H, qa, J=7.0 Hz, =CH—CH₂), 2.22 (2H, m, NHCOCH₂—), 2.95 (1H, t, J=7.5 Hz, —CH(CO₂tBu)₂), 3.54 (1H, dt, J=9.2 and 6.8 Hz, —OCH₂—), 3.69 (1H, dt, J=9.2 and 6.5 Hz, —OCH₂—), 3.80 (1H, s, H-5'), 3.83 (1H, d, J$_{AB}$=11.1 and J$_{AX}$=4.1 Hz, H-1), 3.88 (1H, d, J$_{AB}$=11.1 Hz, and J$_{BX}$=3.4 Hz, H-1), 4.03–4.09 (2H, m, H-6' and H-2'), 4.25 (1H, d, J=12.2 Hz, H-6'), 4.50–4.55 (1H, m, H-2), 4.55 (1H, d, J=3.5 Hz, H-4'), 5.07 (1H, d, J=3.4 Hz, H-1'), 5.45 (1H, dd, J=10.5 and 3.5Hz, H-3'), 5.50 (1H, s, —OCHO—), 5.53 (1H, dd, J=15.1 and 7.6 Hz, H-4), 5.60 (1H, t, J=7.6 Hz, H-3), 3.88 (1H, dt, J=15.1 and 7.0 Hz, H-5), 6.17 (1H, d, J=9.3 Hz, —NH—), 7.33–7.37, 7.42–7.60 and 8.03–8.09 (15H, 3 sets of m, aromatic H).

I. (2S,3R,4E)-3-Benzoyloxy-2-hexadecanoylamino-1-[2-O-(5,5-di-tert-butyloxycarbonylpent-1-yl)-3-O-benzoyl-α-D-galactopyranosyloxy]-4-octadecene

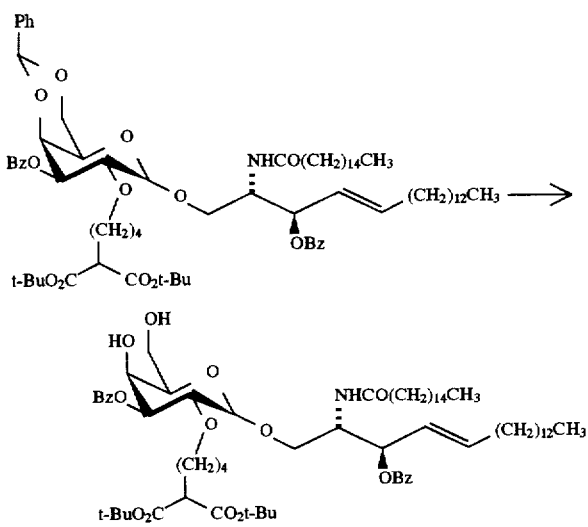

(2S,3R,4E)-3-Benzoyloxy-2-hexadecanoylamino-1-[2-O-(5,5-di-tert-butyloxycarbonylpent-1-yl)-3-O-benzoyl-4,6-O-benzylidene-α-D-galactopyranosyloxy]-4-octadecene (0.225 g, 0.178 mmol) was reacted as described in Example 1-M and afforded the title compound (0.158 g, 75%).

IR (CH$_2$Cl$_2$) $\nu_{max}$ (cm$^{-1}$): 3650–3100 (OH and NH), 2920, 2850 (C—H), 1720, 1650 (C=O).

$^1$H NMR 400 MHz (CDCl$_3$) δ (ppm): 0.89 (6H, t, J=6.7 Hz, 2×—CH$_3$), 1.24–1.33 (48H, m, —(CH$_2$)$_{11}$— and —(CH$_2$)$_{13}$—), 1.43 (18H, 2s, 2×—OtBu), 1.51–1.74 (6H, m, —(CH$_2$)$_3$—), 1.99–2.06 (2H, m, =CH—CH$_2$—), 2.22 (2H, m, —NHCOCH$_2$—), 2.50 (1H, t, J=6.2 Hz, —OH—6'), 2.63 (1H, d, J=3.0 Hz, —OH—4'), 2.94 (1H, t, J=7.5 Hz, —CH(CO$_2$tBu)$_2$), 3.52 (1H, dt, J=9.3 and 6.8 Hz, —OCH$_2$—), 3.69 (1H, dt, J=9.3 and 6.4 Hz, —OCH$_2$—), 3.83–3.93 (5H, m, H-1, H-3' and H-6'), 3.99 (1H, dd, J=10.4 and 3.6 Hz, H-2'), 4.34 (1H, br s, H-4'), 4.58 (1H, m, H-2), 5.07 (1H, d, J=3.6 Hz, H-1'), 5.38 (1H, dd, J=10.4 and 3.1 Hz, H-3'), 5.53 (1H, dd, J=15.0 and 7.5 Hz, H-4), 5.59 (1H, t, H-3), 5.89 (1H, dt, J=15.0 and 6.8 Hz, H-5), 6.18 (1H, d, J=9.4 Hz, —NH—), 7.44–7.50, 7.56–7.62 and 8.03–8.09 (10H, 3 sets of m, aromatic H).

Anal. Calcd. for C$_{69}$H$_{111}$NO$_{14}$: C, 70.32; H, 9.49; N, 1.19. Found: C, 70.27; H, 9.42; N, 1.19.

EXAMPLE 4

(2S,3R,4E)-3-Benzoyloxy-2-hexadecanoylamino-1-[2-O-(5,5-dicarboxypent-1-yl)-3-O-benzoyl-α-D-galactopyranosyloxy]-4-octadecene

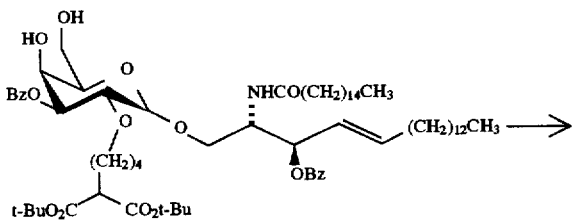

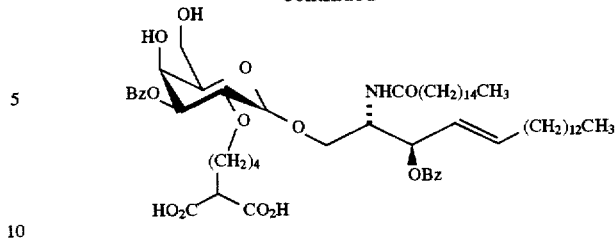

(2S,3R,4E)-3-Benzoyloxy-2-hexadecanoylamino-1-[2-O-(5,5-di-tert-butyloxycarbonylpent-1-yl)-3-O-benzoyl-α-D-galactopyranosyloxy]-4-octadecene (0.173 g, 0.147 mmol) was reacted as described in Example 2 and gave the title compound (0.082 g, 52%) as a white solid.

IR (KBr) $\nu_{max}$ (cm$^{-1}$): 3700–3100 (OH and NH), 2920, 2850 (C—H), 1720, 1650 (C=O).

$^1$H NMR 400 MHz (pyridine-d$_5$) δ (ppm): 0.85 (6H, t, J=6.6 Hz, 2×—CH$_3$), 1.24–1.41 (48H, m, —(CH$_2$)$_{11}$— and —(CH$_2$)$_{13}$—), 1.68–1.77 (2H, m, —(CH$_2$)—), 1.88 , 2.05 and 2.30 (3×2H, 3m, —(CH$_2$)$_2$— and =CH—CH$_2$—), 2.51 (2H, t, J=7.3 Hz, —NHCOCH$_2$—), 3.69–3.71 (1H, m, —OCH$_2$—), 3.78 (1H, t, J=7.4 Hz, —CH(CO$_2$H)$_2$), 3.83–3.87 (1H, m, —OCH$_2$—), 4.26 (1H, dd, J=10.8 and 5.9 Hz, H-6'), 4.38–4.46 (3H, m, H-1 and H-6'), 4.59 (1H, t, J=6.0 Hz, H-5'), 4.64 (1H, dd, J=10.5 and 3.4 Hz, H-2'), 4.97 (1H, d, J=2.7 Hz, H-4'), 5.21 (1H, m, H-2), 5.57 (1H, d, J=3.4 Hz, H-1'), 5.91–5.97 (2H, m, H-3' and H-4), 6.10 (1H, dt, J=15.4 and 6.7 Hz, H-5), 6.28 (1H, t, J=6.8 Hz, H-3), 7.38–7.51 and 8.23–8.28 (10H, 2 sets of m, aromatic H), 8.95 (1H, d, J=8.7 Hz, —NH—).

EXAMPLE 5

(2S,3R,4E)-3-Benzoyloxy-2-hexadecanoylamino-1-[6-O-(3,3-di-tert-butyloxycarbonylprop-1-yl)-α-D-galactopyranosyloxy]-4-octadecene A. Ethyl 3,4-O-isopropylidene-6-O-(1,1-dimethyl-1-methoxymethyl)-1-thio-β-D-galactopyranoside

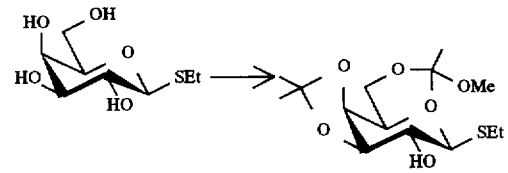

A suspension of ethyl thio-β-D-galactopyranoside [R.U. Lemieux, Can. J. Chem., 29, 1079 (1951)] (15.0 g, 66.9 mmol) in 2,2-dimethoxypropane (300 mL) was treated with p-toluenesulfonic acid (0.370 g). The mixture was stirred for 26 hours at 23° C. Triethylamine (600 μL) was added and the mixture was stirred for 10 more minutes. The mixture was then concentrated in vacuo, and the residue was purified by silica gel chromatography (70% to 80 % ethyl acetate/hexane+0.1% triethylamine) and gave the title compound (16.96 g, 75%) as a colorless oil.

IR (neat) $\nu_{max}$ (cm$^{-1}$): 3450 (broad, OH), 2990, 2940 (C—H), 1740.

$^1$H NMR 400 MHz (CDCl$_3$) δ (ppm): 1.33 (3H, t, J=7.5 Hz, —SCH$_2$CH$_3$), 1.33, 1.36, 1.37 and 1.53 (12H, 4s, 2×—C(CH$_3$)$_2$), 2.42 (1H, d, J=1.9 Hz, —OH), 2.75 (2H, m, —SCH$_2$—), 3.24 (3H, s, —OCH$_3$), 3.58 (1H, ddd, J=10.2, 7.1 and 1.9 Hz, H-2), 3.70 (2H, d, J=5.9 Hz, H-6 and H-4), 3.88 (1H, td, J=6.1 and 2.1 Hz, H-5), 4.06 (1H, dd, J=7.1 and 5.5 Hz, H-3), 4.23 (1H, d, J=2.1 Hz, H-6), 4.25 (1H, d, J=10.2 Hz, H-1).

B. Ethyl 3,4-O-isopropylidene-2-O-p-methoxybenzyl-1-thio-β-D-galactopyranoside

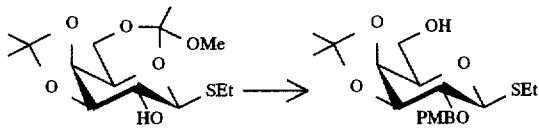

A stirred suspension of sodium hydride (60% in oil, 5.38 g, 134.5 mmol) in N,N-dimethylformamide (50 mL) at 5° C. was treated with a solution of ethyl 3,4-O-isopropylidene-6-O-(1,1-dimethyl-1-methoxymethyl)-1-thio-β-D-galactopyranoside (14.96 g, 44.2 mmol) in N,N-dimethylformamide (100 mL). The mixture was stirred at 23° C. for 1 hour. The mixture was then cooled down to 5° C. and p-methoxybenzyl chloride (13.5 g, 88.4 mmol) was added. The mixture was stirred at 23° C. for 45 minutes. The mixture was cooled down again to 5° C. and water (50 mL) was added dropwise. The mixture was then diluted with water (500 mL) and extracted with ethyl acetate (700 mL). The organic layer was washed with 5% aqueous hydrochloric acid (3×300 mL) and brine (200 mL), dried over anhydrous magnesium sulfate and concentrated. The residue was purified by precipitation in ethyl acetate/hexane and afforded the title compound (12.54 g, 74%) as a white solid.

m.p.: 88.5°–89.5° C.

$[\alpha]_D^{22}$: –0.2° (c=1.0, CHCl$_3$).

IR (KBr) $v_{max}$ (cm$^{-1}$): 3230 (broad, OH), 2980, 2930 (C—H), 1610, 1515.

$^1$H NMR 400 MHz (CDCl$_3$) δ (ppm): 1.31 (3H, t, J=7.5 Hz, —SCH$_2$CH$_3$), 1.36 and 1.46 (2×3H, 2 s, —C(CH$_3$)$_2$), 2.07 (1H, m, —OH-6), 2.73 (2H, m, —SCH$_2$—), 3.45 (1H, dd, J=9.6 and 6.4 Hz, H-2), 3.76–3.84 and 3.94–3.98 (3H, 2m, H-5 and H-6), 3.81 (3H, s, —OCH$_3$), 4.23 (1H, d, $J_{AB}$=5.7 Hz, and $J_{AX}$=1.9 Hz, H-4), 4.25 (1H, dd, $J_{AB}$=5.7 Hz, and $J_{BX}$=6.4 Hz, H-3), 4.43 (1H, d, J=9.6 Hz, H-1), 4.70 (1H, d, $J_{AB}$=11.0 Hz, —CH$_2$OAr), 4.78 (1H, d, $J_{AB}$=11.0 Hz, —OCH$_2$Ar), 6.87–6.90 and 7.34–7.38 (4H, 2 sets of m, aromatic H).

Anal. Calcd. for C$_{19}$H$_{28}$O$_6$S: C, 59.35; H, 7.34; S, 8.32. Found: C, 59.38; H, 7.29; S, 8.62.

C. Ethyl 3,4-O-isopropylidene-2-O-p-methoxybenzyl-6-O-(tert-butyloxycarbonylmethyl)-1-thio-β-D-galactopyranoside

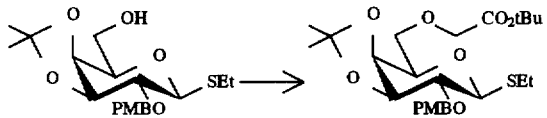

A stirred solution of ethyl 3,4-O-isopropylidene-2-O-p-methoxybenzyl-1-thio-β-D-galactopyranoside (12.6 g, 32.7 mmol) in dichloromethane (200 mL) was treated with an aqueous solution of sodium hydroxide (14M, 90 mL) followed by tert-butylbromoacetate (30.36 g, 155.7 mmol) and tetrabutylammonium chloride (21.75 g, 78.3 mmol). The mixture was vigorously stirred at 23° C. for 1.25 hours, then diluted with cold water (150 mL) and ethyl ether (750 mL). The organic phase was separated and washed with water (3×350 mL), and brine (350 mL), dried over anhydrous magnesium sulfate, filtered and concentrated. The residue was purified by silica gel chromatography (20 to 35% ethyl acetate/hexane) and afforded the title compound (14.46 g, 89%) as a pale yellow oil.

$[\alpha]_D^{22}$: –23°(c=1.0, CHCl$_3$).

IR (neat) $v_{max}$ (cm$^{-1}$): 2980, 2930 (C—H), 1745 (C=O), 1610, 1515.

$^1$H NMR 400 MHz (CDCl$_3$) δ (ppm): 1.31 (3H, t, J=7.4 Hz, —SCH$_2$CH$_3$), 1.36 and 1.45 (2×3H, 2 s, —C(CH$_3$)$_2$), 1.49 (9H, s, —OtBu), 2.73 (2H, —SCH$_2$—), 3.44 (1H, m, H-2), 3.76 (1H, dd, J=10.5 and 7.1 Hz, H-6), 3.81 (3H, s, —OCH$_3$), 3.88 (1H, dd, J=10.5 and 4.7 Hz, H-6), 3.96 (1H, brt, H-5), 4.02 (1H, d, $J_{AB}$=16.3 Hz, —OCH$_2$CO—), 4.10 (1H, d, $J_{AB}$=16.3 Hz, —OCH$_2$CO—), 4.22–4.24 (2H, m, H-3 and H-4), 4.43 (1H, d, J=9.6 Hz, H-1), 4.71 (1H, d, $J_{AB}$=11.0 Hz, —OCH$_2$Ar), 4.77 (1H, d, $J_{AB}$=11.0 Hz, —OCH$_2$Ar), 6.87–6.90 and 7.34–7.37 (4H, 2 sets of m, aromatic H).

Anal. Calcd. for C$_{25}$H$_{38}$O$_8$S: C, 60.22; H, 7.68; S, 6.43. Found: C, 60.09; H, 7.57; S, 6.61.

D. Ethyl 3,4-O-isopropylidene-2-O-p-methoxybenzyl-6-O-(2-hydroxyeth-1-yl)-1-thio-β-D-galactopyranoside

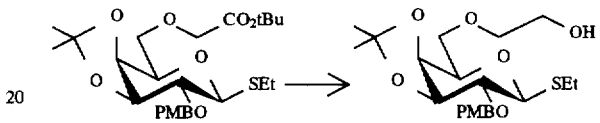

Ethyl 3,4-O-isopropylidene-2-O-p-methoxybenzyl-6-O-(t-butyloxycarbonylmethyl)-1-thio-β-D-galactopyranoside (14.34 g, 28.7 mmol) was reacted by the general procedure as described in Example 1-D and afforded the title compound (12.01 g, 97%) as a clear oil.

$[\alpha]_D^{22}$: –8° (c=0.74, CHCl$_3$).

IR (neat) $v_{max}$ (cm$^{-1}$): 3470 (broad, OH), 2930, 2870 (C—H), 1610, 1515.

$^1$H NMR 400 MHz (CDCl$_3$) δ (ppm): 1.31 (3H, t, J=7.4 Hz, —SCH$_2$CH$_3$), 1.37 and 1.46 (2×3H, 2 s, —C(CH$_3$)$_2$), 2.34 (1H, t, J=6.0 Hz, —OH), 2.71 (2H, m, —SCH$_2$—), 3.46 (1H, dd, J=9.6 and 5.9 Hz, H-2), 3.48–3.81 (6H, m, H-6 and —O(CH$_2$)$_2$OH), 3.81 (3H, s, —OCH$_3$), 3.91 (1H, brt, H-5), 4.22–4.26 (2H, m, H-3 and H-4), 4.43 (1H, d, J=9.6 Hz, H-1), 4.70 (1H, d, $J_{AB}$=11.0 Hz, —OCH$_2$Ar), 4.78 (1H, d, $J_{AB}$=11.0 Hz, —OCH$_2$Ar), 6.86–6.89 and 7.35–7.37 (4H, 2 sets of m, aromatic H).

E. Ethyl 3,4-O-isopropylidene-2-O-p-methoxybenzyl-6-O-(2-methanesulfonyloxyeth-1-yl)-1-thio-β-D-galactopyranoside

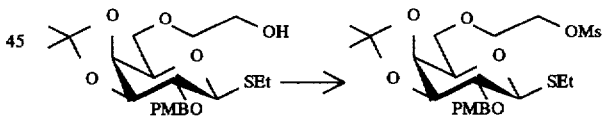

Ethyl 3,4-O-isopropylidene-2-O-p-methoxybenzyl-6-O-(2-hydroxyeth-1-yl)-1-thio-β-D-galactopyranoside (11.89 g, 27.67 mmol) was reacted by the general procedure as described in Example 1-E and afforded the title compound (13.47 g, 96%) as an oil.

$^1$H NMR 200 MHz (CDCl$_3$) δ (ppm): 1.29 (3H, t, J=7.5 Hz, —SCH$_2$CH$_3$), 1.34 and 1.44 (2×3H, 2 s, —C(CH$_3$)$_2$), 2.70 (2H, m, —SCH$_2$—), 3.05 (3H, s, —SO$_2$CH$_3$), 3.42 (1H, dd, J=9.5 and 5.9 Hz, H-2), 3.74–3.90 and 4.34–4.43 (7H, 2 sets of m, H-6, H-5 and —O(CH$_2$)$_2$—OMs), 3.79 (3H, s, —OCH$_3$), 4.17 (1H, d, $J_{AB}$=5.7 Hz and $J_{AX}$=2.0 Hz, H-4), 4.23 (1H, dd, $J_{AB}$=5.7 Hz and $J_{BX}$=5.7 Hz, H-3), 4.40 (1H, d, J=9.5 Hz, H-1), 4.68 (1H, d, $J_{AB}$=11.0 Hz, —OCH$_2$Ar), 4.76 (1H, d, $J_{AB}$=11.0 Hz, —OCH$_2$Ar), 6.84–6.89 and 7.32–7.36 (4H, 2 sets of m, aromatic H).

F. Ethyl 3,4-O-isopropylidene-2-O-p-methoxybenzyl-6-O-(3,3-di-tert-butyloxycarbonylprop-1-yl)-1-thio-β-D-galactopyranoside

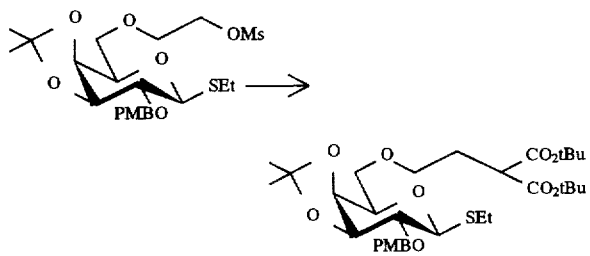

Ethyl 3,4-O-isopropylidene-2-O-p-methoxybenzyl-6-O-(2-methanesulfonyloxyeth-1-yl)-1-thio-β-D-galactopyranoside (6.73 g, 13.27 mmol) was reacted by the general procedure as described in Example 1-F and gave the title compound (5.98 g, 72%) as a colorless oil.

$[\alpha]_D^{22}$: −8° (c=1.1, CHCl₃).

IR (neat) $\nu_{max}$ (cm$^{-1}$): 2980, 2930, 2870 (C—H), 1740 and 1720 (C=O), 1610, 1515.

¹H NMR 400 MHz (CDCl₃) δ (ppm): 1.31 (3H, t, J=7.4 Hz, —SCH₂CH₃), 1.37 and 1.45 (2×3H, 2 s, —C(CH₃)₂), 1.46 (18H, s, 2×—OtBu), 2.07 (2H, m, —C H₂—CH(CO₂tBu)₂), 2.72 (2H, m, —SCH₂—), 3.34 (1H, t, J=7.4 Hz, —CH(CO₂tBu)₂), 3.43 (1H, m, H-2), 3.51 (1H, dt, J$_{AB}$=9.9 Hz, and J$_{AX}$=6.2 Hz, —OCH₂—), 3.58 (1H, dt, J$_{AB}$=9.9 Hz, and J$_{BX}$=6.2 Hz, —OCH₂—), 3.67 (1H, dd, J$_{AB}$=10.1 Hz and J$_{AX}$=6.8 Hz, H-6), 3.69 (1H, dd, J$_{AB}$=10.1 Hz and J$_{BX}$=5.5 Hz, H-6), 3.81 (3H, s, —OCH₃), 3.84 (1H, dd, J=5.4 and 6.8 Hz, H-5), 4.19–4.21 (2H, m, H-3 and H-4), 4.42 (1H, d, J=9.7 Hz, H-1), 4.70 (1H, d, J$_{AB}$=11.0 Hz, —OCH₂Ar), 4.78 (1H, d, J$_{AB}$=11.0 Hz, —OCH₂Ar), 6.86–6.90 and 7.35–7.37 (4H, 2 sets of m, aromatic H).

Anal. Calcd. for C₃₂H₅₀O₁₀S·0.15 CH₂Cl₂: C, 60.38; H, 7.93; S, 5.01. Found: C, 60.46; H, 7.84; S, 5.67.

G. (2S,3R,4E)-3-Benzoyloxy-2-azido-1-[6-O-(3,3-di-tert-butyloxycarbonylprop-1-yl)-3,4-O-isopropylidene-2-O-p-methoxybenzyl-α-D-galactopyranosyloxy]-4-octadecene and (2S,3R,4E)-3-benzoyloxy-2-azido-1-[6-O-(3,3-di-tert-butyloxycarbonylprop-1-yl)-3,4-O-isopropylidene-2-O-p-methoxybenzyl-β-D-galactopyranosyloxy]-4-octadecene

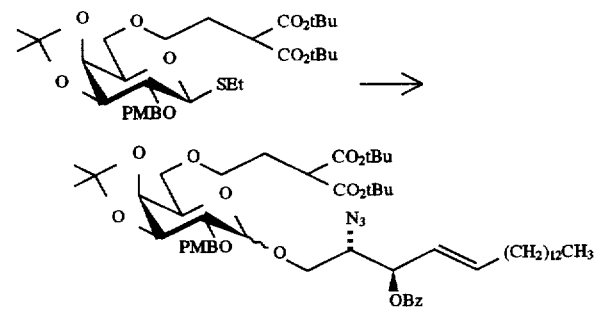

Ethyl 3,4-O-isopropylidene-2-O-p-methoxybenzyl-6-O-(3,3-di-tert-butyloxycarbonylprop-1-yl)-1-thio-β-D-galactopyranoside (1.187 g, 1.89 mmol) and (2S,3R,4E)-2-azido-3-benzoyloxy-4-octadecen-1-ol (0.507 g, 1.18 mmol) were reacted by the general procedure as described in Example 1-K except that dichloromethane was used as solvent. The reaction afforded the α-anomer (0.467 g, 40%) and the β-anomer (0.644 g, 55%) of the title compound as colorless oils.

α-anomer $[\alpha]_D^{22}$: +25° (c=0.96, CHCl₃).

IR (neat) $\nu_{max}$ (cm$^{-1}$): 2980, 2920, 2850 (C—H), 2100 (—N₃), 1725 (C=O), 1515.

¹H NMR 400 MHz (CDCl₃) δ (ppm): 0.89 (3H, t, J=6.7 Hz, —CH₃), 1.25–1.31 (20H, m, —(CH₂)₁₀—), 1.34–1.48 (2H, m, —CH₂—), 1.34 and 1.40 (6H, 2 S, —C(CH₃)₂), 1.46 (18H, s, 2×—OtBu), 2.05–2.11 (4H, m, =CH—C H₂— and —CH₂—CH(CO₂tBu)₂), 3.34 (1H, t, J=7.4 Hz, —CH(CO₂tBu)₂), 3.47–3.62 and 3.82–3.86 (5H, 2 sets of m, H-1, H-2' and —OCH₂—), 3.60 (1H, dd, J$_{AB}$=10.0 Hz, and J$_{AX}$=7.1 Hz, H-6'), 3.66 (1H, J$_{AB}$=10.0 Hz and J$_{BX}$=5.6 Hz, H-6'), 3.78 (3H, S, —OCH₃), 3.96 (1H, m, H-2), 4.16 (1H, br d, J=5.8 Hz, H-3'), 4.20 (1H, dd, J=5.8 and 2.6 Hz, H-4'), 4.33 (1H, dd, J=7.1 and 5.9 Hz, H-5'), 4.65 (1H, d, J$_{AB}$=12.1 Hz, —OCH₂Ar), 4.70 (1H, d, J$_{AB}$=12.1 Hz, —OCH₂Ar), 4.79 (1H, d, J=3.4 Hz, H-1'), 5.58 (1H, dd, J=14.7 and 7.9 Hz, H-4), 5.64 (1H, dd, J=7.9 and 4.3 Hz, H-3), 5.94 (1H, dt, J=14.7 and 6.7 Hz, H-5), 6.83–6.85, 7.27–7.32, 7.45–7.49, 7.53–7.61 and 8.07–8.09 (9H, 5 sets of m, aromatic H).

Anal. Calcd. for C₅₅H₈₃N₃O₁₃: C, 66.44; H, 8.41; N, 4.23. Found: C, 66.28; H, 8.38; N, 4.30.

β-anomer $[\alpha]_D^{22}$: −4° (c=1.2, CHCl₃).

IR (neat) $\nu_{max}$ (cm$^{-1}$): 2980, 2925, 2850 (C—H), 2100 (—N₃), 1725 (C=O), 1515.

¹H NMR 400 MHz (CDCl₃) δ (ppm): 0.89 (3H, t, J=6.9 Hz, —CH₃), 1.25–1.31 (20H, m, —(CH₂)₁₀—), 1.35–1.46 (2H, m, —CH₂—), 1.35 and 1.38 (6H, 2 s, —C(CH₃)₂), 1.46 (18H, s, 2×—OtBu), 2.03–2.09 (4H, m, =CH—CH₂— and —CH₂—CH(CO₂tBu)₂), 3.32 (1H, t, J=7.3 Hz, —C H(CO₂tBu)₂), 3.40 (1H, m, H-2'), 3.48 (1H, dt, J=9.9 and 6.2 Hz, —OCH₂—), 3.54–3.63 (1H, m overlapped by H-1 and H-6', —OCH₂—), 3.58 (1H, dd, J=9.8 and 5.8 Hz, H-1), 3.61 (1H, dd, J=9.9 and 6.5 Hz, H-6'), 3.69 (1H, dd, J=9.9 and 6.1 Hz, H-6'), 3.79 (3H, s, —OCH₃), 3.79–3.84, 4.00–4.04 and 4.12–4.15 (2×1H and 2H, 3 sets of m, H-2, H-3', H-4' and H-5'), 3.96 (1H, dd, J=9.8 and 7.0 Hz, H-1), 4.28 (1H, d, J=8.0 Hz, H-1'), 4.76 (1H, d, J$_{AB}$32 11.3 Hz, —OCH₂Ar), 4.78 (1H, d, J$_{AB}$=11.3 Hz, —OCH₂Ar), 5.58 (1H, dd, J=15.4 and 8.0 Hz, H-4), 5.72 (1H, dd, J=8.0 and 3.9 Hz, H-3), 5.93 (1H, dt, J=15.4 and 6.7 hz, H-5), 6.87–6.89, 7.35–7.37, 7.45–7.49, 7.57–7.60 and 8.06–8.10 (9H, 5 sets of m, aromatic H).

Anal. Calcd. for C₅₅H₈₃N₃O₁₃·0.3 CH₂Cl₂: C, 65.13; H, 8.26; N, 4.12. Found: C, 65.15; H, 8.20; N, 3.87.

H. (2S,3R,4E)-3-Benzoyloxy-2-hexadecanoylamino-1-[6-O-(3,3-di-tert-butyloxycarbonylprop-1-yl)-3,4-O-isopropylidene-2-O-p-methoxybenzyl-α-D-galactopyranosyloxy]-4-octadecene

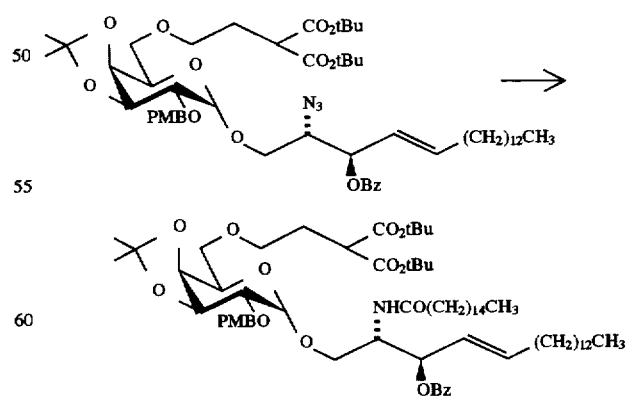

(2S,3R,4E)-3-Benzoyloxy-2-azido-1-[6-O-(3,3-di-tert-butyloxycarbonylprop-1-yl)-3,4-O-isopropylidene-2-O-p-methoxybenzyl-α-D-galactopyranosyloxy]-4-octadecene (0.713 g, 0.717 mmol) was reacted by the general procedure as described in Example 1-L and afforded the title compound (0.612 g, 71%) as a white solid.

m.p.: 47.5°–48.5° C.

$[\alpha]_D^{22}$: +42° (c=0.97, CHCl$_3$).

IR (neat) $v_{max}$ (cm$^{-1}$): 3300 (NH), 2980, 2920, 2850 (C—H), 1745, 1720 (C=O), 1545,1515.

$^1$H NMR 400 MHz (CDCl$_3$) δ (ppm): 0.88–0.91 (6H, m, 2×—CH$_3$), 1.23–1.39 (46H, m, —(CH$_2$)$_{13}$ and —(CH$_2$)$_{10}$—), 1.34 and 1.39 (6H, 2 s, —C(CH$_3$)$_2$), 1.46 (18H, s, 2×—OtBu), 1.59–1.67 (2H, m, —CH$_2$—), 2.00 (2H, qa, J=6.7 Hz, =CH—CH$_2$—), 2.04–2.18 (4H, m, —NHCOCH$_2$— and —CH$_2$—CH(CO$_2$tBu)$_2$), 3.31 (1H, t, J=7.3 Hz, —CH(CO$_2$tBu)$_2$), 3.46–3.61 (3H, m, —OCH$_2$— and H-2'), 3.59 (1H, dd, J$_{AB}$=10.0 Hz and J$_{AX}$=7.0 Hz, H-6'), 3.64 (1H, dd, J$_{AB}$=10.0 Hz and J$_{BX}$=5.2 Hz, H-6'), 3.75 (1H, dd, J$_{AB}$=11.2 Hz and J$_{AX}$=4.0 Hz, H-1), 3.78 (3H, s, —OCH$_3$), 3.79 (1H, dd, J$_{AB}$=11.2 Hz and J$_{BX}$=4.0 Hz, H-1), 4.15–4.19 (2H, m, H-3' and H-4'), 4.28 (1H, br t, H-5'), 4.49 (1H, m, H-2), 4.67 (2H, s, —OCH$_2$Ar), 4.75 (1H, d, J=3.5 Hz, H-1'), 5.51 (1H, dd, J=15.3 and 7.6 Hz, H-4), 5.62 (1H, t, J=7.6 Hz, H-3), 5.81 (1H, dt, J=15.3 and 6.7 Hz, H-5), 6.07 (1H, d, J=9.3 Hz, —NH—), 6.82–6.84, 7.27–7.30, 7.44–7.48, 7.56–7.60 and 8.05–8.07 (9H, 5 sets of m, aromatic H).

Anal. Calcd. for C$_{71}$H$_{115}$NO$_{14}$: C, 70.73; H, 9.24; N, 1.18. Found: C, 70.73; H, 9.48; N, 1.27.

EXAMPLE 6

(2S,3R,4E)-3-Benzoyloxy-2-hexadecanoylamino-1-[6-O-(3,3-di-carboxyprop-1-yl)-α-D-galactopyranosyloxy]-4-octadecene

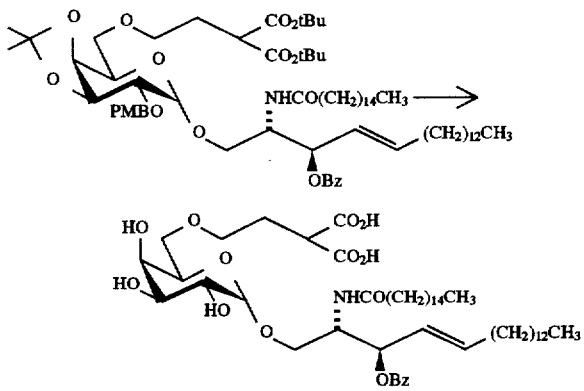

(2S,3R,4E)-3-Benzoyloxy-2-hexadecanoylamino-1-[6-O-(3,3-di-tert-butyloxycarbonylprop-1-yl)-3,4-O-isopropylidene-2-O-p-methoxybenzyl-α-D-galactopyranosyloxy]-4-octadecene (0.210 g, 0.174 mmol) was treated with anisole (40 μL, 0.348 mmol) followed by 90% aqueous trifluoroacetic acid (4 mL) at 50° C. This mixture was stirred for 5 minutes at 50° C. and then the ice-bath was removed and this was stirred for 10 minutes. Toluene was added and the mixture was evaporated under vacuo and coevaporated with toluene (2×). This was repeated until there was no starting material left. The residue was dried under vacuo, dissolved in chloroform and filtered on Millex LCR carthridge. The solution was triturated with acetonitrile. The residue was recrystallized form chloroform/acetonitrile to give the title compound (80 mg, 50%) as a white solid.

$^1$H NMR 400 MHz (pyridine-d$_5$) δ (ppm): 0.85 (6H, t, J=6.7 Hz, 2×—CH$_3$), 1.23–1.37 (46H, m, —(CH$_2$)$_{10}$— and —(CH$_2$)$_{13}$—), 1.85 (2H, m, —CH$_2$—), 2.10 (2H, qa, J=6.9 Hz, —CH$_2$—CH(CO$_2$H)$_2$),2.46 (2H, t, J=7.4 Hz, —NHCOCH$_2$—), 2.74 (2H, qa, J=6.6 Hz, =CH—CH$_2$—), 3.92–3.99, 4.08–4.13 and 4.17–4.22 (3×2H, 3 sets of m, —OCH$_2$—, H-1, H-3' and —CH(CO$_2$H)$_2$), 4.43 (1H, br d, J=2.9 Hz, H-4'), 4.45 (2H, s, H-6'), 4.53 (1H, br t, H-5'), 4.61 (1H, dd, J=9.0 and 3.6 Hz, H-2'), 5.22 (1H, m, H-2), 5.36 (1H, d, J=3.6 Hz, H-1'), 6.01 (1H, dd, J=15.5 and 7.2 Hz, H-4), 6.13 (1H, dt, J=15.5 and 6.6 Hz, H-5), 6.35 (1H, br t, H-3), 7.39–7.45, 7.48–7.52 and 8.24–8.71 (5H, 3 sets of m, aromatic H), 8.75 (1H, d, J=8.7 Hz, —NH—).

Preparation of the sodium salt of the title compound

The diacid from the above procedure (0.159 g, 0.170 mmol) was dissolved in dioxane (10 mL) and filtered on Millex LCR 0.5 m. This solution was treated with an aqueous solution of sodium bicarbonate (28 mg, 0.329 mmol in 5 mL of water). The resulting suspension was then diluted with water to get a slightly cloudy solution which was lyophilized to give the sodium salt of the title compound (0.176 g, 100%) as a white fluffy solid.

IR (neat) $v_{max}$ (cm$^{-1}$): 3600–3000 (NH), 2920, 2850 (C—H), 1715, 1650, 1590 (C=O).

$^1$H NMR 400 MHz (CD$_3$OD) δ (ppm): 0.89 (6H, t, J=6.8 Hz, 2×—CH$_3$), 1.26–1.39 (46H, m, —(CH$_2$)$_{10}$— and —(CH$_2$)$_{13}$—), 1.59 (2H, m, —CH$_2$—), 2.05–2.14 and 2.20–2.24 (4H and 2H, 2 sets of m, —NHCOCH$_2$—, =CH—CH$_2$— and —CH$_2$—CH(CO$_2$Na)$_2$), 3.17 (1H, t, J=7.0 Hz, —CH(CO$_2$Na)$_2$), 3.43–3.49, 3.55–3.60 and 3.71–3.75 (7H, 3 sets of m, H-1, H-6', —OCH$_2$—, H-3' and H-2'), 3.80 (1H, dd, J=10.6 and 5.0 Hz, H-1), 3.86 (1H, br t, H-5'), 3.94 (1H, br s, H-4'), 4.45 (1H, m, H-2), 4.73 (1H, d, J=2.9 Hz, H-1'), 5.56 (1H, dd, J=15.1 and 7.8 Hz, H-4), 5.64 (1H, br t, H-3), 5.90 (1H, dt, J=15.1 and 6.9 Hz, H-5), 7.45–7.49, 7.58–7.60 and 8.00–8.02 (5H, 3 sets of m, aromatic H).

EXAMPLE 7

(2S,3R,4E)-3-Benzoyloxy-2-hexadecanoylamino-1-[6-O-(3,3-di-tert-butyloxycarbonylprop-1-yl)-β-D-galactopyranosyloxy]-4-octadecene

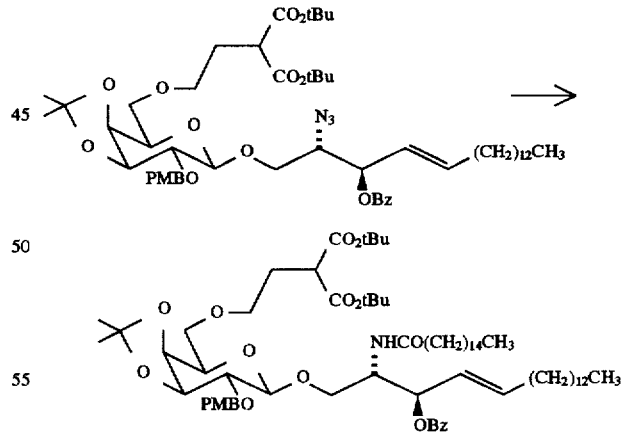

(2S,3R,4E)-3-benzoyloxy-2-azido-1-[6-O-(3,3-di-tert-butyloxycarbonylprop-1-yl)-3,4-O-isopropylidene-2-O-p-methoxybenzyl-β-D-galactopyranosyloxy]-4-octadecene described in Example 5-G (1.10 g, 1.11 mmol) was reacted by the general procedure as described in Example 1-L and afforded the title compound (0.555 g, 52%)

$[\alpha]_D^{22}$: +5° (c=1.05, CHCl$_3$).

IR (KBr) $v_{max}$ (cm$^{-1}$): 3325 (NH), 3910 and 2850 (C—H), 1730, 1705 and 1650 (C=O).

$^1$H NMR 400 MHz (CDCl$_3$) δ (ppm): 0.88–0.91 (6H, m, 2×—CH$_3$), 1.23–1.31 (49H, m, —(CH$_2$)$_{10}$—, —(CH$_2$)$_{13}$ and —C(CH$_3$)$_2$), 1.36 (3H, s, —C(CH$_3$)$_2$), 1.45 and 1.46 (18H, 2 s, 2×—OtBu), 1.46–1.56 (2H, m, —CH$_2$—), 1.79 (2H, m, —CH$_2$—CH(CO$_2$H)$_2$), 1.98–2.08 (4H, m, —NHCOCH$_2$— and =CH—CH$_2$—), 3.31 (1H, t, J=7.3 Hz, —CH(CO$_2$H)$_2$), 3.43–3.49 (2H, m, —OCH$_2$— and H-2'), 3.55 (1H, dt, J=10.0 and 6.3 Hz, —OCH$_2$—), 3.52–3.62 (2H, m, H-6' and H-1), 3.66 (1H, dd, J=10.0 and 6.1 Hz, H-6'), 3.79 (3H, s, —OCH$_3$), 3.81 (1H, td, J=6.2 and 1.5 Hz, H-5'), 4.14–4.26 (4H, m, H-1, H-1', H-3' and H-4'), 4.44 (1H, m, H-2), 4.59 (1H, d, J=10.8 Hz, —OCH$_2$Ar), 4.80 (1H, d, J=10.8 Hz, —OCH$_2$Ar), 5.46 (1H, dd, J=15.1 and 7.5 Hz, H-4), 5.54 (1H, t, J=7.5 Hz, H-3), 5.84 (1H, dt, J=15.0 and 6.7 Hz, H-5), 6.22 (1H, d, J=9.4 Hz, —NH—), 6.85–6.87, 7.23–7.32, 7.42–7.46, 7.53–7.58 and 8.05–8.08 (9H, 5 sets of m, aromatic H).

Anal. Calcd. for C$_{71}$H$_{115}$NO$_{14}$: C, 70.73; H, 9.24; N, 1.18. Found: C, 70.76; H, 9.55; N, 1.34.

EXAMPLE 8

(2S,3R,4E)-3-Benzoyloxy-2-hexadecanoylamino-1-
[6-O-(3,3-di-tert-carboxyprop-1-yl)-β-D-
galactopyranosyloxy]-4-octadecene

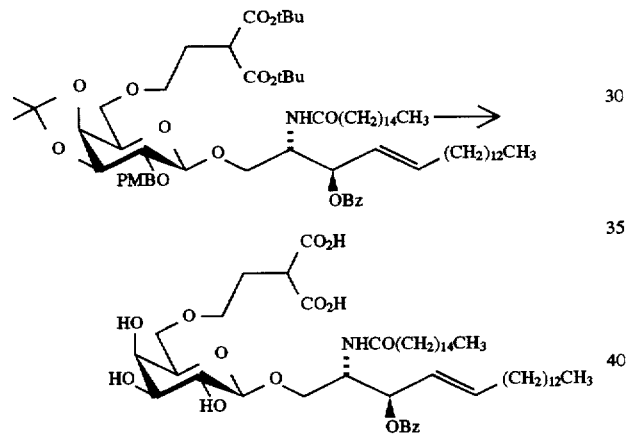

(2S,3R,4E)-3-Benzoyloxy-2-hexadecanoylamino-1-[6-O-(3,3-di-tert-butyloxycarbonylprop-1-yl)-β-D-galactopyranosyloxy]-4-octadecene (0.260 g, 0.22 mmol) was reacted by the general procedure as described in Example 6 and afforded the title compound (0.162 g, 77%) as a white solid.

m.p.: 115°–116° C.

$^1$H NMR 400 MHz (pyridine-d$_5$) δ (ppm): 0.85 (6H, t, J=6.8 Hz, 2×—CH$_3$), 1.20–1.37 (46H, m, —(CH$_2$)$_{13}$— and —(CH$_2$)$_{10}$—), 1.83 (2H, m, —CH$_2$—), 1.99 (2H, qa, —C H$_2$—CH(CO$_2$tBu)$_2$), 2.42 (2H, t, J=7.4 Hz, —NHCOC H$_2$—), 2.69 (2H, qa, =CH—CH$_2$—), 3.90 (1H, dt, J$_{AB}$=9.6 Hz and J$_{AX}$=6.3 Hz, —OCH$_2$—), 3.85 (1H, dt, J$_{AB}$=9.6 Hz and J$_{BX}$=6.3 Hz, —OCH$_2$—), 3.98 (1H, dd, J=9.4 and 6.0 Hz, H-6'), 4.04 (1H, t, J=6.0 Hz, H-5'), 4.09 (1H, dd, J=9.3 and 3.3 Hz, H-3'), 4.17–4.22 (3H, m, H-1, H-6' and —CH (CO$_2$tBu)$_2$), 4.43 (1H, d, J=3.2 Hz, H-4'), 4.46 (1H, dd, J=9.3 and 7.9 Hz, H-2'), 4.65 (1H, dd, J=10.7 and 5.8 Hz, H-1), 4.84 (1H, d, J=7.7 Hz, H-1'), 5.13 (1H, m, H-2), 5.88 (1H, dd, J=15.4 and 7.3 Hz, H-4), 6.01 (1H, dt, J=15.4 and 6.6 Hz, H-5), 6.20 (1H, br t, H-3), 7.37–7.41, 7.45–7.49 and 8.21–8.23 (5H, 3 sets of m, aromatic H), 8.70 (1H, d, J=6.4 Hz, —NH—).

Preparation of the sodium salt of the title compound

The diacid from the above procedure (0.152 g, 0.163 mmol) was reacted by the general procedure as described in Example 6 and afforded the sodium salt of the title compound (0.154 g, 97%) as a white fluffy solid.

IR (KBr) ν$_{max}$ (cm$^{-1}$): 3700–3000 (NH and OH), 2920, 2850 (C—H), 1705, 1650 and 1595 (C=O).

$^1$H NMR 400 MHz (CD$_3$OD) δ (ppm): 0.89 (6H, m, 2×—CH$_3$), 1.27–1.44 (46H, m, —(CH$_2$)$_{13}$— and —(CH$_2$)$_{10}$—), 1.59 (2H, m, —CH$_2$—), 2.03–2.06 and 2.17–2.22 (2H and 4H, 2 sets of m, —NHCOCH$_2$—, =CH—CH$_2$— and —CH$_2$—CH(CO$_2$Na)$_2$), 3.15 (1H, t, J=7.1 Hz, —CH(CO$_2$Na)$_2$), 3.29–3.54 (7H, m, H-6', H-5', H-3', H-2' and —OCH$_2$—), 3.62 (1H, dd, J=10.1 and 3.7 Hz, H-1), 3.85 (1H, d, J=3.1 Hz, H-4'), 4.10 (1H, dd, J=10.1 and 5.2 Hz, H-1), 4.19 (1H, d, J=7.5 Hz, H-1'), 4.43 (1H, m, H-2), 5.48–5.57 (2H, m, H-3 and H-4), 5.88 (1H, dt, J=14.4 and 7.0 Hz, H-5), 7.46–7.49, 7.58–7.62 and 8.00–8.02 (5H, 3 sets of m, aromatic H).

EXAMPLE 9

(2S,3R,4E)-3-Benzoyloxy-2-hexadecanoylamino-1-
[6-O-(3,3-di-tert-butyloxycarbonylprop-1-yl)-2-O-
benzoyl-α-D-galactopyranosyloxy]-4-octadecene A. (2S,3R,4E)-3-Benzoyloxy-2-hexadecanoylamino-1-[6-O-(3,3-di-tert-butyloxycarbonylprop-1-yl)-3,4-O-isopropylidene-β-D-galactopyranosyloxy]-4-octadecene

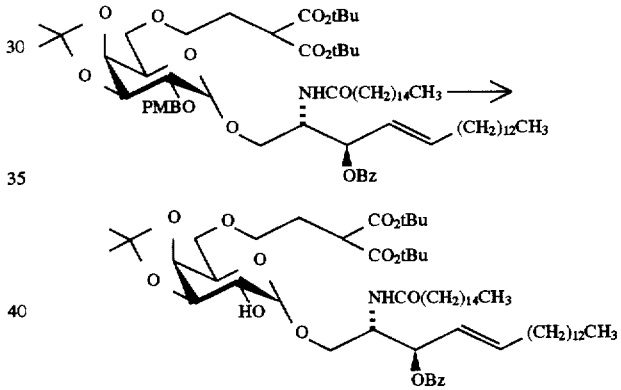

A solution of (2S,3R,4E)-3-benzoyloxy-2-hexadecanoylamino-1-[6-O-(3,3-di-tert-butyloxycarbonylprop-1-yl)-3,4-O-isopropylidene-2-O-p-methoxybenzyl-α-D-galactopyranosyloxy]-4-octadecene described in Example 5-H (0.466 g, 0.382 mmol) in dichloromethane (9 mL) and water (1 mL) was treated with 2,3-dichloro-5,6-dicyano-1,4-benzoquinone (130 mg, 0.573 mmol) at 5° C. The mixture was vigorously stirred at 5° C. for 30 minutes and then at 23° C. for 1 hour. The mixture was diluted with dichloromethane (100 mL) and washed with saturated sodium bicarbonate/10% aqueous sodium thiosulfate (1:1) (60 mL), 10% aqueous sodium thiosulfate (60 mL) and brine (60 mL). The organic phase was dried over anhydrous magnesium sulfate, filtered and concentrated. The residue was purified by silica gel chromatography (30 to 50% ethyl acetate/hexane) and afforded the title compound (0.349 g, 82%).

[α]$_D^{22}$: +34° (c=1.06, CHCl$_3$).

IR (neat) ν$_{max}$ (cm$^{-1}$): 3600–3100 (OH and NH), 2920, 2850 (C—H), 1725 and 1645 (C=O).

$^1$H NMR 400 MHz (CDCl$_3$) δ (ppm): 0.89 (6H, t, J=6.7 Hz, 2×—CH$_3$), 1.26–1.37 (46H, m, —(CH$_2$)$_{10}$— and —(CH$_2$)$_{13}$—), 1.35 (3H, s, —C(CH$_3$)$_2$), 1.46 (18H, s, 2×—OtBu), 1.49 (3H, s, —C(CH$_3$)$_2$), 1.51–1.62 (2H, m, —CH$_2$—), 2.02–2.13 and 2.15–2.25 (4H and 2H, 2 sets of m, —NHCOCH$_2$—, =CH—CH$_2$— and —CH$_2$—CH(CO$_2$tBu)$_2$), 2.75 (1H, br s, —OH), 3.31 (1H, t, J=7.3 Hz, —CH(CO$_2$tBu)$_2$), 3.49–3.67 (4H, m, —OCH$_2$—, H-6' and H-2'), 3.79 (1H, dd, J$_{AB}$=10.9 and J$_{AX}$=4.5 Hz, H-1), 3.82 (1H, br d, J=4.2 Hz, H-4'), 3.86 (1H, dd, J$_{AB}$=10.9 and J$_{BX}$=3.4 Hz, H-1), 4.22 (1H, dd, J=6.5 and 2.0 Hz, H-5'), 4.21–4.30 (2H, m, H-3' and H-6'), 4.53 (1H, m, H-2), 4.75 (1H, d, J=3.7 Hz, H-1'), 5.56 (1H, dd, J=15.3 and 7.5 Hz, H-4), 5.68 (1H, t, J=7.5 Hz, H-3), 5.89 (1H, dt, J=15.3 and 6.7 Hz, H-5), 6.24 (1H, d, J=9.4 Hz, —NH—), 7.27–7.29, 7.44–7.50, 7.57–7.60 and 8.03–8.08 (5H, 4 sets of m, aromatic H).

Anal. Calcd. for C$_{61}$H$_{107}$NO$_{13}$.0.1 CH$_2$Cl$_2$: C, 68.52; H, 10.09; N, 1.31. Found: C, 68.52; H, 9.68; N,1.43.

B. (2S,3R,4E)-3-Benzoyloxy-2-hexadecanoylamino-1-[6-O-(3,3-di-tert-butyloxycarbonylprop-1-yl)-3,4-O-isopropylidene-2-O-benzoyl-α-D-galactopyranosyloxy]-4-octadecene

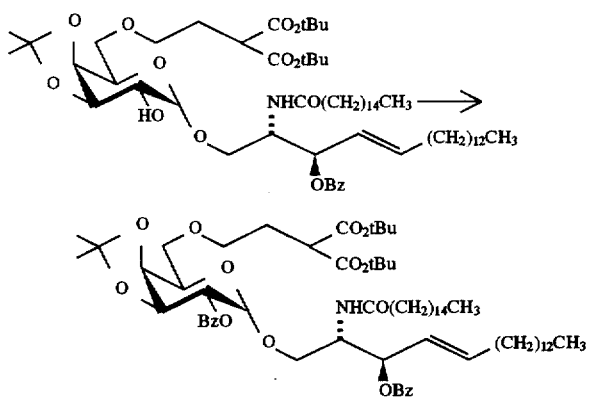

(2S,3R,4E)-3-Benzoyloxy-2-hexadecanoylamino-1-[6-O-(3,3-di-tert-butyloxycarbonylprop-1-yl)-3,4-O-isopropylidene-α-D-galactopyranosyloxy]-4-octadecene (0.330 g, 0.30 mmol) was reacted by the general procedure as described in Example 1-J and afforded the title compound (0.310 g, 87%) as a beige waxy solid.

[α]$_D^{22}$: +52° (c=1.03, CHCl$_3$).

IR (neat) ν$_{max}$ (cm$^{-1}$): 3600–3150 (NH), 2930, 2850 (C—H), 1725 and 1650 (C=O).

$^1$H NMR 400 MHz (CDCl$_3$) δ (ppm): 0.89 (6H, t, J=6.7 Hz, 2×—CH$_3$), 1.24–1.31 (46H, m, —(CH$_2$)$_{10}$— and —(CH$_2$)$_{13}$—), 1.37 (3H, s, —C(CH$_3$)$_2$), 1.42–1.56 (2H, m, —CH$_2$—), 1.47 (18H, s, 2×—OtBu), 1.54 (3H, s, —C(CH$_3$)$_2$), 2.00 (2H, m, qa, J=6.9 Hz, =CH—CH$_2$—), 2.05–2.13 (4H, m, —NHCOCH$_2$— and —CH$_2$—CH(CO$_2$tBu)$_2$), 3.34 (1H, t, J=7.3 Hz, —CH(CO$_2$tBu)$_2$), 3.51–3.71 (4H, m, —OCH$_2$—, H-6' and H-1), 3.74 (1H, dd, J=10.1 and 5.3 Hz, H-6'), 3.82 (1H, dd, J=10.8 and 4.5 Hz, H-1), 4.25–4.28 (1H, m, H-5'), 4.30 (1H, dd, J=5.5 and 2.3 Hz, H-4'), 4.47 (1H, dd, J=7.6 and 5.5 Hz, H-3'), 4.45–4.52 (1H, m, H-2), 5.04 (1H, d, J=3.6 Hz, H-1'), 5.19 (1H, dd, J=7.6 and 3.6 Hz, H-2'), 5.50 (1H, dd, J=15.1 and 7.5 Hz, H-4), 5.56 (1H, br t, H-3), 5.79 (1H, dt, J=15.1 and 6.9 Hz, H-5), 5.84 (1H, d, J=9.4 Hz, —NH—), 7.39–7.45, 7.53–7.58 and 7.98–8.05 (10H, 3 sets of m, aromatic H).

Anal. Calcd. for C$_{70}$H$_{111}$NO$_{14}$: C, 70.61; H, 9.40; N, 1.18. Found: C, 70.55; H, 9.33; N, 1.35.

EXAMPLE 10

(2S,3R,4E)-3-Benzoyloxy-2-hexadecanoylamino-1-[6-O-(3,3-di-carboxyprop-1-yl)-2-O-benzoyl-α-D-galactopyranosyloxy]-4-octadecene

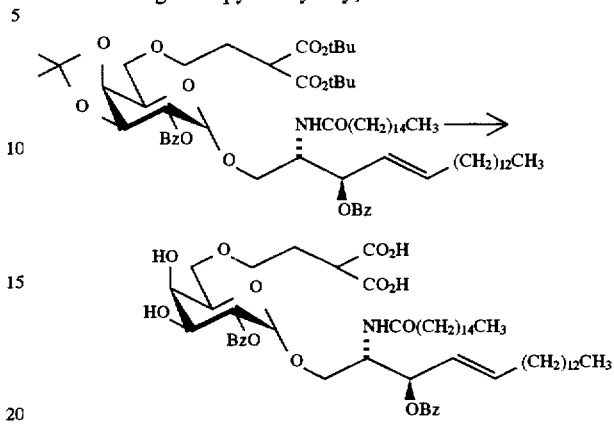

(2S,3R,4E)-3-Benzoyloxy-2-hexadecanoylamino-1-[6-O-(3,3-di-tert-butyloxycarbonylprop-1-yl)-α-D-galactopyranosyloxy]-4-octadecene (0.150 g, 0.126 mmol) was reacted by the general procedure as described in Example 6 and afforded the title compound (0.104 g, 80%) as a white solid.

m.p.: 115°–116° C.

$^1$H NMR 400 MHz (pyridine-d$_5$) δ (ppm): 0.85 (6H, t, J=6.6 Hz, 2×—CH$_3$), 1.23–1.33 (46H, m, —(CH$_2$)$_{10}$— and —(CH$_2$)$_{13}$—), 1.81 (2H, m, —CH$_2$—), 2.08 (2H, qa, J=6.9 Hz, =CH—CH$_2$—), 2.37 (2H, t, J=7.3 Hz, —NHCOCH$_2$—), 2.74 (2H, m, —CH$_2$—CH(CO$_2$H)$_2$), 3.90–4.03 (3H, m, —OCH$_2$— and —CH(CO$_2$H)$_2$), 4.09 (1H, dd, J=9.5 and 6.3 Hz, H-6'), 4.19–4.23 (2H, m, H-6' and H-3'), 4.45 (1H, dd, J=10.3 and 3.7 Hz, H-1), 4.57–4.61 (1H, m overlapped by H-5', H-4'), 4.59 (1H, br t, H-5'), 4.77 (1H, dd, J=10.3 and 2.9 Hz, H-1), 5.23 (1H, m, H-2), 5.61 (1H, d, J=3.6 Hz, H-1'), 5.98 (1H, dd, J=15.6 and 7.3 Hz, H-4), 6.07–6.14 (2H, m, H-5 and H-2'), 6.27 (1H, br t, H-3), 7.35–7.40, 7.45–7.47, 8.17–8.19 and 8.27–8.29 (10H, 4 sets of m, aromatic H), 8.73 (1H, d, J=9.1 Hz, —NH—).

Anal. Calcd. for C$_{59}$H$_{91}$NO$_{14}$: C, 68.25; H, 8.83; N, 1.35. Found: C, 68.30; H, 8.72; N, 1.54.

Preparation of the sodium salt of the title compound

The diacid from the above procedure (0.096 g, 0.092 mmol) was reacted by the general procedure as described in Example 6 and afforded the sodium salt of the title compound (0.092 g, 92%) as a white fluffy solid.

IR (KBr) ν$_{max}$ (cm$^{-1}$): 3700–3000 (NH), 2920, 2850 (C—H), 1725, 1645 and 1585 (C=O).

$^1$H NMR 400 MHz (CD$_3$OD) δ (ppm): 0.89 (6H, t, J=6.7 Hz, 2×—CH$_3$), 1.25–1.35 (46H, m, —(CH$_2$)$_{13}$— and —(CH$_2$)$_{10}$—), 1.47 (2H, m, —CH$_2$—), 1.97–2.11 (6H, m, —NHCOCH$_2$—, =CH—CH$_2$— and —CH$_2$—CH—(CO$_2$Na)$_2$), 3.20 (1H, br t, —CH(CO$_2$Na)$_2$), 3.48–3.52 (3H, m, —OCH2— and H-6'), 3.59–3.66 (2H, m, H-1 and H-6'), 3.83 (1H, dd, J=10.3 and 4.3 Hz, H-1), 3.99 (1H, br t, J=6.4 Hz, H-5'), 4.09 (1H, br d, H-4'), 4.18 (1H, dd, J=10.4 and 3.1 Hz, H-3'), 4.43 (1H, m, H-2), 5.07 (1H, d, J=3.7 Hz, H-1'), 5.20 (1H, dd, J=10.3 and 3.6 Hz, H-2'), 5.50–5.53 (2H, m, H-4 and H-3), 5.83 (1H, td, H-5), 7.40–7.44, 7.54–7.58, 7.90–7.92 and 8.01–8.03 (10H, 4 sets of m, aromatic H).

EXAMPLE 11

(2S,3R,4E)-3-Benzoyloxy-2-hexadecanoylamino-1-[3-O-(5,5-di-tert-butyloxycarbonylpentyl)-α-D-galactopyranosyloxy]-4-octadecene A. Ethyl 6-O-t-butyldimethylsilyl-3,4-O-isopropylidene-2-O-p-methoxybenzyl-1-thio-β-D-galactopyranoside

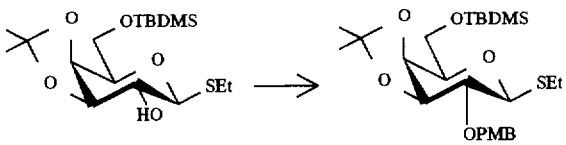

A solution of ethyl 6-O-t-butyldimethylsilyl-3,4-O-isopropylidene-1-thio-β-D-galactopyranoside described in Example 1-B (12.4 g, 32.7 mmol) in N,N-dimethylformamide (45 mL) was added to a suspension of sodium hydride (1.35 g of 80% in mineral oil, 45.0 mmol) in N,N-dimethylformamide (90 mL) and the resulting mixture was stirred at 22° C. for 2 hours. The reaction mixture was then cooled to 0°–5° C., treated dropwise with p-methoxybenzyl chloride (8.1 mL, 59.8 mmol) and stirred at 22° C. for 2 hours. The reaction mixture was cooled again in an ice bath and treated dropwise with water (20 mL). The reaction mixture was then diluted with water (300 mL) and extracted with ether (3×300 mL). The combined extracts were washed with brine, dried over anhydrous magnesium sulfate and evaporated. The residual oil was purified on silica gel chromatography (9×12 cm, 0 to 10% ethyl acetate/toluene) and gave the title compound (10.5 g, 64%) as an oil.

IR (NaCl, film) $v_{max}$ (cm$^{-1}$): 1612 (aromatic) and 1516.

$^1$H NMR 200 MHz (CDCl$_3$) δ (ppm): 0.06 (6H, s, SiCH$_3$), 0.88 (9H, s, Sit-Bu), 1.29 (3H, t, J=7.4 Hz, —SCH$_2$CH$_3$), 1.34 and 1.44 (2×3H, 2s, —C(CH$_3$)$_2$), 2.7 (2H, m, —SCH$_2$CH$_3$), 3.41 (1H, dd, J=6.1 and 9.9 Hz, H-2), 3.79 (3H, s, —OCH$_3$), 3.7–3.9 (3H, m, H-5 and H-6), 4.15–4.25 (2H, m, H-3 and H-4 overlapping), 4.39 (1H, d, J=9.9 Hz, H-1), 4.70 (1H, d, J$_{AB}$=11.0 Hz, —OCH$_2$ of 4-methoxybenzyl), 4.74 (1H, d, J$_{AB}$=11.0 Hz, —OCH$_2$ of 4-methoxybenzyl), 6.86 (2H, d, J=8.7 Hz, H-3 of 4-methoxybenzyl) and 7.35 (2H, d, J=8.7 Hz, H-2 of 4-methoxybenzyl).

B. Ethyl 2-O-p-methoxybenzyl-1-thio-β-D-galactopyranoside

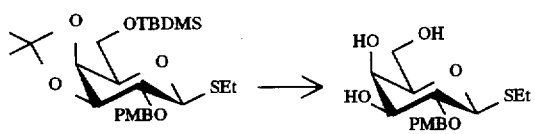

A solution of ethyl 6-O-t-butyldimethylsilyl-3,4-O-isopropylidene-2-O-para-methoxybenzyl-1-thio-β-D-galactopyranoside (10.50 g, 21.05 mmol) in 80% aqueous acetic acid (100 mL) was heated at 60° C. for 1.5 hours. The cooled mixture was evaporated under vacuum and the last traces of acetic acid removed by co-evaporation with toluene. Chromatography of the residue on silica gel (7×13 cm, 0 to 10% methanol/chloroform) gave the title compound (5.67 g, 78%) as a solid. Recrystallization from dichloromethane gave a white solid.

m.p.: 131°–132° C.

$[\alpha]_D^{22}$: +22.70° (c=1.0, CHCl$_3$).

IR (KBr) $v_{max}$ (cm$^{-1}$): 3500 and 3300 (broad, OH) and 1605 (aromatic).

$^1$H NMR 400 MHz (CDCl$_3$) δ (ppm): 1.35 (3H, t, J=7.5 Hz, —SCH$_2$CH$_3$), 2.22 (1H, m, —OH), 2.50 (1H, d, J=4.4 Hz, —OH), 2.73–2.87 (3H, m, OH and —SCH$_2$CH$_3$), 3.5–3.6 (2H, m, H-2 and H-5 overlapping), 3.61 (1H, m, H-3), 3.82 (3H, s, —OCH$_3$), 3.84 (1H, m, H-6), 3.95 (1H, m, H-6), 4.03 (1H, br s, H-4), 4.44 (1H, d, J=9.4 Hz, H-1), 4.63 and 4.92 (2H, 2d, J=10.8 Hz, —CH$_2$OAr), 6.91 (2H, d, J=8.6 Hz, H-3 of 4-methoxybenzyl) and 7.34 ppm (2H, d, J=8.6 Hz, H-2 of 4-methoxybenzyl).

Anal. Calcd. for C$_{16}$H$_{24}$O$_6$S: C, 55.80; H, 7.02; S, 9.31. Found: C, 55.64; H, 6.78; S, 9.23.

C. Ethyl 2-O-p-methoxybenzyl-4,6-di-O-benzylidene-1-thio-β-D-galactopyranoside

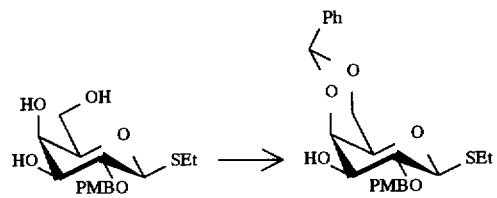

A suspension of ethyl 2-O-para-methoxybenzyl-1-thio-β-D-galactopyranoside (6.11 g, 17.7 mmol) in acetonitrile was treated with benzaldehyde dimethyl acetal (4.38 mL, 29.2 mmol), followed by p-toluenesulfonic acid (0.337 g, 1.77 mmol) at 22° C. for 1.5 hours. The mixture was neutralized with triethylamine (1.7 mL) and concentrated under reduced pressure. The residue was dissolved in ethyl acetate (175 mL) and washed with a saturated solution of sodium bicarbonate (2×25 mL), water (25 mL) and brine (25 mL). The organic layer was dried over anhydrous magnesium sulfate, filtered and concentrated. The residual yellow oil was purified by silica gel chromatography (~110 mL, 10% to 35% ethyl acetate/toluene) and afforded the title compound (4.72 g, 62%) as a colorless oil.

$[\alpha]_D^{22}$: +14.1° (c=1.0, CHCl$_3$).

IR (KBr) $v_{max}$ (cm$^{-1}$): 3600–3250 (broad, OH) and 1610, 1510 (aromatic C=C).

$^1$H NMR 400 MHz (CDCl$_3$) δ (ppm): 1.36 (3H, t, J=7.4 Hz, —CH$_3$), 2.52 (1H, d, J=8.3 Hz, —OH), 2.81 (2H, m, —SCH$_2$—), 3.47 (1H, br d, H-5), 3.64 (1H, t, H-2), 3.77 (1H, td, J=8.6 and 3.5 Hz, H-3), 3.80 (3H, s, —OCH$_3$), 4.03 (1H, dd, J=12.5 and 1.7 Hz, H-6), 4.25 (1H, d, J=3.5 Hz, H-4), 4.35 (1H, dd, J=12.5 and 1.2 Hz, H-6), 4.44 (1H, d, J=9.5 Hz, H-1), 4.72 (1H, d, J$_{AB}$=10.3 Hz, —CH$_2$Ph), 4.88 (1H, d, J$_{AB}$=10.3 Hz, —CH$_2$Ph), 5.57 (1H, s, —OCHO—), 6.87–6.92, 7.15–7.19, 7.25–7.32, 7.36–7.43 and 7.50–7.54 (9H, 5 sets of m, aromatic H).

Anal. Calcd. for C$_{23}$H$_{28}$O$_6$S.0.2 H$_2$O: C, 63.34; H, 6.56. Found: C, 63.42; H, 6.40.

D. Ethyl 2-O-p-methoxybenzyl-4,6-di-O-benzylidene-3-(4-bromobut-1-yl)-1-thio-β-D-galactopyranoside

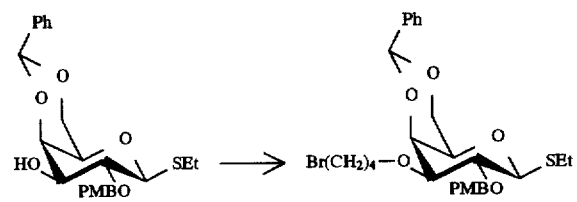

Ethyl 2-O-p-methoxybenzyl-4,6-di-O-benzylidene-1-thio-β-D-galactopyranoside (3.5 g, 8.1 mmol) was reacted by the general procedure as described in Example 3-A and afforded the title compound (2.7 g, 59%).

IR (CH$_2$Cl$_2$) $v_{max}$(cm$^{-1}$): 3050, 2980 (C—H), 1610, 1515 (aromatic C=C).

$^1$H NMR 400 MHz (CDCl$_3$) δ (ppm): 1.35 (3H, t, J=7.5 Hz, —CH$_3$), 1.76–1.82 and 1.96–2.03 (2×2H, 2 sets of m, —(CH$_2$)$_2$—), 2.81 (2H, m, —SCH$_2$—), 3.38–3.44 (3H, m, H-5 and —CH$_2$Br), 3.46 (1H, dd, J=9.1 and 3.2 Hz, H-3), 3.61 (1H, dt, J=9.2 and 6.0 Hz, —OCH$_2$—), 3.75 (1H, dt, J=9.2 and 6.1 Hz, —OCH$_2$—), 3.78 (1H, br t, H-2), 3.81 (3H, s, —OCH$_3$), 4.03 (1H, dd, J=12.3 and 1.6 Hz, H-6), 4.32 (1H, d, J=3.2 Hz, H-4), 4.36 (1H, dd, J=12.3 and 1.3 Hz, H-6), 4.44 (1H, d, J=9.6 Hz, H-1), 4.72 (1H, d, J$_{AB}$=9.8 Hz, —OCH$_2$Ar), 4.81 (1H, d, J$_{AB}$=9.8 Hz, —OCH$_2$Ar), 5.55 (1H, s, —OCHO—), 6.87–6.90, 7.33–7.41 and 7.52–7.55 (9H, 3 sets of m, aromatic H).

Anal. Calcd. for C$_{27}$H$_{35}$O$_6$SBr: C, 57.14; H, 6.22. Found: C, 57.38; H, 6.14.

E. Ethyl 2-O-p-methoxybenzyl-4,6-di-O-benzylidene-3-(5,5-di-tert-butyloxycarbonylpent-1-yl)-1-thio-β-D-galactopyranoside Ethyl 2-O-p-methoxybenzyl-4,6-di-O-benzylidene-3-(4-bromobut-1-yl)-1-thio-β-D-galactopyranoside (1.5 g, 2.64 mmol) was reacted by the general procedure as described in Example 3-B and afforded the title compound (1.52 g, 82%) as a white solid.

IR (CH$_2$Cl$_2$) v$_{max}$ (cm$^{-1}$): 3050, 2980 (C—H), 1740, 1720 (C=O).

$^1$H NMR 400 MHz (CDCl$_3$) δ (ppm): 1.34 (3H, t, J=7.5 Hz, —CH$_3$), 1.45 (18H, s, 2×—OtBu), 1.58, 1.68 and 1.83 (3×2H, —(CH$_2$)$_3$—), 2.80 (2H, m, —SCH$_2$—), 3.10 (1H, t, J=7.5 Hz, —CH(CO$_2$tBu)$_2$), 3.42 (1H, br s, H-5), 3.45 (1H, dd, J=9.2 and 3.5 Hz, H-3), 3.59 (1H, dt, J=9.2 and 6.6 Hz, —OCH$_2$—), 3.71 (1H, dt, J=9.2 and 6.7 Hz, —OCH$_2$—), 3.76–3.84 (1H, m overlapped by —OCH$_3$, H-2), 3.81 (3H, s, —OCH$_3$), 4.03 (1H, dd, J=12.3 and 1.5 Hz, H-6), 4.30 (1H, d, J=3.4 Hz, H-4), 4.34 (1H, dd, J=12.3 and 1.2 Hz, H-6), 4.43 (1H, d, J=9.6 Hz, H-1), 4.74 (1H, d, J$_{AB}$=9.9 Hz, —CH$_2$OAr), 4.78 (1H, d, J$_{AB}$=9.9 Hz, —OCH$_2$Ar), 5.54 (1H, s, —OCHO—), 6.85–6.92, 7.30–7.40 and 7.49–7.54 (9H, 3 sets of m, aromatic H).

Anal. Calcd. for C$_{38}$H$_{54}$O$_{10}$S: C, 64.93; H, 7.74. Found: C, 64.94; H, 7.64.

F. (2S,3R,4E)-3-Benzoyloxy-2-azido-1-[3-O-(5,5-di-tert-butyloxycarbonylpent-1-yl)-2—O-p-methoxybenzyl-4,6-O-benzylidene-α-D-galactopyranosyloxy]-4-octadecene and (2S,3R,4E)-3-benzoyloxy-2-azido-1-[3-O-(5,5-di-tert-butyloxycarbonylpent-1-yl)-2-O-p-methoxybenzyl-4,6-O-benzylidene-β-D-galactopyranosyloxy]-4-octadecene Ethyl 2-O-p-methoxybenzyl-4,6-di-O-benzylidene-3-(5,5-di-tert-butyloxycarbonylpent-1-yl)-1-thio-β-D-galactopyranoside (1.185 g, 1.68 mmol) and (2S,3R,4E)-2-azido-3-benzoyloxy-4-octadecen-1-ol (0.540 g, 1.68 mmol) were reacted by the general procedure as described in Example 1-K except that acetonitrile was used as solvent. This afforded the α-anomer (0.694 g, 39%) and the β-anomer (0.453 g, 25%) of the title compound.

α-anomer

IR (CH$_2$Cl$_2$) v$_{max}$ (cm$^{-1}$): 3050, 2980, 2930 and 2860 (C—H), 1720 (C=O).

$^1$H NMR 400 MHz (CDCl$_3$) δ (ppm): 0.89 (3H, t, J=6.8 Hz, —CH$_3$), 1.26 (20H, m, —(CH$_2$)$_{10}$—), 1.36–1.59 (4H, m, —(CH$_2$)$_2$—), 1.45 and 1.45 (18H, 2 s, 2×—OtBu), 1.67 and 1.83 (2×2H, 2 sets of m, —(CH$_2$)$_2$—), 2.08 (2H, qa, J=6.9 Hz, =CH—CH$_2$—), 3.10 (1H, t, J=7.5 Hz, —CH(CO$_2$tBu)$_2$), 3.56–3.76 (5H, m, —OCH$_2$—, H-1 and H-2), 3.79 (3H, s, —OCH$_3$), 3.83 (1H, dd, J=10.2 and 3.1 Hz, H-3'), 3.96 (1H, dd, J=10.2 and 3.5 Hz, H-2'), 3.94–3.99 (1H, m overlapped by H-2', H-5'), 4.07 (1H, dd, J=12.3 and 1.2 Hz, H-6'), 4.23 (1H, d, J=12.3 Hz, H-6'), 4.33 (1H, d, J=3.1 Hz, H-4'), 4.56 (1H, d, J=11.6 Hz, —OCH$_2$Ar), 4.75 (1H, d, J=11.6 Hz, —OCH$_2$Ar), 4.85 (1H, d, J=3.5 Hz, H-1'), 5.55 (1H, s, —OCHO—), 5.55–5.64 (1H, m overlapped by H-3, H-4), 5.63 (1H, dd, J=7.9 and 4.0 Hz, H-3), 5.93 (1H, dt, J=14.5 and 6.9 Hz, H-5), 6.82–6.85, 7.17–7.39, 7.45–7.53, 7.58–7.62 and 8.06–8.08 (14H, 5 sets of m, aromatic H).

Anal. Calcd. for C$_{61}$H$_{87}$N$_3$O$_{13}$: C, 68.45; H, 8.19; N, 3.93. Found: C, 68.46; H, 8.03; N, 3.94.

β-anomer

IR (CH$_2$Cl$_2$) v$_{max}$ (cm$^{-1}$): 3050, 2980, 2930 and 2850 (C—H), 1720 (C=O).

$^1$H NMR 400 MHz (CDCl$_3$) δ (ppm): 0.89 (3H, t, J=6.8 Hz, —CH$_3$), 1.24–1.42 (20H, m, —(CH$_2$)$_{10}$—), 1.42–1.61 (4H, m, —(CH$_2$)$_2$—), 1.45 and 1.45 (18H, 2 s, 2×—OtBu), 1.67 and 1.82 (2×2H, 2 sets of m, —(CH$_2$)$_2$—), 0.04 (2H, m, =CH—CH$_2$—), 3.09 (1H, t, J=7.5 Hz, —CH(CO$_2$tBu)$_2$), 3.38 (1H, br s, H-5'), 3.43 (1H, dd, J=9.7 and 3.5 Hz, H-3'), 3.57–3.63 (2H, m, —OCH$_2$— and H-2), 3.69 (1H, dt, J=9.1 and 6.7 Hz, —OCH$_2$—), 3.77 (1H, dd, J=9.6 and 7.7 Hz, H-2'), 3.79 (3H, s, —OCH$_3$), 3.99–4.08 (3H, m, H-1 and H-6'), 4.25 (1H, d, J=3.5 Hz, H-4'), 4.32 (1H, dd, J=12.3 and 0.9 Hz, H-6'), 4.40 (1H, d, J=7.7 Hz, H-1'), 4.73 (1H, d, J$_{AB}$=10.4 Hz, —OCH$_2$Ar), 4.82 (1H, d, J$_{AB}$=10.4 Hz, —OCH$_2$Ar), 5.55 (1H, s, —OCHO—), 5.58 (1H, dd, J=15.3 and 7.9 Hz, H-4), 5.71 (1H, dd, J=8.0 and 3.6 Hz, H-3), 5.90 (1H, dt, J=15.3 and 6.8 Hz, H-5), 6.82–6.90, 7.01–7.60 and 8.07–8.10 (14H, 3 sets of m, aromatic H).

Anal. Calcd. for C$_{61}$H$_{87}$N$_3$O$_{13}$: C, 68.45; H, 8.19; N, 3.93. Found: C, 68.57; H, 8.03; N, 3.92.

G. (2S,3R,4E)-3-Benzoyloxy-2-hexadecanoylamino-1-[3-O-(5,5-di-tert-butyloxycarbonylpent-1-yl)-2-O-p-methoxybenzyl-4,6-O-benzylidene-α-D-galactopyranosyloxy]-4-octadecene

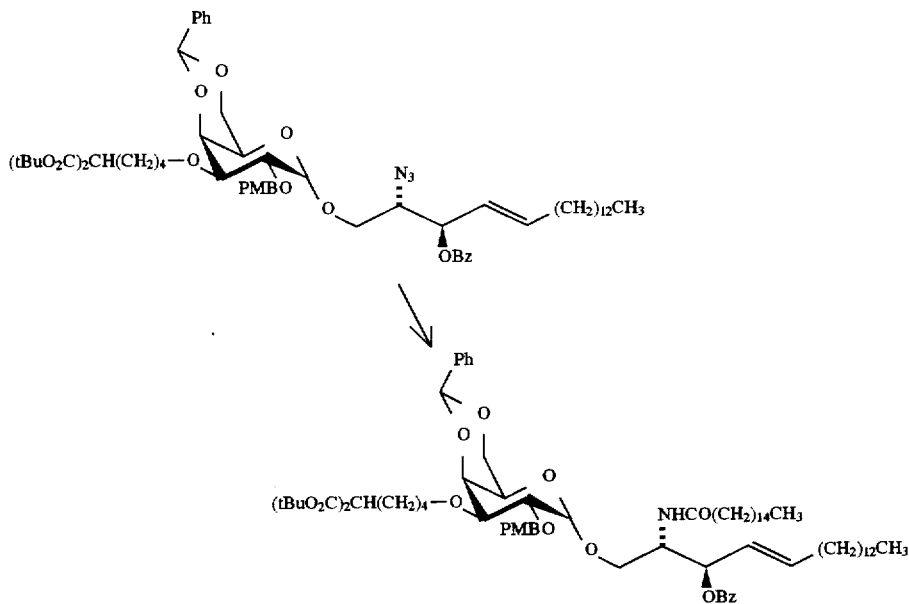

(2S,3R,4E)-3-Benzoyloxy-2-azido-1-[3-O-(5,5-di-tert-butyloxycarbonylpent-1-yl)-2-O-p-methoxybenzyl-4,6-O-benzylidene-α-D-galactopyranosyloxy]-4-octadecene (0.718 g, 0.67 mmol) was reacted by the general procedure as described in Example 1-L and afforded the title compound (0.710 g, 83%) as a white solid.

IR $(CH_2Cl_2)$ $v_{max}$ $(cm^{-1})$: 3440 (NH), 3050, 2990, 2930 and 2860 (C—H), 1720,1670 (C=O).

$^1$H NMR 400 MHz $(CDCl_3)$ δ (ppm): 0.89 (6H, t, J=6.7 Hz, 2×—CH$_3$), 1.24–1.27 (46H, m, —(CH$_2$)$_{13}$— and —(CH$_2$)$_{10}$—), 1.42–1.45 (2H, m, —CH$_2$—), 1.45 (18H, 2 s, 2×—OtBu), 1.5–1.62 (2H, m, —CH$_2$—), 1.68, 1.85, 2.00 and 2.09 (4×2H, 4 sets of m, —NHCOC$\underline{H}_2$—, =CH—C$\underline{H}_2$— and —(CH$_2$)$_2$—), 3.10 (1H, t, J=7.5 Hz, —CH(CO$_2$tBu)$_2$), 3.57 (1H, dt, J=9.0 and 6.7 Hz, —OCH$_2$—), 3.64–3.69 (1H, m, —OCH$_2$—), 3.69 (1H, br s, H-5'), 3.76–3.83 (3H, m, H-1 and H-2'), 3.78 (3H, s, —OCH$_3$), 3.95 (1H, dd, J=10.1 and 3.5 Hz, H-3'), 4.05 (1H, d, J=11.7 Hz, H-6'), 4.21 (1H, d, J=1 1.7 Hz, H-6'), 4.31 (1H, br d, H-4'), 4.48 (1H, m, H-2), 4.62 (1H, d, J$_{AB}$=11.1 Hz, —OCH$_2$Ar), 4.72 (1H, d, J$_{AB}$=11.1 Hz, —OCH$_2$Ar), 4.88 (1H, d, J=3.5 Hz, H-1'), 5.48 (1H, dd, J=15.3 and 7.6 Hz, H-4), 5.54 (1H, s, —OCHO—), 5.59 (1H, t, J=7.4 Hz, H-3), 5.79 (1H, dt, J=15.3 and 6.7 Hz, H-5), 5.99 (1H, d, J=9.1 Hz, —NH—), 6.81–6.83, 7.30–7.38, 7.45–7.53, 7.57–7.61 and 8.04–8.06 (14H, 5 sets of m, aromatic H).

Anal. Calcd. for $C_{77}H_{119}NO_{14}$: C, 72.10; H, 9.35; N, 1.09. Found: C, 72.19; H, 9.31; N, 1.23.

H. (2S,3R,4E)-3-Benzoyloxy-2-hexadecanoylamino-1-[3-O-(5,5-di-tert-butyloxycarbonylpent-1-yl)-4,6-O-benzylidene-α-D-galactopyranosyloxy]-4-octadecene

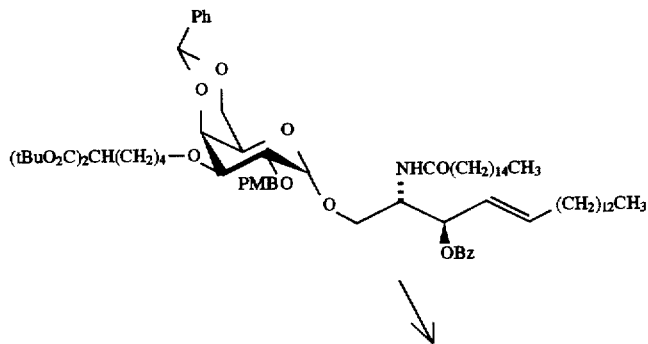

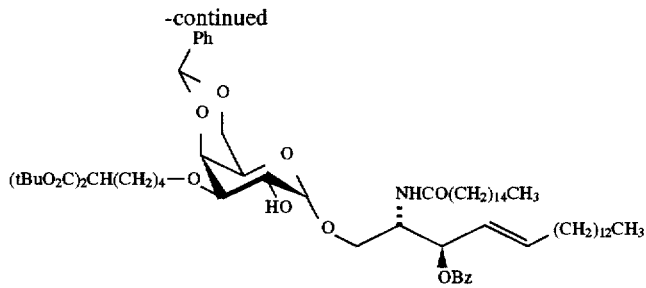

(2S,3R,4E)-3-Benzoyloxy-2-hexadecanoylamino-1-[3-O-(5,5-di-tert-butyloxycarbonylpent-1-yl)-2-O-p-methoxybenzyl-4,6-O-benzylidene-α-D-galactopyranosyloxy]-4-octadecene (0.675 g, 0.53 mmol) was reacted by the general procedure as described in Anal. Calcd. for $C_{69}H_{111}NO_{13}$: C, 71.28; H, 9.62; N, 1.20. Found: C, 71.21; H, 9.52; N, 1.34.

I. (2S,3R,4E)-3-Benzoyloxy-2-hexadecanoylamino-1-[3-O-(5,5-di-tert-butyloxycarbonylpent-1-yl)-α-D-galactopyranosyloxy]-4-octadecene

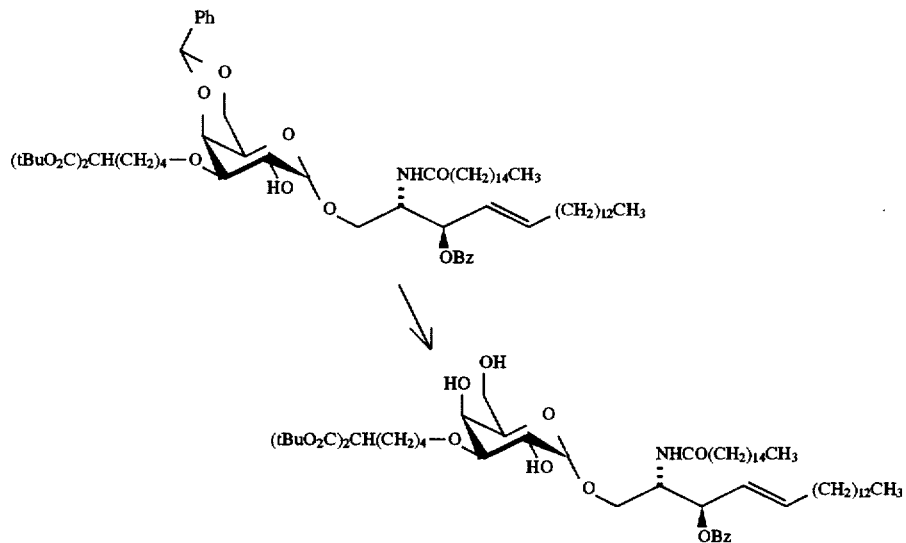

Example 9-A and afforded the title compound (0.549 g, 90%) as an amorphous beige solid.

IR $(CH_2Cl_2)$ $v_{max}$ $(cm^{-1})$: 3700, 3600 3440 (NH and OH), 3050, 2980, 2930 and 2860 (C—H), 1720, 1675 (C=O).

$^1$H NMR 400 MHz $(CDCl_3)$ δ (ppm): 0.89 (6H, t, J=6.7 Hz, 2×—$CH_3$), 1.26 (46H, m, —$(CH_2)_{13}$— and —$(CH_2)_{10}$—), 1.40–1.52 (2H, m, —$CH_2$—), 1.45 and 1.46 (18H, 2 s, 2×—OtBu), 1.59–1.70 (4H, m, —$(CH_2)_2$—), 1.83 and 2.20 (2×2H, 2 sets of m, —NHCOC$H_2$— and —C$H_2$—CH(CO$_2$tBu)$_2$), 2.05 (2H, qa J=6.9 Hz, =CH—C$H_2$—), 2.50 (1H, br s, —OH), 3.11 (1H, t, J=7.5 Hz, —CH(CO$_2$tBu)$_2$), 3.54 (1H, dt, J=9.0 and 6.6 Hz, —OCH$_2$—), 3.62 (1H, dd, J=10.1 and 3.3 Hz, H-3'), 3.69 (1H, dt, J=9.0 and 6.6 Hz, —OCH$_2$—), 3.74 (1H, br s, H-5'), 3.76 (1H, dd, J=11.0 and 6.1 Hz, H-1), 3.93 (1H, dd, J=11.0 and 3.8 Hz, H-1), 4.06–4.13 (1H, m, H-2'), 4.08 (1H, dd, J=12.4 and 1.2 Hz, H-6'), 4.26 (1H, dd, J=12.4 and 1.0 Hz, H-6'), 4.32 (1H, br d, H-4'), 4.55 (1H, m, H-2), 4.99 (1H, d, J=3.7 Hz, H-1'), 5.53 (1H, dd, J=15.3 and 7.4 Hz, H-4), 5.54 (1H, s, —OCHO—), 5.63 (1H, brt, H-3), 5.88 (1H, dt, J=15.3 and 6.9 Hz, H-5), 5.90 (1H, d, J=9.3 Hz, —NH—), 7.30–7.38, 7.45–7.58, 7.58–7.62 and 8.03–8.05 (10H, m, aromatic H).

(2S,3R,4E)-3-Benzoyloxy-2-hexadecanoylamino-1-[3-O-(5,5-di-tert-butyloxycarbonylpent-1-yl)-4,6-O-benzylidene-α-D-galactopyranosyloxy]-4-octadecene (0.260 g, 0.22 mmol) was reacted by the general procedure as described in Example 1-M and afforded the title compound (0.173 g, 74%) as a gummy white solid.

IR $(CH_2Cl_2)$ $v_{max}$ $(cm^{-1})$: 3700–3400 (NH and OH), 3050, 2980, 2930 and 2860 (C—H), 1720, 1675 (C=O).

$^1$H NMR 400 MHz $(CDCl_3)$ δ (ppm): 0.89 (6H, t, J=6.7 Hz, 2×—$CH_3$), 1.26–1.37 (46H, m, —$(CH_2)_{13}$— and —$(CH_2)_{10}$—), 1.41–1.51 (2H, m, —$CH_2$—), 1.47 (18H, s, 2×—OtBu), 1.53–1.73 (4H, m, —$(CH_2)_2$—), 1.82–1.88 (2H, m, —C$H_2$—CH(CO$_2$tBu)$_2$), 2.05 (2H, qa, J=6.9 Hz, =CH—C$H_2$—), 2.20 (2H, m, —NHCOC$H_2$—), 2.68 (1H, br s, —OH), 3.15 (1H, t, J=7.4 Hz, —CH(CO$_2$tBu)$_2$), 3.45 (1H, t, J=9.7 and 3.2 Hz, H-3'), 3.62–3.71 (2H, m, —OCH$_2$—), 3.77 (1H, dd, J=11.1 and 5.7 Hz, H-1), 3.82–3.99 (5H, m, H-1, H-2', H-5' and H-6'), 4.12 (1H, d, J=3.0 Hz, H-4'), 4.56 (1H, m, H-2), 4.90 (1H, d, J=3.9 Hz, H-1'), 5.53 (1H, dd, J=15.3 and 7.4 Hz, H-4), 5.63 (1H, br t, H-3), 5.90 (1H, dt, J=15.3 and 6.9 Hz, H-5), 5.96 (1H, d, J=9.3 Hz, —NH—), 7.45–7.49, 7.58–7.62 and 8.03–8.05 (5H, 3 sets of m, aromatic H).

EXAMPLE 12

(2S,3R,4E)-3-Benzoyloxy-2-hexadecanoylamino-1-[3-O-(5,5-di-carboxypent-1-yl)-α-D-galactopyranosyloxy]-4-octadecene

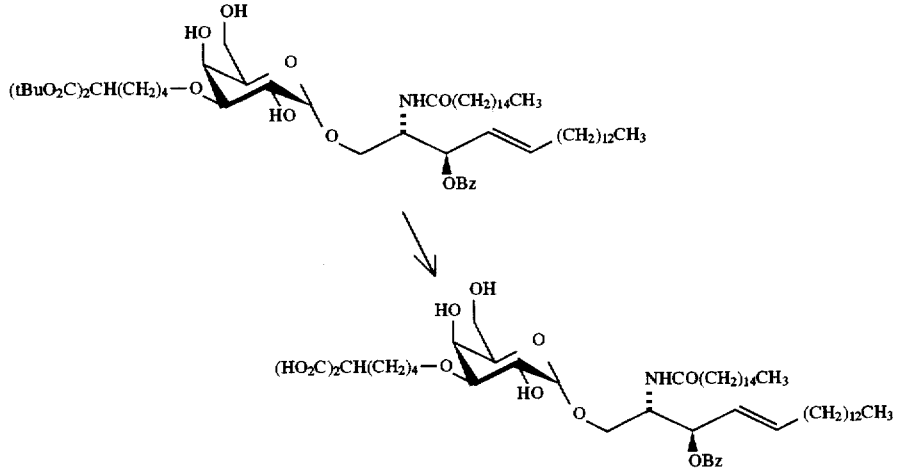

(2S,3R,4E)-3-Benzoyloxy-2-hexadecanoylamino-1-[3-O-(5,5-di-tert-butyloxycarbonylpent-1-yl)-(α-D-galactopyranosyloxy]-4-octadecene (0.165 g, 0.154 mmol) was reacted by the general procedure as described in Example 2, procedure No. 2 and afforded the title compound (0.124 g, 80%) as a white solid.

IR (nujol) $v_{max}$ (cm$^{-1}$): 3650–3100 (NH and OH), 2930 and 2850 (C—H), 1730,1640 (C=O).

$^1$H NMR 400 MHz (pyridine-d$_5$) δ (ppm): 0.85 (6H, t, J=6.7 Hz, 2×—CH$_3$), 1.24–1.36 (46H, m, —(CH$_2$)$_{13}$— and —(CH$_2$)$_{10}$—), 1.64–1.75 (4H, m, —(CH$_2$)$_2$—), 1.84 (2H, m, —CH$_2$—), 2.04 (2H, qa, J=6.8 Hz, =CH—CH$_2$—), 2.28 (2H, m, —CH$_2$—CH(CO$_2$H)$_2$), 2.47 (2H, t, J=7.4 Hz, —NHCOCH$_2$—), 3.51–3.53 and 3.72–3.74 (2×1H, 2 sets of m, —OCH$_2$—), 3.83 (1H, t, J=7.4 Hz, —CH(CO$_2$H)$_2$), 3.96 (1H, dd, J=10.0 and 3.0 Hz, H-3'), 4.17 (1H, dd, J=10.8 and 6.6 Hz, H-6'), 4.35–4.53 (4H, m, H-6', H-1 and H-5'), 4.60 (1H, br d, H-4'), 4.68 (1H, dd, J=10.0 and 3.8 Hz, H-2'), 5.22 (1H, m, H-2), 5.36 (1H, d, J=3.8 Hz, H-1'), 5.97 (1H, dd, J=15.5 and 7.1 Hz, H-4), 6.13 (1H, dt, J=15.5 and 6.8 Hz, H-5), 6.36 (1H, br t, H-3), 7.39–7.43, 7.50–7.53 and 8.24–8.26 (5H, 3 sets of m, aromatic H), 8.91 (1H, d, J=8.7 Hz, —NH—).

Preparation of the sodium salt of the title compound

The diacid from the above procedure (0.118 g, 0.117 mmol) was reacted by the general procedure as described in Example 6 and afforded the title compound (0.121 g, 98%) as a white fluffy solid.

IR (nujol) $v_{max}$ (cm$^{-1}$): 3650–3100 (broad, NH and OH), 2920 and 2850 (broad, C—H), 1710, 1640 and 1585 (C=O).

EXAMPLE 13

(2S,3R,4E)-3-Benzoyloxy-2-hexadecanoylamino-1-[3-O-(5,5-di-tert-butyloxycarbonylpent-1-yl)-β-D-galactopyranosyloxy]-4-octadecene A. (2S,3R,4E)-3-Benzoyloxy-2-hexadecanoylamino-1-[3-O-(5,5-di-tert-butyloxycarbonylpent-1-yl)-2-O-p-methoxybenzyl-4,6-O-benzylidene-β-D-galactopyranosyloxy]-4-octadecene

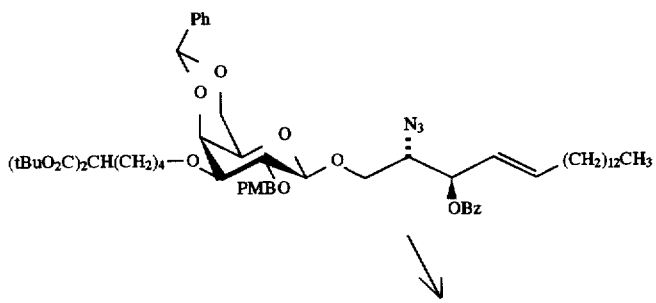

-continued

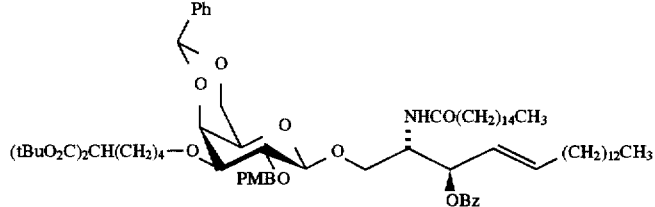

(2S,3R,4E)-3-Benzoyloxy-2-azido-1-[3-O-(5,5-di-tert-butyloxycarbonylpent-1-yl)-2-O-p-methoxybenzyl-4,6-O-benzylidene-β-D-galactopyranosyloxy]-4-octadecene described in Example 11-F (0.624 g, 0.58 mmol) was reacted by the general procedure as described in Example 1-L and afforded the title compound (0.506 g, 68%) as a white solid.

IR (CH$_2$Cl$_2$) $v_{max}$ (cm$^{-1}$): 3440 (NH), 3050, 2990, 2930 and 2860 (C—H), 1720,1670 (C=O).

$^1$H NMR 400 MHz (CDCl$_3$) δ (ppm): 0.87–0.91 (6H, m, 2×—CH$_3$), 1.23–1.31 (46H, m, —(CH$_2$)$_{13}$— and —(CH$_2$)$_{10}$—), 1.39–1.52 (4H, m, —(CH$_2$)$_2$—), 1.44 and 1.45 (18H, 2 s, 2×—OtBu), 1.64–1.71, 1.76–1.91 and 1.96–2.03 (2H, 4H and 2H, —NHCOCH$_2$—, =CH—CH$_2$—, —CH$_2$—CH(CO$_2$tBu)$_2$ and —CH$_2$—), 3.08 (1H, t, J=7.5 Hz, —CH(CO$_2$tBu)$_2$), 3.36 (1H, br s, H-5'), 3.43 (1H, dd, J=9.6 and 3.5 Hz, H-3'), 3.57 (1H, dt, J=9.1 and 6.6 Hz, —OCH$_2$—), 3.60–3.79 (2H, m, H-1 and —OCH$_2$—), 3.76 (1H, dd, J=9.6 and 7.8 Hz, H-2'), 3.79 (3H, s, —OCH$_3$), 4.05 (1H, dd, J=11.6 and 1.2 Hz, H-6'), 4.22–4.29 (1H, d overlapped by H-1 and H-4', H-6'), 4.24 (1H, dd, J=11.1 and 3.2 Hz, H-1), 4.25 (1H, d, J=3.5 Hz, H-4'), 4.32 (1H, d, J=7.8 Hz, H-1'), 4.45 (1H, m, H-2), 4.64 and 4.78 (2H, 2 d, J=10.4 Hz, —OCH$_2$Ar), 5.48 (1H, dd, J=15.3 and 7.3 Hz, H-4), 5.54 (1H, s, —OCHO—), 5.60 (1H, t, J=7.3 Hz, H-3), 5.83 (1H, dt, J=15.3 and 6.7 Hz, H-5), 6.19 (1H, d, J=9.1 Hz, —NH—), 6.85–6.87, 7.22–7.28, 7.32–7.45, 7.52–7.56 and 8.05–8.07 (14H, 5 sets of m, aromatic H).

Anal. Calcd. for C$_{77}$H$_{119}$NO$_{14}$·0.3 H$_2$O: C, 71.79; H, 9.36; N, 1.09. Found: C71.84; H, 9.26; N, 1.20.

B. (2S,3R,4E)-3-Benzoyloxy-2-hexadecanoylamino-1-[3-O-(5,5-di-tert-butyloxycarbonylpent-1-yl)-4,6-O-benzylidene-β-D-galactopyranosyloxy]-4-octadecene (2S,3R,4E)-3-Benzoyloxy-2-hexadecanoylamino-1-[3-O-(5,5-di-tert-butyloxycarbonylpent-1-yl)-2-O-p-methoxybenzyl-4,6-O-benzylidene-β-D-galactopyranosyloxy]-4-octadecene (0.502 g, 0.39 mmol) was reacted by the general procedure as described in Example 9-A and afforded the title compound (0.403 g, 89%) as an amorphous beige solid.

IR (CH$_2$Cl$_2$) $v_{max}$ (cm$^{-1}$): 3550–3300 (NH and OH), 3050, 2980, 2930 and 2860 (C—H), 1720, 1670 (C=O).

$^1$H NMR 400 MHz (CDCl$_3$) δ (ppm): 0.89 (6H, t, J=6.8 Hz, 2×—CH$_3$), 1.24–1.36 (46H, m, —(CH$_2$)$_{13}$— and —(CH$_2$)$_{10}$—), 1.38–1.50 (2H, m, —CH$_2$—), 1.45 and 1.45 (18H, 2 s, 2×—OtBu), 1.53–1.71 (4H, m, —(CH$_2$)$_2$—), 1.77–1.85, 1.96–2.05 and 2.16 (3×2H, —NHCOCH$_2$—, =CH—CH$_2$— and —CH$_2$—CH(CO$_2$tBu)$_2$), 3.10 (1H, t, J=7.4 Hz, —CH(CO$_2$tBu)$_2$), 3.12 (1H, br s, —OH), 3.34 (1H, dd, J=9.6 and 3.4 Hz, H-3'), 3.42 (1H, br s, H-5'), 3.54 (1H, dt, J=9.1 and 6.6 Hz, —OCH$_2$—), 3.71 (1H, dt, J=9.1 and 6.6 Hz, —OCH$_2$—), 3.81 (1H, dd, J=11.4 and 3.9 Hz, H-1), 3.89 (1H, dd, J=9.6 and 7.8 Hz, H-2'), 4.07 (1H, dd, J=12.3 and 1.3 Hz, H-6'), 4.18 (1H, dd, J=11.4 and 4.8 Hz, H-1), 4.26 (1H, d, J=3.2 Hz, H-4'), 4.30 (1H, d, J=12.3 Hz, H-6'), 4.34 (1H, d, J=7.8 Hz, H-1'), 4.49 (1H, m, H-2), 5.51 (1H, dd, J=15.3 and 7.2 Hz, H-4), 5.53 (1H, s, —OCHO—), 5.62 (1H, br t, H-3), 5.87 (1H, dt, J=15.3 and 6.7 Hz, H-5), 6.42 (1H, d, J=9.1 Hz, —NH—), 7.30–7.37, 7.41–7.45, 7.48–7.57 and 8.03–8.05 (10H, m, aromatic H).

Anal. Calcd. for C$_{69}$H$_{111}$NO$_{13}$: C, 71.28; H, 9.62; N, 1.20. Found: C, 71.08; H, 9.54; N, 1.35.

C. (2S,3R,4E)-3-Benzoyloxy-2-hexadecanoylamino-1-[3-O-(5,5-di-tert-butyloxycarbonylpent-1-yl)-β-D-galactopyranosyloxy]-4-octadecene

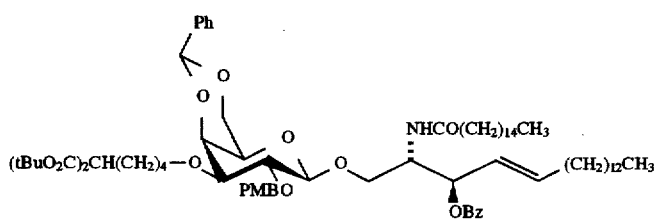

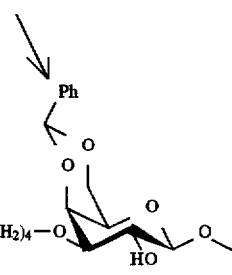

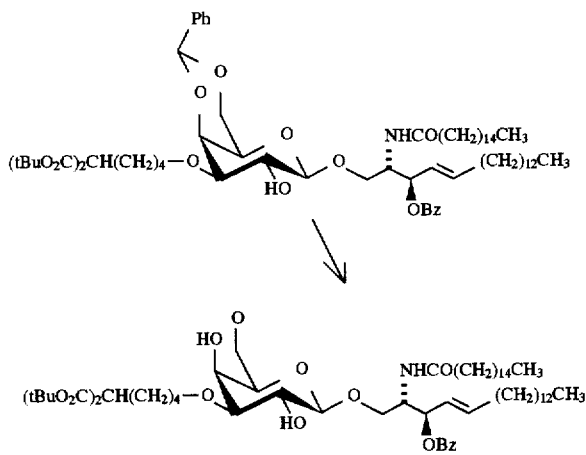

(2S,3R,4E)-3-Benzoyloxy-2-hexadecanoylamino-1-[3-O-(5,5-di-tert-butyloxycarbonylpent-1-yl)-4,6-O-benzylidene-β-D-galactopyranosyloxy]-4-octadecene (0.397 g, 0.34 mmol) was reacted by the general procedure as described in Example 1-M and afforded the title compound (0.308 g, 84%) as a white amorphous solid.

IR (CH$_2$Cl$_2$) $v_{max}$ (cm$^{-1}$): 3700–3300 (NH and OH), 3050, 2980, 2930 and 2850 (C—H), 1720, 1670 (C=O).

$^1$H NMR 400 MHz (CDCl$_3$) δ (ppm): 0.89 (6H, t, J=6.7 Hz, 2×—CH$_3$), 1.25–1.35 (46H, m, —(CH$_2$)$_{13}$— and —(CH$_2$)$_{10}$—), 1.40–1.49 (2H, m, —CH$_2$—), 1.47 (8H, s, 2×—OtBu), 1.53–1.71 (4H, 2 sets of m, —(CH$_2$)$_2$—), 1.84, 2.04 and 2.19 (3×2H, 3 sets of m, —NHCOCH$_2$—, =CH—CH$_2$— and —CH$_2$—CH(CO$_2$tBu)$_2$), 2.77 and 2.90 (2H, 2 br s, 2×—OH), 3.13–3.17 (1H. br s, —OH), 3.15 (1H, t, J=7.4 Hz, —CH(CO$_2$tBu)$_2$), 3.24 (1H, dd, J=9.4 and 3.2 Hz, H-3'), 3.45 (1H, br t, H-5'), 3.59 (1H, dt, J=9.2 and 6.5 Hz, —OCH$_2$—), 3.68–3.77 (3H, m, —OCH$_2$—, H-6' and H-2'), 3.82 (1H, dd, J=11.2 and 4.3 Hz, H-1), 3.93 (1H, dd, J=12.0 and 6.0 Hz, H-6'), 4.02–4.06 (2H, m, H-1 and H-4'), 4.30 (1H, d, J=7.7 Hz, H-1'), 4.56 (1H, m, H-2), 5.51 (1H, dd, J=15.3 and 7.5 Hz, H-4), 5.65 (1H, br t, H-3), 5.90 (1H, dt, J=15.3 and 6.7 Hz, 6.13 (1H, d, J=9.4 Hz, —NH—), 7.44–7.48, 7.53–7.61 and 8.03–8.05 (5H, 3 sets of m, aromatic H).

Anal. Calcd. for C$_{62}$H$_{107}$NO$_{13}$.0.5 H$_2$O: C, 68.73; H, 10.05; N, 1.29. Found: C, 68.79; H, 9.92; N, 1.45.

EXAMPLE 14

(2S,3R,4E)-3-Benzoyloxy-2-hexadecanoylamino-1-[3-O-(5,5-di-carboxypent-1-yl)-β-D-galactopyranosyloxy]-4-octadecene

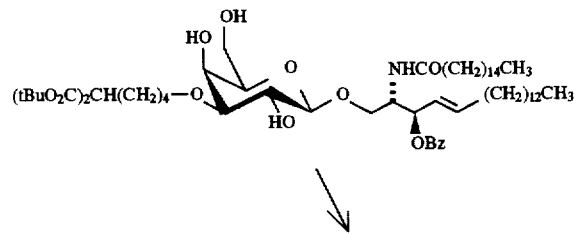

(2S,3R,4E)-3-Benzoyloxy-2-hexadecanoylamino-1-[3-O-(5,5-di-tert-butyloxycarbonylpent-1-yl)-β-D-galactopyranosyloxy]-4-octadecene (0.290 g, 0.27 mmol) was reacted by the general procedure as described in Example 2, procedure No. 2 and afforded the title compound (0.142 g, 55%) as a white solid.

IR (nujol) $v_{max}$ (cm$^{-1}$): 3700–3000 (NH and OH), 2920 and 2850 (broad, C—H), 1715, 1630 (C=O).

$^1$H NMR 400 MHz (pyridine-d$_5$) δ (ppm): 0.86 (6H, t, J=6.6 Hz, 2×—CH$_3$), 1.24–1.37 (46H, m, —(CH$_2$)$_{13}$— and —(CH$_2$)$_{10}$—), 1.70–1.86, 1.98 and 2.30 (6H and 2×2H, —(CH$_2$)$_2$—, —CH$_2$—, =CH—CH$_2$— and —CH$_2$—CH(CO$_2$H)$_2$), 2.44 (2H, t, J=7.4 Hz, —NHCOCH$_2$—), 3.65 (1H, dd, J=9.3 and 3.0 Hz, H-3'), 3.63–3.71 (1H, m, —OCH$_2$—), 3.83 (1H, t, J=7.4 Hz, —CH(CO$_2$H)$_2$), 3.81–3.87 (1H, m, —OCH$_2$—), 4.02 (1H, t, J=6.0 Hz, H-5'), 4.15 (1H, dd, J=10.9 and 4.4 Hz, H-1), 4.39 (1H, dd, J=10.9 and 6.0 Hz, H-6'), 4.45 (1H, dd, J=10.9 and 6.0 Hz, H-6'), 4.51 (1H, dt, J=9.3 and 7.7 Hz, H-2'), 4.57 (1H, dd, J=10.9 and 5.1 Hz, H-1), 4.59 (1H, br d, J=2.8 Hz, H-4'), 4.89 (1H, d, J=7.7 Hz, H-1'), 5.11 (1H, m, H-2), 5.88 (1H, dd, J=15.4 and 7.4 Hz, H-4), 6.02 (1H, dt, J=15.4 and 6.5 Hz, H-5), 6.20 (1H, br t, H-3), 7.35–7.39, 7.35–7.39 and 8.20–8.22 (5H, 3 sets of m, aromatic H), 8.70 (1H, d, J=10.9 Hz, —NH—).

Preparation of the sodium salt of the title compound

The diacid from the above procedure (0.138 g, 0.14 mmol) was reacted by the general procedure as described in Example 6 and afforded the sodium salt of the title compound (0.138 g, 98%) as a white fluffy solid.

IR (nujol) $v_{max}$ (cm$^{-1}$): 3700–3000 (NH), 2920 and 2850 (broad, C—H), 1715, 1585 (C=O).

$^1$H NMR 400 MHz (CD$_3$OD) δ (ppm): 0.89 (6H, t, J=6.8 Hz, 2×—CH$_3$), 1.27–1.43 (48H, m, —(CH$_2$)$_{13}$— and (CH$_2$)$_{11}$—), 1.58–1.66 (4H, m, —(CH$_2$)$_2$—) 2.05, and 2.18–2.24 (3×2H, —NHCOCH$_2$—, =CH—CH$_2$— and —CH$_2$—CH(CO$_2$Na)$_2$), 3.09 (1H, t, J=7.1 Hz, —CH(CO$_2$Na)$_2$), 3.20 (1H, dd, J=9.6 and 3.01 Hz, H-3'), 3.42–3.75 (7H, m, H-2', H-5', H-6', —OCH$_2$— and H-1), 4.01 (1H, br d, H-4'), 4.13 (1H, dd, J=10.4 and 5.0 Hz, H-1), 4.22 (1H, d, J=7.7 Hz, H-1'), 4.42 (1H, m, H-2), 5.51 (1H, dd, J=15.0 and 7.8 Hz, H-4), 5.58 (1H, br t, H-3), 5.89 (1H, dt, J=15.0 and 6.8 Hz, H-5), 7.45–7.48, 7.57–7.61 and 8.00–8.02 (5H, 3 sets of m, aromatic H).

EXAMPLE 15

(2S,3R 4E)-3-Benzoyloxy-2-hexadecanoylamino-1-[3-O-(5,5-di-tert-butyloxycarbonylpent-1-yl)-2-O-benzoyl-α-D-galactopyranosyloxy]-4-octadecene A. (2S,3R,4E)-3-Benzoyloxy-2-hexadecanoylamino-1-[3-O-(5,5-di-tert-butyloxycarbonylpent-1-yl)-4,6-O-benzylidene-2-O-benzoyl-α-D-galactopyranosyloxy]-4-octadecene

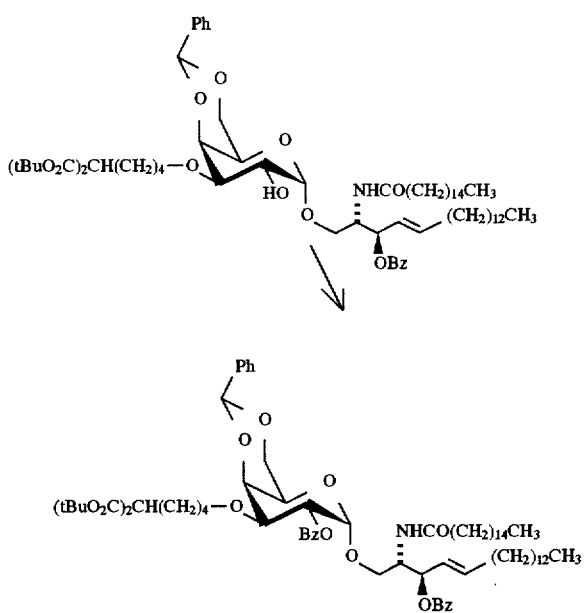

(2S,3R,4E)-3-Benzoyloxy-2-hexadecanoylamino-1-[3-O-(5,5-di-tert-butyloxycarbonylpent-1-yl)-4,6-O-benzylidene-α-D-galactopyranosyloxy]-4-octadecene described in Example 11-H (0.260 g, 0.22 mmol) was reacted by the general procedure as described in Example 1-J and afforded the title compound (0.262 g, 95%) as a white gummy solid.

IR (CH$_2$Cl$_2$) ν$_{max}$ (cm$^{-1}$): 3440 (NH), 3050, 2980, 2930 and 2850 (C—H), 20 1720, 1675 (C=O).

$^1$H NMR 400 MHz (CDCl$_3$) δ (ppm): 0.89 (6H, m, 2×—CH$_3$), 1.25–1.38 (48H, m, —(CH$_2$)$_{13}$— and —(CH$_2$)$_{11}$—), 1.42 and 1.43 (18H, 2 s, 2×—OtBu), 1.54–1.63 (4H, m, —(CH$_2$)$_2$—),1.74 (2H, m, —CH$_2$—CH(CO$_2$tBu)$_2$), 2.02 (4H, m, —NHCOCH$_2$— and =CH—CH$_2$—), 2.97 (1H, t, J=7.5 Hz, —CH(CO$_2$tBu)$_2$), 3.55 (1H, dt, J=9.2 and 6.6 Hz, —OCH$_2$—), 3.65–3.70 (2H, m, —OCH$_2$— and H-1), 3.81 (1H, s, H-5'), 3.86 (1H, dd, J=11.0 and 4.0 Hz, H-1), 3.99 (1H, dd, J=10.5 and 3.4 Hz, H-3'), 4.11 (1H, d, J=12.5 Hz, H-6'), 4.30 (1H, dd, J=12.5 and 0.9 Hz, H-6'), 4.41 (1H, br d, H-4'), 4.53 (1H, m, H-2), 5.33 d, J=3.7 Hz, H-1'), 5.45 (1H, dd, J=10.4 and 7.4 Hz, H-2'), 5.48 (1H, dd, J=7.3 and 14.7 hz, H-4), 5.53 (1H, t, J=7.3 Hz, H-3), 5.60 (1H, s, —OCHO—), 5.64 (1H, d, J=9.3 Hz, —NH—), 5.78 (1H, dt, J=14.7 and 6.7 Hz, H-5), 7.32–7.46, 7.54–7.60 and 7.97–8.04 (15H, 3 sets of m, aromatic H).

Anal. Calcd. for C$_{76}$H$_{115}$NO$_{14}$: C,72.06; H,9.15; N,1.11. Found: C, 72.13; H, 9.11; N, 1.29.

B. (2S,3R,4E)-3-Benzoyloxy-2-hexadecanoylamino-1-[3-O-(5,5-di-tert-butyloxycarbonylpent-1-yl)-2-O-benzoyl-(α-D-galactopyranosyloxy]-4-octadecene

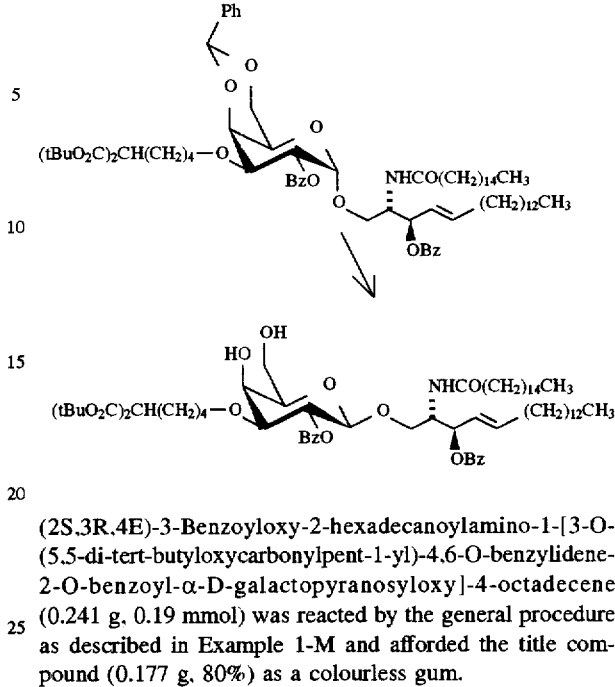

(2S,3R,4E)-3-Benzoyloxy-2-hexadecanoylamino-1-[3-O-(5,5-di-tert-butyloxycarbonylpent-1-yl)-4,6-O-benzylidene-2-O-benzoyl-α-D-galactopyranosyloxy]-4-octadecene (0.241 g, 0.19 mmol) was reacted by the general procedure as described in Example 1-M and afforded the title compound (0.177 g, 80%) as a colourless gum.

IR (CH$_2$Cl$_2$) ν$_{max}$ (cm$^{-1}$): 3700–3430 (NH and OH), 3050, 2980, 2930 and 2850 (C—H), 1720, 1675 (C=O). $^1$H NMR 400 MHz (CDCl$_3$) δ (ppm): 0.89 (6H, t, J=6.7 Hz, 2×—CH$_3$), 1.24–1.31 (46H, m, —(CH$_2$)$_{13}$— and —(CH$_2$)$_{10}$—), 1.38–1.47 (2H, m, —CH$_2$—), 1.44 (18H, s, 2×—OtBu), 1.50–1.57 (4H, m, —(CH$_2$)$_2$—), 1.66–1.81 (2H, m, —CH$_2$—CH(CO$_2$tBu)$_2$), 1.98–2.14 (4H, m, =CH—CH$_2$— and —NHCOCH$_2$—), 2.48 (1H, br s, —OH—6'), 2.78 (1H, s, —OH—4'), 2.99 (1H, t, J=7.5 Hz, —CH(CO$_2$tBu)$_2$), 3.56 (1H, dt, J=9.3 and 6.2 Hz, —OCH$_2$—), 3.67 (1H, dt, J=9.3 and 6.5 Hz, —OCH$_2$—), 3.75 (1H, dd, J=11.1 and 6.0 Hz, H-1), 3.81 (1H, dd, J=11.1 and 3.9 Hz, H-1), 3.84 (1H, dd, J=10.3 and 3.3 Hz, H-3'), 3.85–3.91 (1H, m, H-6'), 3.96–4.01 (2H, m, H-6' and H-5'), 4.20 (1H, br d, H-4'), 4.54 (1H, m, H-2), 5.20 (1H, d, J=3.8 Hz, H-1'), 5.31 (1H, dd, J=10.1 and 3.8 Hz, H-2'), 5.49 (1H, dd, J=15.0 and 7.3 Hz, H-4), 5.55 (1H, br t, H-3), 5.81 (1H, d, J=10.0 Hz, —NH—), 5.82 (1H, dt overlapped by —NH—, H-5), 7.40–7.46, 7.54–7.60 and 7.98–8.01 (10H, 3 sets of m, aromatic H).

EXAMPLE 16

(2S,3R,4E)-3-Benzoyloxy-2-hexadecanoylamino-1-[3-O-(5,5-di-carboxypent-1-yl)-2-O-benzoyl-α-D-galactopyranosyloxy]-4-octadecene

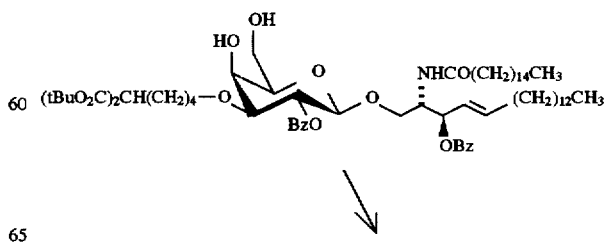

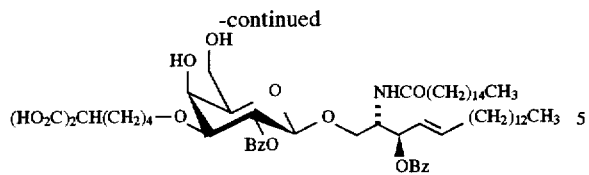

(2S,3R,4E)-3-Benzoyloxy-2-hexadecanoylamino-1-[3-O-(5,5-di-tert-butyloxycarbonylpent-1-yl)-2-O-benzoyl-α-D-galactopyranosyloxy]-4-octadecene (0.175 g, 0.148 mmol) was reacted by the general procedure as described in Example 2, procedure No. 2 and afforded the title compound (0.094 g, 57%) as a white solid.

IR (nujol) $v_{max}$ (cm$^{-1}$): 3650–3100 (broad, NH and OH), 2930 and 2850 (C—H), 1720, 1650 (C=O).

$^1$H NMR 400 MHz (pyridine-d$_5$) δ (ppm): 0.85 (6H, br t, 2×—CH$_3$), 1.24 (46H, m, —(CH$_2$)$_{13}$— and —(CH$_2$)$_{10}$—), 1.56–1.63, 1.77–1.88, 1.99–2.04 and 2.20 (4H and 3×2H, —(CH$_2$)$_2$—, —CH$_2$—, —CH$_2$—CH(CO$_2$H)$_2$ and =CH—CH$_2$—), 2.41 (2H, t, J=7.4 Hz, —NHCOCH$_2$—), 3.57–3.50 (1H, m, —OCH$_2$—), 3.69–3.72 (2H, m, —OCH$_2$— and —CH(CO$_2$H)$_2$), 4.04 (1H, dd, J=10.3 and 6.9 Hz, H-1), 5.28 (1H, dd, J=10.4 and 1.9 Hz, H-3'), 4.41–4.50 (3H, m, H-6— and H-1), 4.58 (1H, t, J=5.9 Hz, H-5;), 4.71 (1H, br s, H-4'), 5.23 (1H, m, H-2), (1H, d, J=3.5 Hz, H-1'), 5.92 (1H, dd, J=15.4 and 7.3 Hz, H-4), 6.07 (1H, dt, J=15.4 and 6.5 Hz, H-5), 6.13 (1H, dd, J=10.4 and 3.4 Hz, H-2'), 6.24 (1H, br t, H-3), 7.36–7.40, 7.47–7.52, 8.16–8.18 and 8.36–8.71 (10H, 4 sets of m, aromatic H), 8.85 (1H, d, J=8.9 Hz, —NH—).

Preparation of the sodium salt of the title compound

The diacid from the above procedure (0.091 g, 0.085 mmol) was reacted by the general procedure as described in Example 6 and afforded the title compound (0.094 g, 99%) as a white fluffy solid.

IR (nujol) $v_{max}$ (cm$^{-1}$): 3650–3100 (broad, NH and OH), 2920 and 2850 (C—H), 1720, 1595 (C=O).

$^1$H NMR 400 MHz (CD$_3$OD) δ (ppm): 0.84 (6H, t, J=6.8 Hz, 2×—CH$_3$), 1.20–1.28 (48H, m, —(CH$_2$)$_{13}$— and —(CH$_2$)$_{11}$—), 1.39–1.54, 1.79 and 1.93–2.07 (4H, 2H and 4H, —(CH$_2$)$_2$—, —CH$_2$—CH(CO$_2$Na)$_2$, =CH—CH$_2$— and —NHCOCH$_2$—), 2.96 (1H, br t, —CH(CO$_2$Na)$_2$), 3.43–3.48 (1H, m, —OCH$_2$—), 3.53 (1H, dd, J=10.6 and 6.0 Hz, H-1), 3.63 (1H, m, —OCH$_2$—), 3.67 and 3.71 (2H, 2 d, J$_{AB}$=11.4 Hz, H-6'), 3.82 (1H, dd, J=10.5 and 3.5 Hz, H-3'), 3.85–3.89 (2H, m, H-5' and H-1), 4.12 (1H, brs, H-4'), 4.74 (1H, m, H-2), 5.03 (1H, d, J=3.7 Hz, H-1'), 5.19 (1H, dd, J=10.3 and 3.7 Hz, H-2'), 5.40–5.49 (2H, m, H-3 and H-4), 5.77 (1H, dt, J=14.3 and 6.7 Hz, H-5), 7.34–7.42, 7.50–7.55, 7.84–7.86 and 7.91–7.93 (10H, 4 sets of m, aromatic H).

EXAMPLE 17

(2S,3R,4E)-3-Benzoyloxy-2-hexadecanoylamino-1-[2-O-(5,5-di-tert-butyloxycarbonylpent-1-yl)-3-O-benzoyl-β-D-galactopyranosyloxy]-4-octadecene A. (2S,3R,4E)-3-Benzoyloxy-2-hexadecanoylamino-1-[2-O-(5,5-di-tert-butyloxycarbonylpent-1-yl)-3-O-benzoyl-4,6-O-benzylidene-β-D-galactopyranosyloxy]-4-octadecene

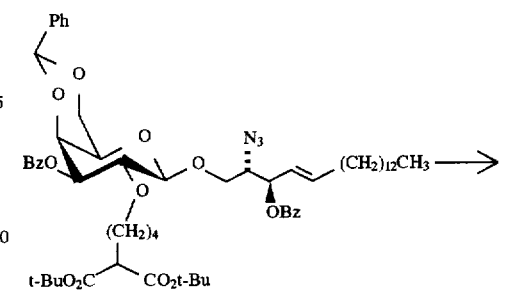

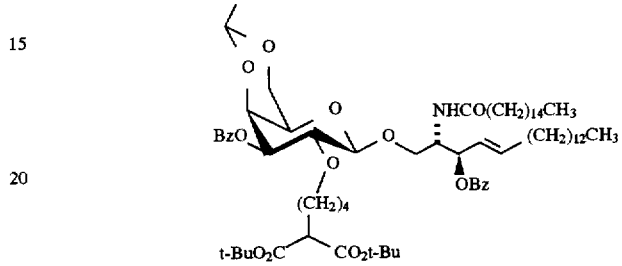

(2S,3R,4E)-3-benzoyloxy-2-azido-1-[2-O-(5,5-di-tert-butyloxycarbonylpent-1-yl)-3-O-benzoyl-4,6-O-benzylidene-β-D-galactopyranosyloxy]-4-octadecene described in Example 3-G (0.371 g, 0.35 mmol) was reacted by the general procedure as described in Example 1-L to give the title compound (0.364 g, 82%) as a beige solid.

IR (CH$_2$Cl$_2$) $v_{max}$ (cm$^{-1}$): 3400 (NH), 3050, 2930, 2850 (C—H), 1720, 1670 (C=O).

$^1$H NMR 400 MHz (CDCl$_3$) δ (ppm): 0.89 (6H, m, 2×—CH$_3$), 1.14–1.36 (48H, m, —(CH$_2$)$_{13}$— and —(CH$_2$)$_{11}$—), 1.41 and 1.42 (18H, 2 s, 2×—OtBu), 1.41–1.51 and 1.58–1.67 (6H, 2 sets of m, —CH$_2$—CH(CO$_2$tBu)$_2$ and —(CH$_2$)$_2$—), 2.03 (2H, qa, J=7.0 Hz, =CH—CH$_2$—), 2.15 (2H, m, —NHCOCH$_2$—), 2.87 (1H, t, J=7.5 Hz, —CH(CO$_2$tBu)$_2$), 3.54 (1H, br s, H-5'), 3.59 (1H, dt, J=9.4 and 6.9 Hz, —OCH$_2$—), 3.75–3.86 (3H, m, —OCH$_2$—, H-2' and H-1), 4.06 (1H, d, J=11.9 Hz, H-6'), 4.16 (1H, dd, J=11.2 and 4.6 Hz, H-1), 4.28 (1H, d, J=11.9 Hz, H-6'), 4.44 (1H, d, J=7.9 Hz, H-1'), 4.46 (1H, d, J=3.8 Hz, H-4'), 4.50 (1H, m, H-2), 5.08 (1H, dd, J=10.1 and 3.8 Hz, H-3'), 5.50 (1H, s, —OCHO—), 5.53 (1H, dd, J=15.3 and 7.4 Hz, H-4), 5.67 (1H, br t, H-3), 5.87 (1H, dt, J=15.3 and 7.0 Hz, H-5), 6.21 (1H, d, J=8.8 Hz, —NH—), 7.34–7.38, 7.42–7.49, 7.54–7.60 and 8.04–8.09 (15H, 4 sets of m, aromatic H).

Anal. Calcd. for C$_{76}$H$_{115}$NO$_{14}$: C, 72.06; H, 9.15; N,1.11. Found: C, 72.09; H, 9.10; N, 1.29.

B. (2S,3R,4E)-3-Benzoyloxy-2-hexadecanoylamino-1-[2-O-(5,5-di-tert-butyloxycarbonylpent-1-yl)-3-O-benzoyl-β-D-galactopyranosyloxy]-4-octadecene

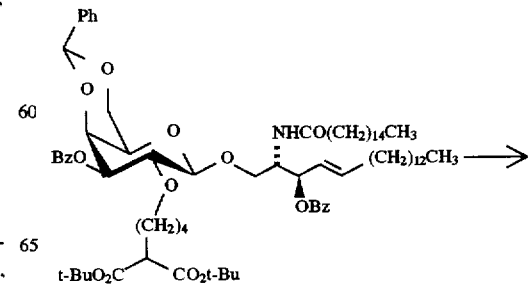

81

-continued

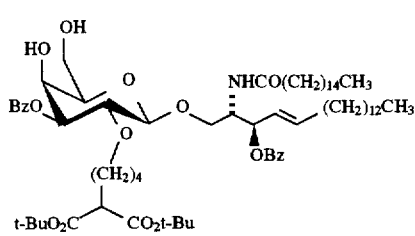

(2S,3R,4E)-3-Benzoyloxy-2-hexadecanoylamino-1-[2-O-(5,5-di-tert-butyloxycarbonylpent-1-yl)-3-O-benzoyl-4,6-O-benzylidene-β-D-galactopyranosyloxy]-4-octadecene (0.436 g, 0.27 mmol) was reacted by the general procedure as described in Example 1-M and afforded the title compound (0.259 g, 81%) as a white solid.

IR (CH$_2$Cl$_2$) $v_{max}$ (cm$^{-1}$): 3600, 3450–3350 (NH and OH), 3050, 2930, 2850 (C—H), 1720, 1675 (C=O).

$^1$H NMR 400 MHz (CDCl$_3$) δ (ppm): 0.89 (6H, t, J=6.8 Hz, 2×—CH$_3$), 1.19–1.39 (48H, m, —(CH$_2$)$_{13}$— and —(CH$_2$)$_{11}$—), 1.43 (18H, s, 2×—OtBu), 1.46–1.53 and 1.58–1.73 (2H and 4H, —CH$_2$—CH(CO$_2$tBu)$_2$ and —(CH$_2$)$_2$—), 2.03–2.25 (2H, br s, 2×—OH), 2.05 (2H, qa, J=6.9 Hz, =CH—CH$_2$—), 2.19 (2H, m, —NHCOCH$_2$—), 2.89 (1H, t, J=7.5 Hz, —CH(CO$_2$tBu)$_2$), 3.43 (1H, br t, J=3.4 Hz, H-5'), 3.60 (1H, dt, J=9.4 and 6.6 Hz, —OCH$_2$—), 3.67 (1H, dd, J=12.5 and 3.2 Hz, H-6'), 3.75–3.85 (4H, m, H-2', H-1, H-6' and —OCH$_2$—), 4.01 (1H, dd, J=10.5 and 2.7 Hz, H-1), 4.27 (1H, d, J=2.9 Hz, H-4'), 4.44 (1H, d, J=7.6 Hz, H-1'), 4.62 (1H, m, H-2), 4.98 (1H, dd, J=10.0 and 3.0 Hz, H-3'), 5.55 (1H, dd, J=15.4 and 7.9 Hz, H-4), 5.77 (1H, t, J=7.9 Hz, H-3), 5.86 (1H, d, J=9.4 Hz, —NH—), 5.95 (1H, dt, J=15.4 and 6.9 Hz, H-5), 7.46–7.49, 7.57–7.62 and 8.05–8.10 (10H, 3 sets of m, aromatic H).

Anal. Calcd. for C$_{69}$H$_{111}$NO$_{14}$: C, 70.32; H, 9.49; N, 1.19. Found: C, 70.78; H, 9.52; N, 1.30.

EXAMPLE 18

(2S,3R,4E)-3-Benzoyloxy-2-hexadecanoylamino-1-[2-O-(5,5-di-carboxypent-1-yl)-3-O-benzoyl-β-D-galactopyranosyloxy]-4-octadecene

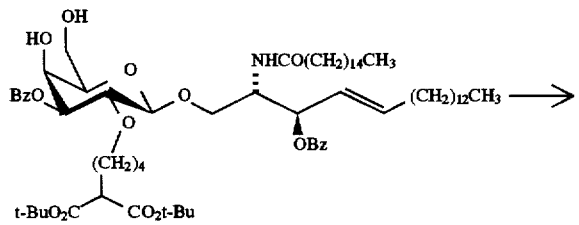

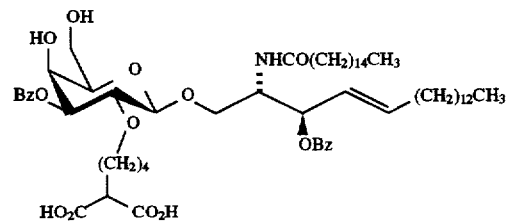

(2S,3R,4E)-3-Benzoyloxy-2-hexadecanoylamino-1-[2-O-(5,5-di-tert-butyloxycarbonylpent-1-yl)-3-O-benzoyl-β-D-galactopyranosyloxy]-4-octadecene (0.240 g, 0.2 mmol) was reacted by the general procedure as described in

82

Example 2 and gave the title compound (0.139 g, 65%) as a 20 white solid.

IR (nujol) $v_{max}$ (cm$^{-1}$): 3700–3100 (NH and OH), 2930, 2850 (C—H), 1715, 1645 (C=O).

$^1$H NMR 400 MHz (pyridine-d$_5$) δ (ppm): 0.85 (6H, t, J=6.7 Hz, 2×—CH$_3$), 1.24 (44H, br s, —(CH$_2$)$_{12}$— and —(CH$_2$)$_{10}$—), 1.41, 1.67–1.92, 2.04 and 2.24–2.32 (2H, 6H, 2×2H, 4 sets of m, 2×—CH$_2$—, —(CH$_2$)$_2$—, —CH$_2$—CH(CO$_2$H)$_2$ and =CH—CH$_2$—), 2.49 (2H, t, J=7.4 Hz, —NHCOCH$_2$—), 3.73 (1H, t, J=7.4 Hz, —CH(CO$_2$H)$_2$), 3.90 (1H, m, —OCH$_2$—), 4.07 (1H, t, J=6.2 Hz, H-5'), 4.19 (1H, m, —OCH$_2$—), 4.27 (1H, dd, J=10.4 and 5.2 Hz, H-1), 4.32 (1H, dd, J=10.9 and 6.1 Hz, H-6'), 4.37–4.43 (2H, m, H-2' and H-6'), 4.52 (1H, dd, J=10.4 and 6.7 Hz, H-1), 4.91–4.93 (2H, m, H-1' and H-4'), 5.25 (1H, m, H-2), 5.57 (1H, dd, J=10.1 and 3.1 Hz, H-3'), 5.94 (1H, dd, J=15.4 and 7.3 Hz, H-4), 6.12 (1H, dt, J=15.4 and 6.7 Hz, H-5), 6.28 (1H, br t, H-3), 7.19–7.50 and 8.24–8.26 (10H, 2 sets of m, aromatic H), 8.60 (1H, d, J=8.7 Hz, —NH—).

Preparation of the sodium salt of the title compound

The diacid (0.134 g, 0.13 mmol) from the above procedure was reacted by the general procedure as described in Example 6 and afforded the title compound (0.140 g, 100%) of the sodium salt of the title compound.

IR (nujol) $v_{max}$ (cm$^{-1}$): 3650–3100 (NH and OH), 2920, 2850 (C—H), 1720, 1650, 1595 (C=O).

$^1$H NMR 400 MHz (CD$_3$OD) δ (ppm): 0.89 (6H, t, J=6.8 Hz, 2×—CH$_3$), 1.25–1.31 (46H, m, —(CH$_2$)$_{13}$— and —(CH$_2$)$_{10}$—), 1.40, 1.49, 1.59 and 1.73 (4×2H, 4 sets of m, —CH$_2$—, —(CH$_2$)$_2$— and —CH$_2$—CH(CO$_2$Na)$_2$), 2.09 (2H, qa, J=6.9 Hz, =CH—CH$_2$—), 2.18–2.24 (2H, m, —NHCOCH$_2$—), 2.97 (1H, br t, —CH(CO$_2$Na)$_2$), 3.56–3.66 (4H, m, H-5', H-6', H-1 and —OCH$_2$—), 3.69 (1H, dd, J=10.1 and 7.7 Hz, H-2'), 3.77–3.83 (1H, m, —OCH$_2$—), 3.84 (1H, dd, J=10.7 and 5.4 Hz, H-1), 3.99 (1H, dd, J=10.5 and 6.3 Hz, H-6'), 4.11 (1H, d, J=3.1 Hz, H-4'), 4.43 (1H, d, J=7.7 Hz, H-1'), 4.51 (1H, m, H-2), 4.94 (1H, dd, J=10.1 and 3.3 Hz, H-3'), 5.56 (1H, dd, J=15.2 and 7.7 Hz, H-4), 5.65 (1H, br t, H-3), 5.91 (1H, dt, J=15.2 and 6.9 Hz, H-5), 7.45–7.51, 7.58–7.61 and 7.99–8.08 (10H, 3 sets of m aromatic H).

EXAMPLE 19

(2S,3R,4E)-3-Benzoyloxy-2-hexadecanoylamino-1-[2-O-(3,3-di-tert-butyloxycarbonylprop-1-yl)-3,4-O-isopropylidene-6-O-tert-butyldimethylsilyl-α-D-galactopyranosyloxy]-4-octadecene A. (2S,3R,4E)-3-Benzoyloxy-2-azido-1-[2-O-(3,3-di-tert-butyloxycarbonylprop-1-yl)-3,4-O-isopropylidene-6-O-tert-butyldimethylsilyl-α-D-galactopyranosyloxy]-4-octadecene and (2S,3R,4E)-3-benzoyloxy-2-azido-1-[2-O-(3,3-di-tert-butyloxycarbonylprop-1-yl)-3,4-O-isopropylidene-6-O-tert-butyldimethylsilyl-β-D-galactopyranosyloxy]-4-octadecene

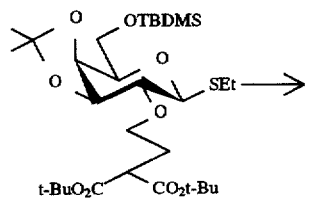

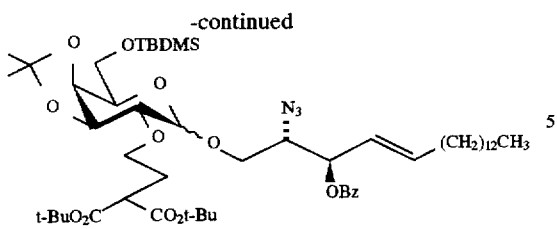

Ethyl 3,4-O-isopropylidene-6-O-tert-butyldimethylsilyl-2-O-(3,3-di-tert-butyloxycarbonylprop-1-yl)-1-thio-β-D-galactopyranoside described in Example 1-F (0.81 g, 1.30 mmol) and (2S,3R,4E)-2-azido-3-benzoyloxy-4-octadecen-1-ol (0.375 g, 0.87 mmol) were reacted by the general procedure as described in Example 1-K and afforded the α-anomer (0.155 g, 18%) and the β-anomer (0.050 g, 6%) of the title compound.

α-anomer $^1$H NMR 400 MHz (CDCl$_3$) δ (ppm): 0.08 (6H, m, —Si(CH$_3$)$_2$), 0.89 (3H, t overlapped by —SitBu, —CH$_3$), 0.91 (9H, s, —SitBu), 0.92–1.40 (22H, m, —(CH$_2$)$_{11}$—), 1.33 (3H, s, —C(CH$_3$)$_2$), 1.45 (18H, s, 2×—OtBu), 1.50 (3H, s, —C(CH$_3$)$_2$), 2.05–2.09 (4H, m, =CH—C<u>H</u>$_2$— and —C<u>H</u>$_2$—CH(CO$_2$tBu)$_2$), 3.43–3.47 (2H, m, —CH(CO$_2$tBu)$_2$ and H-2), 3.53 (1H, dd, J=10.7 and 8.0 Hz, H-1), 3.63 (1H, dt, J=9.8 and 6.0 Hz, —OCH$_2$—), 3.72 (1H, dt, J=9.8 and 6.0 Hz, —OCH$_2$—), 3.78 (1H, dd, J=10.0 and 6.6 Hz, H-6'), 3.84–3.88, 4.00–4.05 and 4.21–4.27 (3×1H, 3 sets of m, H-1, H-5' and H-6'), 3.85 (1H, dd, J=6.5 and 3.3 Hz, H-2'), 4.03 (1H, dd, J=6.5 and 2.2 Hz, H-3'), 4.22 (1H, dd, J=5.6 and 2.2 hz, H-4'), 4.91 (1H, d, J=3.4 Hz, H-1'), 5.55–5.60 (2H, m, H-3 and H-4), 5.93 (1H, br dt, H-5), 7.44–7.48, 7.56–7.60 and 8.06–8.08 (5H, 3 sets of m, aromatic H).

β-anomer $^1$H NMR 400 MHz (CDCl$_3$) δ (ppm): 0.06 (6H, S, —Si(CH$_3$)$_2$), 0.89 (12H, m, —SitBu and —CH$_3$), 1.24 (20H, m, —(CH$_2$)$_{10}$—), 1.31 (3H, s, —C(CH$_3$)$_2$), 1.34–1.50 (2H, m, —CH$_2$—), 1.44 and 1.45 (18H,2 s, 2×—OtBu), 1.51 (3H, s, —C(CH$_3$)$_2$), 2.04–2.14 (4H, m, =CH—C<u>H</u>$_2$— and —C<u>H</u>$_2$—CH(CO$_2$tBu)$_2$), 3.24 (1H, t, J=7.3 Hz, —CH(CO$_2$tBu)$_2$), 3.42 (1H, br t, H-2'), 3.61 (1H, dd, J=10.3 and 5.0 Hz, H-1), 3.70–3.76 (2H, m, H-2 and —OCH$_2$—), 3.78–3.93 (1H, m, —OCH$_2$—), 3.80 (1H, dd, J=10.0 and 5.8 Hz, H-6'), 3.86 (1H, dd, J=10.0 and 7.2 Hz, H-6'), 3.90 (1H, dd, J=10.2 and 7.7 Hz, H-1), 4.01–4.06 (2H, m, H-3' and H-5'), 4.16 (1H, dd, J=5.6 and 1.8 Hz, H-4'), 4.20 (1H, d, J=7.8 Hz, H-1'), 5.56 (1H, dd, J=14.8 and 8.0 Hz, H-4), 5.62 (1H, dd, J=8.0 and 4.0 Hz, H-3), 5.93 (1H, dt, J=14.8 and 6.7 Hz, H-5), 7.42–7.46, 7.55–7.58 and 8.05–8.07 (5H, 3 sets of m, aromatic H).

B. (2S,3R,4E)-3-Benzoyloxy-2-hexadecanoylamino-1-[2-O-(3,3-di-tert-butyloxycarbonylprop-1-yl)-3,4-O-isopropylidene-6-O-tert-butyldimethylsilyl-α-D-galactopyranosyloxy]-4-octadecene

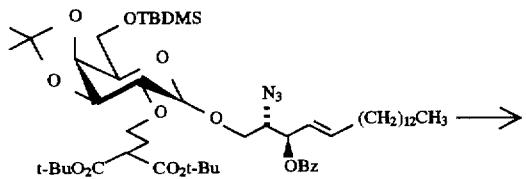

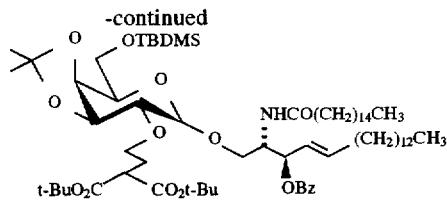

(2S,3R,4E)-3-Benzoyloxy-2-azido-1-[2-O-(3,3-di-tert-butyloxycarbonylprop-1-yl)-3,4-O-isopropylidene-6-O-tert-butyldimethylsilyl-α-D-galactopyranosyloxy]-4-octadecene (0.230 g, 0.233 mmol) was reacted by the general procedure as described in Example 1-L and afforded the title compound (0.168 g, 60%).

$[\alpha]_D^{22}$: +40° (c=1.0, CHCl$_3$).

IR (film) ν$_{max}$ (cm$^{-1}$): 3290 (NH), 2920, 2850 (C—H), 1740, 1715, 1640 (C=O).

$^1$H NMR 400 MHz (CDCl$_3$) δ (ppm): 0.07 (6H, s, —Si(CH$_3$)$_2$), 0.90 (15H, m, —SitBu and 2×—CH$_3$), 1.25–1.27 (46H, m, —(CH$_2$)$_{10}$— and —(CH$_2$)$_{13}$—), 1.31 (3H, s, —C(CH$_3$)$_2$), 1.43 and 1.45 (18H, 2 s, —OtBu), 1.46 (3H, s, —C(CH$_3$)$_2$), 1.49–1.62 (4H, m, —CH$_2$— and —C<u>H</u>$_2$—CH(CO$_2$tBu)$_2$), 2.00–2.09 and 2.13–2.22 (2×2H, 2 sets of m, —NHCOC<u>H</u>$_2$— and =CH—C<u>H</u>$_2$—), 3.40 (1H, dd, J=6.3 and 3.3 Hz, H-2'), 3.46 (1H, t, J=7.5 Hz, —CH(CO$_2$tBu)$_2$), 3.57–3.70 (3H, m, —OCH$_2$— and H-1), 3.74 (1H, dd, J=9.8 and 6.3 Hz, H-6'), 3.83 (1H, dd, J=9.8 and 7.1 Hz, H-6'), 3.88 (1H, dd, J=10.6 and 3.6 Hz, H-1), 4.00 (1H, br t, H-5'), 4.18–4.21 (2H, m, H-3' and H-4'), 4.49 (1H, m, H-2), 4.79 (1H, d, J=3.2 Hz, H-1'), 5.54 (1H, dd, J=15.3 and 7.5 Hz, H-4), 5.65 (1H, br t, H-3), 5.89 (1H, dt, J=15.3 and 6.7 Hz, H-5), 6.59 (1H, d, J=8.8 Hz, —NH—), 7.42–7.46, 7.53–7.58 and 8.03–8.05 (5H, 3 sets of m, aromatic H).

Anal. Calcd. for C$_{69}$H$_{121}$NO$_{13}$Si: C, 69.02; H, 10.16; N, 1.17. Found: C, 69.05; H, 10.12; N, 1.23.

EXAMPLE 20

(2S,3R,4E)-3-Benzoyloxy-2-hexadecanoylamino-1-[2-O-(3,3-di-carboxyprop-1-yl)-α-D-galactopyranosyloxy]-4-octadecene

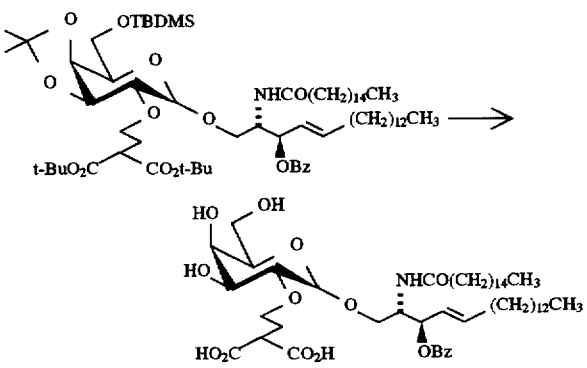

(2S,3R,4E)-3-Benzoyloxy-2-hexadecanoylamino-1-[2-O-(3,3-di-tert-butyloxycarbonylprop-1-yl)-3,4-O-isopropylidene-6-O-tert-butyldimethylsilyl-α-D-galactopyranosyloxy]-4-octadecene (0.155 g, 0.129 mmol) was reacted by the general procedure as described in Example 6 and afforded the title compound (0.081 g, 67%) as a beige solid.

$^1$H NMR 400 MHz (pyridine-d$_5$) δ (ppm): 0.85 (6H, t, J=6.7 Hz, 2×—CH$_3$), 1.23–1.39 (46H, m, —(CH$_2$)$_{13}$— and —(CH$_2$)$_{10}$—), 1.81–1.90 and 2.00 (2×2H, 2 sets of m, —C H₂—CH(CO₂H)₂ and —CH₂—), 2.53 (2H, t, J=7.4 Hz, —NHCOCH₂—), 2.76 (2H, qa, J=6.6 Hz, =CH—CH₂—), 4.07 (1H, dt, J=9.3 and 6.2 Hz, —OCH₂—), 4.16 (1H, dt, J=9.3 and 6.0 Hz, —OCH₂—), 4.23 (1H, dd, J=10.7 and 6.6 Hz, H-6'), 4.28–4.35 and 4.43–4.55 (7H, 2 sets of m, H-1, H-2', H-3', H-4', H-6', H-5' and —CH(CO₂H)₂), 4.38 (1H, dd, J=10.4 and 4.8 Hz, H-1), 5.17–5.22 (1H, m, H-2), 3.52 (1H, d, J=3.5 Hz, H-1'), 5.92 (1H, J=15.4 and 7.3 Hz, H-4), 6.08 (1H, dt, J=15.4 and 6.6 Hz, H-5), 6.29 (1H, br t, H-3), 7.36–7.40, 7.45–7.49 and 8.24–8.28 (5H, 3 sets of m, aromatic H), 8.80 (1H, d, J=8.6 Hz, —NH—).

Preparation of the sodium salt of the title compound

The diacid from the above procedure (0.083 g, 0.089 mmol) was reacted by the general procedure as described in Example 6 and afforded the 20 sodium salt of the title compound (0.085 g, 97%) as a beige foam.

IR (film) $v_{max}$ (cm⁻¹): 3700–3000 (NH), 2920, 2850 (C—H), 1720, 1650,1600 (C=O).

¹H NMR 400 MHz (CD₃OD) δ (ppm): 0.83 (6H, m, 2×—CH₃), 1.21–1.39 (46H, m, —(CH₂)₁₃— and —(CH₂)₁₀—), 1.53 (2H, m, —CH₂—),1.98–2.19 (6H —NHCOCH₂—, =CH—CH₂— and —CH₂—CH(CO₂Na)₂), 5.21 (1H, t, J=6.9 Hz, —CH(CO₂Na)₂), 3.46–3.80 (10H, m, H-1, H-2', H-3', H-4', H-5', H-6' and —OCH₂—), 4.35 (1H, m, H-2), 4.88 (1H, d, J=2.5 Hz, H-1'), 5.46 (1H, dd, J=14.8 and 8.0 Hz, H-4), 5.53 (1H, br t, H-3), 5.84 (1H, dt, J=14.8 and 6.4 Hz, H-5), 7.39–7.43, 7.51–7.55 and 7.96–7.98 (5H, 3 sets of m, aromatic H).

EXAMPLE 21

(2S,3R,4E)-3-Benzoyloxy-2-hexadecanoylamino-1-[2-O-(5,5-di-tert-butyloxycarbonylpent-1-yl)-3-O-benzoyl-4,6-di-O-acetyl-α-D-galactopyranosyloxy]-4-octadecene

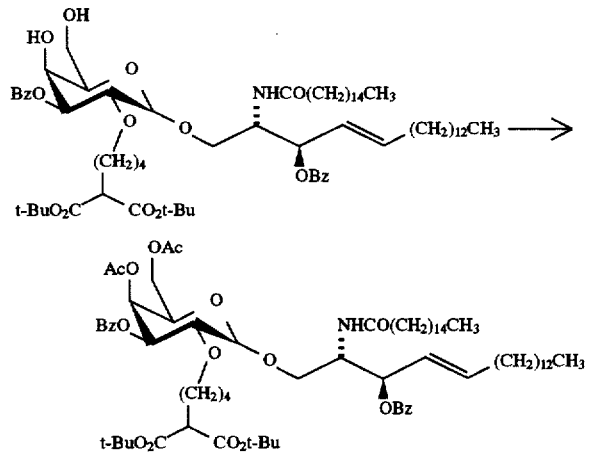

A solution of (2S,3R,4E)-3-benzoyloxy-2-hexadecanoylamino-1-[2-O-(5,5-di-tert-butyloxycarbonylpent-1-yl)-3-O-benzoyl-α-D-galactopyranosyloxy]-4-octadecene described in Example 3-1 (0.234 g, 0.198 mmol) in pyridine (1 mL) was treated with acetic anhydride (2 mL) at 5° C. The resulting mixture was stirred at 22° C. overnight, then concentrated under vacuum with toluene (2 mL). The residue was co-evaporated with toluene (3×2 mL) and purified by silica gel chromatography (0 to 28% ethyl acetate/hexane) to give the title material (0.248 g, 99%) as a colorless oil.

IR (CH₂Cl₂) $v_{max}$ (cm⁻¹): 3700, 3440 (N—H), 3050, 2980, 2930, 2920, 2840 (C—H), 1745, 1720, 1670 (C=O).

¹H NMR 400 MHz (CDCl₃) δ (ppm): 0.89 (6H, br t, 2×—CH₃), 1.23–1.38 (48H, m, —(CH₂)₁₃— and —(CH₂)₁₁—), 1.43 (18H, s, 2×—OtBu), 1.52–1.75 (6H, m, —CH₂—CH(CO₂tBu)₂ and —(CH₂)₂—), 1.98–2.06 (2H, m, =CH—CH₂—), 2.03 and 2.10 (2×3H, 2 s, 2×—OAc), 2.24 (2H, m, —NHCOCH₂—), 2.95 (1H, t, J=7.5 Hz, —CH(CO₂tBu)₂), 3.51 (1H, dt, J=9.2 and 6.8 Hz, —OCH₂—), 3.68 (1H, dt, J=9.2 and 6.5 Hz, —OCH₂—), 3.79 (1H, dd, J=10.9 and 3.3 Hz, H-1), 3.84–3.87 (2H, m, H-1 and H-2'), 4.03 (1H, dd, $J_{AB}$=11.3 and $J_{AX}$=7.1 Hz, H-6'), 4.10 (1H, dd, $J_{AB}$=11.3 and J=$_{BX}$5.9 Hz, H-6'), 4.23 (1H, br t, H-5'), 4.54 (1H, m, H-2), 5.01 (1H, d, J=3.5 Hz, H-1'), 5.48 (1H, dd, J=10.5 and 3.4 Hz, H-3'), 5.54 (1H, dd, J=15.2 and 7.8 Hz, H-4), 5.58 (1H, d, J=3.4 Hz, H-4'), 5.63 (1H, t, J=7.8 Hz, H-3), 5.90 (1H, dt, J=15.2 and 6.7 Hz, H-5), 6.10 (1H, d, J=9.3 Hz, —NH—), 7.44–7.47, 7.53–7.59, 7.96–7.98 and 8.04–8.06 (10H, 4 sets of m, aromatic H).

Anal. Calcd. for C₇₃H₁₁₅NO₁₆: C, 69.44; H, 9.18; N, 1.11. Found: C, 69.49; H, 9.12; N, 1.22.

EXAMPLE 22

(2S,3R,4E)-3-Benzoyloxy-2-hexadecanoylamino-1-[2-O-(5,5-di-carboxypent-1-yl)-3-O-benzoyl-4,6-di-O-acetyl-α-D-galactopyranosyloxy]-4-octadecene

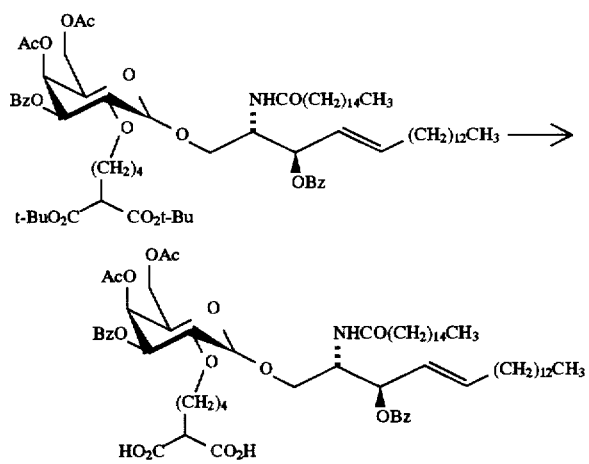

(2S,3R,4E)-3-Benzoyloxy-2-hexadecanoylamino-1-[2-O-(5,5-di-tert-butyloxycarbonylpent-1-yl)-3-O-benzoyl-4,6-di-O-acetyl-α-D-galactopyranosyloxy]-4-octadecene (0.231 g, 0.18 mmol) was reacted by the general procedure as described in Example 6 and afforded the title compound (0.156 g, 72%) as a beige solid.

IR (nujol) $v_{max}$ (cm⁻¹): 3700–2400 (broad, O—H, N—H and C—H), 1750,1725, 1640 (C=O).

¹H NMR 400 MHz (pyridine-d₅) δ (ppm): 0.86 (6H, t, J=6.6 Hz, 2×—CH₃), 1.25 (44H, m, —(CH₂)₁₂— and —(CH₂)₁₀—), 1.42, 1.65–1.76 and 1.89 (2H, 4H and 2H, 3 sets of m, —(CH₂)₂— and 2×—CH₂—), 2.04 and 2.09 (6H, 2 s, 2×—OAc), 2.04–2.12 (2H, m, —CH₂—CH(CO₂H)₂), 2.28 (2H, m, =CH—CH₂—), 2.52 (2H, m, —NHCOCH₂—), 3.65 (1H, dt, J=9.2 and 6.8 Hz, —OCH₂—), 3.77 (1H, t, J=7.4 Hz, —CH(CO₂H)₂), 3.83 (1H, dt, J=9.2 and 6.2 Hz, —OCH₂—), 4.23 (1H, dd, J=10.6 and 5.8 Hz, H-1), 4.28 (1H, dd, J=10.1 and 3.5 Hz, H-2'), 4.38–4.44 (2H, m, H-6' and H-1), 4.50 (1H, dd, J=11.2 and 6.1 Hz, H-6'), 4.67 (1H, br t, H-5'), 5.17 (1H, m, H-2), 5.54 (1H, d, J=3.4 Hz, H-1'), 5.90–5.99 (3H, m, H-3', H-4 and H-4'), 6.09 (1H, dt, J=15.4 and 6.7 Hz, H-5), 6.27 (1H, t, J=7.1 Hz, H-3), 7.43–7.53 and 8.24–8.29 (10H, 2 sets of m, aromatic H), 8.97 (1H, d, J=8.7 Hz, —NH—).

Preparation of the sodium salt of the title compound

The diacid from the above procedure (0.150 g, 0.13 mmol) was reacted by the general procedure as described in Example 6 and afforded the sodium salt of the title compound (0.158 g, 100%).

IR (nujol) $v_{max}$ (cm$^{-1}$): 3700–3100 (broad, N—H), 2920, 2850 (C—H), 1750, 1725, 1650, 1600 (C=O).

$^1$H NMR 400 MHz (CD$_3$OD) δ (ppm): 0.89 (6H, br t, 2×—CH$_3$), 1.25–1.39 (48H, m, —(CH$_2$)$_{11}$— and —(CH$_2$)$_{13}$—), 1.50, 1.62,1.77 (3×2H, 3 sets of m, 3×—CH$_2$—), 1.97 and 2.06 (6H, 2 s, 2×—OAc), 1.97–2.08 (2H, m, =CH—CH$_2$—), 2.25 (2H, t, J=7.4 Hz, —NHCOCH$_2$—), 2.99 (1H, t, J=6.9 Hz, —CH(CO$_2$Na)$_2$), 3.49 (1H, m, —OCH$_2$—), 3.60 (1H, dt, J=9.2 and 7.2 Hz, —OCH$_2$—), 3.75 (1H, dd, J=10.4 and 5.5 Hz, H-1), 3.89 (1H, dd overlapped by H-2', H-1), 3.91 (1H, dd overlapped by H-1, H-2'), 4.02 (1H, dd, J$_{AB}$=11.2 and J$_{AX}$=7.0 Hz, H-6'), 4.10 (1H, dd, J$_{AB}$=11.2 and J$_{BX}$=6.2 Hz, H-6'), 4.29 (1H, br t, H-5'), 4.47 (1H, m, H-2), 5.08 (1H, d, J=3.5 Hz, H-1'), 5.44 (1H, dd, J=10.5 and 3.5 Hz, H-3'), 5.53 (1H, br d, H-4'), 5.54 (1H, dd, J=15.0 and 7.8 Hz, H-4), 5.62 (1H, t, J=7.6 Hz, H-3), 5.93 (1H, dt, J==15.0 and 6.8 Hz, H-5), 7.46–7.50, 7.58–7.62, 7.94–7.96 and 8.02–8.05 (10H, 4 sets of m, aromatic H).

EXAMPLE 23

(2S,3R,4E)-3-Benzoyloxy-2-hexadecanoylamino-1-[4-O-(3,3-di-tert-butyloxycarbonylprop-1-yl)-α-D-galactopyranosyloxy]-4-octadecene A. Ethyl 4,6-O-benzylidene-2,3-di-O-para-methoxybenzyl-1-thio-β-D-galactopyranoside

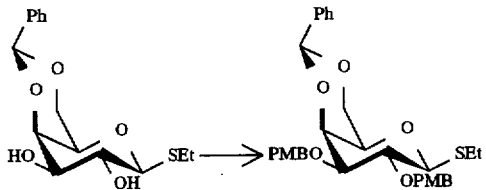

A solution of ethyl 4,6-O-benzylidene-1-thio-β-D-galactopyranoside [Nilsson & all. J. Carboxy. Chem. 10(6) 1023 (1991)] (2.0 g, 6.4 mmol) in dimethylformamide (25 mL) was added under argon to a suspension of sodium hydride (2.0 g, 8.33 mmol, previously washed with hexane). The mixture was allowed to stir for 1.5 h after which para-methoxybenzyl chloride (4.75 mL, 29.0 mmol) was added in slowly. The reaction mixture was allowed to react at ~22° C. for 18 h, cooled down to 5° C. and treated slowly with cold 1M aqueous sodium bicarbonate solution. The crude aqueous mixture was extracted with ethyl acetate (4×100 mL). The organic extracts were combined, washed with 1M aqueous sodium bicarbonate (2×100 mL), water (3×100 mL), brine (100 mL) and dried over anhydrous magnesium sulfate. The residue upon solvent evaporation was crystallized from ethyl acetate and hexane to give the title compound (2.69 g, 75%).

IR (CH$_2$Cl$_2$) $v_{max}$ (cm$^{-1}$): 3060–2860 (C—H).

$^1$H NMR 200 MHz (CDCl$_3$) δ (ppm): 1.33 (3H, t, J=7.3 Hz, —CH$_3$), 2.60–2.91 (2H, m, —SCH$_2$—), 3.34 (1H, br s, H-5), 3.55 (1H, dd, J=9.2 and 3.5 Hz, H-3), 3.80 (6H, s,2×—OCH$_3$), 3.86 (1H, t, J=9.4 Hz, H-2), 3.96 (1H, dd, J=12.4 and 1.6 Hz, H-6), 4.11 (1H, d, J=3.2 Hz, H-4), 4.30 (1H, dd, J=12.3 and 1.4 Hz, H-6), 4.41 (1H, d, J=9.6 Hz, H-1), 4.70 (1H, d, J$_{AB}$=11.9 Hz, —OCH$_2$Ar), 4.72 (1H, d, J$_{AB}$=11.9 Hz, —OCH$_2$Ar), 4.77 (1H, d, J$_{AB}$=9.8 Hz, —OCH$_2$Ar), 4.82 (1H, d, J$_{AB}$=9.8 Hz, —OCH$_2$Ar), 5.469 (1H, s, —OCHO—), 6.82–6.90, 7.26–7.40, 7.51–7.56 (13H, 3 sets of m, aromatic H).

B. Ethyl 2,3-di-O-para-methoxybenzyl-1-thio-β-D-galactopyranoside

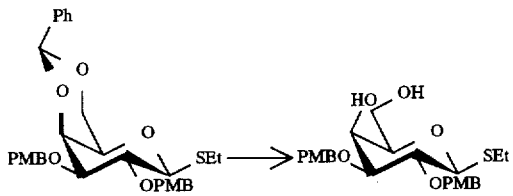

A solution of ethyl 4,6-O-benzylidene-2,3-di-O-para-methoxybenzyl-1-thio-β-D-galactopyranoside (2.6 g, 4.8 mmol) in tetrahydrofuran (80 mL) was treated with 3N aqueous hydrochloric acid (20 mL). The mixture was allowed to react for 30 h after which it was neutralized with solid sodium bicarbonate and diluted with ethyl acetate. The aqueous layer was saturated with sodium chloride and removed. The organic layer was dried over anhydrous magnesium sulfate and the solvent removed under vacuum to give a solid that was triturated in ethyl acetate and hexane and afforded the title material (2.0 g, 90%).

IR (CH$_2$Cl$_2$) $v_{max}$ (cm$^{-1}$): 3600–3200 (OH), 3000–2820 (C—H).

$^1$H NMR 400 MHz (CDCl$_3$) δ (ppm): 1.32 (3H, t, J=7.4 Hz, —CH$_3$), 2.05–2.13 (1H, m, —OH-6), 2.60 (1H, br s, —OH-4), 2.68–2.84 (2H, m, —SCH$_2$—), 3.48 (1H, t, J=5.5 Hz, H-5), 3.53 (1H, dd, J=8.9 and 3.3 Hz, H-3), 3.63 (1H, t, J=9.3 Hz, H-2), 3.76–3.82 (1H, m, H-6), 3.81 and 3.82 (6H, 2s, 2×—OCH$_3$), 3.93–4.00 (1H, m, H-6), 4.01 (1H, br t, J=1.5 Hz, H-4), 4.42 (1H, d, J=9.7 Hz, H-1), 4.63, 4.66, 4.69 (2H, ABq, J=11.7 Hz, —OCH$_2$Ar), 4.70 (1H, d, J$_{AB}$=9.9 Hz, —OCH$_2$Ar), 4.81 (1H, d, J$_{AB}$=11.7 Hz, —OCH$_2$Ar), 6.86–6.90, 7.26–7.35 (8H, 3 sets of m, aromatic H).

C. Ethyl 2,3,6-tri-O-para-methoxybenzyl-1-thio-β-D-galactopyranoside

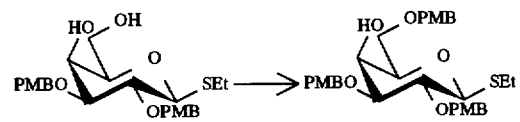

A solution of ethyl 2,3-di-O-para-methoxybenzyl-1-thio-β-D-galactopyranoside (4.18 g, 9.00 mmol) in dimethylformamide (dried over calcium hydride, 20 mL) was treated with sodium hydride (0.416 g, 60% dispersion in oil, 10.4 mmol) and the mixture was stirred at 25° C. for 0.75 hour, then cooled down to -25° C. The mixture was treated dropwise with p-methoxybenzylchloride and stirred at -20° C. for 6 hours. After dilution with ethyl acetate (210 mL), the mixture was washed with water (50 mL and 3×15 mL), dried over anhydrous magnesium sulfate, filtered and concentrated. The residue was purified by silica gel chromatography (6% ethyl acetate/dichloromethane) and afforded the title compound (2.00 g, 38%) along with ethyl 2,3,4,6-tetra-O-para-methoxybenzyl-1-thio-β-D-galactopyranoside (0.726 g, 11%). The title compound was crystallized from isopropanol.

m.p.: 62°–64° C.

[α]$_D^{22}$:+3.6° (c=1.1, CHCl$_3$).

IR (KBr) $v_{max}$ (cm$^{-1}$): 3520 (O—H), 2960, 2930, 2910, 2870, 2840 (C—H), 1615.

$^1$H NMR 400 MHz (CDCl$_3$) δ (ppm): 1.32 (3H, t, J=7.4 Hz, —SCH$_2$CH$_3$), 2.49 (1H, d, J=1.9 Hz, —OH), 2.74 (2H, m, —SCH₂—), 3.51 (1H, dd, J=9.0 and 3.2 Hz, H-3), 3.54 (1H, br t, H-5), 3.64 (1H, br t, H-2), 3.70 (1H, dd, J$_{AB}$=9.9 and J$_{AX}$=5.7 Hz, H-6), 3.75 (1H, dd, J$_{AB}$=9.9 and J$_{BX}$=6.0 Hz, H-6), 3.82 (9H, s, 3×—OCH₃), 4.06 (1H, br s, H-4), 4.41 (1H, d, J=9.7 Hz, H-1) 4.51 and 4.52 (2H, 2 d, J$_{AB}$=11.7 Hz, —OCH₂Ar), 4.65 and 4.67 (2H, 2 d, J$_{AB}$=11.3 Hz, —OCH₂Ar), 4.70 and 4.80 (2H, 2 d, J=9.9 Hz, —OCH₂Ar), 6.81–6.90 and 7.22–7.35 (12H, 2 sets of m, aromatic H).

Anal. Calcd. for C₃₂H₄₀O₈S: C, 65.73; H, 6.90; S, 5.48. Found: C, 65.58; H, 6.84; S, 5.79.

D. Ethyl 2,3,6-tri-O-para-methoxybenzyl-4-O-tert-butyloxycarbonylmethyl-1-thio-β-D-galactopyranoside

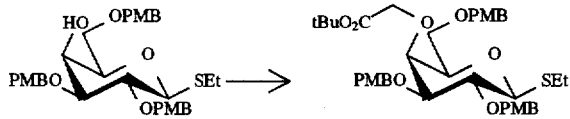

Ethyl 2,3,6-tri-O-para-methoxybenzyl-1-thio-β-D-galactopyranoside (1.6 g, 2.7 mmol) was treated by the general procedure as described in Example 1-C and afforded the title compound (1.23 g, 65%). The title compound was recrystallized form isopropanol.

m.p.: 82°–84° C.
[α]$_D$²²: −6.2° (c=1.1, CHCl₃).
IR (KBr) ν$_{max}$ (cm⁻¹): 2930, 2910 (C—H), 1740 (C=O), 1615.
¹H NMR 400 MHz (CDCl₃) δ (ppm): 1.31 (3H, t, J=7.4 Hz, —SCH₂CH₃), 1.47 (9H, s, —OtBu), 2.75 (2H, m, —SCH₂—), 3.49 (1H, dd, J=9.3 and 2.6 Hz, H-3), 3.54 (1H, t, J=6.1 Hz, H-5), 3.69 (1H, dd, J=9.7 and 5.9 Hz, H-6), 3.81, 3.82 and 3.82 (9H, 3 s, 3×—OCH₃), 3.84 (1H, t, J=9.4 Hz, H-2), 3.90 (1H, br s, H-4), 3.90 (1H, dd overlapped by H-4, H-6), 4.26 and 4.31 (2H, 2 d, J$_{AB}$=16.3 Hz, —OCH₂CO—), 4.40 (1H, d, J=9.6 Hz, H-1), 4.50 (2H, br s, —OCH₂Ar), 4.64 (2H, br s, —OCH₂Ar), 4.69 and 4.80 (2H, 2 s, J$_{AB}$=9.9 Hz, —OCH₂Ar), 6.86–6.89 and 7.26–7.33 (12H, 3 sets of m, aromatic H).

Anal. Calcd. for C₃₈H₅₀O₁₀S: C, 65.31; H, 7.21; S, 4.59. Found: C, 65.12; H, 7.12; S, 4.63.

E. Ethyl 2,3,6-tri-O-para-methoxybenzyl-4-O-(2-hydroxyeth-1-yl)-1-thio-β-D-galactopyranoside

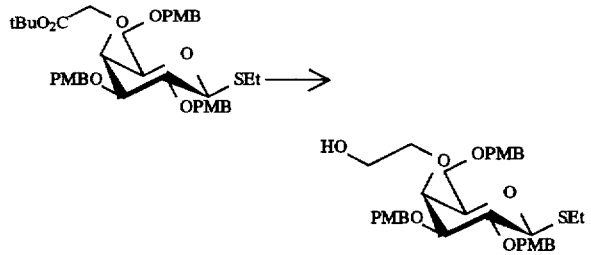

Ethyl 2,3,6-tri-O-para-methoxybenzyl-4-O-tert-butyloxycarbonylmethyl-1-thio-β-D-galactopyranoside (1.14 g, 1.63 mmol) was reacted by the general procedure as described in Example 1-D and afforded the title compound (0.743 g, 73%). The title compound was triturated in hexanes.

m.p.: 48°–50° C.
[α]$_D$²²: +6.8° (c=1.08, CHCl₃).
IR (KBr) ν$_{max}$ (cm⁻¹): 3460 (O—H), 2910,2870 (C—H), 1615.
¹H NMR 400 MHz (CDCl₃) δ (ppm): 1.31 (3H, t, J=7.4 Hz, —SCH₂CH₃), 1.6 (1H, br s, —OH), 2.73 (2H, m, —SCH₂—), 3.49 (1H, dd, J=9.4 and 3.0 Hz, H-3), 3.48–3.82 (7H, m, H-6, H-4, H-5 and —O(CH₂)₂O—), 3.59 (1H, dd, J=9.0 and 5.3 Hz, H-6), 3.70 (1H, t, J=9.6 Hz, H-2), 3.81 and 3.82 (9H, 2 s, 3×—OCH₃), 4.39 (1H, d, J=9.7 Hz, H-1), 4.46 (2H, br s, —OCH₂Ar), 4.69 and 4.71 (2H, 2, d J$_{AB}$=11.4 Hz, —OCH₂Ar), 4.69 (1H, d, J=9.9 Hz, —OCH₂Ar), 4.81 (1H, d, J=9.9 Hz, —OCH₂Ar), 6.86–6.90 and 7.23–7.34 (12H, 2 sets of m, aromatic H).

Anal. Calcd. for C₃₄H₄₄O₉S: C, 64.95; H, 7.05; S, 5.10. Found: C, 64.55; H, 7.00; S, 5.00.

F. Ethyl 2,3,6-tri-O-para-methoxybenzyl-4-O-(2-methanesulfonyloxyeth-1-yl)-1-thio-β-D-galactopyranoside

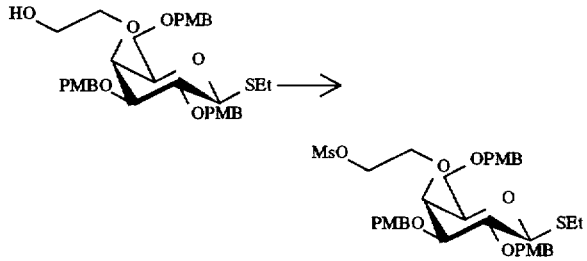

Ethyl 2,3,6-tri-O-para-methoxybenzyl-4-O-(2-hydroxyeth-1-yl)-1-thio-β-D-galactopyranoside (0.490 g, 0.78 mmol) was reacted by the general procedure as described in Example 1-E and afforded the title compound (0.471 g, 86%).

[α]$_D$²²: +11.3° (c=1.3, CHCl₃).
IR (film) ν$_{max}$ (cm⁻¹): 2930, 2870 (C—H), 1610.
¹H NMR 400 MHz (CDCl₃) δ (ppm): 1.30 (3H, t, J=7.4 Hz, —SCH₂CH₃), 2.71 (2H, m, —SCH₂—), 2.99 (3H, s, —OSO₂CH₃), 3.49 (1H, dd, J=9.3 and 2.8 Hz, H-3'), 3.53–3.82 (6H, m, —OCH₂—, H-2, H-4, H-6 and H-5), 3.81 and 3.82 (9H, 2 s, 3×—OCH₃), 4.11 (1H, ddd, J=11.3, 5.2 and 3.3 Hz, —OCH₂—), 4.26 (1H, ddd, J=11.4, 5.1 and 3.3 Hz, —CH₂OMs), 4.34 (1H, ddd, J=11.4, 7.0 and 3.2 Hz, —CH₂OMs), 4.39 (1H, d, J=9.6 Hz, H-1), 4.46 and 4.48 (2H, 2 d, J$_{AB}$=11.4 Hz, —OCH₂Ar), 4.64 and 4.68 (2H, 2 d, J$_{AB}$=11.2 Hz, —OCH₂Ar), 4.68 and 4.78 (2H, 2 d, J$_{AB}$=9.8 Hz, —OCH₂Ar), 6.86–6.91 and 7.24–7.33 (12H, 2 sets of m, aromatic H).

Anal. Calcd. for C₃₅H₄₆O₁₁S₂·0.1 CH₂Cl₂: C, 58.93; H, 6.51; S, 8.96. Found: C, 58.85; H, 6.57; S, 8.60.

G. Ethyl 2,3,6-tri-O-para-methoxybenzyl-4-O-(3,3-di-tert-butyloxycarbonylprop-1-yl)-1-thio-β-D-galactopyranoside

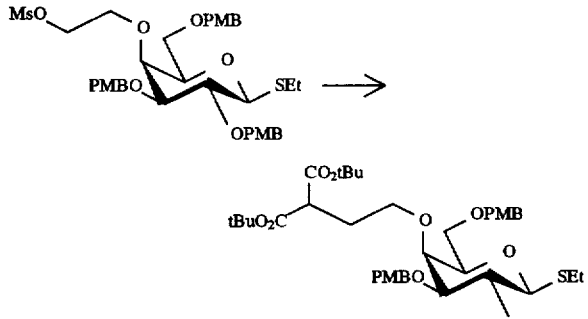

Ethyl 2,3,6-tri-O-para-methoxybenzyl-4-O-(2-methanesulfonyloxyeth-1-yl)-1-thio-β-D-galactopyranoside (0.282 g, 0.40 mmol) was reacted by the general procedure as described in Example 1-F except that tetrahydrofuran was used as solvent instead of a mixture of tetrahydrofuran/dimethylformamide (2:1). This afforded the title compound (0.226 g, 68%).

$[\alpha]_D^{22}$: +8.2° (c=0.7, CHCl$_3$).

IR (film) $v_{max}$ (cm$^{-1}$): 2980, 2930, 2870 (C—H), 1740, 1725 (C=O), 1610.

$^1$H NMR 400 MHz (CDCl$_3$) δ (ppm): 1.30 (3H, t, J=7.4 Hz, —SCH$_2$CH$_3$), 1.45 and 1.47 (2×9H, 2 s, 2×—OtBu), 2.09 (2H, m, —CH$_2$—CH(CO$_2$tBu)$_2$), 2.73 (2H, m, —SCH$_2$—), 3.45 (1H, t, J=7.2 Hz, —CH(CO$_2$tBu)$_2$), 3.46 (1H, dd overlapped by —CH(CO$_2$tBu)$_2$, H-3), 3.49 (1H, br t, H-5), 3.54 (1H, dt, J=9.3 and 6.3 Hz, —OCH$_2$—), 3.60 (1H, dd, J=9.2 and 5.4 Hz, H-6), 3.68 (1H, dd, J=9.2 and 7.5 Hz, H-6), 3.70 (1H, t, J=9.6 Hz, H-2), 3.73 (1H, br d, J=2.4 Hz, H-4), 3.81 and 3.81 (9H, 2 s, 3×—OCH$_3$), 3.98 (1H, dt, J=9.3 and 6.3 Hz, —OCH$_2$—), 4.37 (1H, d, J=9.6 Hz, H-1), 4.46 and 4.49 (2H, 2 d, $J_{AB}$=11.3 Hz, —OCH$_2$Ar), 4.61 and 4.66 (2H, 2 d, $J_{AB}$=11.5 Hz, —OCH$_2$Ar), 4.70 and 4.78 (2H, 2 d, $J_{AB}$=9.8 Hz, —OCH$_2$Ar), 6.84–6.90 and 7.25–7.33 (12H, 2 sets of m, aromatic H).

Anal. Calcd. for C$_{45}$H$_{62}$O$_{12}$S: C, 65.35; H, 7.56; S, 3.88. Found: C, 65.16; H, 7.54; S, 3.77.

H. (2S,3R,4E)-3-Benzoyloxy-2-azido-1-[4-O-(3,3-di-tert-butyloxycarbonylprop-1-yl)-2,3,6-tri-O-para-methoxybenzyl-β-D-galactopyranosyloxy]-4-octadecene and (2S,3R,4E)-3-benzoyloxy-2-azido-1-[2-O-(3,3-di-tert-butyloxycarbonylprop-1-yl)-2,3,6-tri-O-para-methoxybenzyl-β-D-galactopyranosyloxy]-4-octadecene

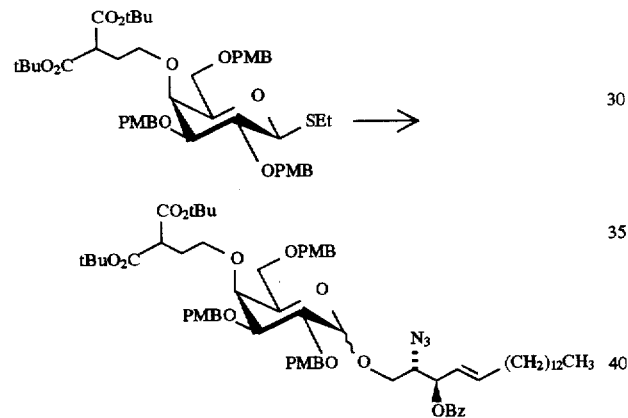

Ethyl 2,3,6-tri-O-para-methoxybenzyl-4-O-(3,3-di-tert-butyloxycarbonylprop-1-yl)-1-thio-β-D-galactopyranoside (2.00 g, 2.42 mmol) and (2S,3R,4E)-2-azido-3-benzoyloxy-4-octadecen-1-ol (0.945 g, 2.20 mmol) were reacted by the general procedure as described in Example 1-K and afforded the α-anomer (1.88 g, 72%) and the β-anomer (0.586 g, 22%) of the title compound.

α-anomer:

$[\alpha]_D^{22}$: +220° (c=0.95, CHCl$_3$).

IR (film) $v_{max}$ (cm$^{-1}$): 2930, 2860 (C—H), 2105 (N$_3$), 1725 (C=O).

$^1$H NMR 400 MHz (CDCl$_3$) δ (ppm): 0.89 (3H, t, J=6.8 Hz, —CH$_3$), 1.24–1.46 (22H, m, —(CH$_2$)$_{11}$—), 1.44 and 1.46 (18H, 2 s, 2×—OtBu), 1.99–2.16 (4H, m, =CH—CH$_2$— and —CH$_2$—CH(CO$_2$tBu)$_2$), 3.37 (1H, t, J=7.4 Hz, —CH(CO$_2$tBu)$_2$), 3.47–3.55 (3H, m, H-6' and —OCH$_2$—), 3.61 (1H, dd, J=9.2 and 6.8 Hz, H-6'), 3.70 (1H, br s, H-4'), 3.72 (1H, dd, J=10.9 and 4.4 Hz, H-1), 3.78, 3.80 and 3.81 (3×3H, 3 s, 3×—OCH$_3$), 3.78–3.99 (5H, m, H-2, H-1, H-2', H-3' and H-5'), 4.46 (2H, br s, —OCH$_2$Ar), 4.60 (1H, d, $J_{AB}$=11.4 Hz, —OCH$_2$Ar), 4.63 (1H, d, $J_{AB}$=11.6 Hz, —OCH$_2$Ar), 4.69 (1H, d, $J_{AB}$=11.4 Hz, —OCH$_2$Ar), 4.73 (1H, d, $J_{AB}$=11.6 Hz, —OCH$_2$Ar), 4.76 (1H, d, J=3.5 Hz, H-1'), 5.53 (1H, dd, J=15.1 and 7.8 Hz, H-4), 5.60 (1H, dd, J=7.8 and 4.1 Hz, H-3), 5.88 (1H, dt, J=15.1 and 6.8 Hz, H-5), 6.82–6.88, 7.15–7.31, 7.44–7.49, 7.56–7.60 and 8.02–8.08 (17H, 5 sets of m, aromatic H).

β-anomer:

$[\alpha]_D^{22}$: -2.4° (c=1.0, CHCl$_3$).

IR (film) $v_{max}$ (cm$^{-1}$): 2930, 2850 (C—H), 2100 (N$_3$), 1725 (C=O).

$^1$H NMR 400 MHz (CDCl$_3$) δ (ppm): 0.89 (3H, t, J=6.7 Hz, —CH$_3$), 1.24–1.46 (22H, m, —(CH$_2$)$_{11}$—), 1.45 and 1.46 (18H, 2 s, 2×—OtBu), 2.00–2.37 (4H, m, =CH—CH$_2$— and —CH$_2$—CH(CO$_2$tBu)$_2$), 3.39–3.43, 3.52–3.59, 3.67–3.77 and 3.87–4.02 (10H, 4 sets of m, H-1, H-2, H-2', H-3', H-6', —OCH$_2$— and —CH(CO$_2$tBu)$_2$), 3.47 (1H, t, J=6.4 Hz, H-5'), 3.69 (1H, br s, H-4'), 3.78 and 3.81 (3H and 6H, 2 s, 3×—OCH$_3$), 4.28 (1H, d, J=7.7 Hz, H-1'), 4.45 (1H, d, $J_{AB}$=11.2 Hz, —OCH$_2$Ar), 4.50 (1H, d, $J_{AB}$=11.2 Hz, —OCH$_2$Ar), 4.61 (1H, d, $J_{AB}$=11.8 Hz, —OCH$_2$Ar), 4.65 (1H, d, $J_{AB}$=11.8 Hz, —OCH$_2$Ar), 4.71 (1H, d, J=10.4 Hz, —OCH$_2$Ar), 4.84 (1H, d, J=10.4 Hz, —OCH$_2$Ar), 5.56 (1H, dd, J=15.4 and 7.9 Hz, H-4), 5.68 (1H, dd, J=7.9 and 3.7 Hz, H-3), 5.89 (1H, dt, J=15.4 and 6.7 Hz, H-5), 6.82–6.90, 7.20–7.33, 7.44–7.48, 7.56–7.60 and 8.07–8.09 (17H, 5 sets of m, aromatic H).

I. (2S,3R,4E)-3-Benzoyloxy-2-hexadecanoylamino-1-[4-O-(3,3-di-tert-butyloxycarbonylprop-1-yl)-2,3,6-tri-O-para-methoxybenzyl-α-D-galactopyranosyloxy]-4-octadecene

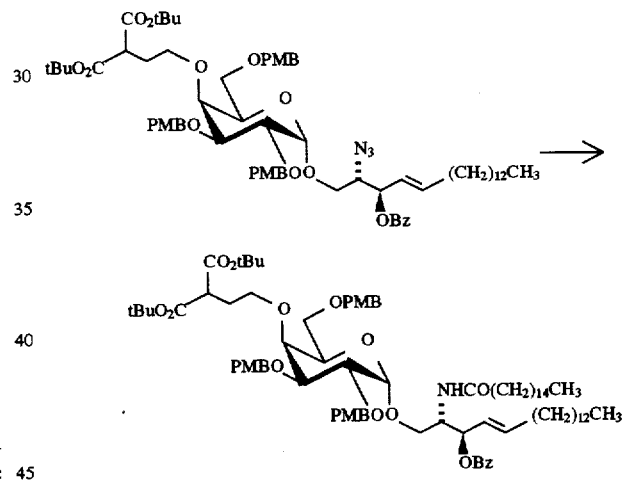

(2S,3R,4E)-3-Benzoyloxy-2-azido-1-[4-O-(3,3-di-tert-butyloxycarbonylprop-1-yl)-2,3,6-tri-O-para-methoxybenzyl-α-D-galactopyranosyloxy]-4-octadecene (1.6 g, 1.34 mmol) was reacted by the general procedure as described in Example 1-L and afforded the title compound (1.71 g, 91%). $[\alpha]_D^{22}$: +33° (c=0.75, CHCl$_3$).

IR (film) max (cm$^{-1}$): 3310 (N—H), 2920, 2850 (C—H), 1745, 1725, 1640 (C=O).

$^1$H NMR 400 MHz (CDCl$_3$) δ (ppm): 0.89 (6H, br t, 2×—CH$_3$), 1.21–1.29 (46H, m, —(CH$_2$)$_{10}$— and —(CH$_2$)$_{13}$—), 1.44 and 1.45 (2×9H, 2 s, 2×—OtBu), 1.55 (2H, m, —CH$_2$—), 1.94–2.13 (6H, m, —CH$_2$—CH(CO$_2$tBu)$_2$, =CH—CH$_2$— and —NHCOCH$_2$—), 3.34 (1H, t, J=7.4 Hz, —CH(CO$_2$tBu)$_2$), 3.47 (1H, dt, J=9.4 and 6.5 Hz, —OCH$_2$—), 3.51–3.59, 3.76–3.81 and 3.93–4.00 (5H, 3 sets of m, H-1, H-6', H-3', H-5' and —OCH$_2$—), 3.65 (1H, dd, J=11.6 and 3.3 Hz, H-1), 3.70 (1H, d, J=1.7 Hz, H-4'), 3.78 and 3.81 (6H and 3H, 2 s, 3×—OCH$_3$), 3.89 (1H, dd, J=10.1 and 3.6 Hz, H-2'), 3.99 (1H, t, J=6.5 Hz, H-5'), 4.40–4.46 (1H, m, H-2), 4.44 (1H, d, $J_{AB}$=11.6 Hz, —OCH$_2$Ar), 4.51 (1H, d, $J_{AB}$=11.6 Hz, —OCH₂Ar), 4.60 (1H, d, J_AB=11.4 Hz, —OCH₂Ar), 4.61 (2H, br d, —OCH₂Ar), 4.67 (1H, d, J_AB=11.4 Hz, —OCH₂Ar), 4.70 (1H, d, J=3.6 Hz, H-1'), 5.47 (1H, dd, J=15.3 and 7.6 Hz, H-4), 5.61 (1H, t, J=7.8 Hz, H-3), 5.81 (1H, dt, J=15.3 and 6.8 Hz, H-5), 6.30 (1H, d, J=9.4 Hz, —NH—), 6.79–6.88, 7.24–7.28, 7.42–7.46, 7.53–7.58 and 8.03–8.05 (17H, 5 sets of m, aromatic H).

J. (2S,3R,4E)-3-Benzoyloxy-2-hexadecanoylamino-1-[4-O-(3,3-di-tert-butyloxycarbonylprop-1-yl)-α-D-galactopyranosyloxy]-4-octadecene

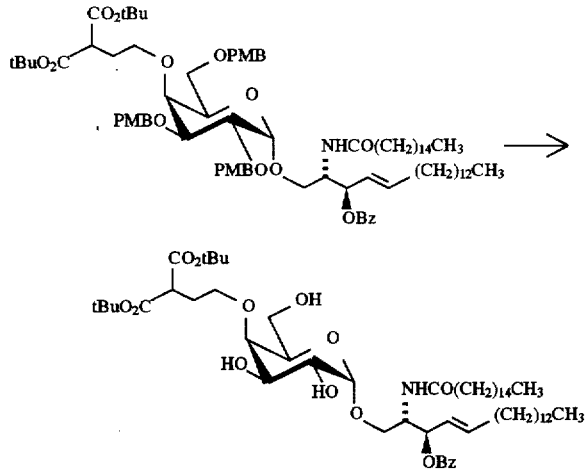

(2S,3R,4E)-3-Benzoyloxy-2-hexadecanoylamino-1-[4-O-(3,3-di-tert-butyloxycarbonylprop-1-yl)-2,3,6-tri-O-para-methoxybenzyl-α-D-galactopyranosyloxy]-4-octadecene (1.10 g, 0.782 mmol) was reacted by the general procedure as described in Example 9-A and afforded the title compound (0.690 g, 85%).

[α]_D²²: +38° (c=1.0, CHCl₃).

IR (film) ν_max (cm⁻¹): 3600–3150 (N—H and O—H), 2925, 2850 (C—H), 1745, 1725, 1645 (C=O).

¹H NMR 400 MHz (CDCl₃) δ (ppm): 0.89 (6H, t, J=6.7 Hz, 2×—CH₃), 1.13–1.26 (46H, m, —(CH₂)₁₀— and —(CH₂)₁₃—), 1.47 (18H, s, 2×—OtBu), 1.57–1.62 (2H, m, —CH₂—), 2.02–2.11 and 2.14–2.21 (4H and 2H, 2 sets of m, —NHCOCH₂—, =CH—CH₂— and —CH₂—CH(CO₂tBu)₂), 2.41 (1H, d, J=8.2 Hz, —OH), 2.66 (1H, t, J=6.0 Hz, —OH-6'), 2.90 (1H, d, J=5.7 Hz, —OH), 3.47 (1H, t, J=7.7 Hz, —CH(CO₂tBu)₂), 3.59 (1H, dt, J=9.5 and 5.5 Hz, —OCH₂—), 3.68–3.93 (9H, m, H-1, H-2', H-3', H-4', H-5', H-6', —OCH₂—), 4.55 (1H, m, H-2), 4.85 (1H, d, J=2.9 Hz, H-1'), 5.53 (1H, dd, J=15.2 and 7.4 Hz, H-4), 5.62 (1H, br t, H-3), 5.85–5.92 (1H, m overlapped by —NH—, H-5), 5.86 (1H, d, J=9.6 Hz, —NH—), 7.45–7.49, 7.58–7.61 and 8.03–8.05 (5H, 3 sets of m, aromatic H).

Anal. Calcd. for C₆₀H₁₀₃NO₁₃.0.3 H₂O: C, 68.51; H, 9.93; N, 1.34. Found: C, 68.41; H, 10.20; N, 1.36.

EXAMPLE 24

(2S,3R,4E)-3-Benzoyloxy-2-hexadecanoylamino-1-[4-O-(3,3-di-carboxyprop-1-yl)-α-D-galactopyranosyloxy]-4-octadecene

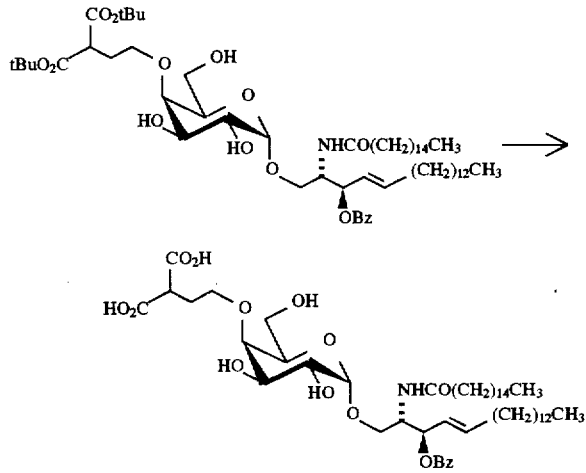

(2S,3R,4E)-3-Benzoyloxy-2-hexadecanoylamino-1-[4-O-(3,3-di-tert-butyloxycarbonylprop-1-yl)-α-D-galactopyranosyloxy]-4-octadecene (0.265 g, 0.253 mmol) was reacted by the general procedure as described in Example 6 and afforded the title material (0.210 g, 89%). [α]_D²²: +35° (c=1.0, CHCl₃).

IR (KBr) ν_max (cm⁻¹): 3700–2300 (broad, N—H and O—H), 2925, 2850 (C—H), 1725, 1645 (C=O).

¹H NMR 400 MHz (pyridine-d₅) δ (ppm): 0.85 (6H, t, J=6.7 Hz, 2×—CH₃), 1.24–1.25 (46H, m, —(CH₂)₁₀— and —(CH₂)₁₃—), 1.84 (2H, m, —CH₂—), 2.01 (2H, m, —CH₂—CH(CO₂H)₂), 2.44 (2H, t, J=7.4 Hz, —NHCOCH₂—), 2.78 (2H, m, =CH—CH₂—), 4.10 (1H, dd, J=10.8 and 6.7 Hz, H-6' or H-1), 4.21 (1H, br s, H-4'), 4.21–4.25, 4.31–4.41, 4.49–4.64 (9H, m, —CH(CO₂H)₂, —OCH₂—, H-2', H-3', H-5', H-6' and H-1), 5.18 (1H, m, H-2), 5.32 (1H, d, J=3.6 Hz, H-1'), 5.92 (1H, dd, J=15.5 and 7.3 Hz, H-4), 6.09 (1H, dt, J=15.5 and 6.4 Hz, H-5), 6.29 (1H, br t, H-3), 7.38–7.42, 7.49–7.52 and 8.21–8.23 (5H, 3 sets of m, aromatic H), 8.77 (1H, d, J=8.8 Hz, —NH—).

Anal. Calcd. for C₅₂H₈₇NO₁₃.0.45 CF₃CO₂H: C, 64.47; H, 8.94; N, 1.34. Found: C, 64.37; H, 8.86; N, 1.49.

Preparation of the sodium salt of the title compound

The above diacid (0.190 g, 0.203 mmol) was reacted by the general procedure as described in Example 6 and afforded the sodium salt of the title compound (0.195 g, 100%) as a white fluffy solid.

IR (KBr) ν_max (cm⁻¹): 3650–3100 (broad, N—H and O—H), 2925, 2850 (C—H), 1720, 1600 (C=O).

¹H NMR 400 MHz (CD₃OD) δ (ppm): 0.89 (6H, t, J=6.8 Hz, 2×—CH₃), 1.26–1.38 (46H, m, —(CH₂)₁₀— and —(CH₂)₁₃—), 1.59 (2H, m, —CH₂—), 2.04–2.09 (4H, m, =CH—CH₂— and —CH₂—CH(CO₂Na)₂), 2.21 (2H, m, —NHCOCH₂—), 3.62–3.83 (11H, m, H-1, H-2', H-3', H-4', H-5', H-6', —OCH₂— and —CH(CO₂Na)₂), 4.41 (1H, m, H-2), 4.73 (1H, d, J=3.1 Hz, H-1'), 5.52 (1H, dd, J=15.2 and 7.7 Hz, H-4), 5.62 (1H, br t, H-3), 5.89 (1H, dt, J=15.2 and 6.8 Hz, H-5), 7.45–7.49, 7.58–7.61 and 8.00–8.03 (5H, 3 sets of m, aromatic H).

EXAMPLE 25

(2S,3R,4E)-3-Benzoyloxy-2-hexadecanoylamino-1-[2-O-(3,3-di-tert-butyloxycarbonylprop-1-yl)-3-O-benzoyl-β-D-galactopyranosyloxy]-4-octadecene

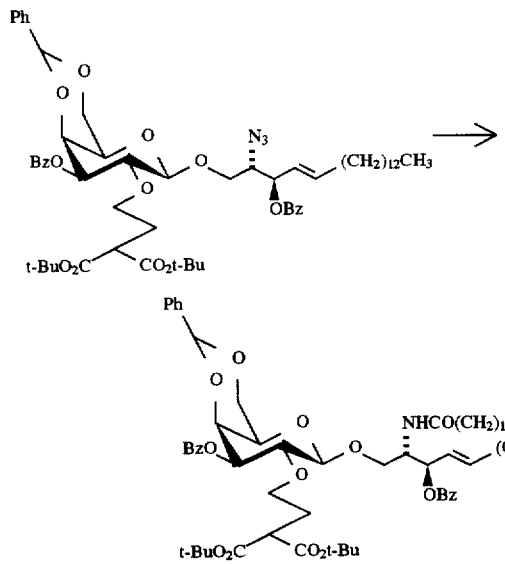

(2S,3R,4E)-3-Benzoyloxy-2-azido-1-[2-O-(3,3-di-tert-butyloxycarbonylprop-1-yl)-3-O-benzoyl-4,6-O-benzylidene-β-D-galactopyranosyloxy]-4-octadecene described in Example 1-K (0.467 g, 0.455 mmol) was reacted by the general procedure as described in Example 1-L and afforded the title compound (0.393 g, 70%).

$[\alpha]_D^{22}$: +36° (c=1.3, CHCl$_3$).

IR (film) $v_{max}$ (cm$^{-1}$): 2920, 2850 (C—H), 1725, 1680 (C=O).

$^1$H NMR 400 MHz (CDCl$_3$) δ (ppm): 0.90 (6H, t, J=6.7 Hz, 2×—CH$_3$), 1.24–1.36 (46H, m, —(CH$_2$)$_{13}$— and —(CH$_2$)$_{10}$—), 1.39 and 1.41 (18H, 2 s, 2×—OtBu), 1.53–1.60 (2H, m, —CH$_2$—), 2.00–2.12 (4H, m, —CH$_2$—CH(CO$_2$tBu)$_2$ and =CH—CH$_2$—), 2.21 (2H, t, J=7.4 Hz, —NHCOCH$_2$—), 3.26 (1H, t, J=7.2 Hz, —CH(CO$_2$tBu)$_2$), 3.50 (1H, br s, H-5'), 3.70 (1H, dt, J=9.6 and 5.9 Hz, —OCH$_2$—), 3.78 (1H, dd, J=10.1 and 7.7 Hz, H-2'), 3.76–3.83 (1H, m overlapped by H-2', —OCH$_2$—), 3.86 (1H, dd, J=11.1 and 3.5 Hz, H-1), 4.00 (1H, d, J=12.2 Hz, H-6'), 4.16–4.20 (2H, m, H-1 and H-6'), 4.41 (1H, d, J=7.7 Hz, H-1'), 4.45 (1H, d, J=3.6 Hz, H-4'), 4.52 (1H, m, H-2), 5.04 (1H, dd, J=10.1 and 3.6 Hz, H-3'), 5.45 (1H, s, —OCHO—), 5.54 (1H, dd, J=15.5 and 7.5 Hz, H-4), 5.69 (1H, t, J=7.5 Hz, H-3), 5.92 (1H, dt, J=15.5 and 6.7 Hz, H-5), 6.72 (1H, d, J=8.7 Hz, —NH—), 7.32–7.60 and 8.04–8.09 (15H, 2 sets of m, aromatic H).

Anal. Calcd. for C$_{74}$H$_{111}$NO$_{14}$: C, 71.75; H, 9.03; N, 1.13. Found: C, 71.77; H, 9.09; N, 1.23.

EXAMPLE 26

(2S,3R,4E)-3-Benzoyloxy-2-hexadecanoylamino-1-[2-O-(3,3-di-carboxyprop-1-yl)-3-O-benzoyl-β-D-galactopyranosyloxy]-4-octadecene

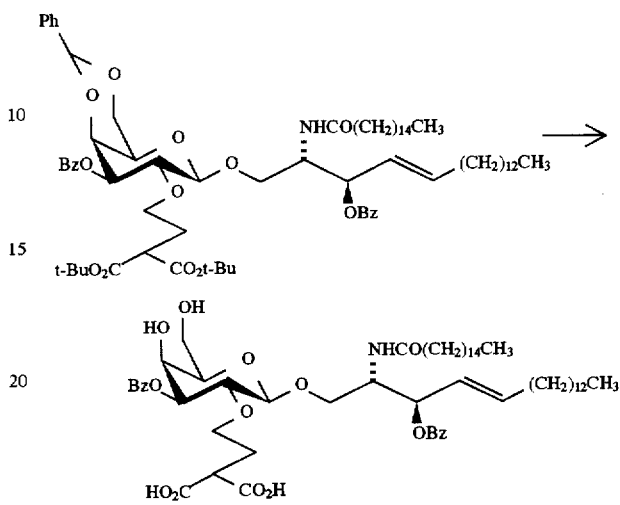

(2S,3R,4E)-3-Benzoyloxy-2-hexadecanoylamino-1-[2-O-(3,3-di-tert-butyloxycarbonylprop-1-yl)-3-O-benzoyl-β-D-galactopyranosyloxy]-4-octadecene (0.350 g, 0.28 mmol) was reacted by the general procedure as described in Example 6 and afforded the title compound (0.120 g, 41%).

$^1$H NMR 400 MHz (pyridine-d$_5$) δ (ppm): 0.85 (6H, t, J=6.7 Hz, 2×—CH$_3$), 1.23–1.41 (46H, m, —(CH$_2$)$_{13}$— and —(CH$_2$)$_{11}$—), 1.87 (2H, m, —CH$_2$—), 2.03 (2H, m, —CH$_2$—CH(CO$_2$H)$_2$), 2.54 (2H, t, J=7.3 Hz, —NHCOCH$_2$—), 2.76 (2H, m, =CH—CH$_2$—), 4.06 (1H, br t, H-5'), 4.20 (1H, t, J=7.2 Hz, —CH(CO$_2$H)$_2$), 4.26 (1H, dd, J=10.5 and 5.7 Hz, H-6'), 4.29–4.39 and 4.47–4.57 (3H, m, —OCH$_2$— and H-1), 4.36 (1H, dd, J=10.7 and 6.7 Hz, H-1), 4.49 (1H, dd, J=10.0 and 7.7 Hz, H-2'), 4.55 (1H, dd, J=10.5 and 6.7 Hz, H-6'), 4.93–4.96 (2H, m, H-1' and H-4'), 5.25 (1H, m, H-2), 5.55 (1H, dd, J=10.1 and 3.1 Hz, H-3'), 5.94 (1H, dd, J=15.4 and 7.1 Hz, H-4), 6.14 (1H, dt, J=15.4 and 6.7 Hz, H-5), 6.29 (1H, br t, H-3), 7.22–7.40, 7.45–7.49 and 8.23–8.28 (10H, m, aromatic H), 8.59 (1H, d, J=8.6 Hz, —NH—).

Anal. Calcd. for C$_{59}$H$_{91}$NO$_{14}$·H$_2$O: C, 67.08; H, 8.87; N, 1.33. Found: C, 67.02; H, 8.75; N, 1.83.

Preparation of the sodium salt of the title compound

The above diacid (0.119 g, 0.11 mmol) was reacted by the general procedure as described in Example 6 and afforded the sodium salt of the title compound (0.092 g, 77%) as a white fluffy solid. IR (KBr) $v_{max}$ (cm$^{-1}$): 3700–3100 (O—H), 2920, 2850 (C—H), 1715, 1650, 1600 (C=O).

$^1$H NMR 400 MHz (CD$_3$OD) δ (ppm): 0.82 (6H, t, J=6.7 Hz, 2×—CH$_3$), 1.19–1.32 (46H, m, —(CH$_2$)$_{13}$— and —(CH$_2$)$_{10}$—), 1.52 (2H, m, —CH$_2$—), 2.00 and 2.20 (4H and 2H, 2 sets of m, —NHCOCH$_2$—, =CH—CH$_2$— and —CH$_2$—CH(CO$_2$Na)$_2$), 3.04 (1H, t, J=7.0 Hz, —CH(CO$_2$Na)$_2$), 3.45–3.51, 3.63–3.70 and 3.76–3.82 (3H, 2H and 1H, 3 sets of m, —OCH$_2$—, H-2', H-5', H-6' and H-1), 3.77 (1H, dd, J=10.7 and 4.1 Hz, H-1), 3.99 (1H, dd, J=10.4 and 6.2 Hz, H-6'), 4.04 (1H, br d, H-4'), 4.34 (1H, d, J=7.6 Hz, H-1'), 4.41 (1H, m, H-2), 4.82 (1H, dd, J=10.2 and 3.4 Hz, H-3'), 5.50 (1H, dd, J=15.3 and 7.2 Hz, H-4), 5.61 (1H, t, J=7.2 Hz, H-3), 5.85 (1H, dt, J=15.3 and 7.6 Hz, H-5), 7.39–7.43, 7.49–7.54 and 7.95–8.02 (10H, m, aromatic H).

EXAMPLE 27

(2S,3R,4E)-3-Benzoyloxy-2-hexadecanoylamino-1-[3-O-(5,5-di-tert-butyloxycarbonylpent-1-yl)-2-O-benzoyl-β-D-galactopyranosyloxy]-4-octadecene A. (2S,3R,4E)-3-Benzoyloxy-2-hexadecanoylamino-1-[3-O-(5,5-di-tert-butyloxycarbonylpent-1-yl)-4,6-O-benzylidene-2-O-benzoyl-β-D-galactopyranosyloxy]-4-octadecene

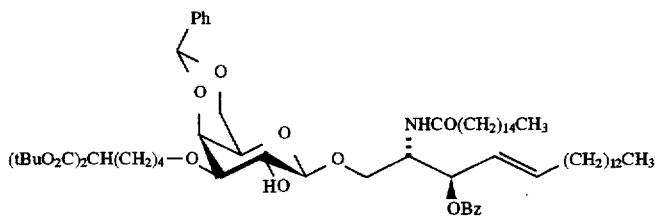

(2S ,3R,4E)-3-Benzoyloxy-2-hexadecanoylamino-1-[3-O-(5,5-di-tert-butyloxycarbonylpent-1-yl)-4,6-O-benzylidene-β-D-galactopyranosyloxy]-4-octadecene described in Example 13-B (0.350 g, 0.305 mmol) was reacted by the general procedure as described in Example 1-J and afforded the title compound (0.277 g, 72%) as a white gummy solid.

IR (CH$_2$Cl$_2$) ν$_{max}$ (cm$^{-1}$): 3050, 2980, 2930, 2850 (C—H), 1722, 1670 (C=O).

$^1$H NMR 400 MHz (CDCl$_3$) δ (ppm): 0.89 (6H, br t, 2×—CH$_3$), 1.11–1.40 and 1.47–1.57 (52H, 2 sets of m, —(CH$_2$)$_{13}$—, —(CH$_2$)$_{11}$— and —(CH$_2$)$_2$—), 1.41 and 1.42 (18H, 2 sx, 2×—OtBu), 1.65 (2H, m, —CH$_2$—CH(CO$_2$tBu)$_2$), 1.79 (2H, br t, —NHCOCH$_2$—), 1.99 (2H, qa, J=6.9 Hz, =CH—CH$_2$—), 2.87 (1H, t, J=7.5 Hz, —CH(CO$_2$tBu)$_2$), 3.45 (1H, dt, J=9.5 and 6.6 Hz, —OCH$_2$—), 3.49 (1H, br s, H-5'), 3.62–3.68 (1H, m overlapped by H-3', —OCH$_2$—), 3.66 (1H, dd, J=10.0 and 3.2 Hz, H-3'), 3.78 (1H, dd, J=10.4 and 4.0 Hz, H-1), 4.09 (1H, dd overlapped by H-1, H-6'), 4.12 (1H, dd, J=10.4 and 4.3 Hz, H-1), 4.27 (1H, d, J=12.0 Hz, H-6'), 4.33 (1H, d, J=3.2 Hz, H-4'), 4.41 (1H, m, H-2), 4.61 (1H, d, J=7.9 Hz, H-1'), 5.49 (1H, dd, J=15.3 and 7.1 Hz, H-4), 5.53 (1H, dd, J=10.0 and 8.0 Hz, H-2'), 5.57 (1H, s, —OCHO—), 5.58 (1H, t, J=6.9 Hz, H-3), 5.81 (1H, dt, overlapped by —NH—, H-5), 5.84 (1H, d, J=8.8 Hz, —NH—), 7.35–7.58 and 8.00–8.05 (15H, 2 sets of m, aromatic H).

Anal. Calcd. for C$_{76}$H$_{125}$NO$_{14}$: C, 72.06; H, 9.15; N, 1.11. Found: C, 72.30; H, 9.12; N, 1.27.

B. (2S,3R,4E)-3-Benzoyloxy-2-hexadecanoylamino-1-[3-O-(5,5-di-tert-butyloxycarbonylpent-1-yl)-2-O-benzoyl-β-D-galactopyranosyloxy]-4-octadecene

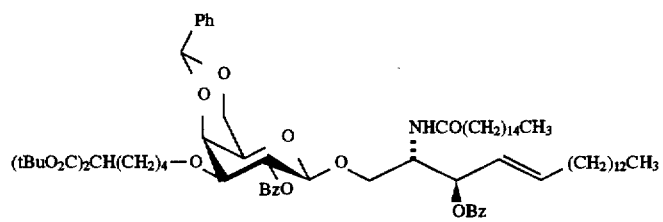

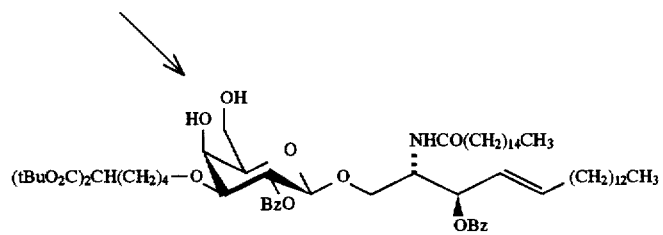

(2S,3R,4E)-3-Benzoyloxy-2-hexadecanoylamino-1-[3-O-(5,5-di-tert-butyloxycarbonylpent-1-yl)-4,6-O-benzylidene-2-O-benzoyl-β-D-galactopyranosyloxy]-4-octadecene (0.257 g, 0.2 mmol) was reacted by the general procedure as described in Example 1-M and afforded the title compound (0.190 g, 81%) as a white solid.

IR (CH$_2$Cl$_2$) v$_{max}$ (cm$^{-1}$): 3700–3400 (O—H), 3050, 2980, 2930, 2850 (C—H), 1722, 1670 (C=O).

$^1$H NMR 400 MHz (CDCl$_3$) δ (ppm): 0.89 (6H, br t, 2×—CH$_3$), 1.24–1.75 (55H, m, —(CH$_2$)$_{13}$—, —(CH$_2$)$_{11}$—, —(CH$_2$)$_2$—, —CH$_2$—CH(CO$_2$tBu)$_2$ and —OH), 1.44 and 1.43 (18H, 2 s, 2×—OtBu), 1.92 (2H, J=7.4 Hz, —NHCOCH$_2$—), 2.01 (2H, qa, J=6.9 Hz, =CH—CH$_2$—), 2.93 (1H, t, J=7.4 Hz, —CH(CO$_2$tBu)$_2$), 3.09 (1H, br s, —OH), 3.46 (1H, dt, J=9.5 and 6.4 Hz, —OCH$_2$—), 3.43–3.53 and 3.62–3.67 (2×2H, 2 sets of m, —OCH$_2$—, H-1 and H-5'), 3.73 (1H, dd, J=12.2 and 3.6 Hz, H-6'), 3.93 (1H, dd, J=12.2 and 6.2 Hz, H-6'), 3.98 (1H, dd, J=9.8 and 2.6 Hz, H-3'), 4.12 (1H, br d, H-4'), 4.44 (1H, m, H-2), 4.48 (1H, d, J=7.9 Hz, H-1'), 5.42 (1H, dd, J=9.7 and 8.1 Hz, H-2'), 5.49 (1H, dd, J=15.3 and 7.9 Hz, H-4), 5.67 (1H, t, J=7.8 Hz, H-3), 5.82 (1H, d, J=9.4 Hz, —NH—), 5.89 (1H, dt, J=15.3 and 6.9 Hz, H-5), 7.33–7.47, 7.52–7.60 and 8.02–8.06 (10H, 3 sets of m, aromatic H).

EXAMPLE 28

(2S,3R,4E)-3-Benzoyloxy-2-hexadecanoylamino-1-[3-O-(5,5-di-carboxypent-1-yl)-2-O-benzoyl-β-D-galactopyranosyloxy]-4-octadecene

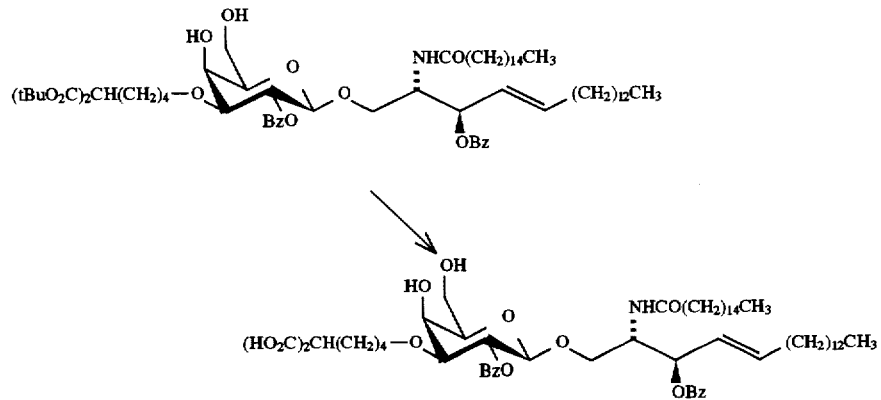

(2S,3R,4E)-3-Benzoyloxy-2-hexadecanoylamino-1-[3-O-(5,5-di-tert-butyloxycarbonylpent-1-yl)-2-O-benzoyl-β-D-galactopyranosyloxy]-4-octadecene (0.182 g, 0.15 mmol) was reacted by the general procedure as described in Example 2, procedure No. 1 and afforded the title compound (0.155 g, 97%) as a beige solid.

IR (nujol) v$_{max}$ (cm$^{-1}$): 3700–2400 (O—H, N—H), 2930, 2850 (broad, C—H), 25 1720,1650 (C=O).

$^1$H NMR 400 MHz (pyridine-d$_5$) δ (ppm): 0.85 (6H, t, J=6.7 Hz, 2×—CH$_3$), 1.20–1.29 and 1.49–1.75 (46H and 6H, 2 sets of m, —(CH$_2$)$_{13}$—, —(CH$_2$)$_{11}$— and —(CH$_2$)$_2$—), 1.93 and 2.07–2.21 (2H and 4H, 2 sets of m, —NHCOCH$_2$—, =CH—CH$_2$—, —CH$_2$—CH(CO$_2$H)$_2$), 3.46 (1H, m, —OCH$_2$—), 3.62 (1H, t, J=7.4 Hz, —CH(CO$_2$H)$_2$), 3.71 (1H, m, —OCH$_2$—), 3.86 (1H, dd, J=9.9 and 2.9 Hz, H-3'), 4.11 (1H, t, J=6.2 Hz, H-5'), 4.30 (1H, dd, J=10.6 and 5.1 Hz, H-1), 4.37–4.42 (2H, m, H-1 and H-6'), 4.48 (1H, dd, J=10.8 and 6.2 Hz, H-6'), 4.68 (1H, d, J=2.7 Hz, H-4'), 5.11 (1H, m, H-2), 5.13 (1H, d, J=7.9 Hz, H-1'), 5.80 (1H, dd, J=15.5 and 7.2 Hz, H-4), 5.92 (1H, dt, J=15.5 and 6.6 Hz, H-5), 6.13 (1H, brt, H-3), 6.26 (1H, dd, J=9.8 and 8.1 Hz, H-2'), 7.36–7.39, 7.45–7.54, 8.19–8.21 and 8.32–8.36 (11H, 4 sets of m, aromatic H and —NH—).

Preparation of the sodium salt of the title compound

The above diacid (0.135 g, 0.13 mmol) was reacted by the general procedure as described in Example 6 and afforded the sodium salt of the title compound (0.139 g, 100%) as a white fluffy solid.

IR (nujol) v$_{max}$ (cm$^{-1}$): 3700–2400 (O—H, N—H), 2930, 2850 (broad, C—H), 1720, 1650, 1600 (C=O).

$^1$H NMR 400 MHz (CD$_3$OD) δ (ppm): 0.83 (6H, br t, 2×—CH$_3$), 1.14–1.46 (52H, m, —(CH$_2$)$_{13}$—, —(CH$_2$)$_{11}$— and —(CH$_2$)$_2$—), 1.67 and 1.80–1.95 (2H and 4H, 2 sets of m, —NHCOCH$_2$—, —CH$_2$—CH(CO$_2$Na)$_2$ and =CH—CH$_2$—), 2.93 (1H, t, J=7.1 Hz, —CH(CO$_2$Na)$_2$), 3.38 (1H, m, —OCH$_2$—), 3.54–3.72 (6H, m, —OCH$_2$—, H-6', H-1, H-5' and H-3'), 3.93 (1H, dd, J=9.9 and 6.3 Hz, H-6'), 4.06 (1H, br s, H-4'), 4.33 (1H, m, H-2), 4.56 (1H, d, J=8.0 Hz, H-1'), 5.29 (1H, brt, H-2'), 5.38 (1H, dd, J=1 5.0 and 7.7 Hz, H-4), 5.44 (1H, br t, H-3), 5.66 (1H, dt, J=15.0 and 6.9 Hz, H-5), 7.37–7.43, 7.51–7.53 and 7.91–7.98 (10H, 3 sets of m, aromatic H).

EXAMPLE 29

(2S,3R,4E)-3-Benzoyloxy-2-hexadecanoylamino-1-[2-O-(5,5-di-tert-butyloxycarbonylpent-1-yl)-3,4-O-isopropylidene-6-O-tert-butyldimethylsilyl-β-D-galactopyranosyloxy]-4-octadecene A. (2S,3R,4E)-3-Benzoyloxy-2-azido-1-[2-O-(5,5-di-tert-butyloxycarbonylpent-1-yl)-3,4-O-isopropylidene-6-O-tert-butyldimethylsilyl-α-D-galactopyranosyloxy]-4-octadecene and (2S,3R,4E)-3-benzoyloxy-2-azido-1-[2-O-(5,5-di-tert-butyloxycarbonylpent-1-yl)-3,4-O-isopropylidene-6-O-tert-butyldimethylsilyl-β-D-galactopyranosyloxy]-4-octadecene

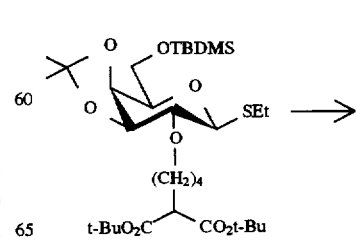

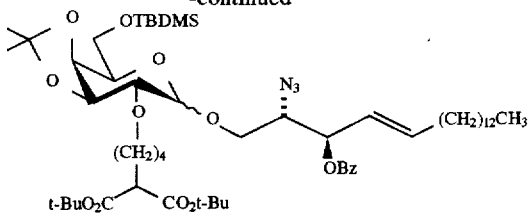

Ethyl 3,4-O-isopropylidene-6-O-tert-butyldimethylsilyl-2-O-(5,5-di-tert-butyloxycarbonylpent-1-yl)-1-thio-β-D-galactopyranoside described in Example 3-B (1.0 g, 1.54 mmol) and (2S,3R,4E)-2-azido-3-benzoyloxy-4-octadecen-1-ol (0.640 g, 1.48 mmol) were reacted by the general procedure as described in Example 1-K except that toluene was used as solvent instead of dioxane. This afforded the a-anomer (0.595 g, 39%) and the β-anomer (0.321 g, 21%) of the title compound.

α-anomer:

IR ($CH_2Cl_2$) $v_{max}$ (cm$^{-1}$): 3050, 2980, 2930, 2855 (C—H), 2105 (—$N_3$), 1720 (C=O).

$^1$H NMR 400 MHz (CDCl$_3$) δ (ppm): 0.08 (6H, s, —Si(CH$_3$)$_2$), 0.89 (3H, t, J=7.0 Hz, —CH$_3$), 0.91 (9H, s, —SitBu), 1.25–1.51 and 1.58–1.66 (26H, 2 sets of m, —(CH$_2$)$_{11}$— and —(CH$_2$)$_2$—), 1.45 (18H, s, 2×—OtBu), 1.33 and 1.51 (2×3H, 2 s, —C(CH$_3$)$_2$—), 1.81 and 2.07 (2×2H, 2 qa, =CH—CH$_2$— and —CH$_2$—CH(CO$_2$tBu)$_2$), 3.11 (1H, t, J=7.5 Hz, —CH(CO$_2$tBu)$_2$), 3.44 (1H, dd, J=6.9 and 3.4 Hz, H-2'), 3.52 (1H, dd, J=10.8 and 8.0 Hz, H-1), 3.61 (2H, t, J=6.7 Hz, —OCH$_2$—), 3.78 (1H, dd, J=10.0 and 6.6 Hz, H-6'), 3.83–3.88 (2H, m, H-1 and H-6'), 3.99 (1H, m, H-2), 4.04 (1H, td, J=6.5 and 2.0 Hz, H-5'), 4.21 (1H, dd, J=5.6 and 2.2 Hz, H-4'), 4.20–4.26 (1H, m overlapped by H-4', H-3'), 4.91 (1H, d, J=3.4 Hz, H-1'), 5.54–5.61 (2H, m, H-3 and H-4), 5.93 (1H, dt, J=14.1 and 6.8 Hz, H-5), 7.44–7.48, 7.56–7.60 and 8.06–8.08 (5H, 3 sets of m, aromatic H).

Anal. Calcd. for C$_{55}$H$_{93}$N$_3$O$_{13}$Si: C, 64.99; H, 9.22; N, 4.13. Found: C, 65.05; H, 8.97; N, 4.23.

β-anomer:

IR ($CH_2Cl_2$) $v_{max}$ (cm$^{-1}$): 3050, 2980, 2930, 2860 (C—H), 2105 (—$N_3$), 1720 (C=O).

$^1$H NMR 400 MHz (CDCl$_3$) δ (ppm): 0.07 (6H, s, —Si(CH$_3$)$_2$), 0.89 (12H, m, —SitBu and —CH$_3$), 1.25–1.52 and 1.61–1.68 (26H, 2 sets of m, —(CH$_2$)$_{11}$— and —(CH$_2$)$_2$—), 1.33 and 1.53 (2×3H, 2 s, —C(CH$_3$)$_2$—), 1.45 (18H, s, 2×—OtBu), 1.83 (2H, qa, J=7.8 Hz, —CH$_2$—CH(CO$_2$tBu)$_2$), 2.07 (2H, qa, J=6.9 Hz, =CH—CH$_2$—), 3.13 (1H, brt, H-2'), 3.25 (1H, t, J=7.4 Hz, —CH(CO$_2$tBu)$_2$), 3.57 (1H, dd, J=10.1 and 5.2 Hz, H-1), 3.69 (1H, dt, J=9.5 and 6.8 Hz, —OCH$_2$—), 3.66–3.82 and 3.98–4.01 (3H, 2 sets of m, H-5', H-2 or —OCH$_2$—), 3.81 (1H, dd, J=9.8 and 6.1 Hz, H-6'), 3.86 (1H, dd, J=9.8 and 7.1 Hz, H-6'), 3.93 (1H, dd, J=10.1 and 7.6Hz, H-1), 4.04 (1H, brt, H-3'), 4.16 (1H, dd, J=5.5 and 1.8 Hz, H-4'), 4.20 (1H, d, J=7.9 Hz, H-1'), 5.57 (1H, dd, J=15.1 and 8.0 Hz, H-4), 5.63 (1H, dd, J=8.0 and 4.0 Hz, H-3), 5.94 (1H, dt, J=15.1 and 6.9 Hz, H-5), 7.44–7.47, 7.56–7.59 and 8.06–8.08 (5H, 3 sets of m, aromatic H).

Anal. Calcd. for C$_{55}$H$_{93}$N$_3$O$_{13}$Si: C, 64.99; H, 9.22; N, 4.13. Found: C, 65.30; H, 9.08; N, 4.16.

B. (2S,3R,4E)-3-Benzoyloxy-2-hexadecanoylamino-1-[2-O-(5,5-di-tert-butyloxycarbonylpent-1-yl)-3,4-O-isopropylidene-6-O-tert-butyldimethylsilyl-β-D-galactopyranosyloxy]-4-octadecene

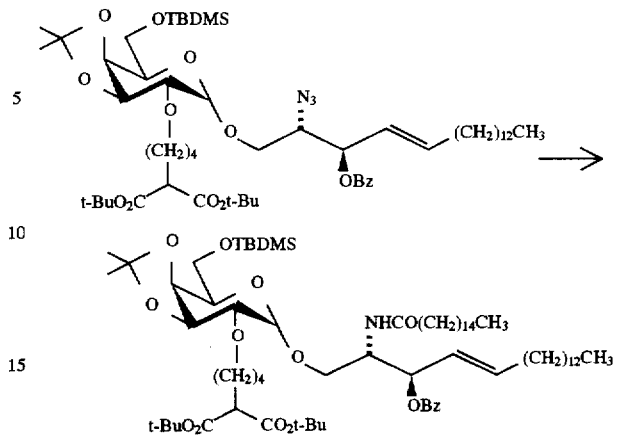

(2S,3R,4E)-3-Benzoyloxy-2-azido-1-[2-O-(5,5-di-tert-butyloxycarbonylpent-1-yl)-3,4-O-isopropylidene-6-O-tert-butyldimethylsilyl-β-D-galactopyranosyloxy]-4-octadecene (0.465 g, 0.45 mmol) was reacted by the general procedure as described in Example 1-L and afforded the title compound (0.406 g, 73%) as a beige solid.

IR ($CH_2Cl_2$) $v_{max}$ (cm$^{-1}$): 3440 (N—H), 3050, 2980, 2930, 2860 (C—H), 1720, 1675 (C=O).

$^1$H NMR 400 MHz (CDCl$_3$) δ (ppm): 0.07 (6H, s, —Si(CH$_3$)$_2$), 0.87–0.90 (15H, m, —SitBu and 2×—CH$_3$), 1.24–1.49 and 1.60–1.63 (76H, m, —(CH$_2$)$_{13}$—, —(CH$_2$)$_{11}$—, —(CH$_2$)$_2$—, 2×—OtBu and —C(CH$_3$)$_2$—), 1.83 and 2.02 (2×2H, 2 qa, —CH$_2$—CH(CO$_2$tBu)$_2$ and =CH—CH$_2$—), 2.20 (2H, m, —NHCOCH$_2$—), 3.12 (1H, t, J=7.5 Hz, —CH(CO$_2$tBu)$_2$), 3.40 (1H, dd, J=6.3 and 3.4 Hz, H-2'), 3.60 (2H, t, J=6.6 Hz, —OCH$_2$—), 3.71–3.77, 3.80–3.86 and 4.18–4.21 (3×2H, 3 sets of m, H-1, H-6', H-4' and H-5'), 4.02 (1H, t, J=6.4 Hz, H-3'), 4.49 (1H, m, H-2), 4.80 (1H, d, J=3.3 Hz, H-1'), 5.53 (1H, dd, J=15.1 and 7.5 Hz, H-4), 5.60 (1H, t, J=7.3 Hz, H-3), 5.87 (1H, dt, J=15.1 and 6.9 Hz, H-5), 6.11 (1H, d, J=9.1 Hz, —NH—), 7.43–7.47, 7.55–7.59 and 8.03–8.05 (5H, 3 sets of m, aromatic H). Anal. Calcd. for C$_{71}$H$_{125}$NO$_{13}$Si: C, 69.40; H, 10.25; N, 1.14. Found: C, 69.40; H, 10.13; N, 1.27.

EXAMPLE 30

(2S,3R,4E)-3-Benzoyloxy-2-hexadecanoylamino-1-[2-O-(5,5-di-carboxypent-1-yl)-α-D-galactopyranosyloxy]-4-octadecene

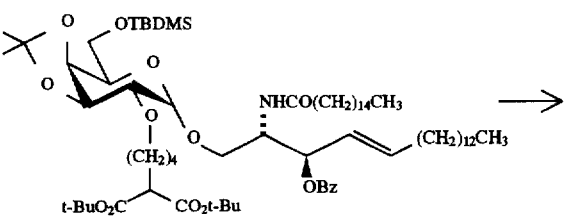

103

-continued

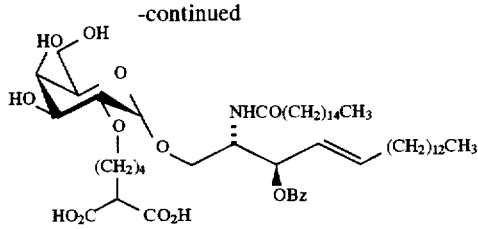

(2S,3R,4E)-3-Benzoyloxy-2-hexadecanoylamino-1-[2-O-(5,5-di-tert-butyloxycarbonylpent-1-yl)-3,4-O-isopropylidene-6-O-tert-butyldimethylsilyl-α-D-galactopyranosyloxy]-4-octadecene (0.376 g, 0.30 mmol) was reacted by the general procedure as described in Example 6 and afforded the title compound (0.175 g, 61%) as a white solid.

IR (nujol) $v_{max}$ (cm$^{-1}$): 3700–3100 (N—H, O—H), 2930, 2860 (C—H), 1720, 1645 (C=O).

$^1$H NMR 400 MHz (pyridine-d$_5$) δ (ppm): 0.85 (6H, t, J=6.7 Hz, 2×—CH$_3$), 1.21–1.40, 1.72–1.78 and 1.84–1.89 (52H, 3 sets of m, —(CH$_2$)$_{13}$—, —(CH$_2$)$_{11}$— and —(CH$_2$)$_2$—), 2.02 and 2.33 (2×2H, 2qa, —CH$_2$—CH(CO$_2$H)$_2$ and =CH—CH$_2$—), 2.51 (2H, t, J=7.4 Hz, —NHCOC H$_2$—), 3.66 (1H, m, —OCH$_2$—), 3.78 (1H, m, —OCH$_2$—), 3.83 (1H, t, J=7.3 Hz, —CH(CO$_2$H)$_2$), 4.18–4.22, 4.37–4.42 and 4.43–4.50 (2H and 6H, H-1, H-6', H-5', H-4', H-3' and H-2'), 5.20 (1H, m, H-2), 5.44 (1H, d, J=3.5 Hz, H-1'), 5.92 (1H, dd, J=15.4 and 7.4 Hz, H-4), 6.09 (1H, dt, J=15.4 and 6.7 Hz, H-5), 6.25 (1H, br t, H-3), 7.41–7.51 and 8.25–8.27 (5H, 2 sets of m, aromatic H), 8.79 (1H, d, J=8.9 Hz, —NH—).

Preparation of the sodium salt of the title compound

The above diacid (0.170 g, 0.18 mmol) was reacted by the general procedure as described in Example 6 and afforded the sodium salt of the title compound (0.172 g, 100%) as a white fluffy solid.

IR (nujol) $v_{max}$ (cm$^{-1}$): 3700–3100 (N—H, O—H), 2920, 2850 (C—H), 1710, 1645, 1585 (C=O).

$^1$H NMR 400 MHz (CD$_3$OD) δ (ppm): 0.83 (6H, t, J=6.8 Hz, 2×—CH$_3$), 1.19–1.38, 1.55, 1.77 (48H, 4H and 2H, 3 sets of m, —(CH$_2$)$_{13}$—, —(CH$_2$)$_{11}$—, —(CH$_2$)$_2$— and —C H$_2$—CH(CO$_2$Na)2), 2.00 (2H, qa, J=6.9 Hz, =CH—C H$_2$—), 2.15 (2H, t, —NHCOCH$_2$—), 3.03 (1H, t, J=7.2 Hz, —CH(CO$_2$Na)$_2$), 3.44 (1H, m, —OCH$_2$—), 3.50 (1H, dd, J=9.9 and 3.6 Hz, H-2'), 3.56–3.65 and 3.73–3.76 (4H and 2H, 2 sets of m, H-1, H-6', —OCH$_2$— and H-3'), 3.69 (1H, t, J=6.0 Hz, H-5'), 3.80 (1H, d, J=3.1 Hz, H-4'), 4.36 (1H, m, H-2), 4.85 (1H, d, J=3.5 Hz, H-1'), 5.45 (1H, dd, J=15.0 and 7.9 Hz, H-4), 5.52 (1H, br t, H-3), 5.84 (1H, dt, J=15.0 and 6.9 Hz, H-5), 7.40–7.44, 7.52–7.56 and 7.95–7.97 (5H, 3 sets of m, aromatic H).

104

EXAMPLE 31

(2S,3R,4E)-3-Benzoyloxy-2-hexadecanoylamino-1-[2-O-(5,5-di-tert-butyloxycarbonylpent-1-yl)-3,4-O-isopropylidene-6-O-tert-butyidimethylsilyl-β-D-galactopyranosyloxy]-4-octadecene

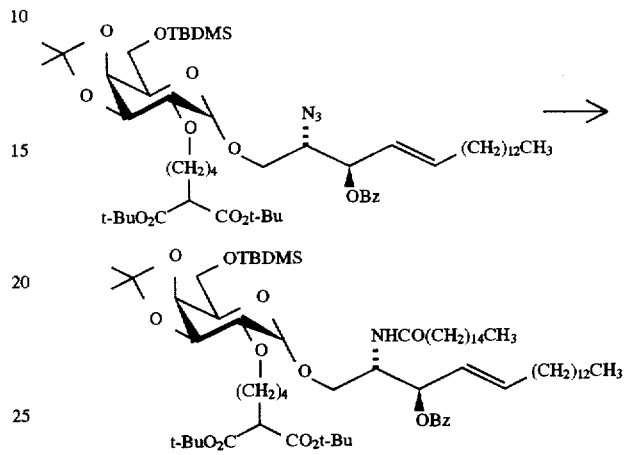

(2S,3R,4E)-3-Benzoyloxy-2-azido-1-[2-O-(5,5-di-tert-butyloxycarbonylpent-1-yl)-3,4-O-isopropylidene-6-O-tert-butyldimethylsilyl-α-D-galactopyranosyloxy]-4-octadecene described in Example 29-A (0.473 g, 0.465 mmol) was reacted by the general procedure as described in Example 1-L and afforded the title compound (0.396 g, 69%) as a slightly yellow oil.

IR (CH$_2$Cl$_2$) $v_{max}$ (cm$^{-1}$): 3690 (N—H), 3050, 2980, 2930, 2860 (C—H), 1720, 1670 (C=O).

$^1$H NMR 400 MHz (CDCl$_3$) δ (ppm): 0.04 and 0.05 (6H, 2 s, —Si(CH$_3$)$_2$), 0.88–0.91 (15H, m, —SitBu and 2×—CH$_3$), 1.32 and 1.51 (2×3H, 2 s, —C(CH$_3$)$_2$—), 1.24–1.39 and 1.47–1.67 (52H, 2 sets of m, —(CH$_2$)$_2$—, —(CH$_2$)$_{13}$— and —(CH$_2$)$_{11}$—), 1.47 (18H, s, 2×—OtBu), 1.80 (2H, qa, J=7.8 Hz, —CH$_2$—CH(CO$_2$tBu)$_2$), 2.02 (2H, qa, J=7.0 Hz, =CH—CH$_2$—), 2.15 (2H, m, —NHCOC H$_2$—), 3.11 (1H, t, J=7.5 Hz, —CH(CO$_2$tBu)$_2$), 3.24 (1H, brt, H-2'), 3.58–3.77 and 4.15–4.18 (5H and 1H, 2 sets of m, —OCH$_2$—, H-6', H-5' and H-1), 3.81 (1H, dd, J=9.5 and 7.3 Hz, H-1 or H-6'), 4.04 (1H, dd, J=5.7 and 6.5 Hz, H-3'), 4.16 (1H, dd, J=5.7 and 1.4 Hz, H-4'), 4.17 (1H, d, J=7.8 Hz, H-1'), 4.46 (1H, m, H-2), 5.51 (1H, dd, J=15.1 and 7.4 Hz, H-4), 5.58 (1H, br t, H-3), 5.86 (1H, dt, J=15.1 and 6.9 Hz, H-5), 6.29 (1H, d, J=9.1 Hz, —NH—), 7.42–7.45, 7.54–7.57 and 8.03–8.06 (5H, 3 sets of m, aromatic H).

Anal. Calcd. for C$_{71}$H$_{125}$NO$_{13}$Si: C, 69.40; H, 10.25; N, 1.14. Found: C, 69.70; H, 10.31; N, 1.24.

EXAMPLE 32

(2S,3R,4E)-3-Benzoyloxy-2-hexadecanoylamino-1-[2-O-(5,5-di-carboxypent-1-yl)-β-D-galactopyranosyloxy]-4-octadecene

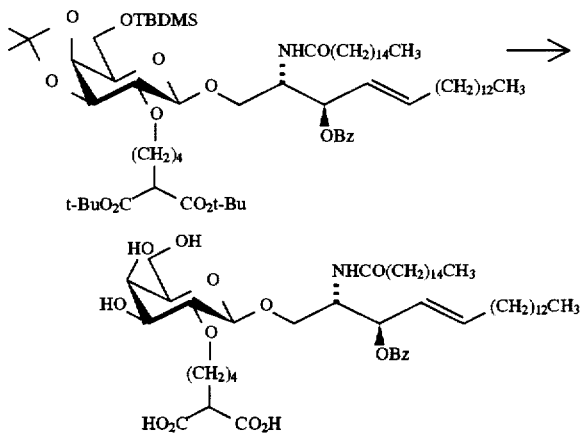

(2S,3R,4E)-3-Benzoyloxy-2-hexadecanoylamino-1-[2-O-(5,5-di-tert-butyloxycarbonylpent-1-yl)-3,4-O-isopropylidene-6-O-tert-butyldimethylsilyl-β-D-galactopyranosyloxy]-4-octadecene (0.358 g, 0.29 mmol) was reacted by the general procedure as described in Example 6 and afforded the title compound (0.217 g, 78%) as a white solid.

IR (nujol) $v_{max}$ (cm$^{-1}$): 3700–2400 (O—H, N—H), 2920, 2850 (C—H), 1710, 1640 (C=O).

$^1$H NMR 400 MHz (pyridine-d$_5$) δ (ppm): 0.85 (6H, t, J=6.8 Hz, 2×—CH$_3$), 1.23–1.44 and 1.79–1.91 (52H, 2 sets of m, —(CH$_2$)$_{13}$—, —(CH$_2$)$_{11}$— and —(CH$_2$)$_2$—), 2.04 (2H, qa, J=6.9 Hz, =CH—CH$_2$—), 2.40 (2H, br qa, —C H$_2$—CH(CO$_2$H)$_2$), 2.48 (2H, t, J=7.4 Hz, —NHCOC H$_2$—), 3.90 (1H, t, J=7.4 Hz, —CH(CO$_2$H)$_2$), 3.92–4.07 (4H, m, H-2', H-3', H-5' and —OCH$_2$—), 4.17–4.24 (1H, m, —OCH$_2$—), 4.23 (1H, dd, J=10.6 and 5.1 Hz, H-1), 4.34 (1H, dd, J$_{AB}$=10.9 and J$_{AX}$=6.0 Hz, H-6'), 4.40 (1H, dd, J$_{AB}$=10.9 and J$_{BX}$=6.0 Hz, H-6'), 4.48 (1H, dd, J=10.6 and 6.3 Hz, H-1), 4.49 (1H, br s, H-4'), 4.79 (1H, d, J=7.0 Hz, H-1'), 5.20 (1H, m, H-2), 5.93 (1H, dd, J=15.4 and 7.4 Hz, H-4), 6.11 (1H, dt, J=15.4 and 6.7 Hz, H-5), 6.26 (1H, brt, H-3), 7.36–7.40, 7.45–7.55 and 8.23–8.25 (5H, 3 sets of m, aromatic H), 8.52 (1H, d, J=8.7 Hz, —NH—).

Preparation of the sodium salt of the title compound

The above diacid (0.168 g, 0.17 mmol) was reacted by the general procedure as described in Example 6 and afforded the sodium salt of the title compound (0.167 g, 100%) as a white fluffy solid.

IR (nujol) $v_{max}$ (cm$^{-1}$): 3700–2500 (O—H, N—H), 2920, 2850 (C—H), 1710, 1640, 1575 (C=O).

$^1$H NMR 400 MHz (CD$_3$OD) δ (ppm): 0.89 (6H, t, J=6.8 Hz, 2×—CH$_3$), 1.25–1.53, 1.59–1.64 and 1.7–1.9 (54H, 3 sets of m, —(CH$_2$)$_{13}$—, —(CH$_2$)$_{11}$—, —C H$_2$—CH(CO$_2$Na)$_2$ and —(CH$_2$)$_2$—), 2.08 (2H, qa, J=6.9 Hz, =CH—CH$_2$—), 2.20 (2H, m, —NHCOCH$_2$—), 3.09 (1H, t, J=6.8 Hz, —CH(CO$_2$Na)$_2$), 3.31–3.29 (1H, m, H-2'), 3.43 (1H, t, J=6.0 Hz, H-5'), 3.48 (1H, dd, J=9.5 and 3.3 Hz, H-3'), 3.64–3.66 (3H, m, —OCH$_2$— and H-6'), 3.76 (1H, dd, J=10.6 and 5.3 Hz, H-1), 3.80 (1H, d, J=3.2 Hz, H-4'), 3.79–3.86 (1H, m, —OCH$_2$—), 3.96 (1H, dd, J=10.6 and 6.3 Hz, H-1), 4.25 (1H, d, J=7.7 Hz, H-1'), 4.47 (1H, m, H-2), 5.55 (1H, dd, J=15.2 and 7.7 Hz, H-4), 5.63 (1H, dd, J=7.5 and 6.0 Hz, H-3), 5.89 (1H, dt, J=15.2 and 6.9 Hz, H-5), 7.44–7.48, 7.57–7.61 and 8.00–8.02 (5H 3 sets of m, aromatic H).

What is claimed is:

1. A compound of the formula

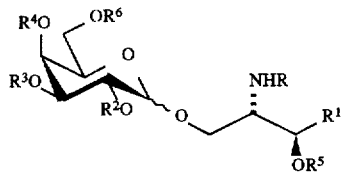

wherein

R is an acyl residue of a fatty acid:

R$^1$ is —(CH=CH)$_m$—(CH$_2$)$_n$—CH$_3$;

R$^2$, R$^3$, R$^4$, R$^5$ and R$^6$ each are independently hydrogen, unsubstituted or substituted (lower)alkanoyl, arylalkyl or arylcarbonyl wherein said substituent is selected from the group consisting of halogen, C$_{1-4}$ alkyl, trifluoromethyl, hydroxy and C$_{1-4}$ alkoxy provided that one of R$^2$, R$^3$, R$^4$ and R$^6$ substituents is —(CH$_2$)$_p$—CH(CO$_2$R$^7$)$_2$;

m is an integer of 0 or 1;

n is an integer of from 5 to 14 inclusive;

p is an integer of from 2 to 6 inclusive; and

R$^7$ is hydrogen, a hydrolyzable ester group or a cation to form a non-toxic pharmaceutically acceptable salt;

or a solvate or hydrate thereof.

2. A compound of claim 1 having the formula

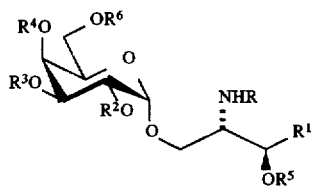

wherein

R is an acyl residue of a fatty acid:

R$^1$ is —(CH=CH)$_m$—(CH$_2$)$_n$—CH$_3$;

R$^2$, R$^3$, R$^4$, R$^5$ and R$^6$ each are independently hydrogen, unsubstituted or substituted (lower)alkanoyl, arylalkyl or arylcarbonyl wherein said substituent is selected from the group consisting of halogen, C$_{1-4}$ alkyl, trifluoromethyl, hydroxy and C$_{1-4}$ alkoxy provided that one of R$^2$, R$^3$, R$^4$ and R$^6$ substituents is —(CH$_2$)$_p$—CH(CO$_2$R$^7$)$_2$;

m is an integer of 0 or 1;

n is an integer of from 5 to 14 inclusive;

p is an integer of from 2 to 6 inclusive; and

R$^7$ is hydrogen, a hydrolyzable ester group or a cation to form a non-toxic pharmaceutically acceptable salt;

or a solvate or hydrate thereof.

3. A compound of claim 1 having the formula

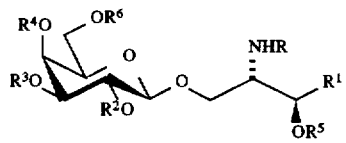

wherein

R is an acyl residue of a fatty acid;

$R^1$ is —(CH=CH)$_m$—(CH$_2$)$_n$—CH$_3$;

$R^2$, $R^3$, $R^4$, $R^5$ and $R^6$ each are independently hydrogen, unsubstituted or substituted (lower)alkanoyl, arylalkyl or arylcarbonyl wherein said substituent is selected from the group consisting of halogen, $C_{1-4}$ alkyl, trifluoromethyl, hydroxy and $C_{1-4}$ alkoxy provided that one of $R^2$, $R^3$, $R^4$ and $R^6$ substituents is —(CH$_2$)$_p$—CH(CO$_2$R$^7$)$_2$;

m is an integer of 0 or 1;

n is an integer of from 5 to 14 inclusive;

p is an integer of from 2 to 6 inclusive; and $R^7$ is hydrogen, a hydrolyzable ester group or a cation to form a non-toxic pharmaceutically acceptable salt; or a solvate or hydrate thereof.

4. A compound of claim 1 wherein $R^2$ is —(CH$_2$)$_p$—CH(CO$_2$R$^7$)$_2$ and $R^3$, $R^4$, $R^5$ and $R^6$ each are independently hydrogen, unsubstituted or substituted (lower)alkanoyl, arylalkyl or arylcarbonyl wherein said substituent is selected from the group consisting of halogen, $C_{1-4}$ alkyl, trifluoromethyl, hydroxy and $C_{1-4}$ alkoxy; p is an integer of from 2 to 6 inclusive; and $R^7$ is hydrogen, a hydrolyzable ester group or a cation to form a non-toxic pharmaceutically acceptable salt; or a solvate or hydrate thereof.

5. A compound of claim 1 wherein $R^3$ is —(CH$_2$)$_p$—CH(CO$_2$R$^7$)$_2$ and $R^2$, $R^4$, $R^5$ and $R^6$ each are independently hydrogen, unsubstituted or substituted (lower)alkanoyl, arylalkyl or arylcarbonyl wherein said substituent is selected from the group consisting of halogen, $C_{1-4}$ alkyl, trifluoromethyl, hydroxy and $C_{1-4}$ alkoxy; p is an integer of from 2 to 6 inclusive; and $R^7$ is hydrogen, a hydrolyzable ester group or a cation to form a non-toxic pharmaceutically acceptable salt; or a solvate or hydrate thereof.

6. A compound of claim 1 wherein $R^4$ is —(CH$_2$)$_p$—CH(CO$_2$R$^7$)$_2$ and $R^2$, $R^3$, $R^5$ and $R^6$ each are independently hydrogen, unsubstituted or substituted (lower)alkanoyl, arylalkyl or arylcarbonyl wherein said substituent is selected from the group consisting of halogen, $C_{1-4}$ alkyl, trifluoromethyl, hydroxy and $C_{1-4}$ alkoxy; p is an integer of from 2 to 6 inclusive; and $R^7$ is hydrogen, a hydrolyzable ester group or a cation to form a non-toxic pharmaceutically acceptable salt; or a solvate or hydrate thereof.

7. A compound of claim 1 wherein $R^6$ is —(CH$_2$)$_p$—CH(CO$_2$R$^7$)$_2$ and $R^2$, $R^3$, $R^4$ and $R^5$ each are independently hydrogen, unsubstituted or substituted (lower)alkanoyl, arylalkyl or arylcarbonyl wherein said substituent is selected from the group consisting of halogen, $C_{1-4}$ alkyl, trifluoromethyl, hydroxy and $C_{1-4}$ alkoxy; p is an integer of from 2 to 6 inclusive; and $R^7$ is hydrogen, a hydrolyzable ester group or a cation to form a non-toxic pharmaceutically acceptable salt; or a solvate or hydrate thereof.

8. A compound of claim 4 wherein $R^2$ is —(CH$_2$)$_p$—CH(CO$_2$R$^7$)$_2$ and $R^3$, $R^4$, $R^5$ and $R^6$ each are independently hydrogen or benzoyl.

9. A compound of claim 5 wherein $R^3$ is —(CH$_2$)$_p$—CH(CO$_2$R$^7$)$_2$ and $R^2$, $R^4$, $R^5$ and $R^6$ each are independently hydrogen or benzoyl.

10. A compound of claim 6 wherein $R^4$ is —(CH$_2$)$_p$—CH(CO$_2$R$^7$)$_2$ and $R^2$, $R^3$, $R^5$ and $R^6$ each are independently hydrogen or benzoyl.

11. A compound of claim 7 wherein $R^6$ is —(CH$_2$)$_p$—CH(CO$_2$R$^7$)$_2$ and $R^2$, $R^3$, $R^4$ and $R^5$ each are independently hydrogen or benzoyl.

12. A compound of claim 2 wherein R is the acyl residue of palmitic acid, lignoceric acid, nervonic acid or stearic acid; and $R^7$ is hydrogen or a cation to form a non-toxic pharmaceutically acceptable salt; or a solvate or hydrate thereof.

13. A compound of claim 3 wherein R is the acyl residue of palmitic acid, lignoceric acid, nervonic acid or stearic acid; and $R^7$ is hydrogen or a cation to form a non-toxic pharmaceutically acceptable salt; or a solvate or hydrate thereof.

14. A compound of claim 2 wherein m is 1; n is 12 and p is 2 or 4.

15. A compound of claim 3 wherein m is 1; n is 12 and p is 2 or 4.

16. A compound of claim 12 wherein R is the acyl residue of palmitic acid.

17. A compound of claim 13 wherein R is the acyl residue of palmitic acid.

18. A compound of claim 1 selected from the group consisting of:

(2S,3R,4E)-3-benzoyloxy-2-hexadecanoylamino-1-[2-O-(3,3-di-carboxyprop-1-yl)-3-O-benzoyl-β-D-galactopyranosyloxy]-4-octadecene;

(2S,3R,4E)-3-benzoyloxy-2-hexadecanoylamino-1-[2-O-(5,5-dicarboxypent-1-yl)-3-O-benzoyl-β-D-galactopyranosyloxy]-4-octadecene;

(2S,3R,4E)-3-benzoyloxy-2-hexadecanoylamino-1-[6-O-(3,3-di-carboxyprop-1-yl)-α-D-galactopyranosyloxy]-4-octadecene;

(2S,3R,4E)-3-benzoyloxy-2-hexadecanoylamino-1-[3-O-(5,5-di-carboxypent-1-yl)-β-D-galactopyranosyloxy]-4-octadecene;

(2S,3R,4E)-3-benzoyloxy-2-hexadecanoylamino-1-[3-O-(5,5-di-carboxypent-1-yl)-β-D-galactopyranosyloxy]-4-octadecene;

(2S,3R,4E)-3-benzoyloxy-2-hexadecanoylamino-1-[2-O-(5,5-di-carboxypent-1-yl)-3-O-benzoyl-β-D-galactopyranosyloxy]-4-octadecene;

(2S,3R,4E)-3-benzoyloxy-2-hexadecanoylamino-1-[4-O-(3,3-di-carboxyprop-1-yl)-α-D-galactopyranosyloxy]-4-octadecene; and (2S,3R,4E)-3-benzoyloxy-2-hexadecanoylamino-1-[2-O-(5,5-di-carboxypent-1-yl)-β-D-galactopyranosyloxy]-4-octadecene or a non-toxic pharmaceutically acceptable salt; or a solvate or hydrate thereof.

19. A method for the treatment of selectin-mediated inflammatory diseases mammal in need thereof, which comprises administering to said mammal a therapeutically effective amount of a compound as defined in claim 1 or a pharmaceutical composition thereof.

20. A method for the treatment of selectin-mediated inflammatory diseases in a mammal in need thereof, which comprises administering to said mammal a therapeutically effective amount of a compound as defined in claim 18 or a pharmaceutical composition thereof.

* * * * *